United States Patent
So et al.

(10) Patent No.: US 11,871,658 B2
(45) Date of Patent: Jan. 9, 2024

(54) COMPOUND FOR ORGANIC ELECTRIC ELEMENT, ORGANIC ELECTRIC ELEMENT USING SAME, AND ELECTRONIC DEVICE THEREOF

(71) Applicant: DUK SAN NEOLUX CO., LTD, Cheonan-si (KR)

(72) Inventors: Ki Ho So, Cheonan-si (KR); Yun Suk Lee, Seongnam-si (KR); Jong Gwang Park, Cheonan-si (KR); Yeon Hee Choi, Cheonan-si (KR); Kyoung Chul Kim, Sejong (KR)

(73) Assignee: Duk San Neolux Co., Ltd.

( * ) Notice: Subject to any disclaimer, the term of this patent is extended or adjusted under 35 U.S.C. 154(b) by 242 days.

(21) Appl. No.: 16/494,235

(22) PCT Filed: Mar. 9, 2018

(86) PCT No.: PCT/KR2018/002858
§ 371 (c)(1),
(2) Date: Sep. 13, 2019

(87) PCT Pub. No.: WO2018/169261
PCT Pub. Date: Sep. 20, 2018

(65) Prior Publication Data
US 2020/0136052 A1    Apr. 30, 2020

(30) Foreign Application Priority Data
Mar. 16, 2017 (KR) .................. 10-2017-0033161

(51) Int. Cl.
H10K 85/60 (2023.01)
C07D 209/88 (2006.01)
C07D 333/76 (2006.01)
C07D 409/12 (2006.01)
C09K 11/06 (2006.01)
H10K 50/11 (2023.01)
H10K 101/10 (2023.01)

(52) U.S. Cl.
CPC ......... *H10K 85/636* (2023.02); *C07D 209/88* (2013.01); *C07D 333/76* (2013.01); *C07D 409/12* (2013.01); *C09K 11/06* (2013.01); *H10K 85/633* (2023.02); *C09K 2211/1018* (2013.01); *H10K 50/11* (2023.02); *H10K 85/615* (2023.02); *H10K 85/626* (2023.02); *H10K 85/6572* (2023.02); *H10K 85/6574* (2023.02); *H10K 85/6576* (2023.02); *H10K 2101/10* (2023.02)

(58) Field of Classification Search
None
See application file for complete search history.

(56) References Cited

U.S. PATENT DOCUMENTS

| | | | |
|---|---|---|---|
| 9,385,335 B2 * | 7/2016 | Pflumm | C09B 57/008 |
| 10,297,758 B2 | 5/2019 | Lee et al. | |
| 2003/0118866 A1 * | 6/2003 | Oh | H01L 51/006 428/690 |
| 2004/0124766 A1 * | 7/2004 | Nakagawa | H01L 51/0064 313/506 |
| 2013/0240858 A1 * | 9/2013 | Nishimura | H01L 27/3211 257/40 |
| 2013/0321375 A1 * | 12/2013 | Ka | G09G 3/3233 345/212 |
| 2016/0005981 A1 | 1/2016 | Kim et al. | |
| 2016/0149140 A1 | 5/2016 | Kang et al. | |
| 2017/0141311 A1 | 5/2017 | Lee et al. | |
| 2017/0200899 A1 | 7/2017 | Kim et al. | |
| 2017/0200903 A1 | 7/2017 | Park et al. | |
| 2018/0083204 A1 | 3/2018 | Kim et al. | |
| 2019/0157560 A1 | 5/2019 | Lee et al. | |
| 2019/0173023 A1 | 6/2019 | Kim et al. | |

FOREIGN PATENT DOCUMENTS

| | | |
|---|---|---|
| CN | 103956436 A | 7/2014 |
| CN | 104356004 A | 2/2015 |
| CN | 107068912 A | 8/2017 |
| JP | 2007180148 A | 7/2007 |
| KR | 20100123172 A | 11/2010 |
| KR | 1020110084798 A | 7/2011 |
| KR | 20110087768 A | 8/2011 |
| KR | 20130024521 A | 3/2013 |
| KR | 1020140145428 A | 12/2014 |
| KR | 20150022461 A | 3/2015 |
| KR | 1020150098062 A | 8/2015 |
| KR | 1020170085183 A | 7/2017 |
| KR | 20180035260 A | 4/2018 |

OTHER PUBLICATIONS

Yun, S. J., Seo, M. H., & Lee, S. (2020). Dibenzofuran derivatives with meta-and para-triphenylamine substituents as hole-transporting materials in organic light-emitting devices. Dyes and Pigments, 175, 108121. (Year: 2020).*
National Phase of PCT/KR2018/002857, Sep. 13, 2019, Ga Eun Lee et al.
U.S. Appl. No. 16/334,527, filed Mar. 19, 2019, Hyong Keun Park et al.
U.S. Appl. No. 16/334,801, filed Mar. 20, 2019, Hyoung Keun Park et al.
International Search Report (in English and Korean) and Written Opinion (in Korean) issued in PCT/KR2018/002858, dated Jun. 15, 2018; ISA/KR.

* cited by examiner

*Primary Examiner* — Dawn L Garrett
(74) *Attorney, Agent, or Firm* — Harness, Dickey & Pierce, P.L.C.

(57) ABSTRACT

The present disclosure provides: a compound capable of enabling high luminous efficiency, a low driving voltage, and an improved lifetime of an element; an organic electric element using the same; and an electronic device thereof.

12 Claims, 20 Drawing Sheets

| Compound | FD-MS | Compound | FD-MS |
|---|---|---|---|
| Sub 1-1 | m/z=495.06($C_{30}H_{19}Cl_2NS$=496.45) | Sub 1-2 | m/z=571.09($C_{36}H_{23}Cl_2NS$=572.55) |
| Sub 1-3 | m/z=554.13($C_{36}H_{24}Cl_2N_2$=555.50) | Sub 1-4 | m/z=554.13($C_{36}H_{24}Cl_2N_2$=555.50) |
| Sub 1-5 | m/z=495.06($C_{30}H_{19}Cl_2NS$=496.45) | Sub 1-6 | m/z=479.08($C_{30}H_{19}Cl_2NO$=480.39) |
| Sub 1-7 | m/z=495.06($C_{30}H_{19}Cl_2NS$=496.45) | Sub 1-8 | m/z=479.08($C_{30}H_{19}Cl_2NO$=480.39) |
| Sub 1-9 | m/z=545.08($C_{34}H_{21}Cl_2NS$=546.51) | Sub 1-10 | m/z=604.15($C_{40}H_{26}Cl_2N_2$=605.56) |
| Sub 1-11 | m/z=554.13($C_{36}H_{24}Cl_2N_2$=555.50) | Sub 1-12 | m/z=630.16($C_{42}H_{28}Cl_2N_2$=631.60) |
| Sub 1-13 | m/z=630.16($C_{42}H_{28}Cl_2N_2$=631.60) | Sub 1-14 | m/z=604.15($C_{40}H_{26}Cl_2N_2$=605.56) |
| Sub 1-15 | m/z=545.08($C_{34}H_{21}Cl_2NS$=546.51) | Sub 1-16 | m/z=595.09($C_{38}H_{23}Cl_2NS$=596.57) |
| Sub 1-17 | m/z=479.08($C_{30}H_{19}Cl_2NO$=480.39) | Sub 1-18 | m/z=554.13($C_{36}H_{24}Cl_2N_2$=555.50) |
| Sub 1-19 | m/z=495.06($C_{30}H_{19}Cl_2NS$=496.45) | Sub 1-20 | m/z=479.08($C_{30}H_{19}Cl_2NO$=480.39) |
| Sub 1-21 | m/z=554.13($C_{36}H_{24}Cl_2N_2$=555.50) | Sub 1-22 | m/z=495.06($C_{30}H_{19}Cl_2NS$=496.45) |
| Sub 1-23 | m/z=495.06($C_{30}H_{19}Cl_2NS$=496.45) | Sub 1-24 | m/z=479.08($C_{30}H_{19}Cl_2NO$=480.39) |
| Sub 1-25 | m/z=529.10($C_{34}H_{21}Cl_2NO$=530.45) | Sub 1-26 | m/z=545.08($C_{34}H_{21}Cl_2NS$=546.51) |
| Sub 1-27 | m/z=529.10($C_{34}H_{21}Cl_2NO$=530.45) | Sub 1-28 | m/z=604.15($C_{40}H_{26}Cl_2N_2$=605.56) |
| Sub 1-29 | m/z=710.14($C_{46}H_{38}Cl_2N_3S$=711.70) | Sub 1-30 | m/z=545.08($C_{34}H_{21}Cl_2NS$=546.51) |
| Sub 1-31 | m/z=529.10($C_{34}H_{21}Cl_2NO$=530.45) | Sub 1-32 | m/z=595.09($C_{38}H_{23}Cl_2NS$=596.57) |
| Sub 1-33 | m/z=882.26($C_{62}H_{40}Cl_2N_2$=883.92) | Sub 1-34 | m/z=680.18($C_{46}H_{30}Cl_2N_2$=681.66) |
| Sub 1-35 | m/z=605.13($C_{40}H_{25}Cl_2NO$=606.55) | Sub 1-36 | m/z=622.11($C_{40}H_{25}Cl_2NS$=622.61) |
| Sub 1-37 | m/z=651.06($C_{40}H_{23}Cl_2NS_2$=652.65) | Sub 1-38 | m/z=651.06($C_{40}H_{23}Cl_2NS_2$=652.65) |

Table 1

FIG. 18

| | | | |
|---|---|---|---|
| Sub 1-39 | m/z=619.11(C$_{40}$H$_{23}$Cl$_2$NO$_2$=620.53) | Sub 1-40 | m/z=635.09(C$_{40}$H$_{23}$Cl$_2$NOS=636.59) |
| Sub 1-41 | m/z=710.14(C$_{46}$H$_{28}$Cl$_2$N$_2$S=711.70) | Sub 1-42 | m/z=545.08(C$_{34}$H$_{21}$Cl$_2$NS=546.51) |
| Sub 1-43 | m/z=529.10(C$_{34}$H$_{21}$Cl$_2$NO=530.45) | Sub 1-44 | m/z=604.15(C$_{40}$H$_{26}$Cl$_2$N$_2$=605.56) |
| Sub 1-45 | m/z=595.09(C$_{38}$H$_{23}$Cl$_2$NS=596.57) | Sub 1-46 | m/z=605.13(C$_{40}$H$_{25}$Cl$_2$NO=606.55) |
| Sub 1-47 | m/z=680.18(C$_{46}$H$_{30}$Cl$_2$N$_2$=681.66) | Sub 1-48 | m/z=635.09(C$_{40}$H$_{23}$Cl$_2$NOS=636.59) |
| Sub 1-49 | m/z=645.16(C$_{43}$H$_{29}$Cl$_2$NO=646.61) | Sub 1-50 | m/z=710.14(C$_{46}$H$_{28}$Cl$_2$N$_2$S=711.10) |
| Sub 1-51 | m/z=545.08(C$_{34}$H$_{21}$Cl$_2$NS=546.51) | Sub 1-52 | m/z=605.13(C$_{40}$H$_{25}$Cl$_2$NO=606.55) |
| Sub 1-53 | m/z=604.15(C$_{40}$H$_{26}$Cl$_2$N$_2$=605.56) | Sub 1-54 | m/z=720.21(C$_{49}$H$_{34}$Cl$_2$N$_2$=721.73) |
| Sub 1-55 | m/z=560.09(C$_{34}$H$_{22}$Cl$_2$N$_2$S=561.52) | Sub 1-56 | m/z=583.11(C$_{37}$H$_{23}$Cl$_2$NO$_2$=584.50) |
| Sub 1-57 | m/z=719.19(C$_{48}$H$_{31}$Cl$_2$N$_3$=720.70) | Sub 1-58 | m/z=651.06(C$_{40}$H$_{23}$Cl$_2$NS$_2$=652.65) |
| Sub 1-59 | m/z=611.12(C39H27Cl2NS=612.61) | Sub 1-60 | m/z=601.05(C$_{36}$H$_{21}$Cl$_2$NS$_2$=602.59) |
| Sub 1-61 | m/z=635.09(C$_{40}$H$_{23}$Cl$_2$NOS=636.59) | Sub 1-62 | m/z=649.17(C$_{42}$H$_{21}$D$_5$Cl$_2$N$_2$O=650.61) |
| Sub 1-63 | m/z=601.05(C$_{36}$H$_{21}$Cl$_2$NS$_2$=602.59) | Sub 1-64 | m/z=660.12(C$_{42}$H$_{26}$Cl$_2$N$_2$S=661.64) |
| Sub 1-65 | m/z=645.13(C$_{42}$H$_{25}$Cl$_2$NO$_2$=646.57) | Sub 1-66 | m/z=809.17(C$_{55}$H$_{33}$Cl$_2$NS=810.84) |
| Sub 1-67 | m/z=601.05(C$_{36}$H$_{21}$Cl$_2$NS$_2$=602.59) | Sub 1-68 | m/z=685.10(C$_{44}$H$_{25}$Cl$_2$NOS=686.65) |
| Sub 1-69 | m/z=601.05(C$_{36}$H$_{21}$Cl$_2$NS$_2$=602.59) | Sub 1-70 | m/z=569.09(C$_{36}$H$_{21}$Cl$_2$NO$_2$=570.47) |
| Sub 1-71 | m/z=601.05(C$_{36}$H$_{21}$Cl$_2$NS$_2$=602.59) | Sub 1-72 | m/z=585.07(C$_{36}$H$_{21}$Cl$_2$NOS=586.53) |
| Sub 1-73 | m/z=660.12(C$_{42}$H$_{26}$Cl$_2$N$_2$S=661.64) | Sub 1-74 | m/z=667.08(C$_{42}$H$_{25}$Cl$_2$NS$_2$=678.69) |
| Sub 1-75 | m/z=635.09(C$_{40}$H$_{23}$Cl$_2$NOS=636.59) | Sub 1-76 | m/z=707.04(C$_{42}$H$_{23}$Cl$_2$NS$_3$=708.73) |
| Sub 1-77 | m/z=766.11(C$_{48}$H$_{28}$Cl$_2$N$_2$S$_2$=767.79) | Sub 1-78 | m/z=585.07(C$_{36}$H$_{21}$Cl$_2$NOS=586.53) |
| Sub 1-79 | m/z=569.09(C$_{36}$H$_{21}$Cl$_2$NO$_2$=570.47) | Sub 1-80 | m/z=644.14(C$_{42}$H$_{26}$Cl$_2$N$_2$O=645.58) |
| Sub 1-81 | m/z=661.10(C$_{42}$H$_{25}$Cl$_2$NOS=662.63) | Sub 1-82 | m/z=619.11(C$_{40}$H$_{23}$Cl$_2$NO$_2$=620.53) |
| Sub 1-83 | m/z=675.08(C$_{42}$H$_{23}$Cl$_2$NO$_2$S=676.61) | Sub 1-84 | m/z=669.13(C$_{44}$H$_{25}$Cl$_2$NO$_2$=670.59) |
| Sub 1-85 | m/z=660.12(C$_{42}$H$_{26}$Cl$_2$N$_2$S=661.64) | Sub 1-86 | m/z=644.14(C$_{42}$H$_{26}$Cl$_2$N$_2$O=645.58) |
| Sub 1-87 | m/z=719.19(C$_{48}$H$_{31}$Cl$_2$N$_3$=720.70) | Sub 1-88 | m/z=710.14(C$_{46}$H$_{28}$Cl$_2$N$_2$S=711.70) |
| Sub 1-89 | m/z=810.18(C$_{54}$H$_{32}$Cl$_2$N$_2$O$_2$=811.76) | Sub 1-90 | m/z=750.13(C$_{48}$H$_{28}$Cl$_2$N$_2$OS=751.73) |
| Sub 1-91 | m/z=710.14(C$_{46}$H$_{28}$Cl$_2$N$_2$S=711.70) | | |

Table 1 (cont.)

FIG. 19

| Compound | FD-MS | Compound | FD-MS |
|---|---|---|---|
| P-1 | m/z=761.29($C_{54}H_{39}N_3S$=761.99) | P-2 | m/z=837.32($C_{60}H_{43}N_3S$=838.09) |
| P-3 | m/z=820.36($C_{60}H_{44}N_4$=821.04) | P-4 | m/z=820.36($C_{60}H_{44}N_4$=821.04) |
| P-5 | m/z=761.29($C_{54}H_{39}N_3S$=761.99) | P-6 | m/z=917.29($C_{64}H_{43}N_3S_2$=918.19) |
| P-7 | m/z=845.34($C_{62}H_{43}N_3O$=846.05) | P-8 | m/z=821.34($C_{60}H_{43}N_3O$=822.02) |
| P-9 | m/z=805.39($C_{58}H_{31}D_{10}N_3O$=806.05) | P-10 | m/z=811.30($C_{58}H_{41}N_3S$=812.05) |
| P-11 | m/z=761.29($C_{54}H_{39}N_3S$=761.99) | P-12 | m/z=845.34($C_{62}H_{43}N_3O$=846.05) |
| P-13 | m/z=795.32($C_{58}H_{41}N_3O$=795.99) | P-14 | m/z=837.32($C_{60}H_{43}N_3S$=838.09) |
| P-15 | m/z=913.35($C_{66}H_{47}N_3S$=914.18) | P-16 | m/z=811.30($C_{58}H_{41}N_3S$=812.05) |
| P-17 | m/z=870.37($C_{64}H_{46}N_4$=871.10) | P-18 | m/z=820.36($C_{60}H_{44}N_4$=821.04) |
| P-19 | m/z=896.39($C_{66}H_{48}N_4$=897.14) | P-20 | m/z=896.39($C_{66}H_{48}N_4$=897.14) |

Table 2

FIG. 25

| P-21 | m/z=995.40(C$_{73}$H$_{49}$N$_5$=996.23) | P-22 | m/z=811.30(C$_{58}$H$_{41}$N$_3$S=812.05) |
|---|---|---|---|
| P-23 | m/z=943.31(C$_{66}$H$_{45}$N$_3$S$_2$=944.23) | P-24 | m/z=911.39(C$_{67}$H$_{49}$N$_3$O=912.15) |
| P-25 | m/z=820.36(C$_{60}$H$_{44}$N$_4$=821.04) | P-26 | m/z=761.29(C$_{54}$H$_{39}$N$_3$S=761.99) |
| P-27 | m/z=745.31(C$_{54}$H$_{39}$N$_3$O=745.93) | P-28 | m/z=905.37(C$_{60}$H$_{55}$N$_3$SSi$_2$=906.35) |
| P-29 | m/z=1051.40(C$_{77}$H$_{53}$N$_3$S=1052.35) | P-30 | m/z=811.30(C$_{58}$H$_{41}$N$_3$S=812.05) |
| P-31 | m/z=863.35(C$_{62}$H$_{45}$N$_3$O$_2$=864.06) | P-32 | m/z=946.40(C$_{70}$H$_{50}$N$_4$=947.20) |
| P-33 | m/z=761.29(C$_{54}$H$_{39}$N$_3$S=761.99) | P-34 | m/z=961.35(C$_{70}$H$_{47}$N$_3$S=962.23) |
| P-35 | m/z=795.32(C$_{58}$H$_{41}$N$_3$O=795.99) | P-36 | m/z=871.36(C$_{64}$H$_{45}$N$_3$O=872.08) |
| P-37 | m/z=811.30(C$_{58}$H$_{41}$N$_3$S=812.05) | P-38 | m/z=795.32(C$_{58}$H$_{41}$N$_3$O=795.99) |
| P-39 | m/z=870.37(C$_{64}$H$_{46}$N$_4$=871.10) | P-40 | m/z=976.36(C$_{70}$H$_{48}$N$_4$S=977.24) |
| P-41 | m/z=811.30(C$_{58}$H$_{41}$N$_3$S=812.05) | P-42 | m/z=895.36(C$_{66}$H$_{45}$N$_3$O=869.11) |
| P-43 | m/z=887.33(C$_{64}$H$_{45}$N$_3$S=888.15) | P-44 | m/z=937.35(C$_{68}$H$_{47}$N$_3$S=938.21) |
| P-45 | m/z=921.37(C$_{68}$H$_{47}$N$_3$O=922.14) | P-46 | m/z=921.37(C$_{68}$H$_{47}$N$_3$O=922.14) |
| P-47 | m/z=977.38(C$_{71}$H$_{51}$N$_3$S=978.27) | P-48 | m/z=1372.60(C$_{102}$H$_{76}$N$_4$O=1373.76) |
| P-49 | m/z=946.40(C$_{70}$H$_{50}$N$_4$=947.20) | P-50 | m/z=977.34(C$_{70}$H$_{47}$N$_3$OS=978.23) |
| P-51 | m/z=963.36(C$_{70}$H$_{49}$N$_3$S=964.24) | P-52 | m/z=917.29(C$_{64}$H$_{43}$N$_3$S$_2$=918.19) |
| P-53 | m/z=917.29(C$_{64}$H$_{43}$N$_3$S$_2$=918.19) | P-54 | m/z=935.35(C$_{68}$H$_{45}$N$_3$O$_2$=936.13) |
| P-55 | m/z=973.27(C$_{64}$H$_{39}$F$_4$N$_3$OS=974.09) | P-56 | m/z=976.36(C$_{70}$H$_{48}$N$_4$S=977.24) |
| P-57 | m/z=811.30(C$_{58}$H$_{41}$N$_3$S=812.05) | P-58 | m/z=795.32(C$_{58}$H$_{41}$N$_3$O=795.99) |
| P-59 | m/z=870.37(C$_{64}$H$_{46}$N$_4$=871.10) | P-60 | m/z=861.32(C$_{62}$H$_{43}$N$_3$S=862.11) |
| P-61 | m/z=871.36(C$_{64}$H$_{45}$N$_3$O=872.08) | P-62 | m/z=946.40(C$_{70}$H$_{50}$N$_4$=947.20) |
| P-63 | m/z=861.32(C$_{62}$H$_{43}$N$_3$S=862.11) | P-64 | m/z=871.36(C$_{64}$H$_{45}$N$_3$O=872.08) |
| P-65 | m/z=901.31(C$_{64}$H$_{43}$N$_3$OS=902.13) | P-66 | m/z=911.39(C$_{67}$H$_{49}$N$_3$O=912.15) |
| P-67 | m/z=895.36(C$_{66}$H$_{45}$N$_3$O=869.11) | P-68 | m/z=976.36(C$_{70}$H$_{48}$N$_4$S=977.24) |
| P-69 | m/z=911.33(C$_{66}$H$_{45}$N$_3$S=912.17) | P-70 | m/z=947.39(C$_{70}$H$_{49}$N$_3$O=948.18) |
| P-71 | m/z=870.37(C$_{64}$H$_{46}$N$_4$=871.10) | P-72 | m/z=986.43(C$_{73}$H$_{54}$N$_4$=987.26) |
| P-73 | m/z=932.30(C$_{64}$H$_{44}$N$_4$S$_2$=933.20) | P-74 | m/z=915.35(C$_{65}$H$_{45}$N$_3$O$_3$=916.09) |
| P-75 | m/z=985.41(C$_{72}$H$_{51}$N$_5$=986.24) | P-76 | m/z=917.29(C$_{64}$H$_{43}$N$_3$S$_2$=918.19) |
| P-77 | m/z=877.35(C$_{63}$H$_{47}$N$_3$S=878.15) | P-78 | m/z=867.27(C$_{60}$H$_{41}$N$_3$S$_2$=868.13) |
| P-79 | m/z=965.26(C$_{64}$H$_{43}$N$_3$OS$_3$=966.25) | P-80 | m/z=915.40(C$_{66}$H$_{41}$D$_5$N$_4$O=916.15) |
| P-81 | m/z=867.27(C$_{60}$H$_{41}$N$_3$S$_2$=868.13) | P-82 | m/z=976.36(C$_{70}$H$_{48}$N$_4$S=977.24) |
| P-83 | m/z=911.35(C$_{66}$H$_{45}$N$_3$O$_2$=912.11) | P-84 | m/z=1261.50(C$_{92}$H$_{67}$N$_3$OS=1262.63) |
| P-85 | m/z=867.27(C$_{60}$H$_{41}$N$_3$S$_2$=868.13) | P-86 | m/z=951.33(C$_{68}$H$_{45}$N$_3$OS=952.19) |
| P-87 | m/z=967.31(C$_{58}$H$_{45}$N$_3$S$_2$=968.25) | P-88 | m/z=925.33(C$_{66}$H$_{43}$N$_3$O$_3$=926.09) |
| P-89 | m/z=867.27(C$_{60}$H$_{41}$N$_3$S$_2$=868.13) | P-90 | m/z=851.30(C$_{60}$H$_{41}$N$_3$OS=852.07) |
| P-91 | m/z=926.34(C$_{65}$H$_{46}$N$_4$S=927.18) | P-92 | m/z=943.31(C$_{66}$H$_{45}$N$_3$S$_2$=944.23) |
| P-93 | m/z=951.33(C$_{68}$H$_{45}$N$_3$OS=952.19) | P-94 | m/z=973.26(C$_{66}$H$_{43}$N$_3$S$_3$=974.27) |

Table 2 (cont.)

FIG. 26

| P-95 | m/z=957.28($C_{66}H_{43}N_3OS_2$=958.21) | P-96 | m/z=1032.33($C_{72}H_{48}N_4S_2$=1033.32) |
|---|---|---|---|
| P-97 | m/z=851.30($C_{60}H_{41}N_3OS$=852.07) | P-98 | m/z=916.38($C_{66}H_{40}D_5N_3O_2$=917.14) |
| P-99 | m/z=910.37($C_{66}H_{46}N_4O$=911.12) | P-100 | m/z=927.33($C_{66}H_{45}N_3OS$=928.17) |
| P-101 | m/z=885.34($C_{64}H_{43}N_3O_2$=886.07) | P-102 | m/z=941.32($C_{66}H_{43}N_3O_2S$=942.15) |
| P-103 | m/z=1016.35($C_{72}H_{48}N_4OS$=1017.26) | P-104 | m/z=935.35($C_{68}H_{45}N_3O_2$=936.13) |
| P-105 | m/z=926.34($C_{66}H_{46}N_4S$=927.18) | P-106 | m/z=910.37($C_{66}H_{46}N_4O$=911.12) |
| P-107 | m/z=985.41($C_{72}H_{51}N_5$=986.24) | P-108 | m/z=976.36($C_{70}H_{48}N_4S$=977.24) |
| P-109 | m/z=960.38($C_{70}H_{48}N_4O$=961.18) | P-110 | m/z=1368.53($C_{101}H_{68}N_4O_2$=1369.68) |
| P-111 | m/z=1016.35($C_{72}H_{48}N_4OS$=1017.26) | P-112 | m/z=976.36($C_{70}H_{48}N_4S$=977.24) |

Table 2 (cont.)

FIG. 27

COMPOUND FOR ORGANIC ELECTRIC ELEMENT, ORGANIC ELECTRIC ELEMENT USING SAME, AND ELECTRONIC DEVICE THEREOF

CROSS-REFERENCE TO RELATED APPLICATIONS

This application is a U.S. National Phase Application under 35 U.S.C. 371 of International Application No. PCT/KR2018/002858, filed on Mar. 9, 2018, which claims the benefit of Korean Patent Application No. 10-2017-0033161, filed on Mar. 16, 2017. The entire disclosures of the above applications are incorporated herein by reference.

TECHNICAL FIELD

The present disclosure relates to a compound for an organic electric element, an organic electric element using same, and an electronic device using same.

BACKGROUND ART

In general, organic light emission refers to a phenomenon in which electric energy is converted into light energy by using an organic material. An organic electric element utilizing organic light emission usually has a structure including an anode, a cathode, and an organic material layer interposed therebetween. In many cases, the organic material layer may have a multilayered structure including multiple layers made of different materials in order to improve efficiency and stability of an organic electric element, and for example, may be composed of a hole injection layer, a hole transport layer, a light emitting layer, an electron transport layer, an electron injection layer, and the like.

Materials used for an organic material layer in an organic electric element may be classified into light emitting materials and charge transport materials, for example, hole injection materials, hole transport materials, electron transport materials, electron injection materials, and the like, according to the function thereof.

Currently, the market for portable displays is on the way to large-area displays, and thus the sizes of displays are increasing. As a result, the larger power consumption than is required in existing portable displays is required. Therefore, the power consumption is a very important factor in portable displays with a limited power source, such as a battery, and efficiency and lifetime issue are also important factors to be solved.

Efficiency, lifetime, driving voltages, and the like are correlated with each other. If the efficiency is increased, the driving voltage is relatively lowered, and as the driving voltage is lowered, the crystallization of an organic material due to Joule heating generated during driving is reduced, and as a result, the lifetime shows a tendency to increase. However, the efficiency cannot be maximized only by simply improving organic material layers. The reason is that both long lifetime and high efficiency can be achieved when there is an optimal combination of energy levels, T1 values, inherent material properties (mobility, interfacial properties, etc.), and the like among the respective layers included in the organic material layer.

As for recent organic light emitting diodes, in order to solve the light emission problem in a hole transport layer, the use of a light emitting auxiliary layer between the hole transport layer and a light emitting layer has been studied, and respective light emitting layers (R, G, B) have different desired properties, and thus it is time to develop different light emitting auxiliary layers according to respective light emitting layers (R, G, B).

In general, electrons are transferred from an electron transport layer to a light emitting layer and holes are transferred from a hole transport layer to the light emitting layer, so that the recombination of the electrons and the holes produces excitons.

However, a material used in the hole transport layer should have a low HOMO value, and thus it mainly has a low T1 value. As a result, the excitons produced from the light emitting layer are transported to the interface of the hole transport layer or to the hole transport layer, resulting in light emission in the interface of the hole transport layer or a charge unbalance in the light emitting layer, thereby causing light emission in the interface of the hole transport layer The light emission in the interface of the hole transport layer causes a deterioration in color purity, a reduction in efficiency, and a shortened lifetime. Therefore, there is an urgent need of the development of a light emitting auxiliary layer, which contains a material having a HOMO level between the HOMO energy level of the hole transport layer and the HOMO energy level of the light emitting layer, has a high T1 value, and hole mobility within an appropriate driving voltage range (within a driving voltage range of a blue element of a full device).

However, this cannot be simply attained by structural characteristics of a core of a material for the light emitting auxiliary layer. A high-efficiency and high-lifetime element can be attained under the core and sub-substituent characteristics of a material for a light emitting auxiliary layer and appropriate combinations between a light emitting auxiliary layer and a hole transport layer and between a light emitting auxiliary layer and a light emitting layer.

Also, there is also a need of the development of material for a hole injection/transport layer and a light emitting auxiliary layer, which have stable characteristics against the Joule heating generated during driving of an element, that is, a high glass transition temperature.

It has been reported that the low glass transition temperatures of the materials for the hole transport layer and the light emitting auxiliary layer result in a deterioration in surface uniformity of thin films during driving of an element and the materials may be deflected due to the heat generated during driving of an element, which greatly affect the lifetime of an element.

Also, OLED elements are formed mainly by deposition, and thus there is a need of the development of a material capable of enduring for a long time, that is, a material having strong heat resistance.

That is, in order to allow the organic electric element to sufficiently exert excellent characteristics thereof, most of all, materials constituting an organic material layer in the element, for examples, a hole injection material, a hole transport material, a light emitting material, an electron transport material, an electron injection material, a material for a light emitting auxiliary layer, and the like should be supported by stable and efficient materials. However, the development of stable and efficient materials for the organic material layer for an organic electric element is not sufficiently achieved. Therefore, the development of new materials is continuously needed, and especially, the development of a material for the light emitting auxiliary layer and a material for the hole transport layer is urgently required.

DETAILED DESCRIPTION OF THE INVENTION

Technical Problem

In order to solve the above-mentioned problems occurring in the prior art, an object of the present disclosure is to provide a compound having an efficient electron blocking ability and hole transport ability and capable of attaining high light-emission efficiency, a low driving voltage, high heat resistance, and improved color purity and lifetime of an element, an organic electric element using same, and an electronic device using same.

Technical Solution

In accordance with an aspect of the present disclosure, there is provided a compound represented by the formula below:

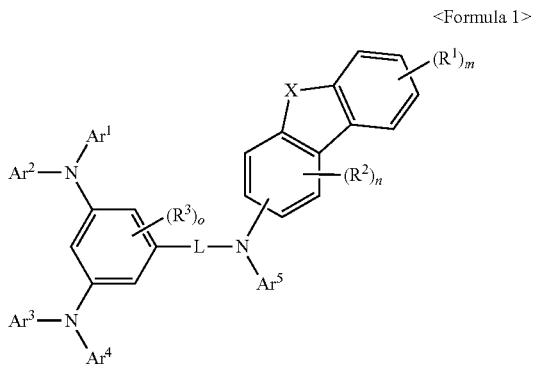

<Formula 1>

In another aspect of the present disclosure, there are provided an organic electric element using the compound represented by the above formula, and an electronic device using same.

Advantageous Effects

According to the present disclosure, a particular compound in which the kind, binding position, and number of an amine group are delimited is used as a material for an organic electric element, and as a result, such a compound has improved hole transport ability and thermal stability, a HOMO energy level and a high Ti value, which facilitate a charge balance in a light emitting layer, and a high refractive index, and thus can improve the light emission efficiency, heat resistance, and lifetime of an organic electric element and lower the driving voltage.

BRIEF DESCRIPTION OF THE DRAWINGS

The FIGURE is a cross-sectional view of an organic light emitting diode according to an embodiment of the present disclosure.

MODE FOR CARRYING OUT THE INVENTION

Figure 1:
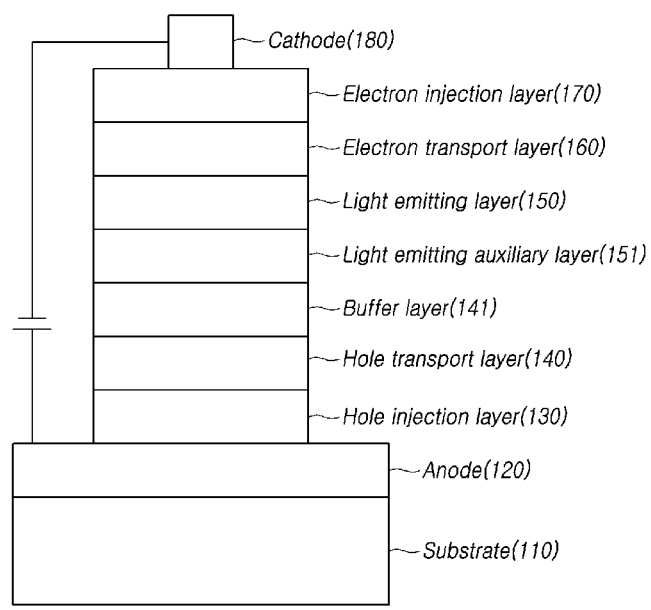
Figure 2:
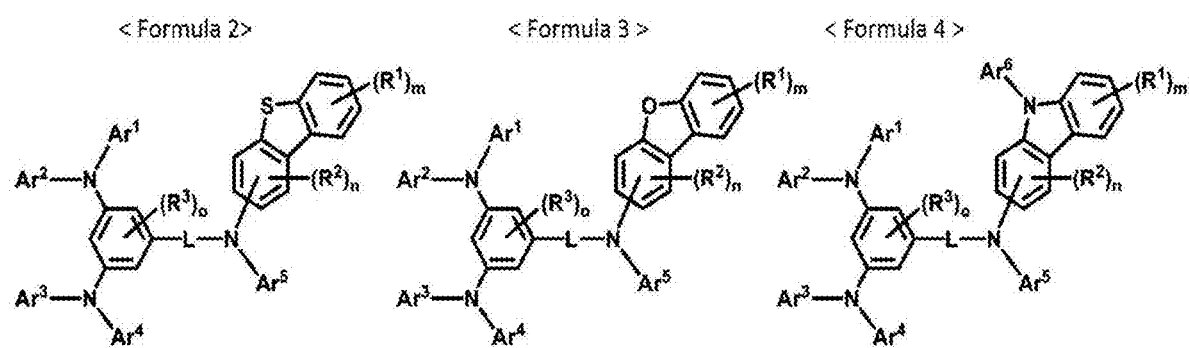
Figure 3:
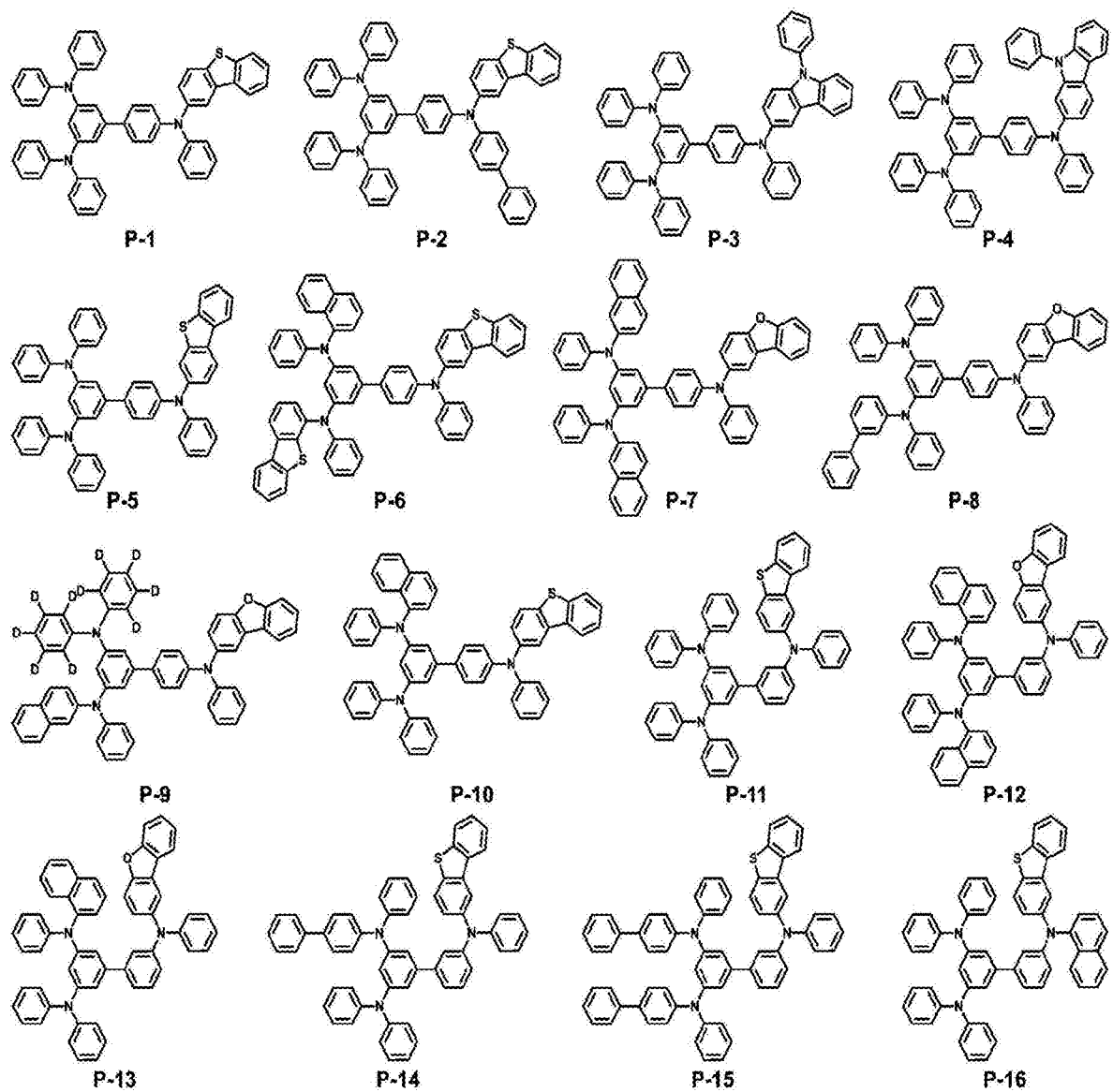
Figure 4:
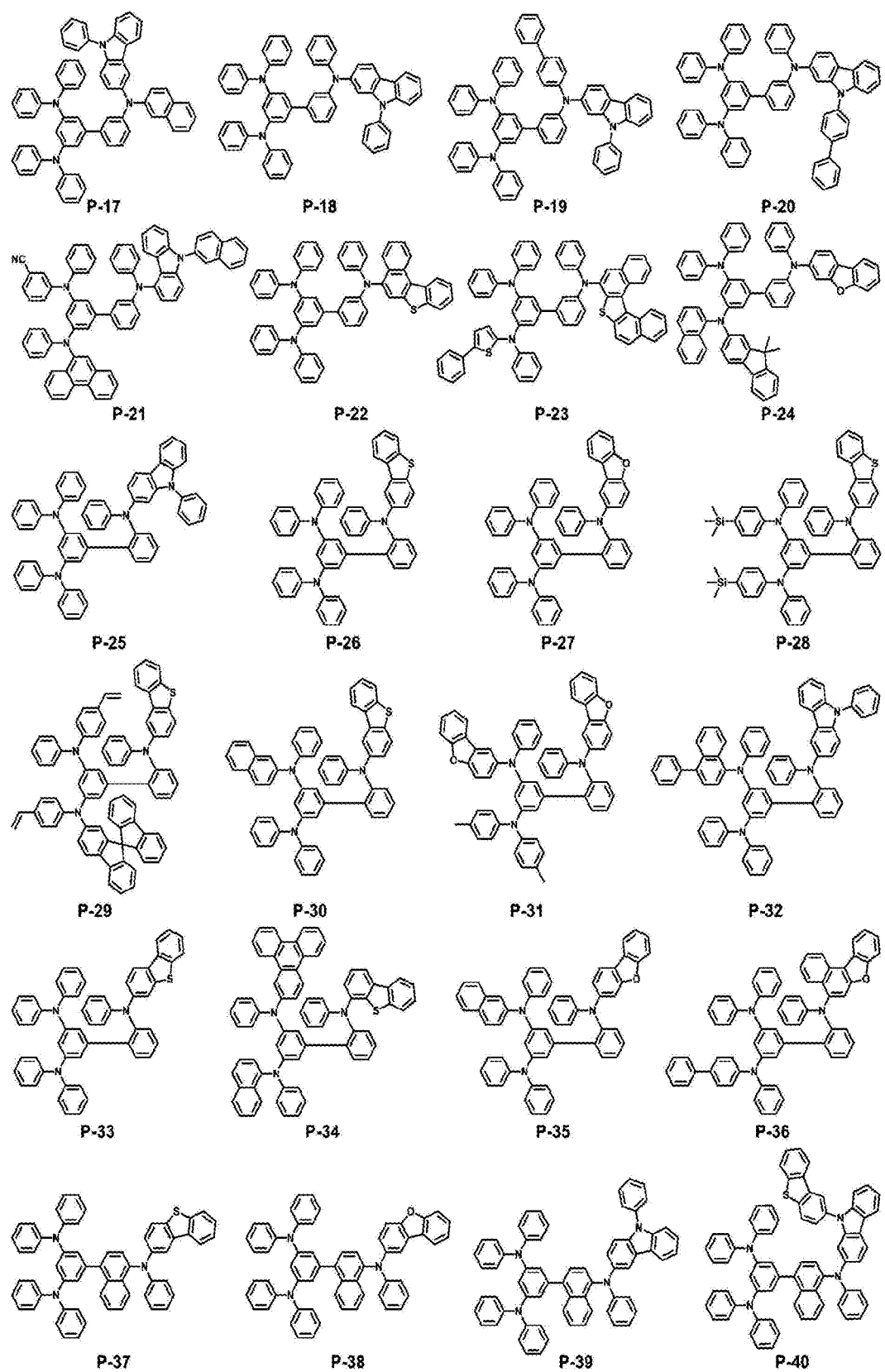
Figure 5:
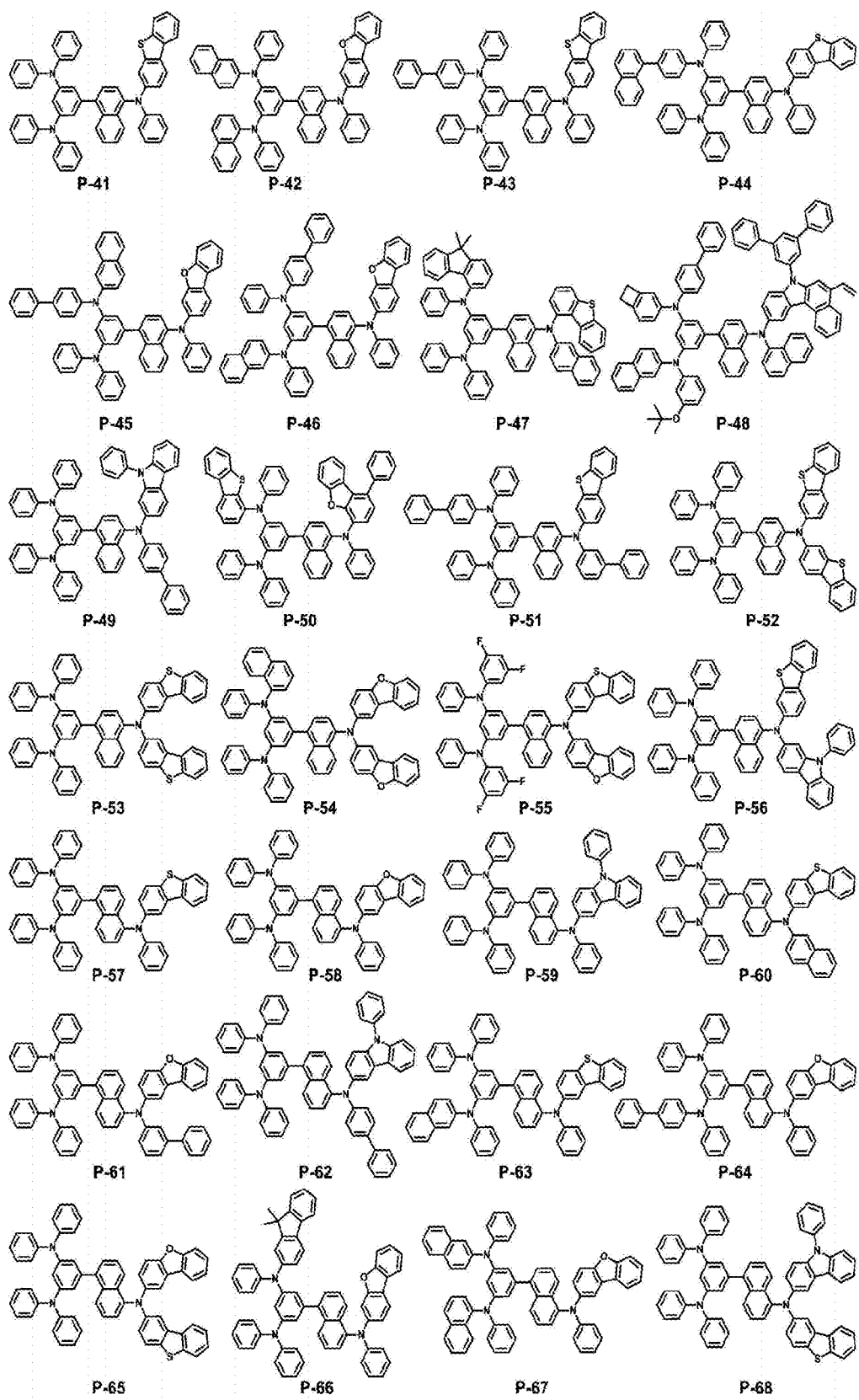
Figure 6:
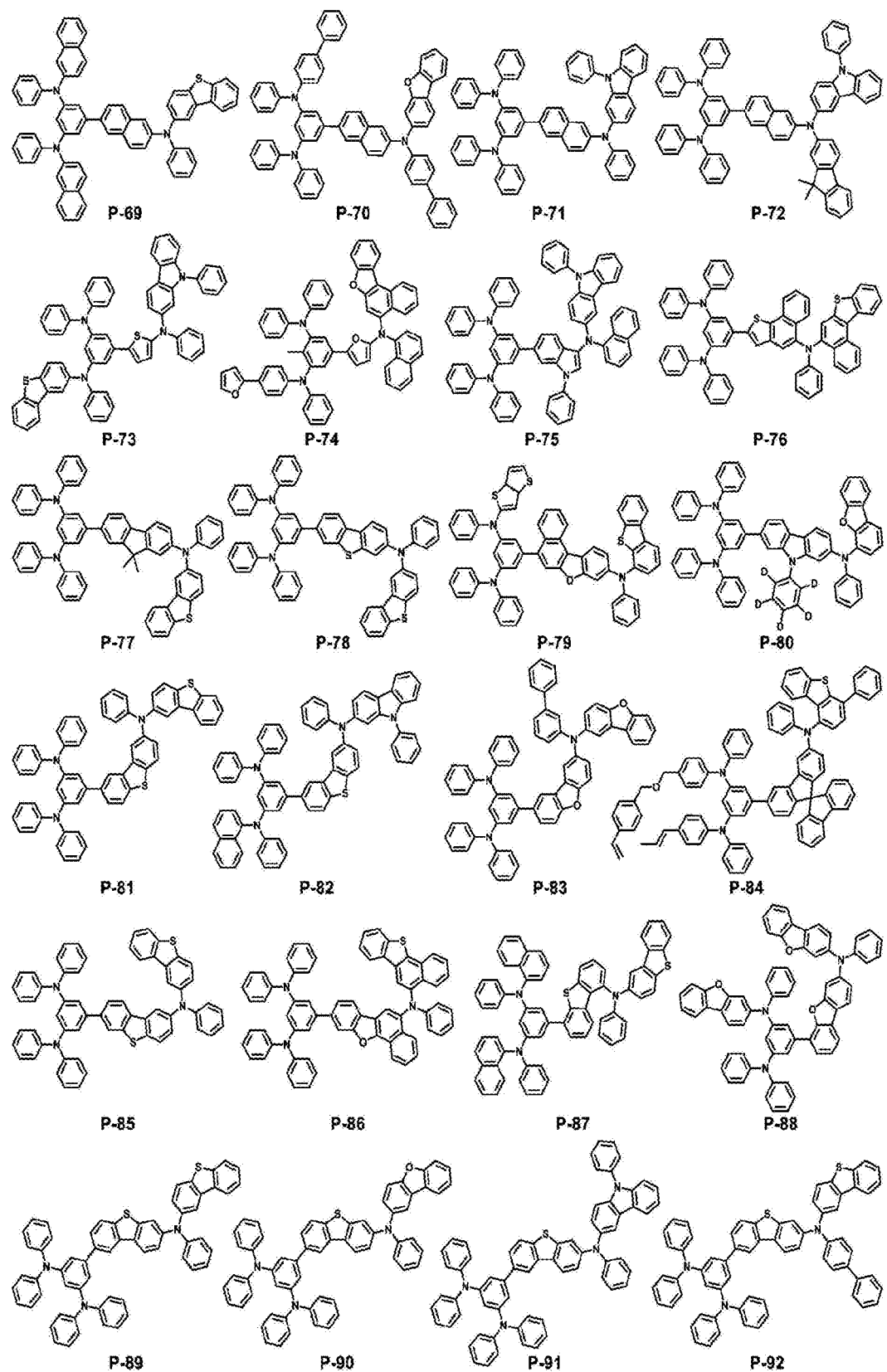
Figure 7:
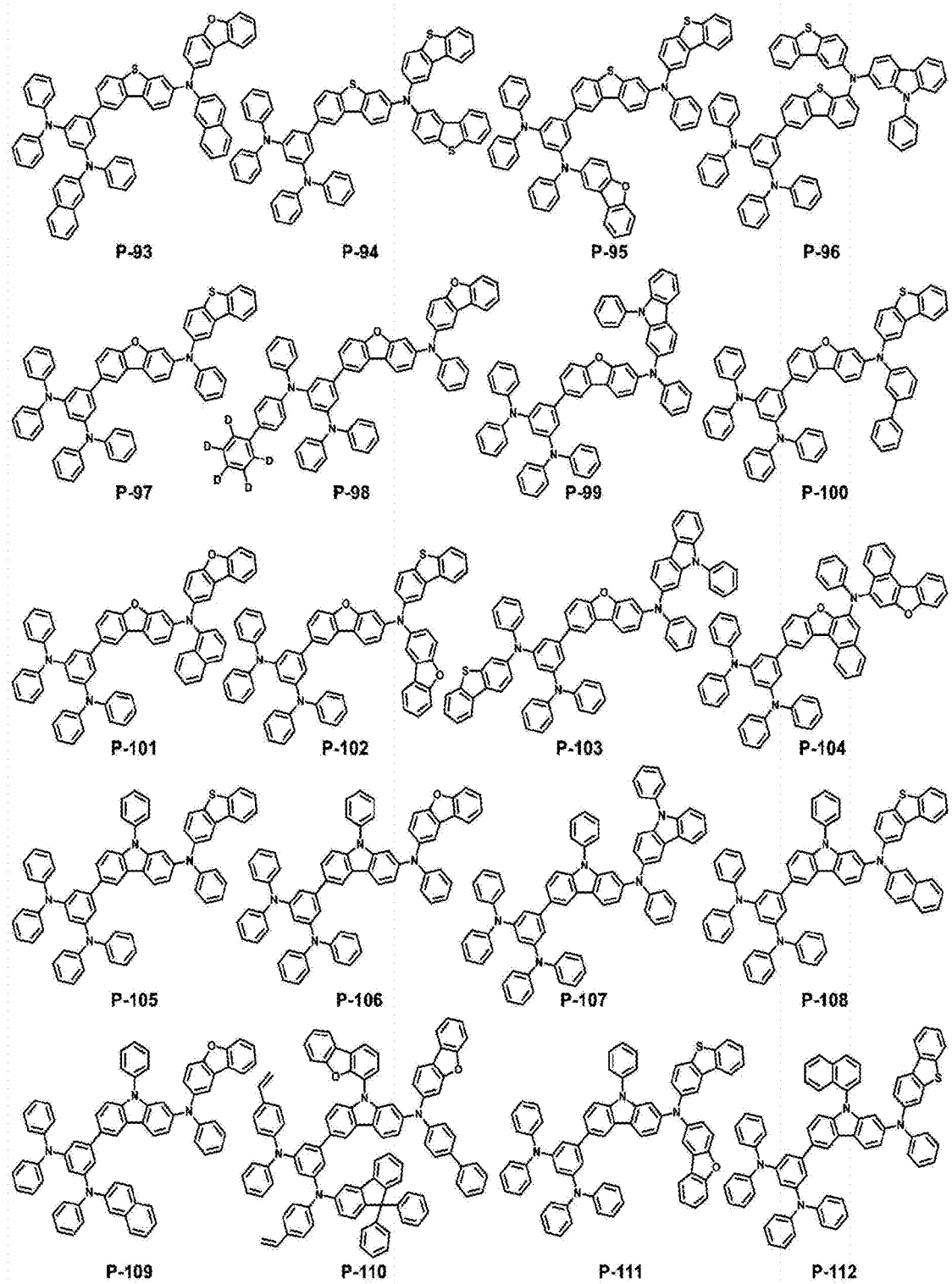
Figure 8:
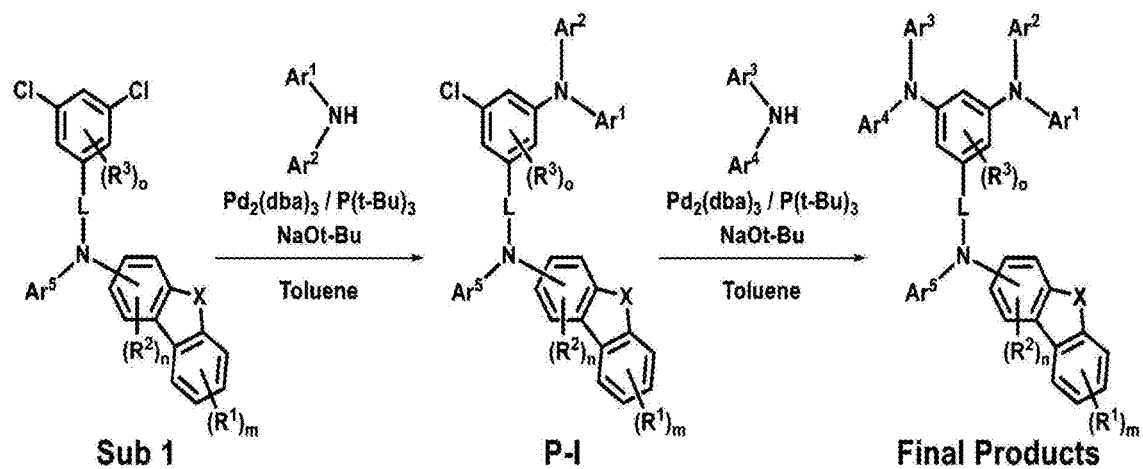
Figure 9:
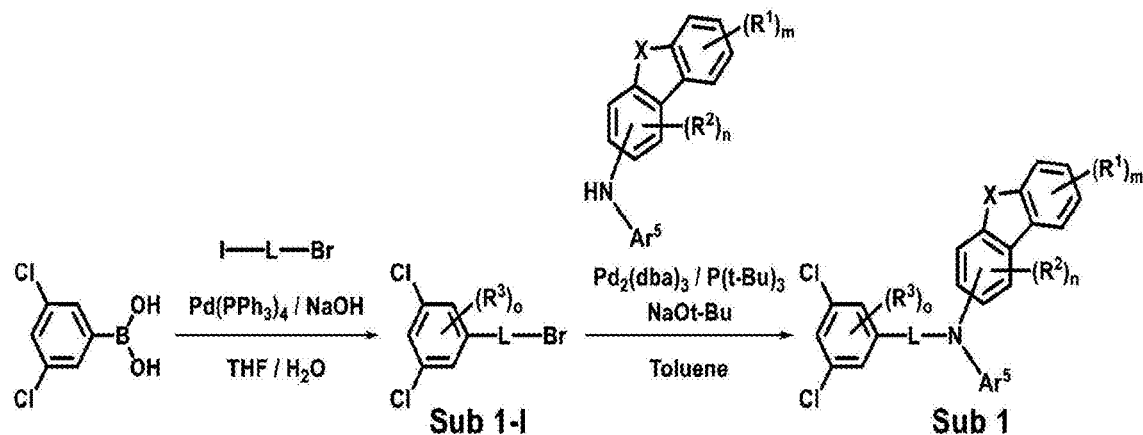
Figure 10:
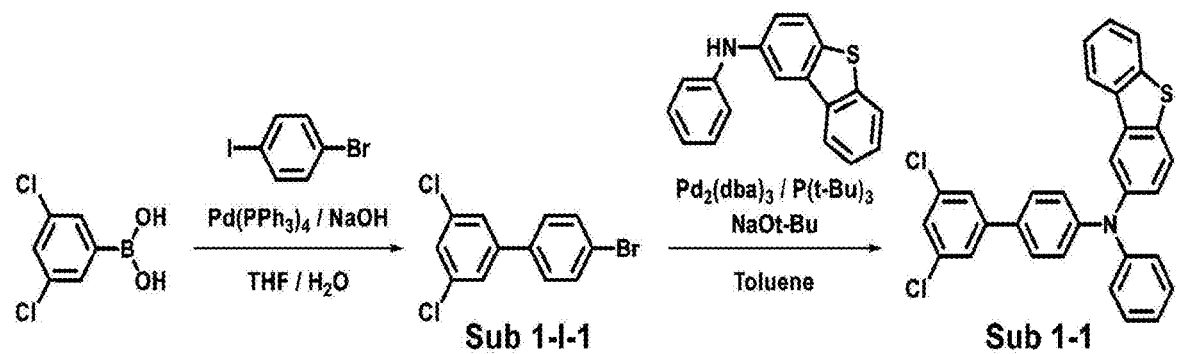
Figure 11:
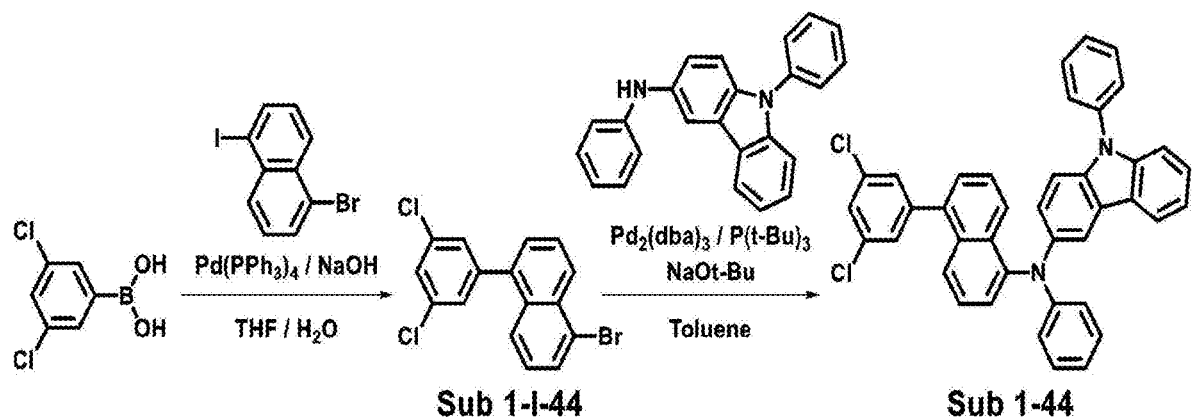
Figure 12:
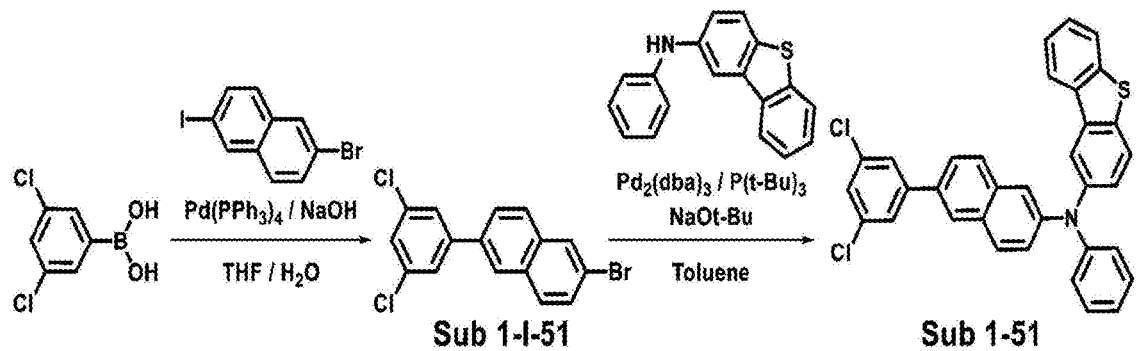
Figure 13:
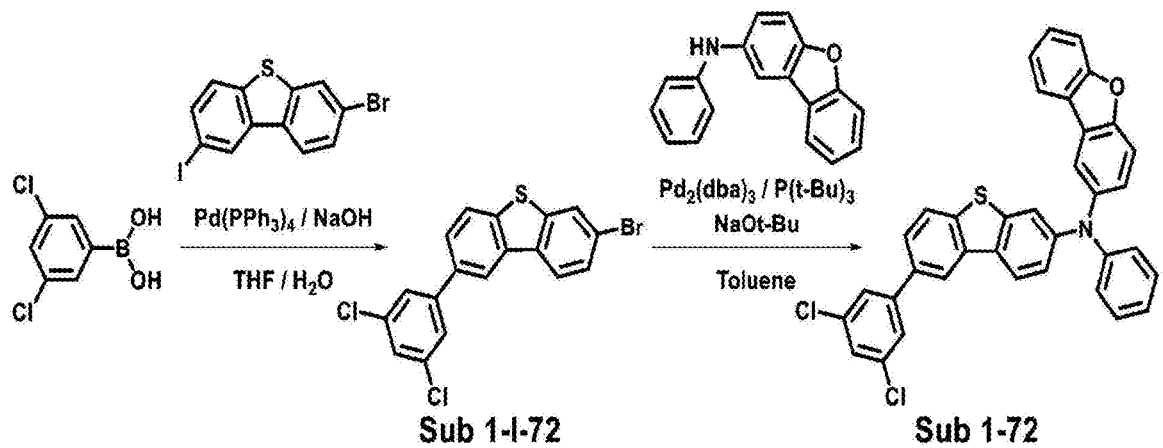
Figure 14:
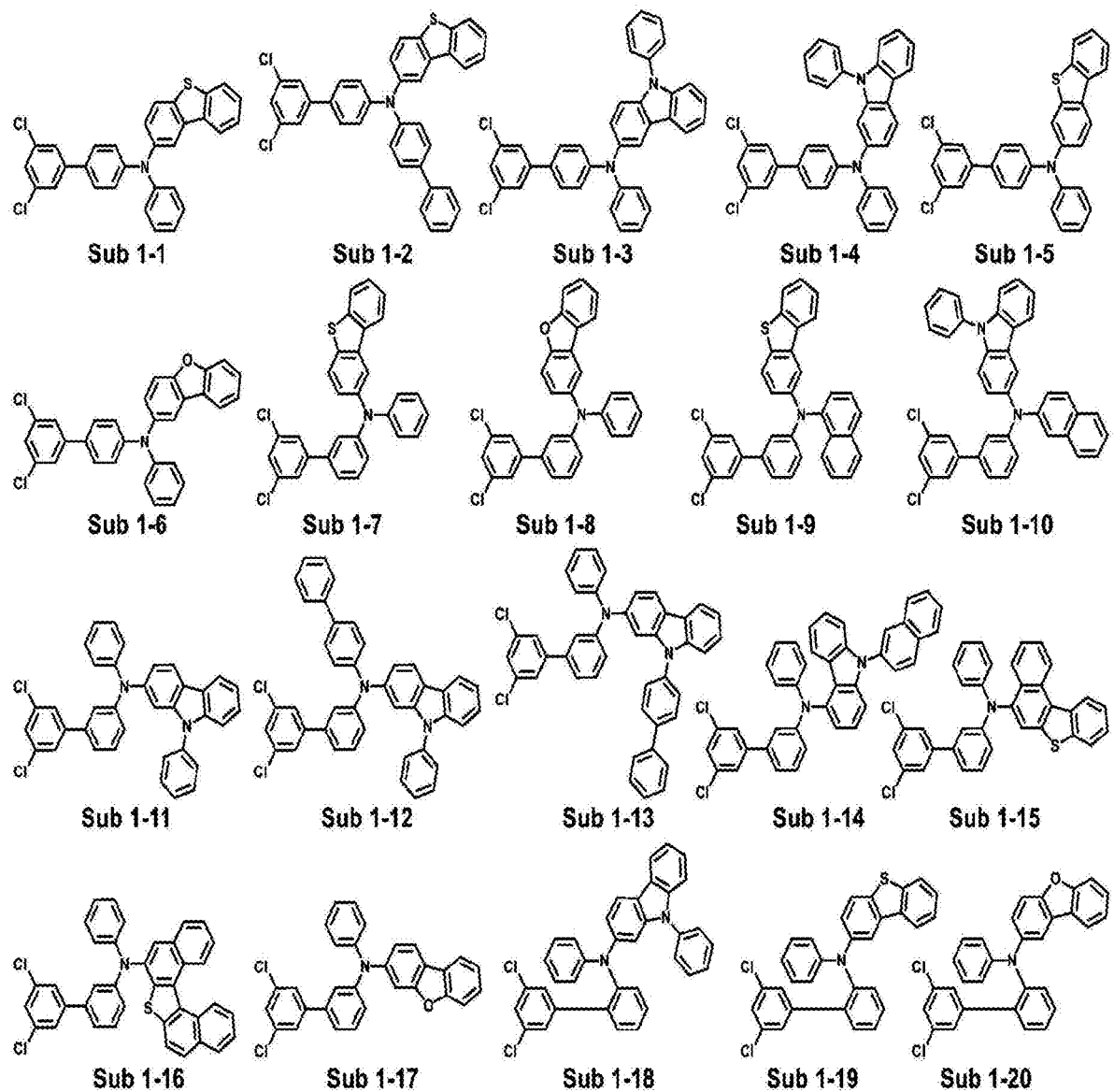
Figure 15:
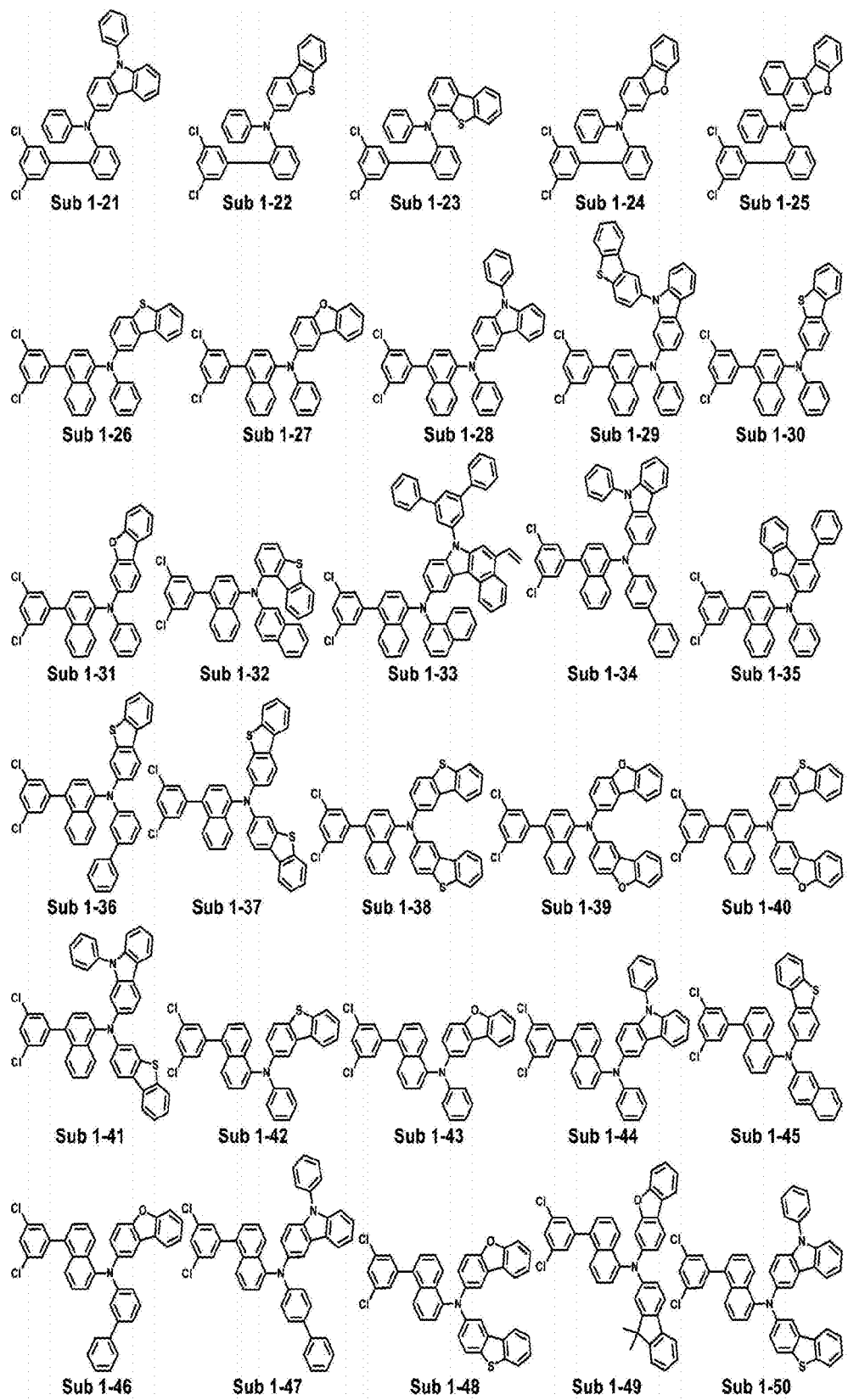
Figure 16:
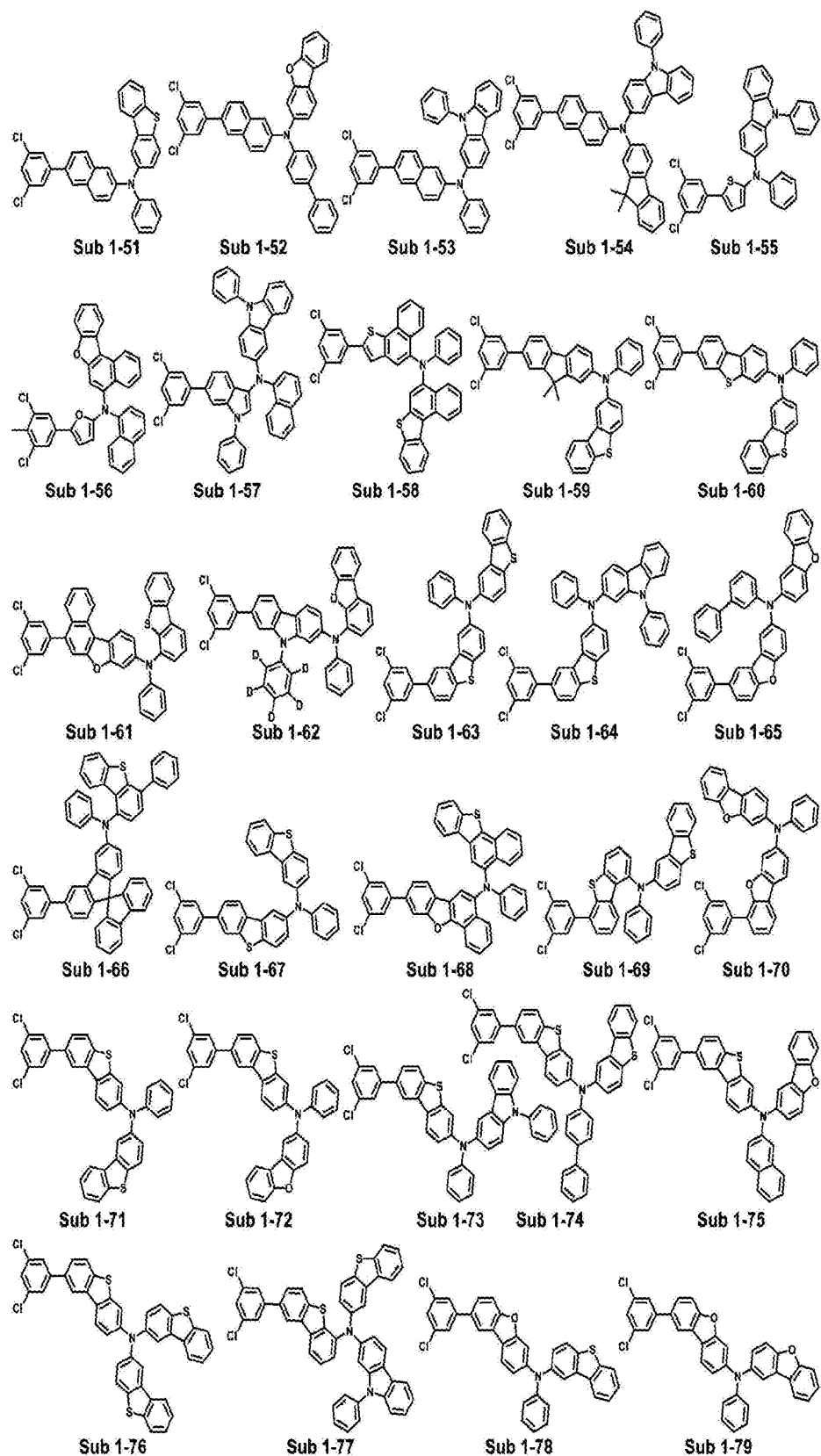
Figure 17:
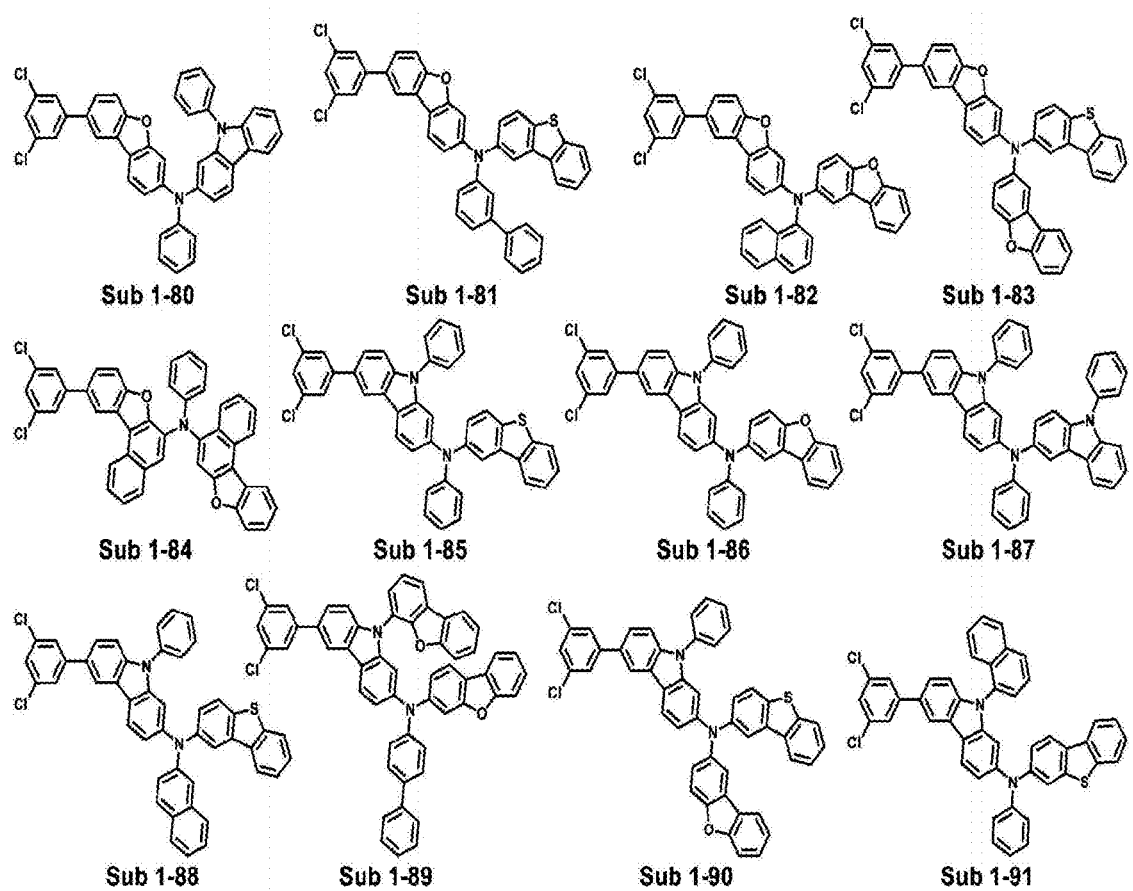
Figure 20:
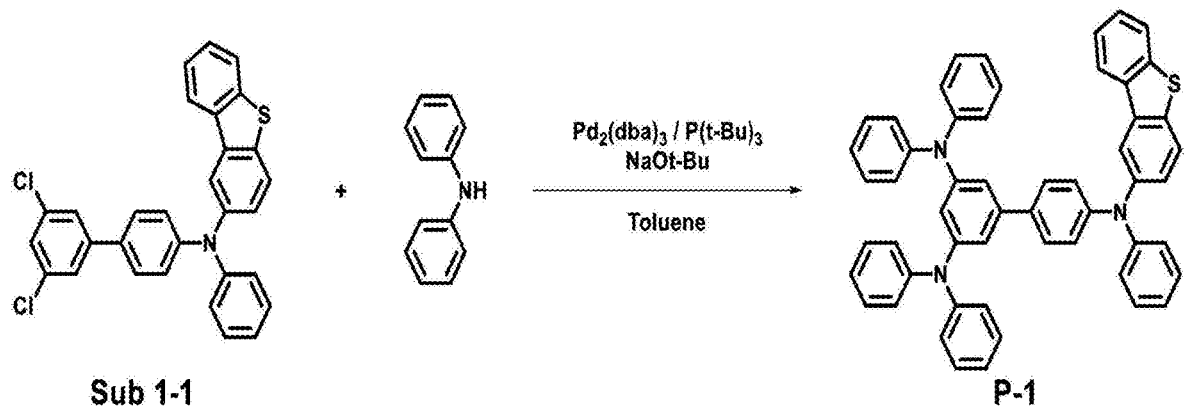
Figure 21:
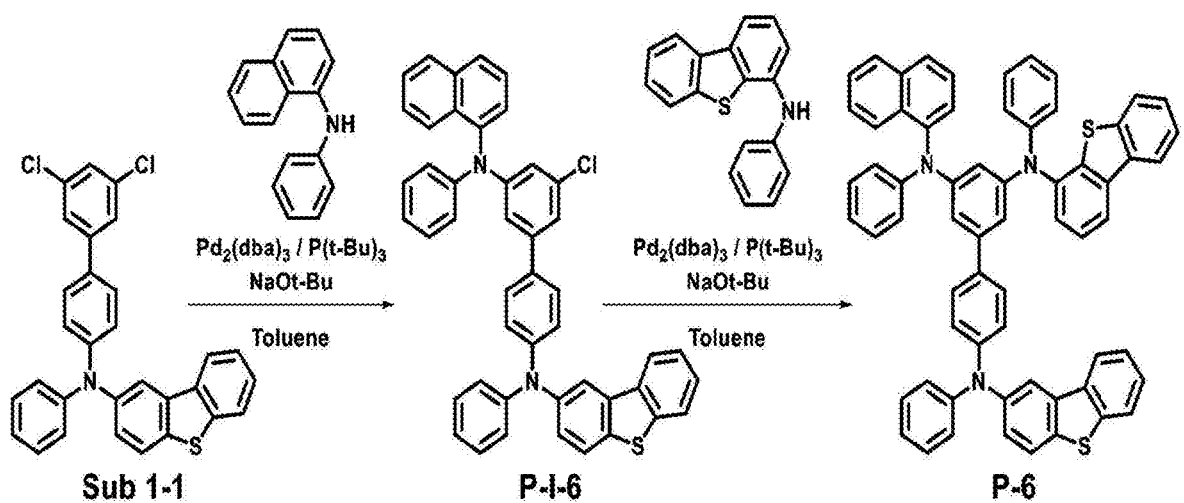
Figure 22:
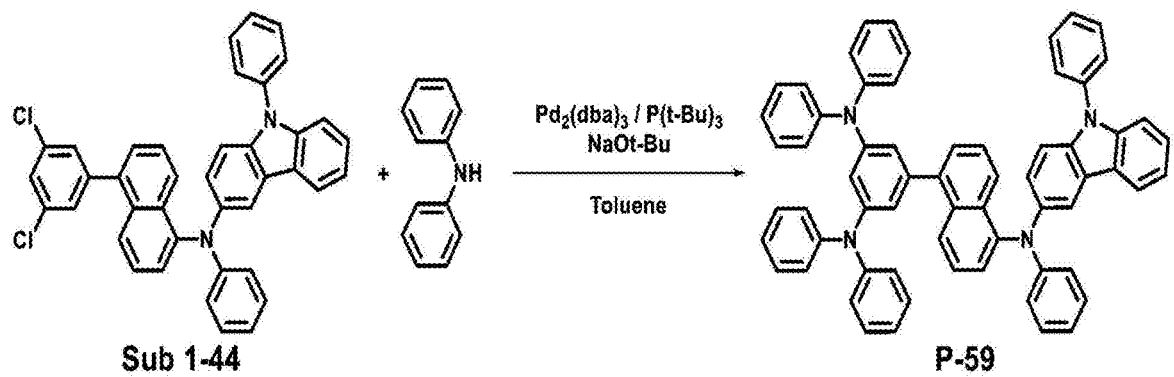
Figure 23:
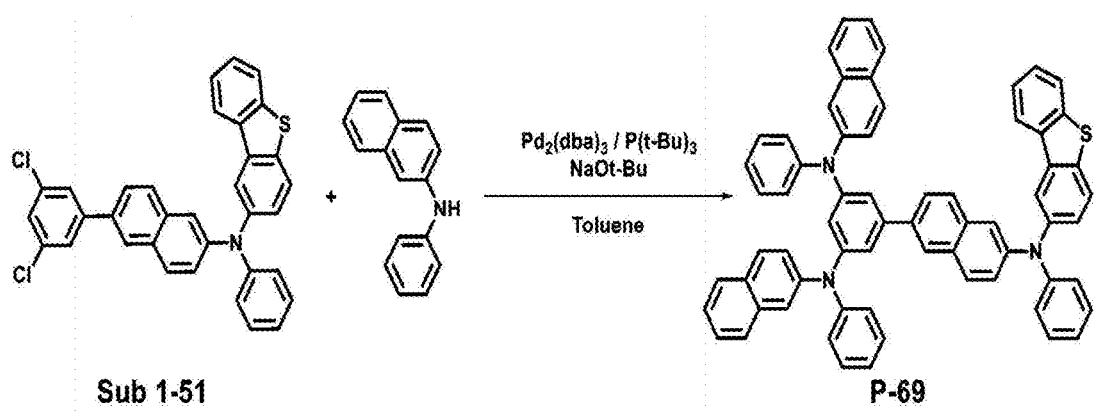
Figure 24:
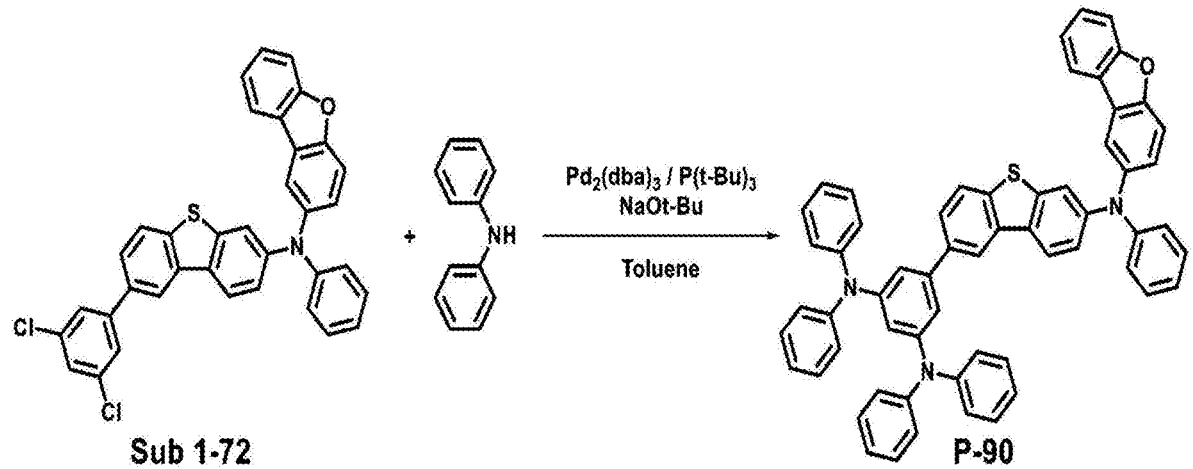

Hereinafter, embodiments of the present disclosure will be described in detail with reference to the accompanying drawings.

In designation of reference numerals to components in each drawing, it should be noted that the same elements would be designated by the same reference numerals although they are shown in different drawings. Further, in the following description of the present disclosure, a detailed description of known functions and configurations incorporated herein will be omitted when it may make the subject matter of the present disclosure rather unclear.

Terms, such as first, second, A, B, (a), (b), or the like may be used herein when describing components of the present disclosure. Each of these terminologies is not used to define an essence, order, or sequence of a corresponding component but used merely to distinguish the corresponding component from other component (s). It should be noted that if it is described in the specification that one component is "connected," "coupled" or "joined" to another component, a third component may be "connected," "coupled," and "joined" between the first and second components, although the first component may be directly connected, coupled or joined to the second component.

As used in the specification and the accompanying claims, unless otherwise stated, the meanings of the terms are as follows.

Unless otherwise stated, the term "halo" or "halogen" as used herein includes fluorine (F), bromine (Br), chlorine (Cl), or iodine (I).

Unless otherwise stated, the term "alkyl" or "alkyl group" as used herein refers to a radical of a saturated aliphatic functional group having 1 to 60 carbon atoms with single bond(s), including a straight-chain alkyl group, a branched-chain alkyl group, a cycloalkyl (alicyclic) group, an alkyl-substituted cycloalkyl group, and a cycloalkyl-substituted alkyl group.

Unless otherwise stated, the term "haloalkyl group" or "halogen alkyl group" as used herein refers to an alkyl group substituted with halogen.

The term "heteroalkyl group" as used herein refers to an alkyl group, of which at least one of carbon atoms is substituted with a hetero atom.

Unless otherwise stated, the term "alkenyl group" or "alkynyl group" as used herein refers to a functional group having 2 to 60 carbon atoms with a double or triple bond and including a straight-chain or branched-chain group, but is not limited thereto.

Unless otherwise stated, the term "cycloalkyl" as used herein refers to alkyl forming a ring having 3 to 60 carbon atoms, but is not limited thereto.

Unless otherwise stated, the term "alkoxyl group", "alkoxy group", or "alkyloxy group" as used herein refers to an alkyl group to which an oxygen radical is attached, the alkyl group having 1 to 60 carbon atoms, but is not limited thereto.

Unless otherwise stated, the term "alkenoxyl group", "alkenoxy group", "alkenyloxyl group", or "alkenyloxy group" as used herein refers to an alkenyl group to which an oxygen radical is attached, the alkenyl group having 2 to 60 carbon atoms, but is not limited thereto.

Unless otherwise stated, the term "aryloxyl group" or "aryloxy group" as used herein refers to an aryl group to which an oxygen radical is attached to, the aryl group having 6 to 60 carbon atoms, but not limited thereto.

Unless otherwise stated, the terms "aryl group" and "arylene group" each as used herein refers to a functional group having 6 to 60 carbon atoms, but are not limited thereto. The aryl group or arylene group herein means to a monocyclic or polycyclic aromatic group, and includes an aromatic ring formed by adjacent substituents involved in linking or reaction. For example, the aryl group may be a phenyl group, a biphenyl group, a terphenyl group, a naphthyl group, an anthracenyl group, a fluorenyl group, a spiro-fluorene group, or a spiro-bifluorene group.

The prefix "aryl" or "ar" refers to a radical substituted with an aryl group. For example, an arylalkyl group is an alkyl group substituted with an aryl group and an arylalkenyl group is an alkenyl group substituted with an aryl group. A radical substituted with an aryl group has carbon atoms described herein.

When prefixes are named subsequently, it means that substituents are listed in the order described first. For example, an arylalkoxy group means an alkoxy group substituted with an aryl group; an alkoxylcarbonyl group means a carbonyl group substituted with an alkoxyl group; and an arylcarbonylalkenyl group means an alkenyl group substitutes with an arylcarbonyl group, wherein the arylcarbonyl group may be a carbonyl group substituted with an aryl group.

Unless otherwise stated, the term "heteroalkyl" as used herein refers to alkyl including at least one heteroatom. Unless otherwise stated, the term "heteroalkyl group" or "heteroarylene group" as used herein refers to an aryl group or arylene group having 2 to 60 carbon atoms and including at least one heteroatom, but is not limited thereto, and includes at least one of a monocyclic ring and a polycyclic ring, and may be formed by linkage of adjacent functional groups.

Unless otherwise stated, the term "heterocyclic group" as used herein refers to a functional group including at least one heteroatom, having 2 to 60 carbon atoms, including at least one of a monocyclic ring and a polycyclic ring. The heterocyclic group may be formed by linkage of adjacent functional groups.

Unless otherwise stated, the term "heteroatom" as used herein represents N, O, S, P, or Si.

Also, the "heterocyclic group" may include a ring containing $SO_2$ instead of carbon constituting a ring. For example, the "heterocyclic group" includes the compound below:

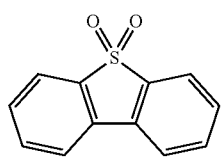 [SMILES: O=S1(=O)c2ccccc2-c2ccccc21]

Unless otherwise stated, the term "aliphatic" as used herein refers to an aliphatic hydrocarbon having 1 to 60 carbon atoms, and the term "aliphatic ring" refers to an aliphatic hydrocarbon ring having 3 to 60 carbon atoms.

Unless otherwise stated, the term "ring" as used herein includes an aliphatic ring having 3 to 60 carbon atoms, an aromatic group having 6 to 60 carbon atoms, a hetero ring having 2 to 60 carbon atoms, or a fusion ring composed of a combination thereof, and includes a saturated or unsaturated group Besides the above-described hetero compounds, the other hetero compounds or hetero radicals include at least one heteroatom, but is not limited thereto.

Unless otherwise stated, the term "carbonyl" as used herein is represented by —COR', wherein R' may be hydrogen, an alkyl group having 1 to 20 carbon atoms, an aryl group having 6 to 30 carbon atoms, a cycloalkyl group having 3 to 30 carbon atoms, an alkenyl group having 2 to 20 carbon atoms, an alkynyl group having 2 to 20 carbon atoms, or a combination thereof.

Unless otherwise stated, the term "ether" as used herein is represented by —R—O—R', wherein R or R' each may be independently hydrogen, an alkyl group having 1 to 20 carbon atoms, an aryl group having 6 to 30 carbon atoms, a cycloalkyl group having 3 to 30 carbon atoms, an alkenyl group having 2 to 20 carbon atoms, an alkynyl group having 2 to 20 carbon atoms, or a combination thereof.

Unless otherwise stated, the term "substituted" in the term "substituted or unsubstituted" as used herein refers to a substitution with at least one substituent selected from the group consisting of deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthiophene group, a $C_6$-$C_{20}$ arylthiophene group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted with deuterium, a $C_8$-$C_{20}$ arylalkenyl group, a silane group, a boron group, a germanium group, and a $C_2$-$C_{20}$ heterocyclic group.

Unless otherwise specified, the formulas used in the present disclosure are applied in the same manner as in the definition of substituents by the definition of an exponent in the formula below.

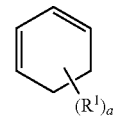

Here, when a is an integer of zero, substituent $R^1$ is absent; when a is an integer of 1, one substitutent $R^1$ is linked to any one of the carbon atoms constituting the benzene ring; and when a is an integer of 2 or 3, substituents $R^1$'s may be the same and different and may be linked to the benzene ring as follows. When a is an integer of 4 to 6, substituents $R^1$'s may be the same and different and may be linked to the benzene ring in a similar manner to that when a is an integer of 2 or 3. The indication of hydrogen atoms linked to carbon constituents of the benzene ring is omitted.

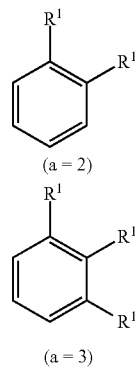

The FIGURE is an exemplary view of an organic electric element according to an embodiment of the present disclosure.

Referring to the FIGURE, an organic electric element 100 according to the present disclosure includes a first electrode 120 formed on a substrate 110, a second electrode 180, and an organic material layer between the first electrode 120 and the second electrode 180, the organic material layer containing the compound according to the present disclosure. Here, the first electrode 120 may be an anode (positive electrode) and the second electrode 180 may be a cathode (negative electrode). In a case of an inverted organic electric element, the first electrode may be a cathode and the second electrode may be an anode.

The organic material layer may include a hole injection layer 130, a hole transport layer 140, a light emitting layer 150, an electron transport layer 160, and an electron injection layer 170, which are formed in sequence on the first electrode 120. Here, the other layers excluding the light emitting layer 150 may not be formed. The organic material layer may further include a hole blocking layer, an electron blocking layer, a light emitting auxiliary layer 151, an electron transport auxiliary layer, a buffer layer 141, or the like, and the electron transport layer 160 or the like may serve as a hole blocking layer.

Although not shown, the organic electric element according to the present disclosure may further include a protective layer or a light efficiency improving layer (capping layer), which is formed on one surface of at least one of the first and second electrodes, the surface being the opposite side to the organic material layer.

The compound according to the present disclosure employed in the organic material layer may be used as a host or dopant for the hole injection layer 130, the hole transport layer 140, the electron transport layer 160, the light emitting auxiliary layer 151, the electron transport auxiliary layer, the electron injection layer 170, or the light emitting layer 150, or a material for the light efficiency improvement layer. Preferably, the compound of the present disclosure may be used as a material for the hole transport layer and/or the light emitting auxiliary layer 151.

Since a band gap, electrical properties, interfacial properties, and the like may vary in spite of the same core depending on the type and position of a substituent to be attached, a selection of the core and a combination of sub-substituent attached to the core are also important. Specially, both long lifetime and high efficiency can be achieved when an optimal combination of energy levels, Ti values, inherent material properties (mobility, interfacial properties, etc.), and the like among the respective layers included in the organic material layer is given.

Accordingly, energy levels, $T_1$ values, and inherent material properties (mobility, interfacial properties, etc.), and the like among the respective layers included in the organic material layer are optimized by forming the hole transport layer and/or the light emitting auxiliary layer 151 using the compound represented by Formula 1 of the present disclosure, so that both the lifetime and efficiency of an organic electric element can be improved.

An organic electric element according to an embodiment of the present disclosure may be manufactured using a physical vapor deposition (PVD) method. For example, the organic electric element may be manufactured by depositing a metal, a metal oxide having conductivity, or an alloy thereof, on the substrate to form the anode 120, forming the organic material layer including the hole injection layer 130, the hole transport layer 140, the light emitting layer 150, the electron transport layer 160, and the electron injection layer 170 thereon, and then depositing a material, which can be used for the cathode 180, thereon. The light emitting auxiliary layer 151 may be further formed between the hole transport layer 140 and the light emitting layer 150, and the electron transport auxiliary layer may be further formed between the light emitting layer 150 and the electron transport layer 160.

Also, the organic material layer may be manufactured to have a smaller number of layers using various polymer materials by, instead of a deposition method, a soluble process or solvent process, for example, a spin coating process, a nozzle printing process, an inkjet printing process, a slot coating process, a dip coating process, a roll-to-roll process, a doctor blading process, a screen printing process, or a thermal transfer method. Since the organic material layer according to the present disclosure may be formed in various ways, the scope of right of the present disclosure is not limited by a method of forming the organic material layer.

The organic electric element according to an embodiment of the present disclosure may be a top emission type, a bottom emission type, or a dual emission type, according to the used materials.

A white organic light emitting device (WOLED) facilitates the implementation of high resolution, has excellent processability, and has an advantage of being produced using conventional LCD color filter techniques. In this regard, various structures for WOLEDs, mainly used as back light units, have been suggested and patented. Representative WOLEDs are: a parallel side-by-side arrangement of red (R), green (G), and blue (B) light-emitting units on a mutual plane: a stacking arrangement of R, G, and B light emitting layers above and below; and a color conversion material (CCM) structure using electroluminescence by a blue (B) organic light emitting layer and photoluminescence from an inorganic fluorescent substance by using the light from the electroluminescence. The present disclosure can be applicable to such WOLEDs.

Further, the organic electric element according to an embodiment of the present disclosure may be any one of an organic light emitting diode (OLED), an organic solar cell, an organic photo conductor (OPC), an organic transistor (organic TFT), and an element for monochromatic or white illumination.

Another embodiment of the present disclosure provides an electronic device including: a display device, which includes the above-described organic electric element of the present disclosure; and a control unit for controlling the display device. Here, the electronic device may be a wired/wireless communication terminal, which is currently used or will be used in the future, and covers all kinds of electronic devices including a mobile communication terminal, such as a cellular phone, a personal digital assistant (PDA), an electronic dictionary, a point-to-multipoint (PMP), a remote controller, a navigation unit, a game player, various kinds of TVs, and various kinds of computers.

Hereinafter, a compound according to an aspect of the present disclosure will be described. A compound according to an aspect of the present disclosure is represented by Formula 1 below.

<Formula 1>

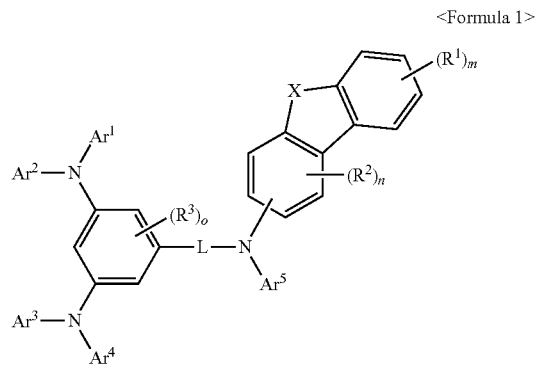

In Formula 1,
1) X is any one of S, O, and $NAr^6$;
2) $Ar^1$ to $Ar^6$ each are independently selected from the group consisting of a $C_6$-$C_{60}$ aryl group, a $C_2$-$C_{60}$ heterocyclic group containing at least one heteroatom of O, N, S, Si, a fluorenyl group, a fused ring group of a $C_6$-$C_{60}$ aromatic ring and a $C_3$-$C_{60}$ aliphatic ring, a $C_1$-$C_{50}$ alkyl group, a $C_2$-$C_{20}$ alkenyl group, a $C_2$-$C_{20}$ alkynyl group, a $C_1$-$C_{30}$ alkoxy group, and a $C_6$-$C_{30}$ aryloxy group;

3) $R^1$ to $R^3$ each are independently selected from the group consisting of deuterium, tritium, halogen, a cyano group, a nitro group, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxy group, and a $C_6$-$C_{30}$ aryloxy group, (in the presence of a plurality of $R^1$'s and $R^2$'s, at least one pair of neighboring $R^1$'s and $R^2$'s independently may bind to each other to form a ring, provided that $R^1$'s and $R^2$'s forming no ring are the same as defined above);

4) m is an integer of 0 to 4, and when m is an integer of 2 or greater, $R^1$'s are the same as or different from each other;

5) n and o each are independently an integer of 0 to 3, and when n and o each are an integer of 2 or greater, $R^2$'s and $R^3$'s each are the same as or different from each other; and 6) L is selected from the group consisting of a $C_6$-$C_{60}$ arylene group, a $C_2$-$C_{60}$ heterocyclic group containing at least one heteroatom selected from the group consisting of O, N, S, Si, and P, a fluorenylene group, a divalent fused ring of a $C_3$-$C_{60}$ aliphatic ring and a $C_6$-$C_{60}$ aromatic ring, and a $C_1$-$C_{60}$ divalent aliphatic hydrocarbon group, wherein the aryl group, arylene group, fluorenyl group, fluorenylene group, heterocyclic group, fused ring group, alkyl group, alkenyl group, alkynyl group, alkoxy group, and aryloxy group each may be further substituted with at least one substituent selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group, and when those substituents are adjacent, the substituents may bind to each other to form a ring.

Here, the aryl group may be an aryl group having 6-60 carbon atoms, preferably 6-40 carbon atoms, and more preferably 6-30 carbon atoms; the heterocyclic group may be a heterocyclic group having 2-60 carbon atoms, preferably 2-30 carbon atoms, and more preferably 2-20 carbon atoms; and the alkyl group may be an alkyl group having 1-50 carbon atoms, preferably 1-30 carbon atoms, more preferably 1-20 carbon atoms, and especially preferably 1-10 carbon atoms.

In the above-described aryl or arylene group, the aryl or arylene group may be independently a phenyl group, a biphenyl group, a terphenyl group, a naphthyl group, or a phenanthryl group, or a phenylene group, a biphenylene group, a terphenylene group, a naphthylene group, or a phenanthrylene group.

Formula 1 above may be represented by one of Formulas 2 to 4 below:

<Formula 2>

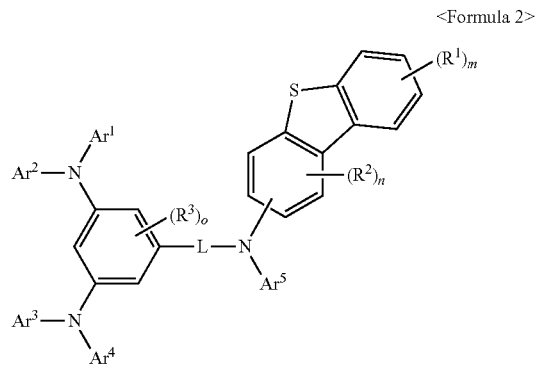

<Formula 3>

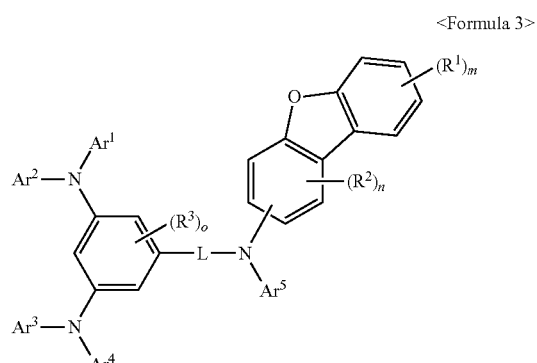

<Formula 4>

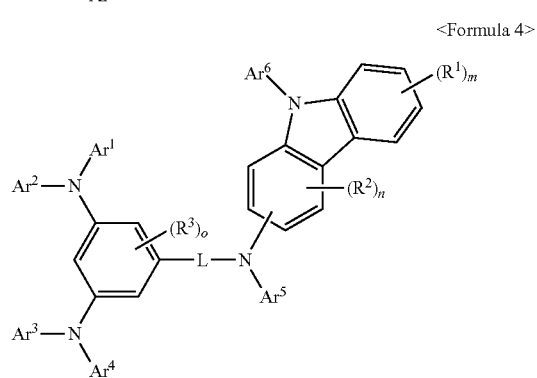

in Formulas 2 to 4, $Ar^1$ to $Ar^6$, L, $R^1$ to $R^3$, m, n, and o are the same as $Ar^1$ to $Ar^6$, L, $R^1$ to $R^3$, m, n, and o defined in Formula 1 above, respectively.

Specifically, L above may be represented by one of Formulas L1 to L6 below:

<Formula L1>

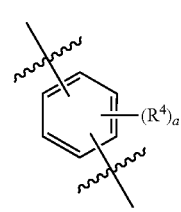

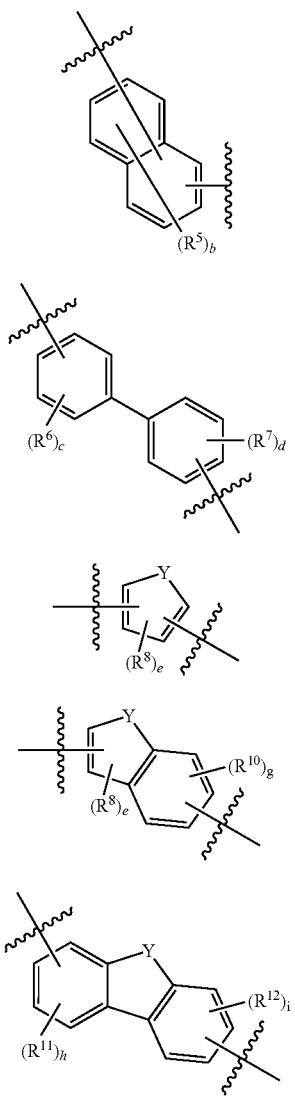

<Formula L2>

<Formula L3>

<Formula L4>

<Formula L4>

<Formula L4> where in Formulas L1 to L6,
1) Y is any one of S, O, NAr$^7$, and CAr$^8$Ar$^9$;
2) Ar$^7$ to Ar$^9$ each are independently selected from the group consisting of a $C_6$-$C_{60}$ aryl group, a fluorenyl group, a $C_2$-$C_{60}$ heterocyclic group containing at least one heteroatom of O, N, S, Si, and P, a fused ring group of a $C_6$-$C_{60}$ aromatic ring and a $C_3$-$C_{60}$ aliphatic ring, a $C_1$-$C_{50}$ alkyl group, a $C_2$-$C_{20}$ alkenyl group, a $C_2$-$C_{20}$ alkynyl group, a $C_1$-$C_{30}$ alkoxy group, and a $C_6$-$C_{30}$ aryloxy group, and Ar$^8$ to Ar$^9$ may bind to each other to form a spiro compound together with a carbon atom to which they are bound;
3) R$^4$ to R$^{12}$ each are independently selected from the group consisting of deuterium, tritium, halogen, a cyano group, a nitro group, an aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxy group, and a $C_6$-$C_{30}$ aryloxy group, (in the presence of a plurality of R$^{10}$'s and R$^{12}$'s, at least one pair of neighboring R$^{10}$'s, R$^{11}$'s, and R$^{12}$'s independently may bind to each other to form a ring, provided that R$^{10}$'s to R$^{12}$'s forming no ring are the same as defined above);
4) a, c, and d each are independently an integer of 0 to 4, and when each of these is an integer of 2 or greater, R$^4$'s, R$^6$'s, and R$^7$'s are the same as or different from each other;
5) b is an integer of 0 to 8, and when b is an integer of 2 or greater, R$^5$'s are the same as or different from each other;
6) e is an integer of 0 to 2, and when e is an integer of 2 or greater, R$^8$'s are the same as or different from each other;
7) f is an integer of 0 or 1; and
8) g, h, and i each are independently an integer of 0 to 3, and when each of these is an integer of 2 or greater, R$^{10}$'s to R$^{12}$'s are the same as or different from each other.

More specifically, the compound represented by Formula 1 may be any one of Compounds P-1 to P-112 shown below, but Formula 1 is not limited thereto.

P-1

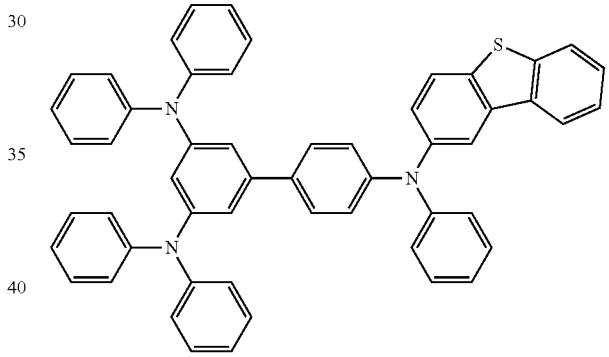

P-2

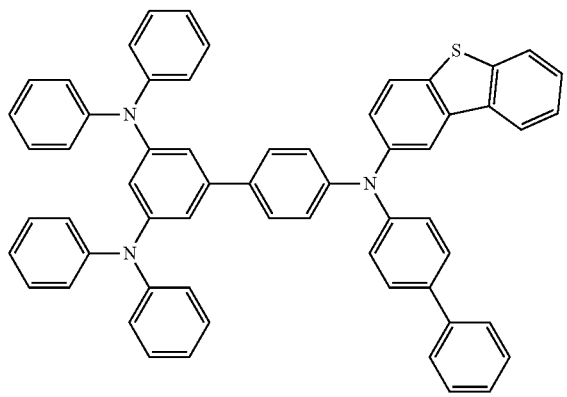

P-3
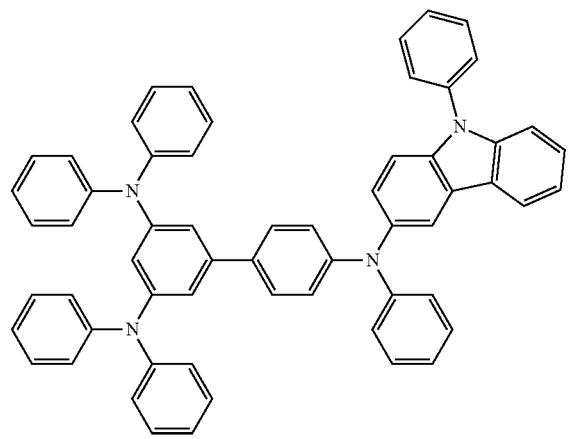
P-4
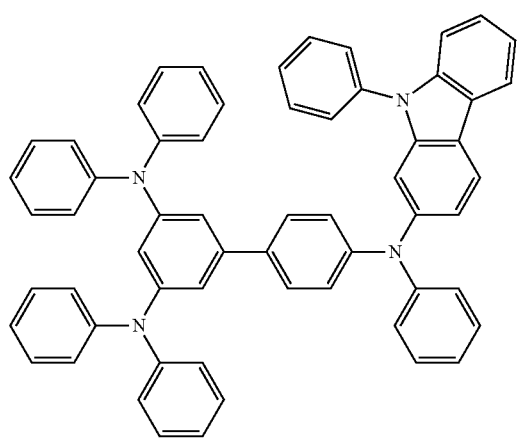
P-5
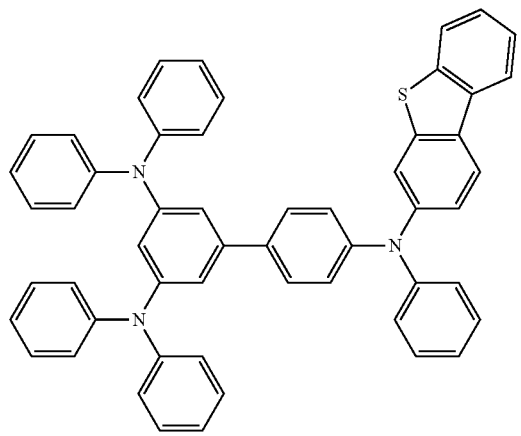
P-6
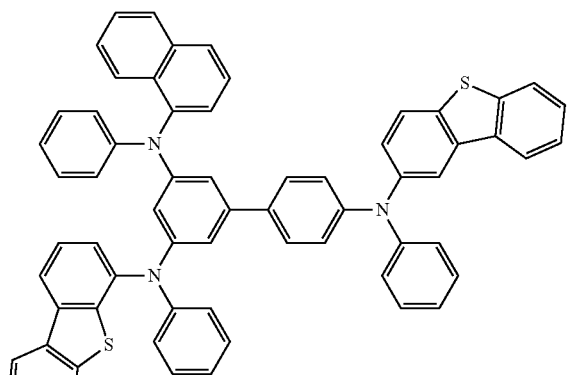
P-7
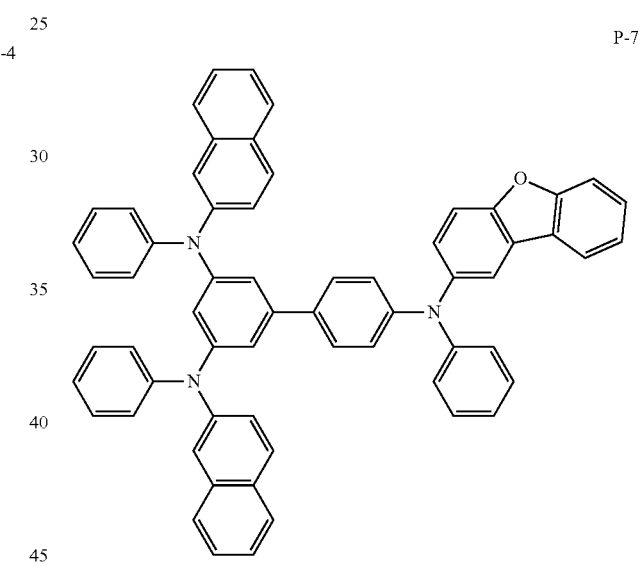
P-8
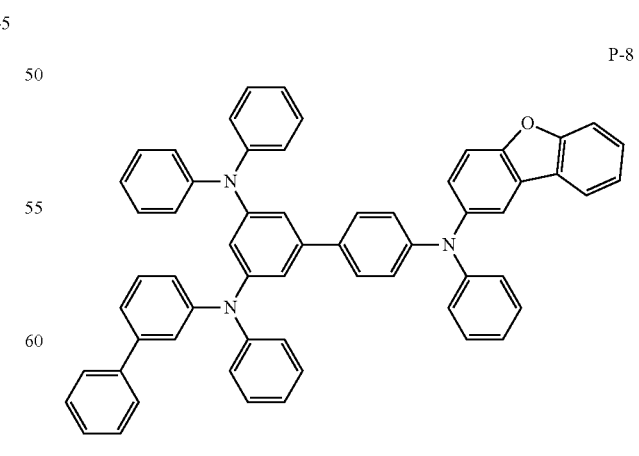

P-9
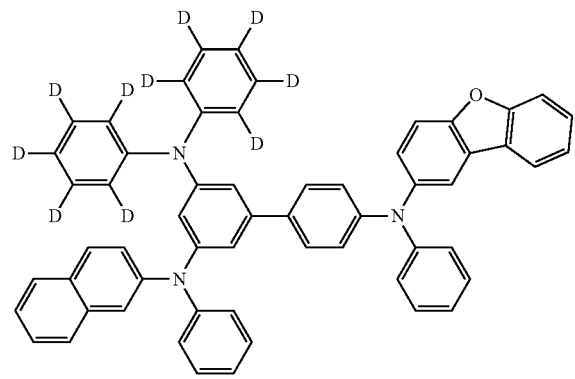
P-12
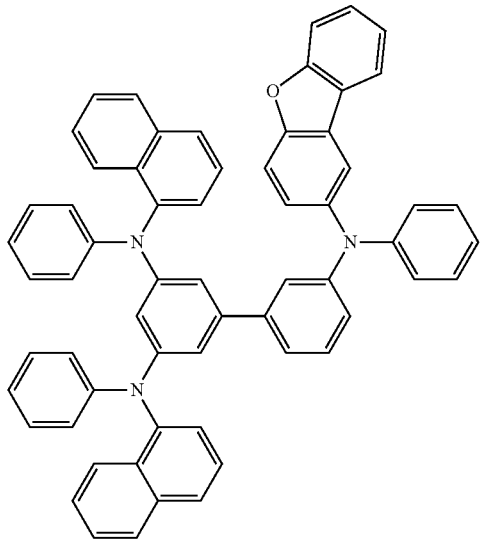
P-10
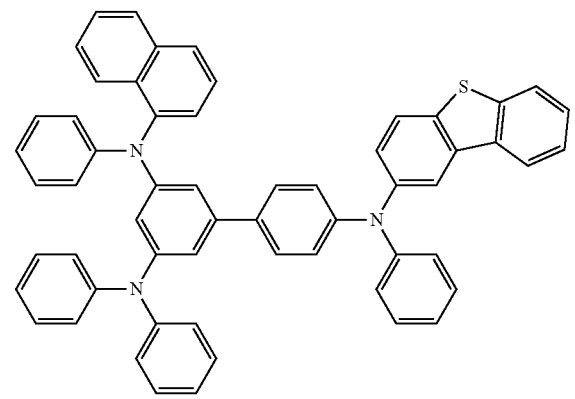
P-13
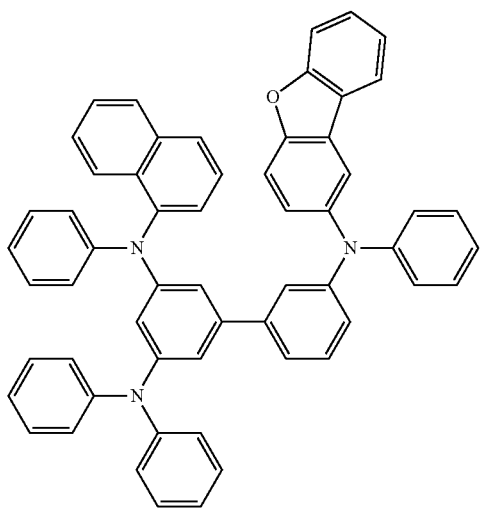
P-11
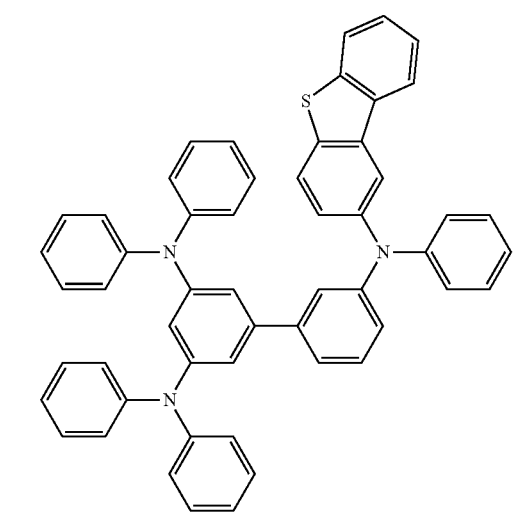
P-14
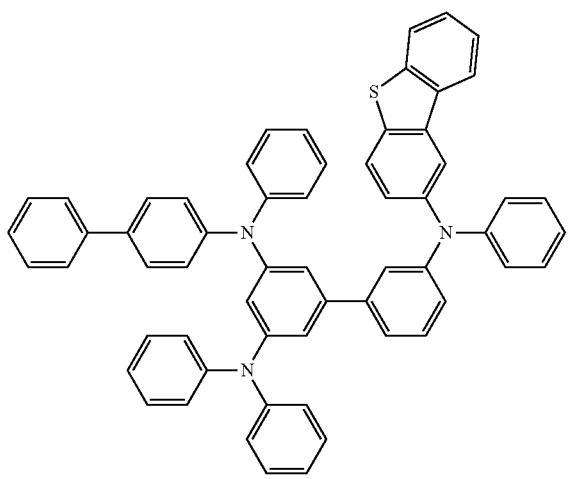

-continued
P-15
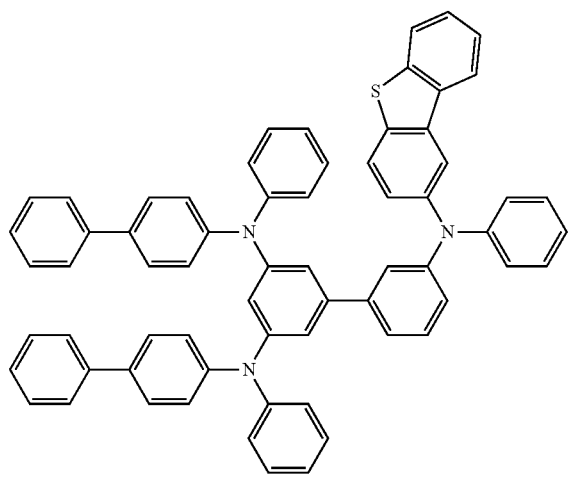
P-16
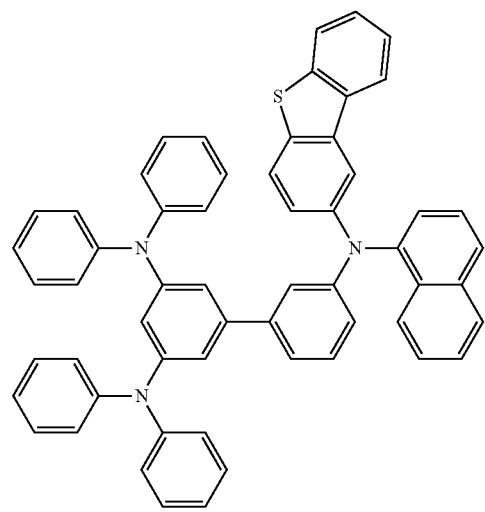
P-17
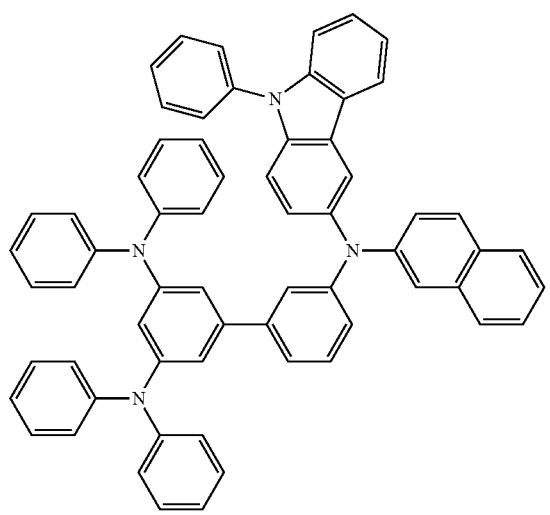
-continued
P-18
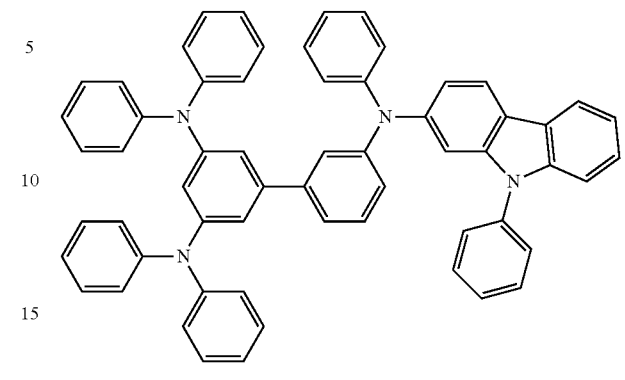
P-19
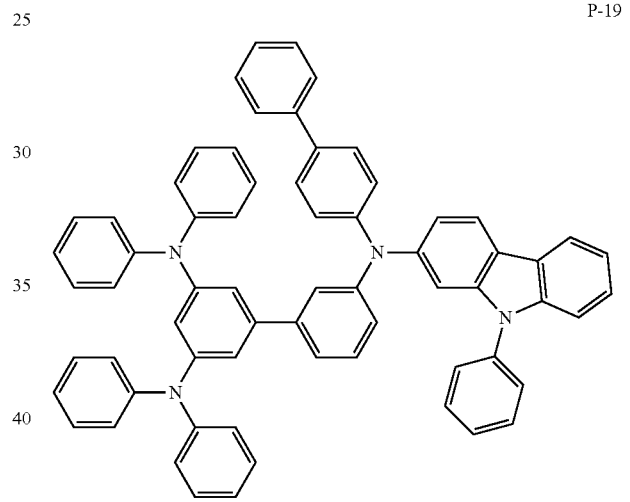
P-20
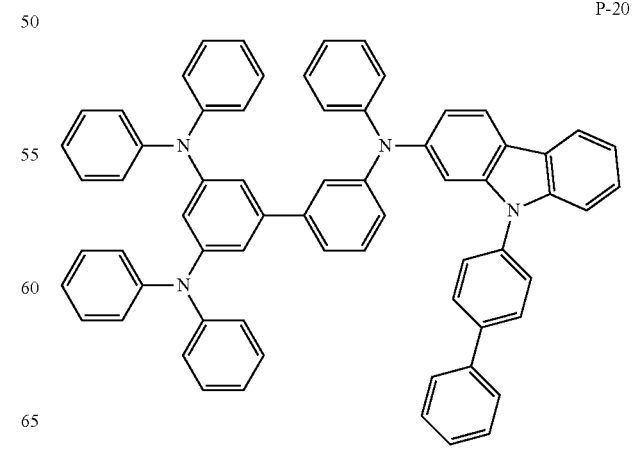

P-21
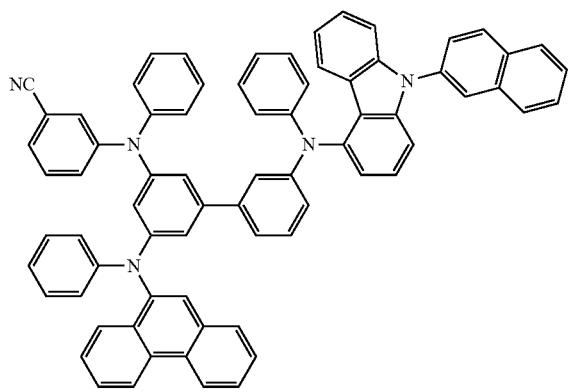
P-25
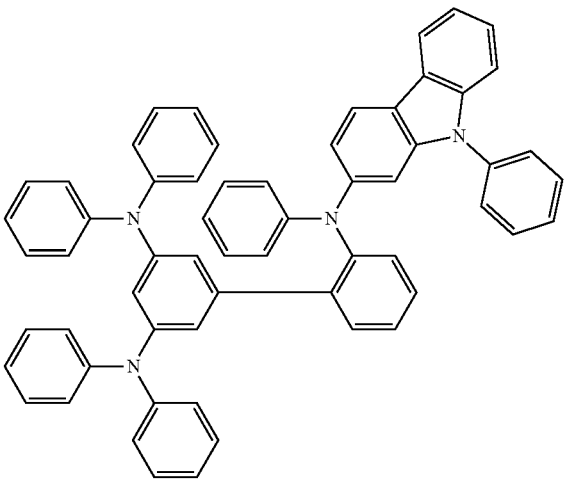
P-22
P-26
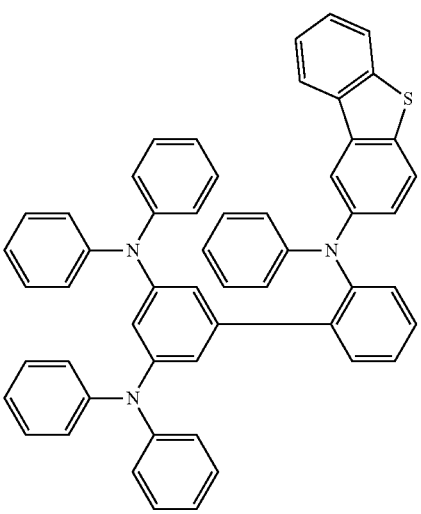
P-23
P-24
P-27
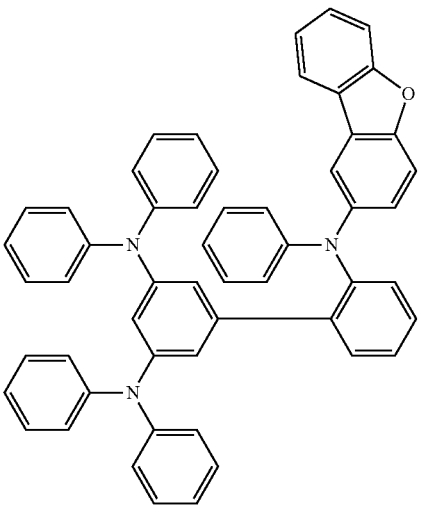

-continued
P-28
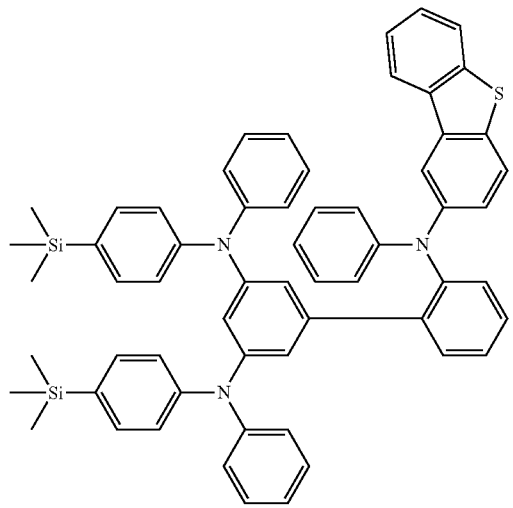
P-29
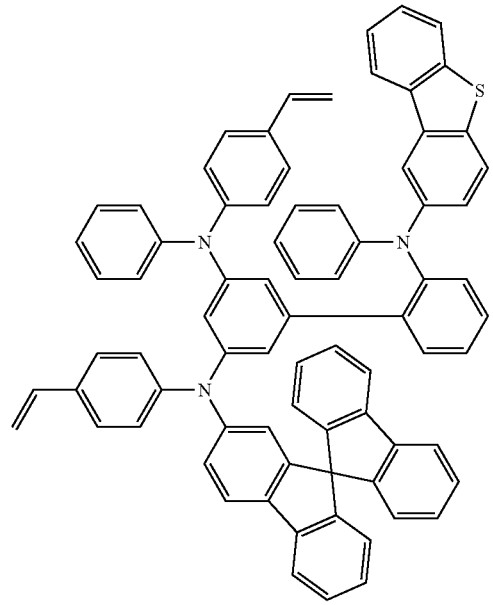
P-30
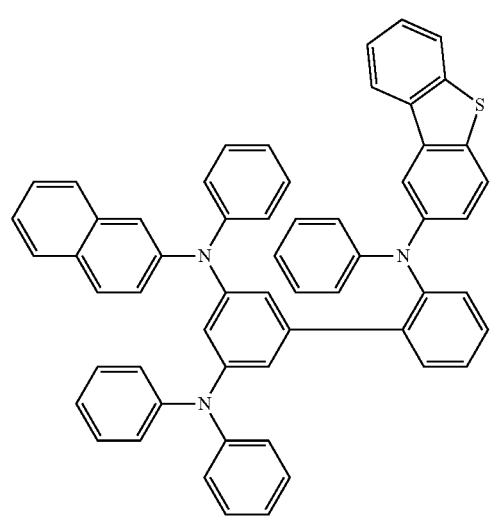
P-31
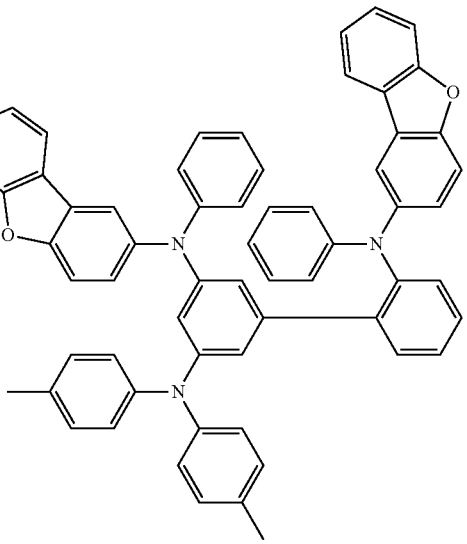
P-32
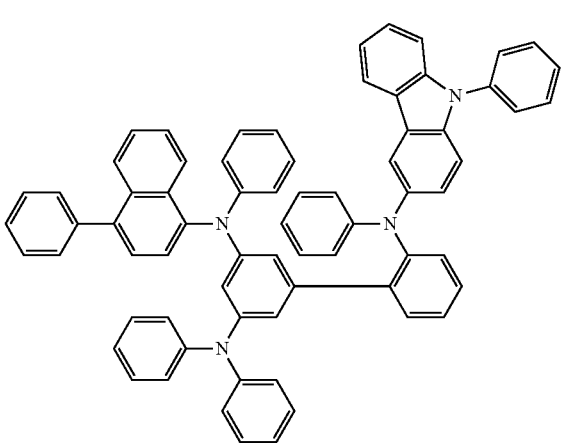
P-33
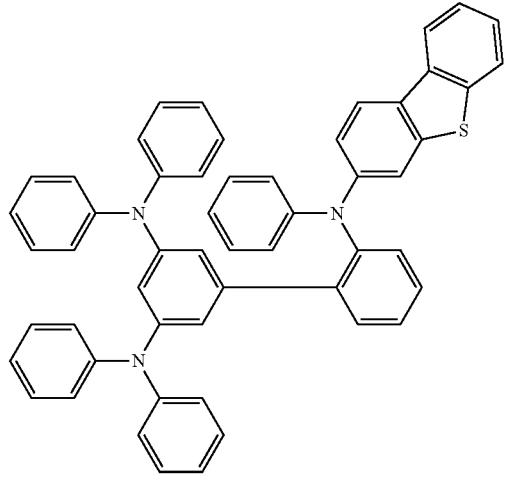

P-34
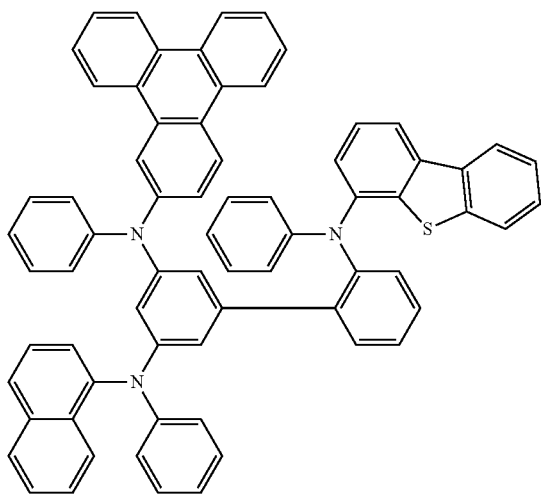
P-35
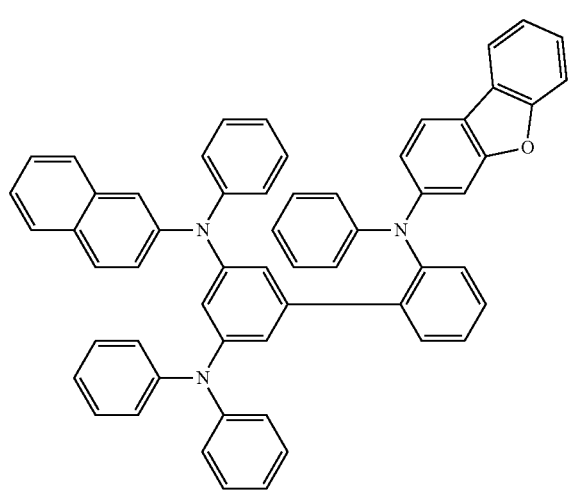
P-36
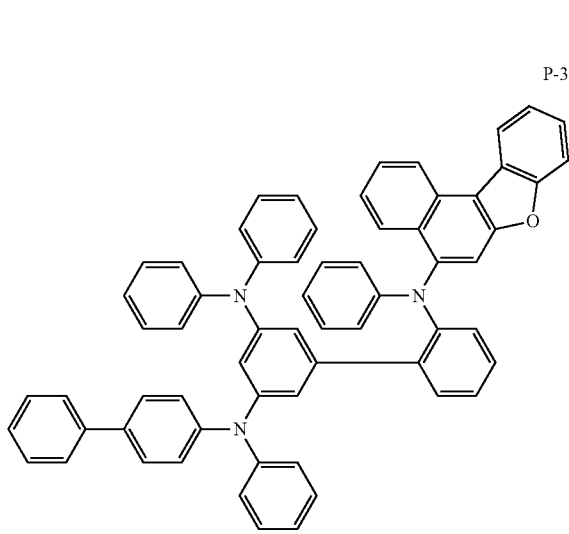
P-37
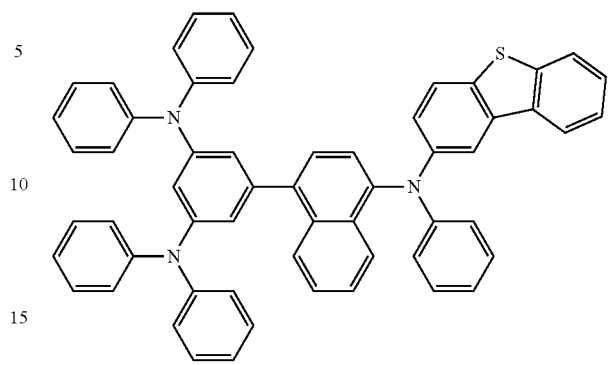
P-38
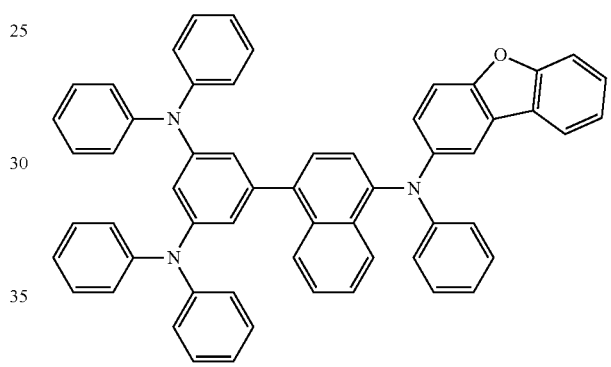
P-39
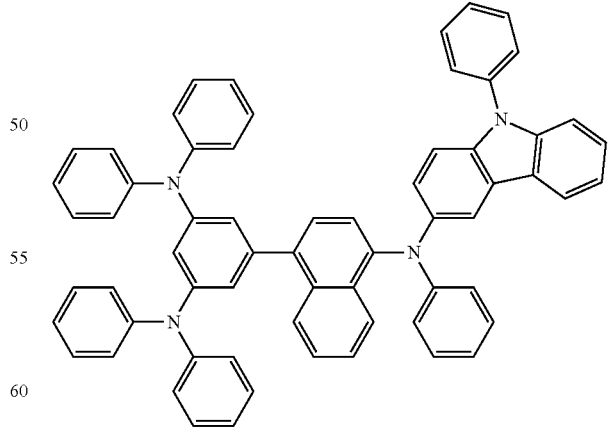

P-40
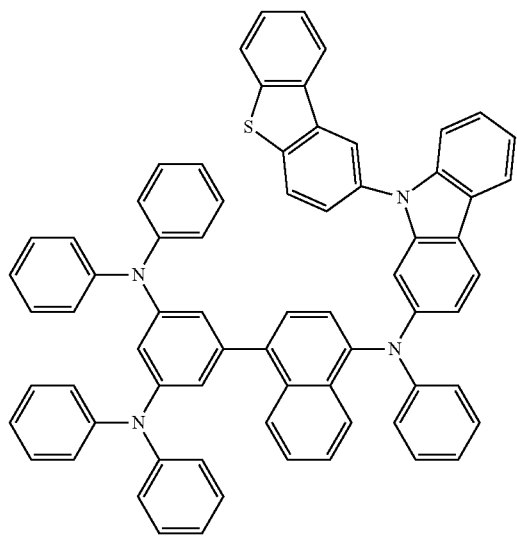
P-41
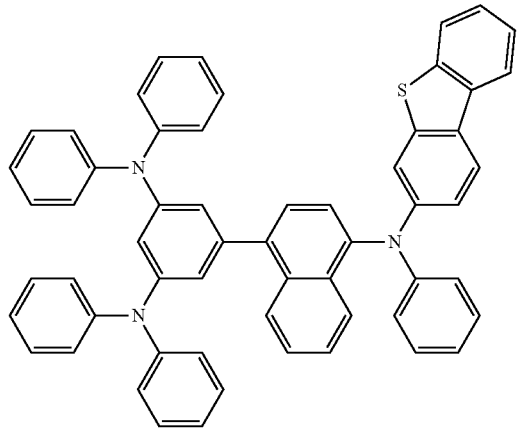
P-42
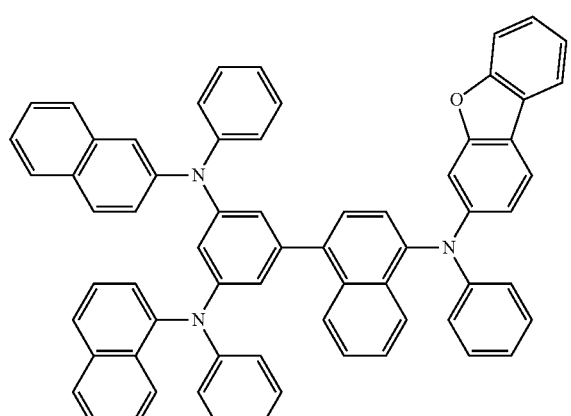
P-43
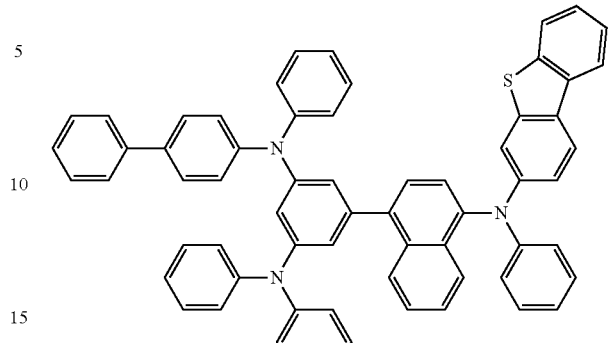
P-44
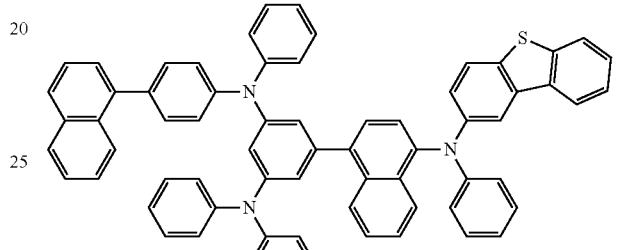
P-45
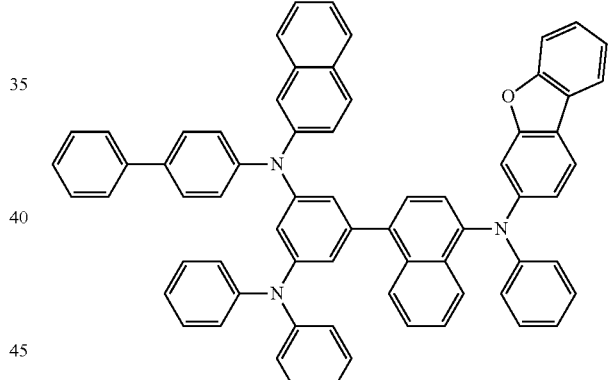
P-46
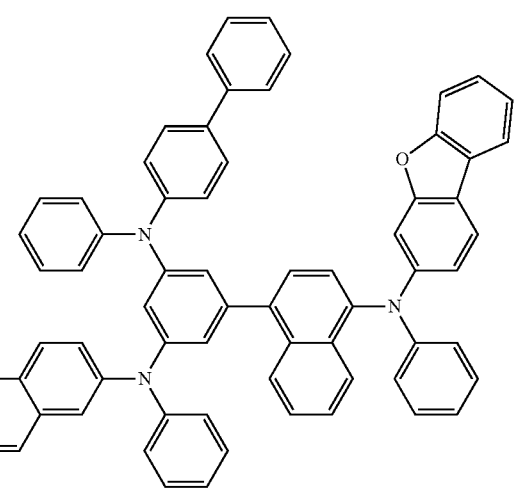

P-47
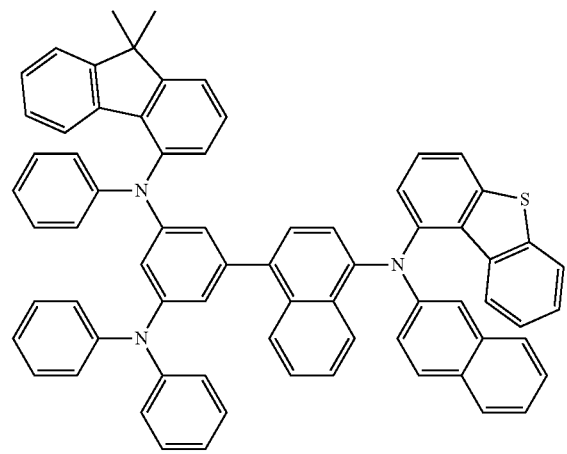
P-48
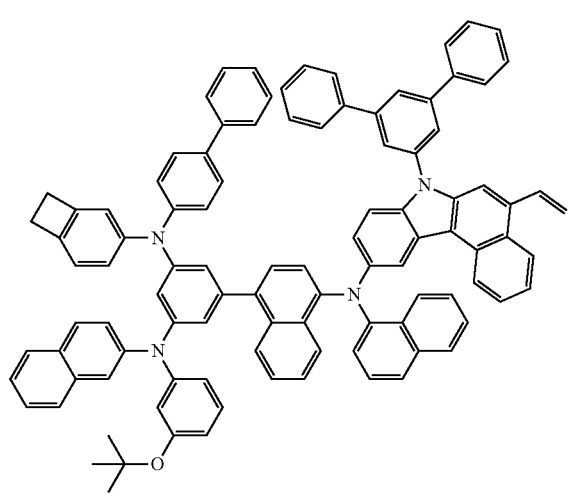
P-49
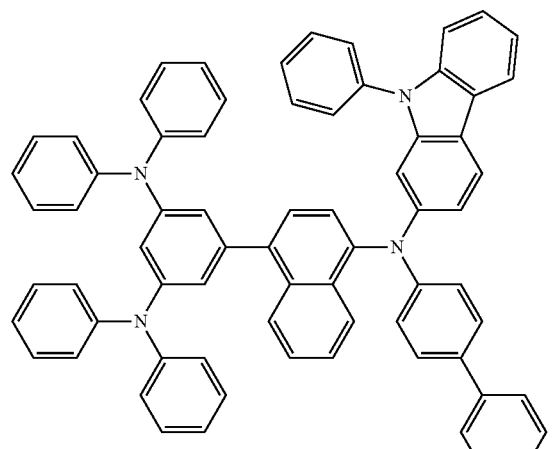
P-50
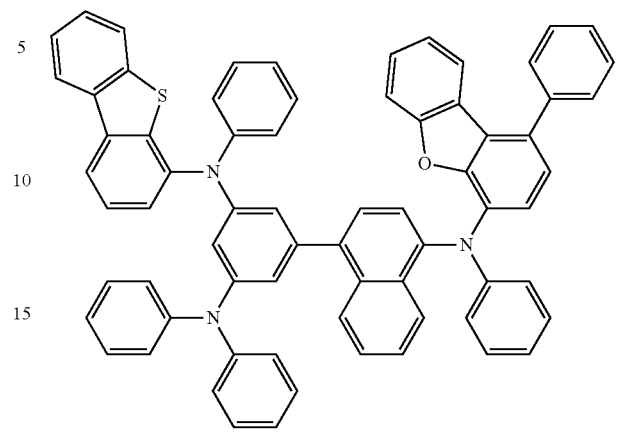
P-51
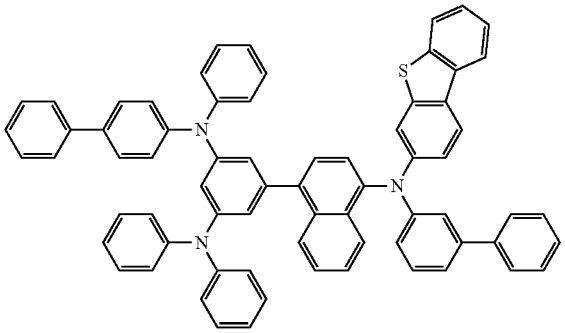
P-52
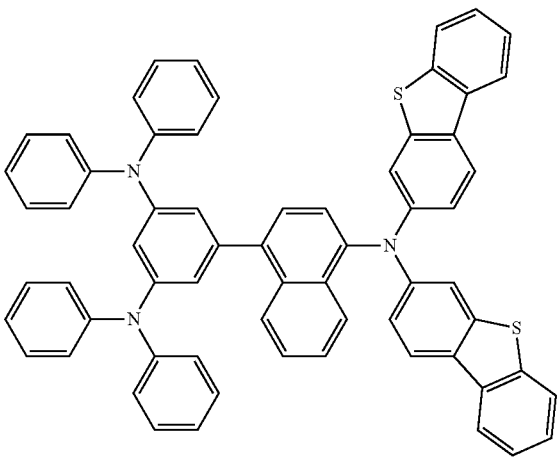

P-53
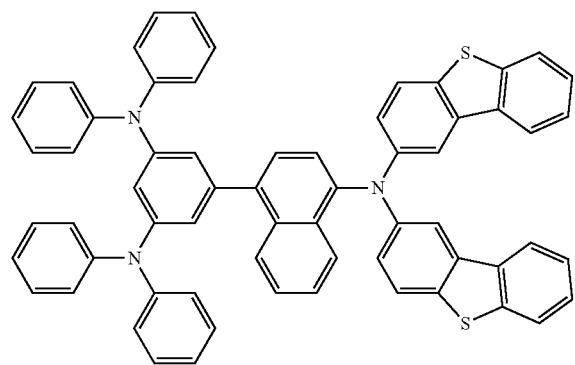
P-54
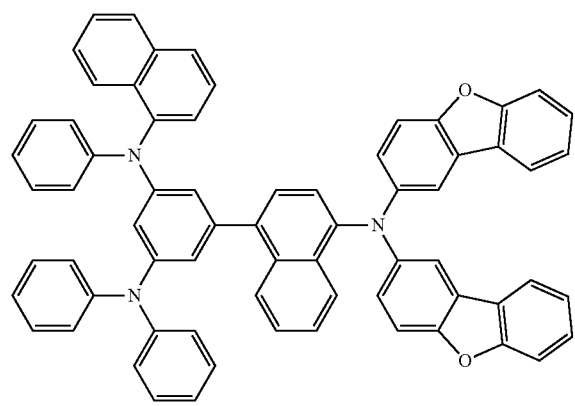
P-55
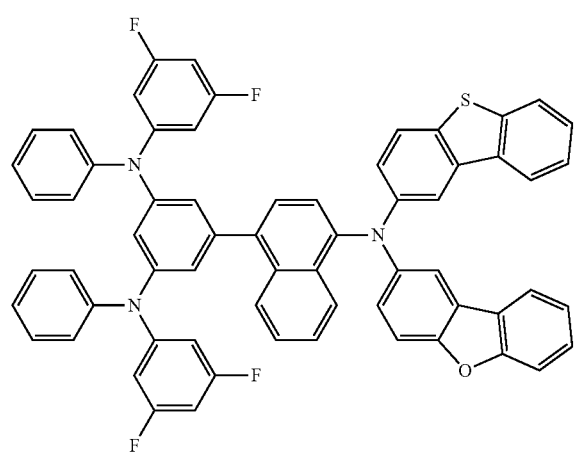
P-56
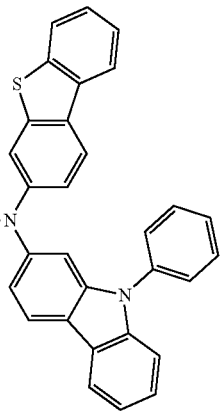
P-57
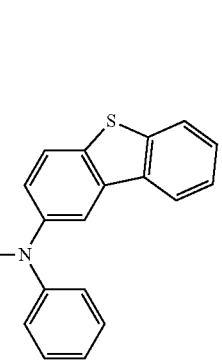
P-58
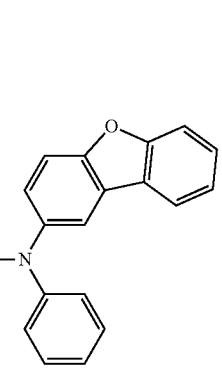
P-59
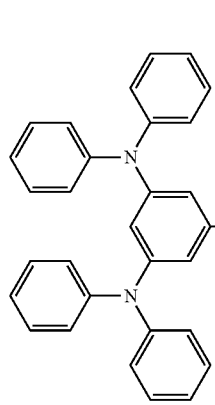

P-60
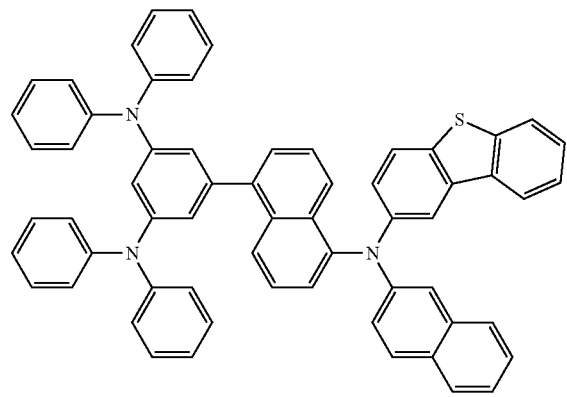
P-61
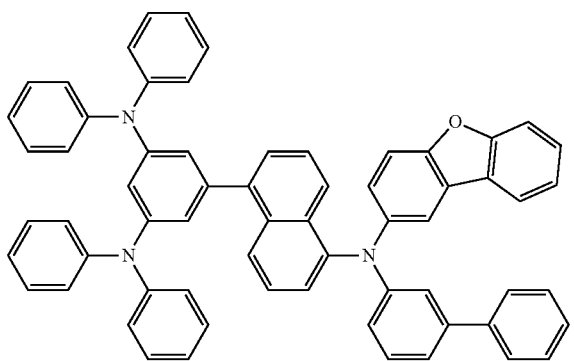
P-62
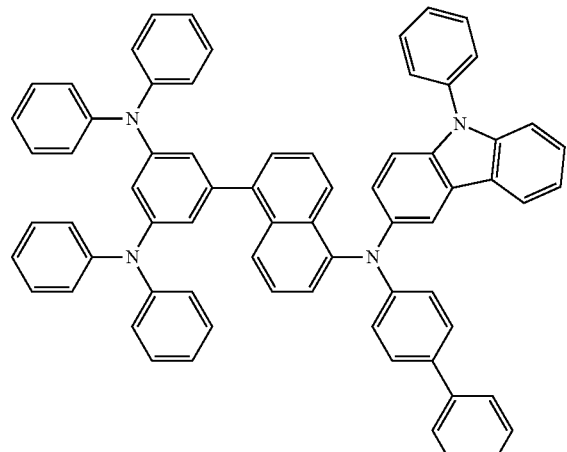
P-63
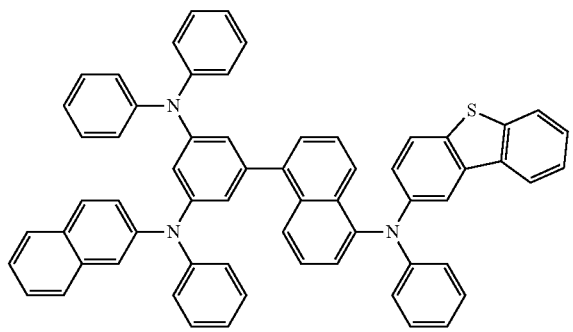
P-64
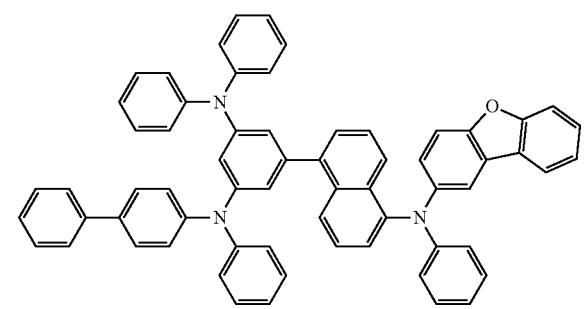
P-65
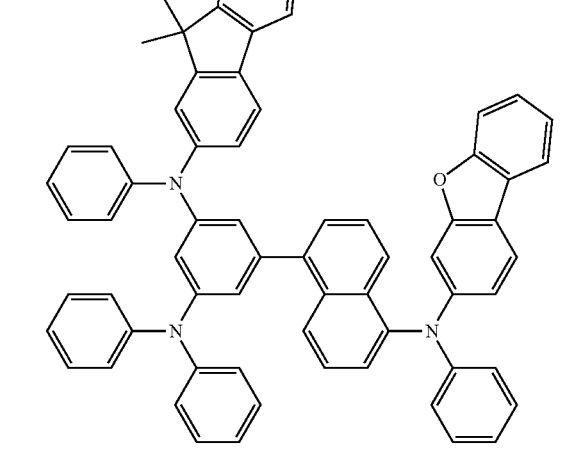
P-66
P-67
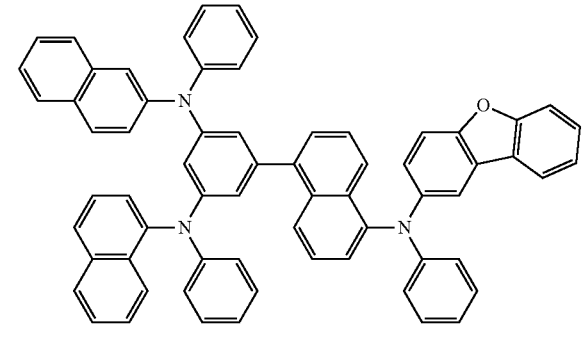

P-68
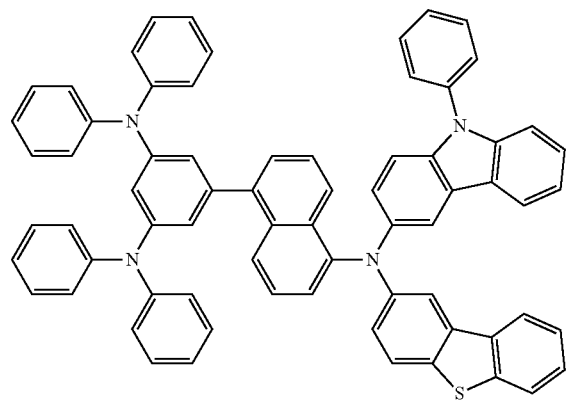
P-69
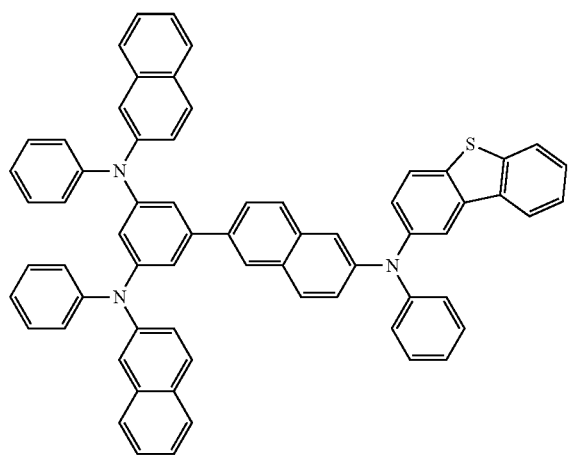
P-70
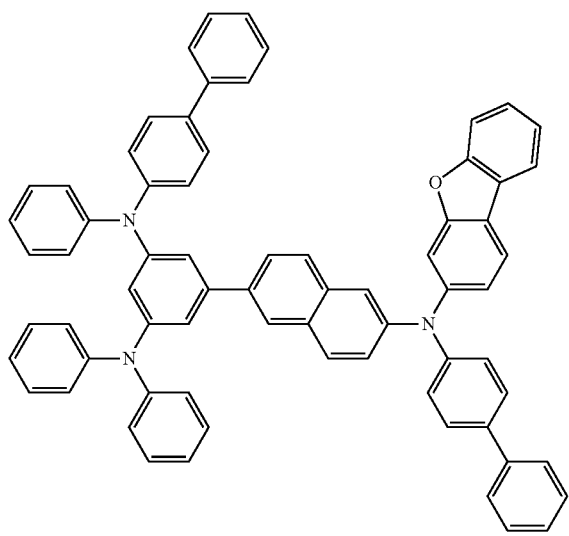
P-71
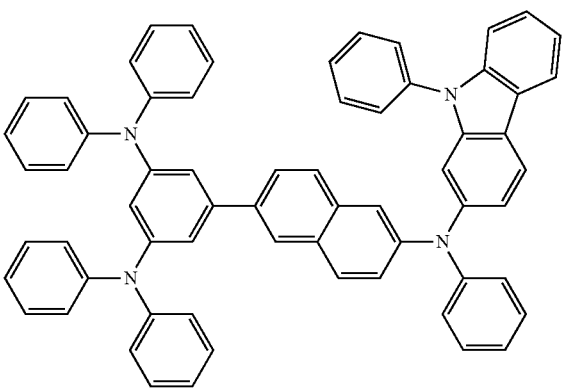
P-72
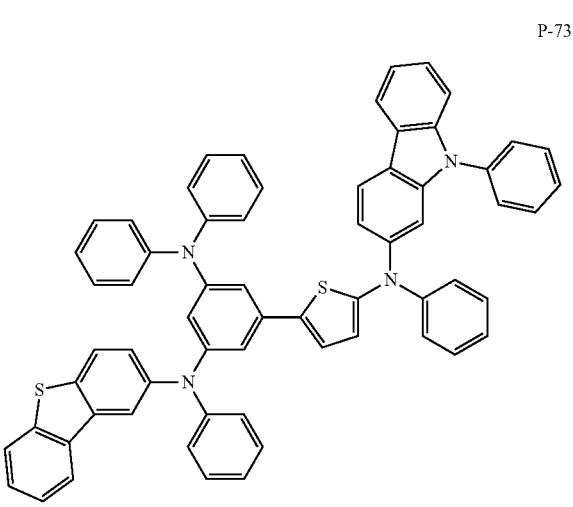
P-73

-continued
P-74
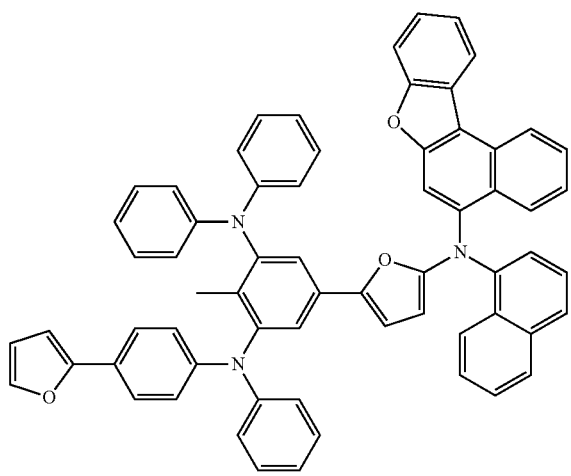
P-77
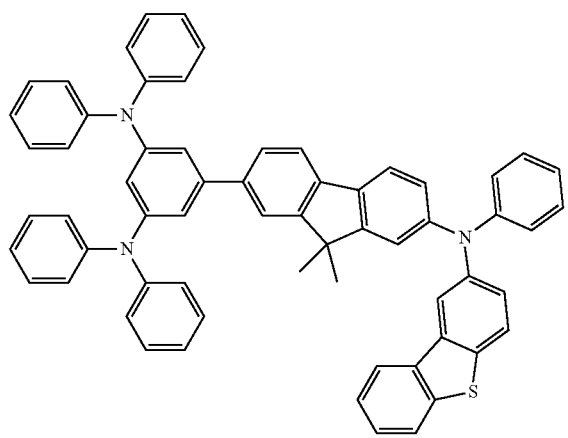
P-75
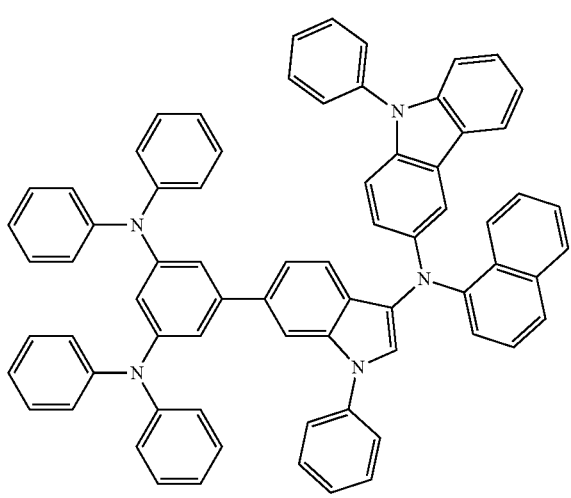
P-78
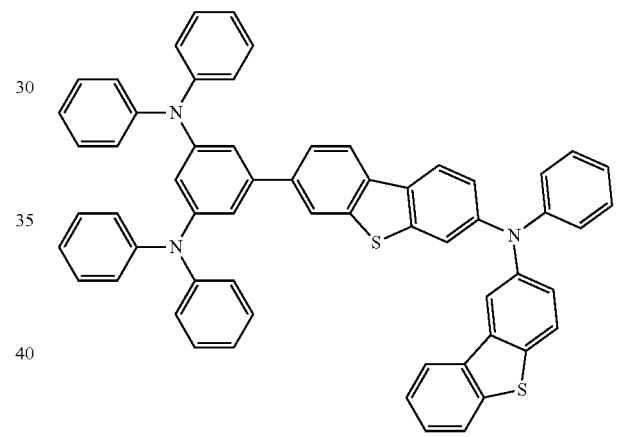
P-76
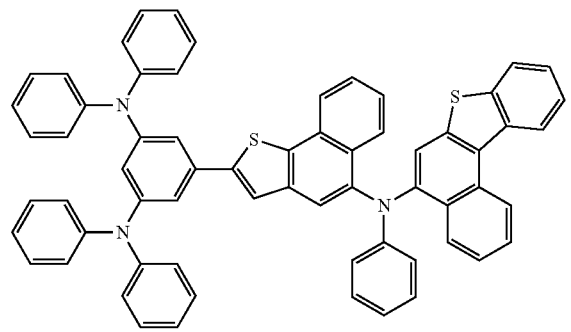
P-79
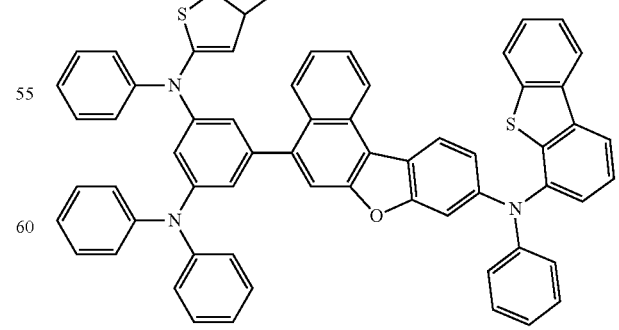

-continued
P-80
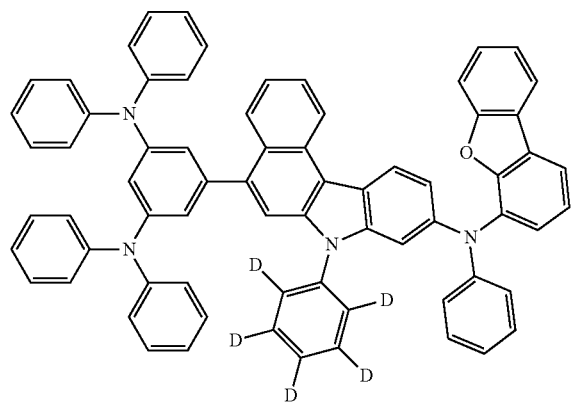
P-81
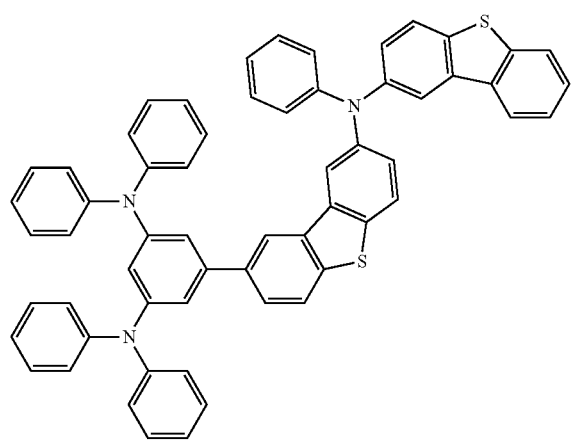
P-82
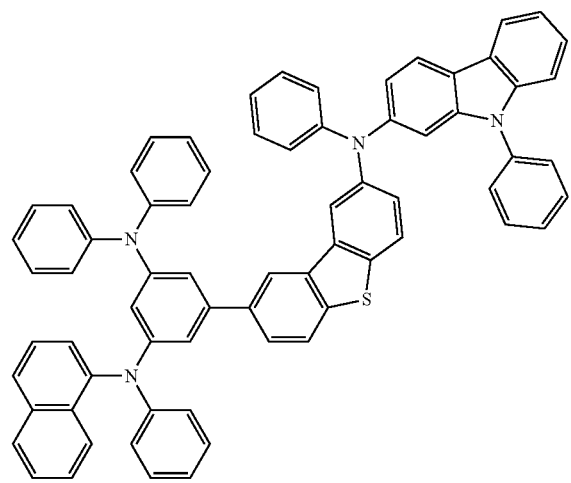
P-83
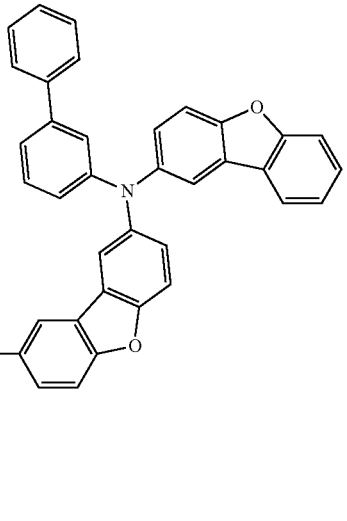
P-84
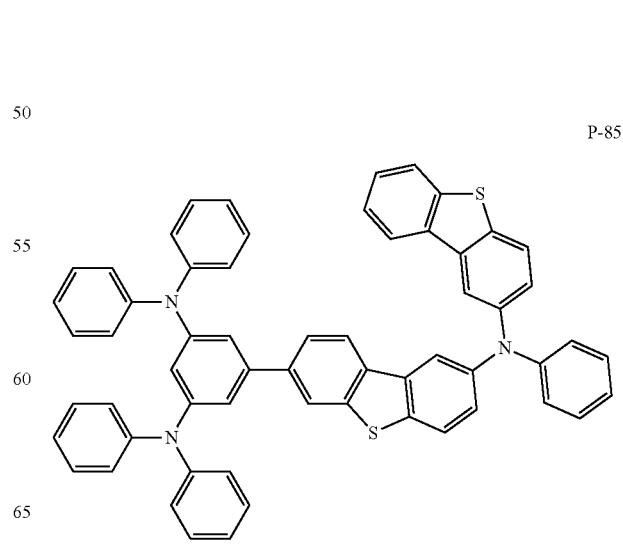
P-85

-continued
P-86
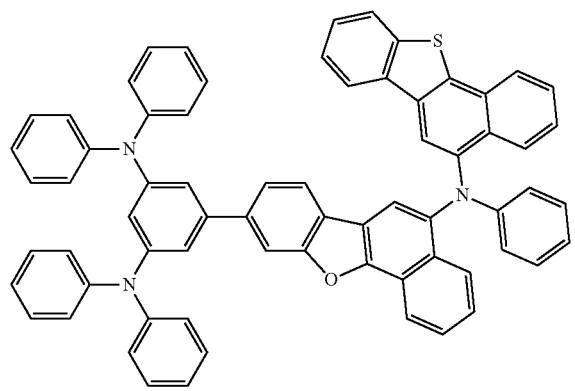
P-87
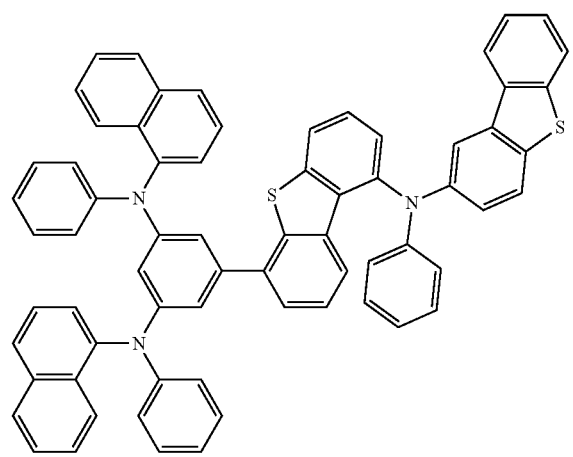
P-88
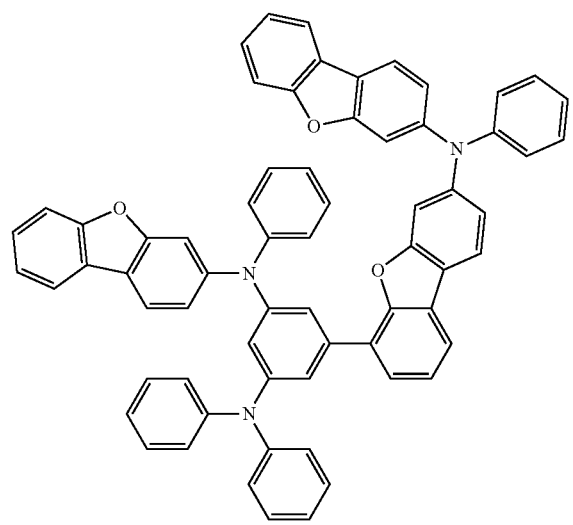
-continued
P-89
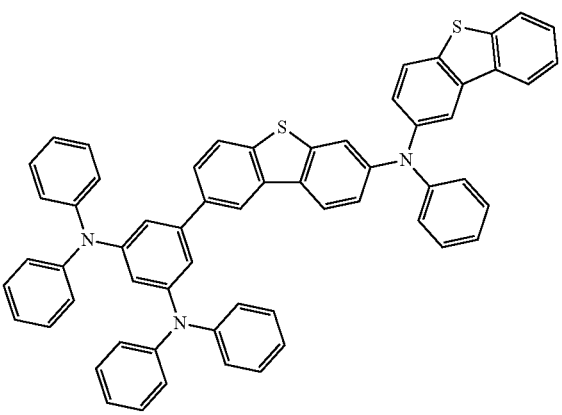
P-90
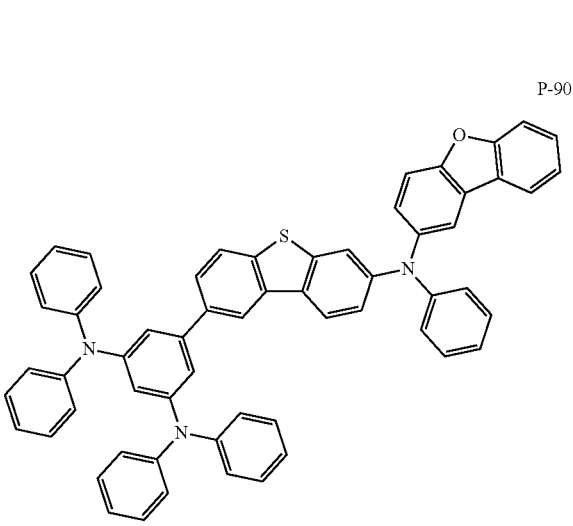
P-91
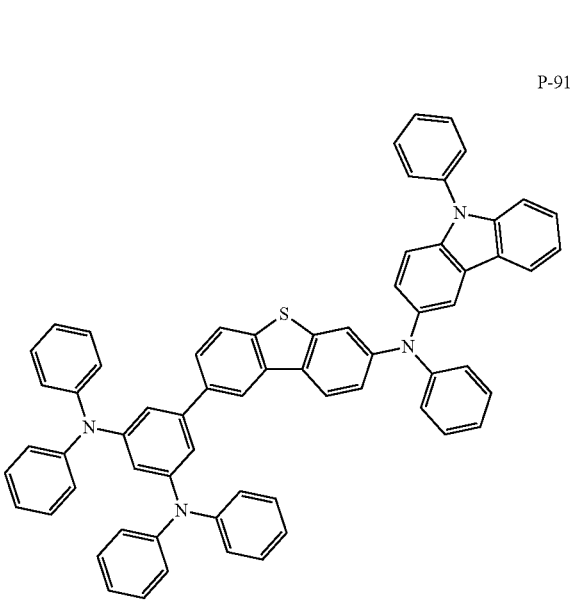

P-92

P-93

P-94

P-95

P-96

P-97

P-98
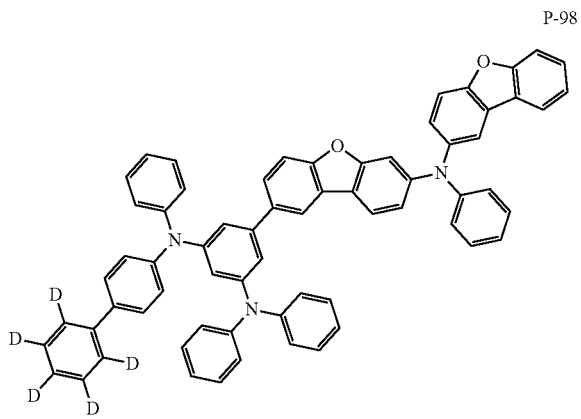
P-99
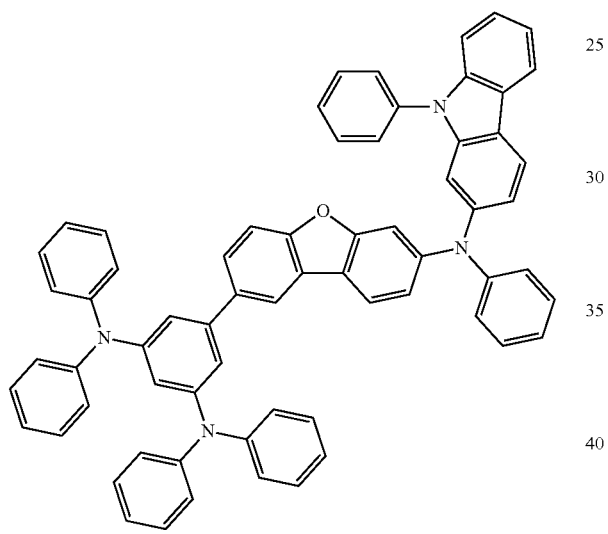
P-100
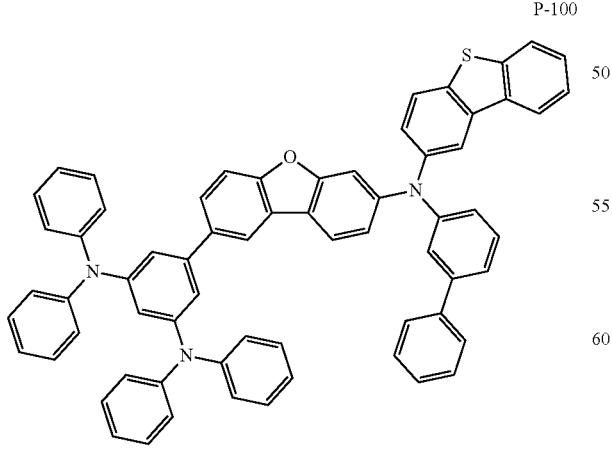
P-101
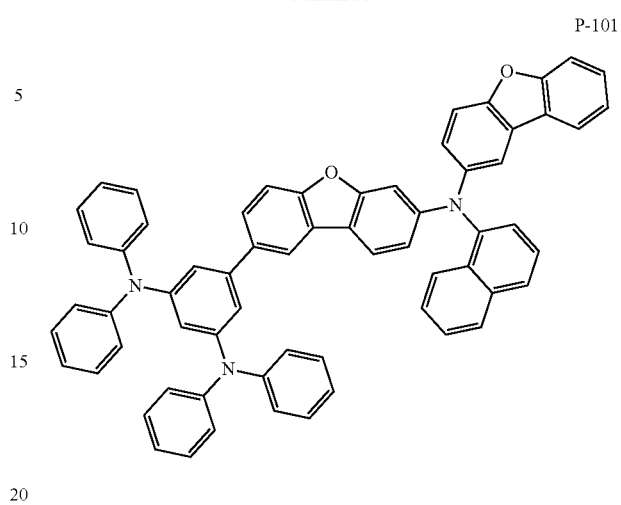
P-102
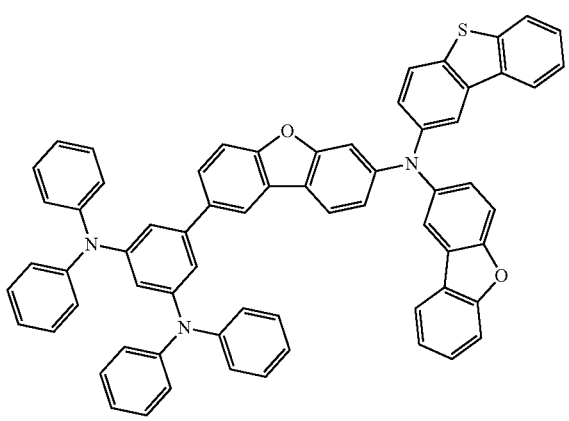
P-103
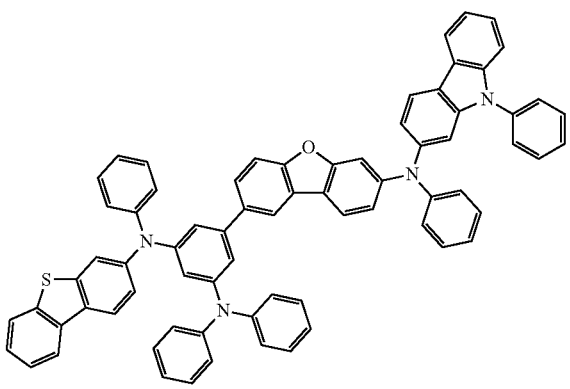

P-104
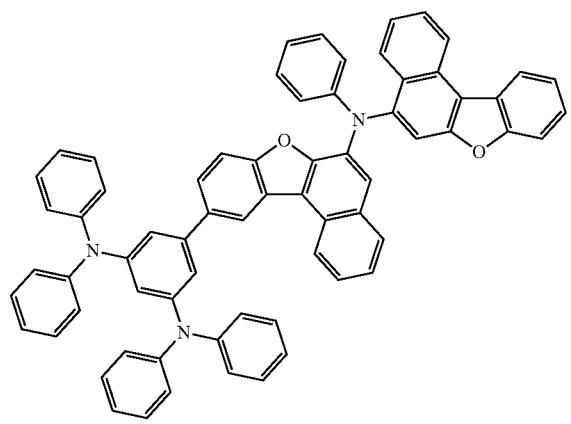
P-105
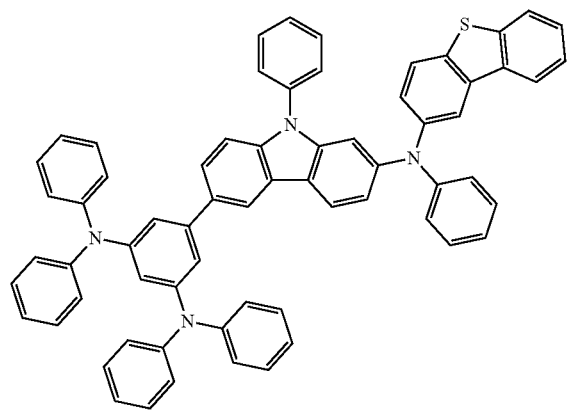
P-106
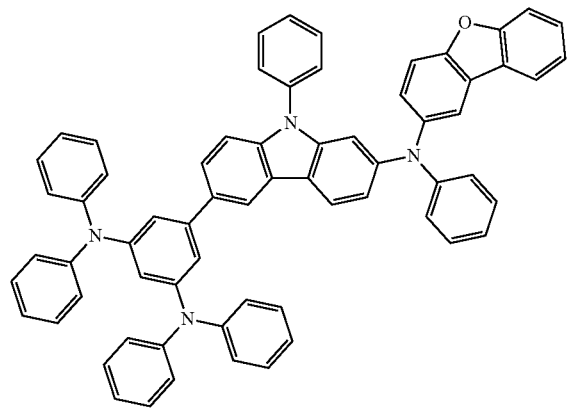
P-107
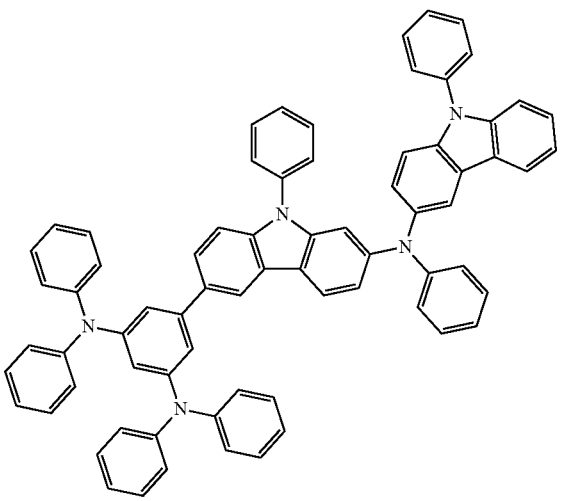
P-108
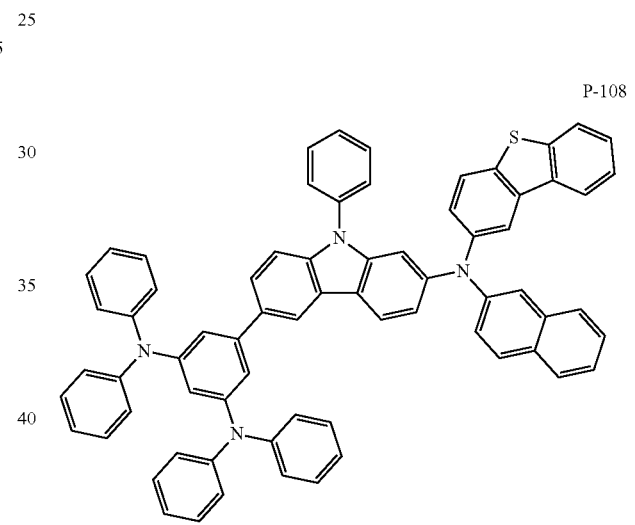
P-109
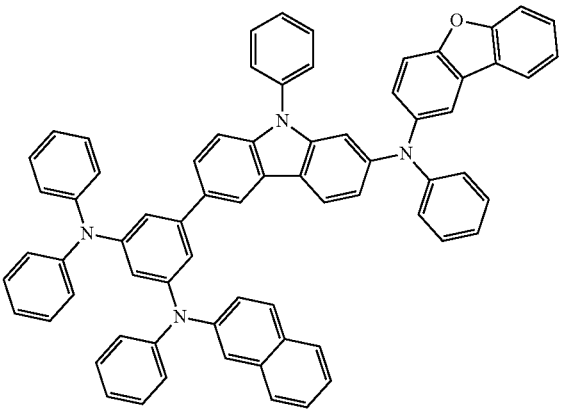

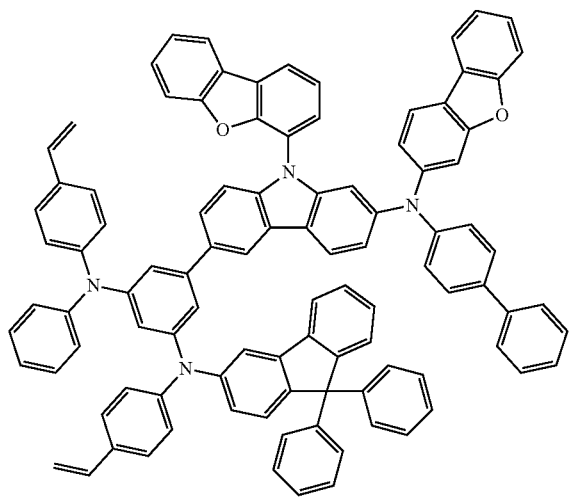

P-110

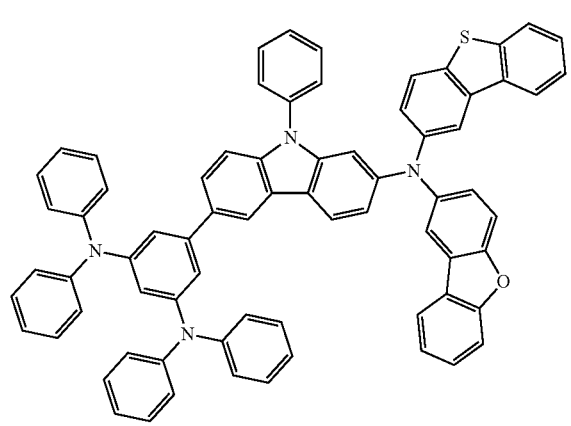

P-111

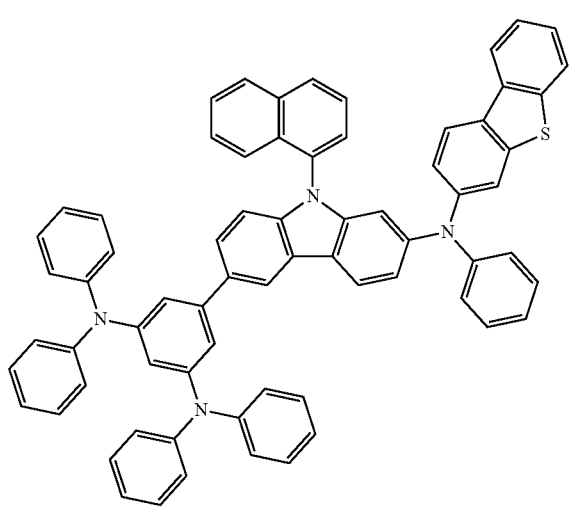

P-112

As another embodiment, the present disclosure provides a compound for an organic electric element, the compound being represented by Formula 1.

As still another embodiment, the present disclosure provides an organic electric element containing the compound represented by Formula 1.

Here, the organic electric element may include: a first electrode; a second electrode; and an organic material layer positioned between the first electrode and the second electrode. The organic material layer may contain the compound represented by Formula 1. The compound represented by Formula 1 may be contained in at least one layer of a hole injection layer, a hole transport layer, a light emitting auxiliary layer, a light emitting layer, an electron transport auxiliary layer, an electron transport layer, and an electron injection layer in the organic material layer. Especially, the compound represented by Formula 1 may be contained in the hole transport layer or the light emitting auxiliary layer.

That is, the compound represented by Formula 1 may be used as a material for a hole injection layer, a hole transport layer, a light emitting auxiliary layer, a light emitting layer, an electron transport auxiliary layer, an electron transport layer, or an electron injection layer. Especially, the compound represented by Formula 1 may be used as a material for the hole transport layer or the light emitting auxiliary layer. The present disclosure provides, specifically, an organic electric element including one of the compounds represented by Formula 1 in the organic material layer, and more specifically, organic electric elements including one of the compounds represented by the above individual Formulas (P-1 to P-112) in the organic material layer.

In still another embodiment, the present disclosure provides an organic electric element characterized in that the compound is contained alone, two or more different kinds of the compounds are contained in a combination, or the compound is contained together with other compounds as a combination of two or more in at least one layer of the hole injection layer, the hole transport layer, the light emitting auxiliary layer, the light emitting layer, the electron transport auxiliary layer, the electron transport layer, and the electron injection layer of the organic material layer. In other words, the compound corresponding to Formula 1 may be contained alone, a mixture of two or more kinds of the compounds of Formula 1 may be contained, or a mixture of the compound of claims 1 to 4 and a compound not corresponding to the present disclosure may be contained in each of the layers. Here, the compound not correspond to the present disclosure may be a single compound or two or more kinds of compounds. Here, when the compound is contained together with other compounds as a combination of two or more kinds of compounds, the other compounds may be compounds that are already known for each organic material layer, or compounds to be developed in the future. Here, the compounds contained in the organic material layer may be composed of only the same kind of compounds, or a mixture of two or more kinds of different compounds represented by Formula 1. More preferably, the organic material layer includes a light emitting layer and a light emitting auxiliary layer, and the light emitting layer contains a phosphorescent green emitter. The compound is contained in the light emitting auxiliary layer.

In still another embodiment of the present disclosure, the present disclosure provides an organic electric element further including a light efficiency improvement layer, which is formed on at least one between one surface of the first electrode, which is the opposite side to the organic material layer, and one surface of the second electrode, which is the opposite side to the organic material layer.

Hereinafter, synthetic examples of the compound represented by Formula 1 and manufacturing examples of the organic electric element according to the present disclosure will be described in detail by way of examples. However, the present disclosure is not limited to the following examples.

SYNTHESIS EXAMPLES

The final products represented by Formula 1 according to the present disclosure may be synthesized via the reaction pathway of Reaction Scheme 1, but are not limited thereto.

I. Synthesis of Sub 1

Sub 1 of Reaction Scheme 1 above may be synthesized by the reaction pathway of Reaction Scheme 2, but is not limited thereto.

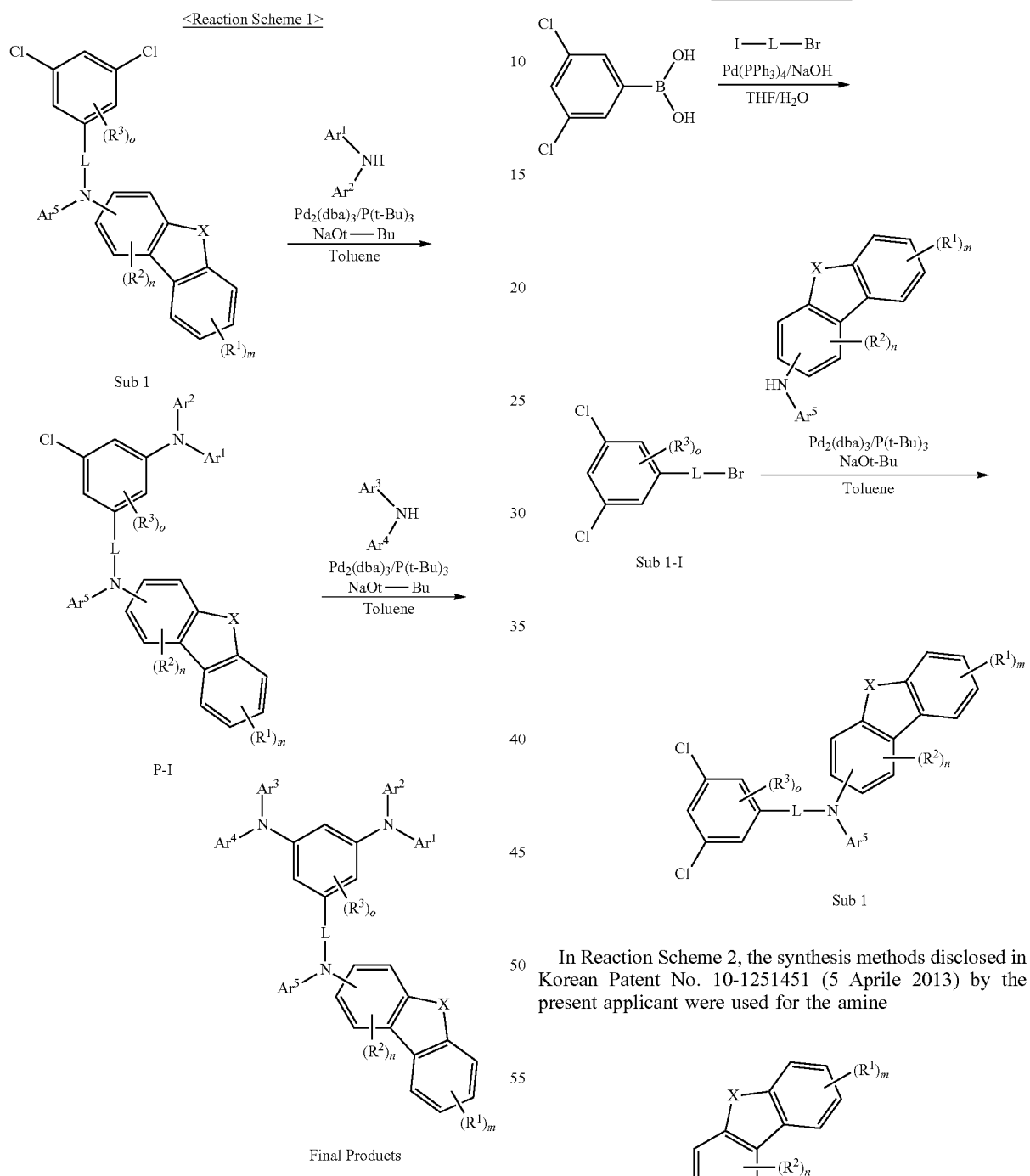

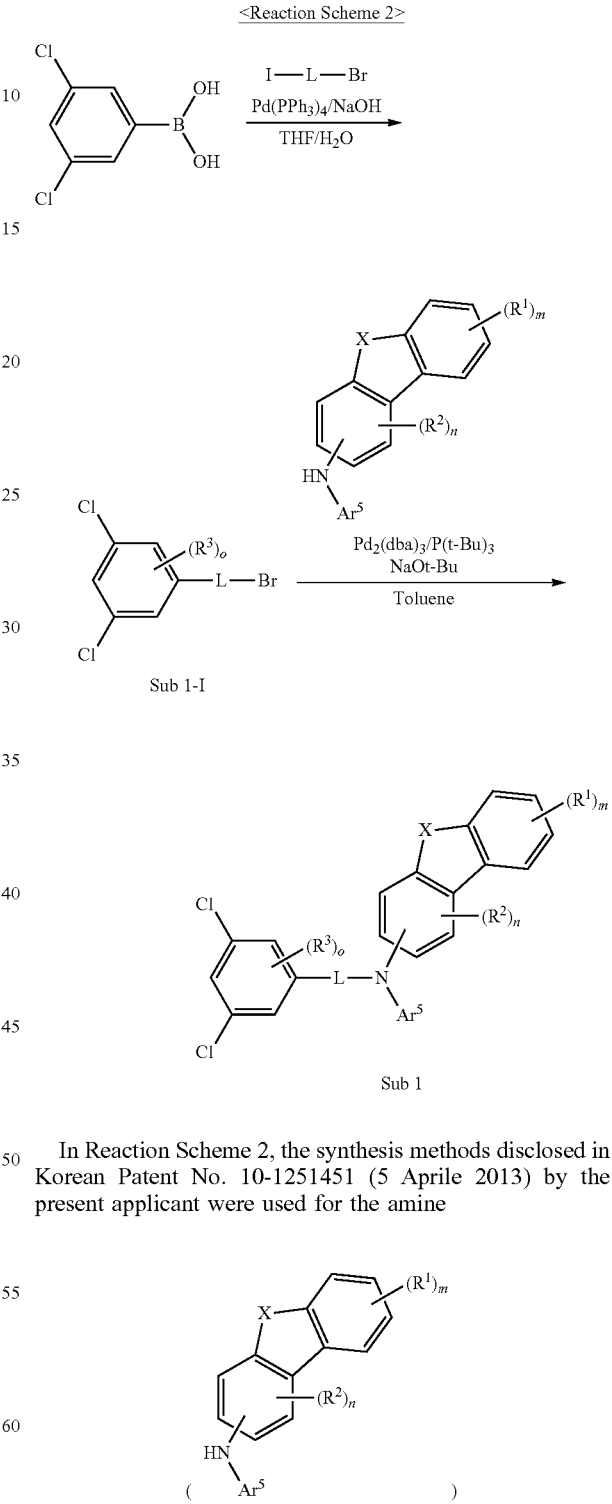

In Reaction Scheme 1, the synthesis methods disclosed in Korean Patent No. 10-1251451 (5 Aprile 2013) by the present applicant were used for amine (HN-Ar$^1$Ar$^2$, HN-Ar$^3$Ar$^4$) reaction products.

In Reaction Scheme 1, X, Ar$^1$ to Ar$^6$, L, R$^1$ to R$^3$, m, n, and o are the same as X, Ar$^1$ to Ar$^6$, L, R$^1$ to R$^3$, m, n, and o defined in Formula 1 above.

In Reaction Scheme 2, the synthesis methods disclosed in Korean Patent No. 10-1251451 (5 Aprile 2013) by the present applicant were used for the amine reaction product.

Synthesis examples of specific compounds pertaining to Sub 1 are as follows.

1. Synthesis Example of Sub 1-1

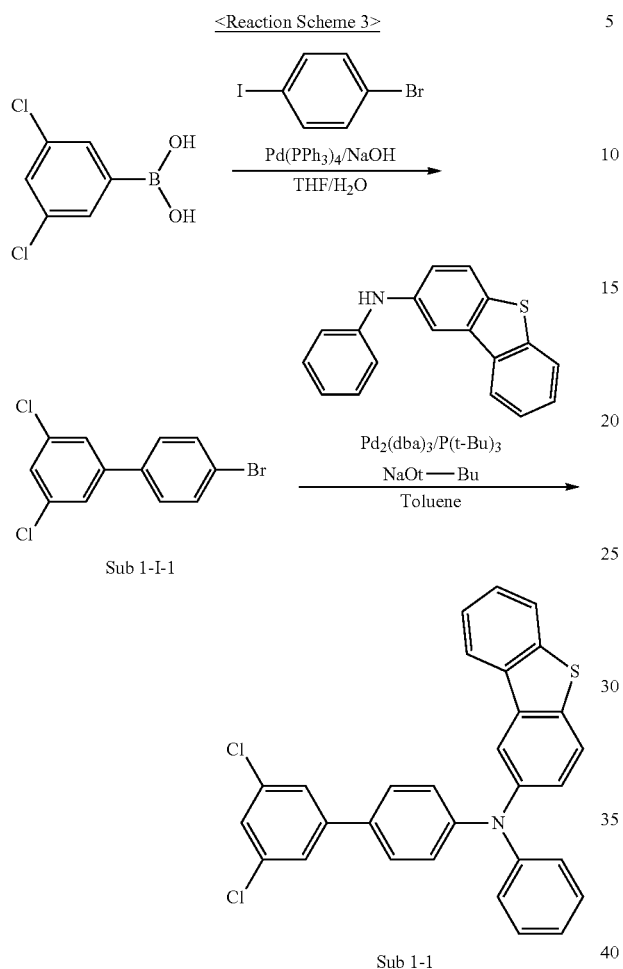

Sub 1-1

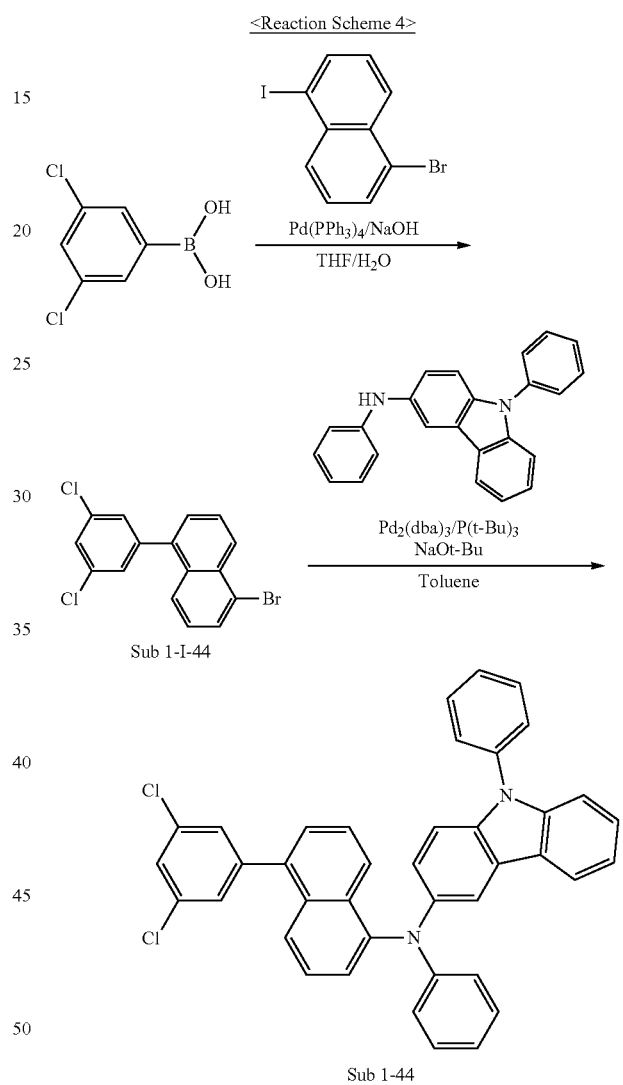

Sub 1-44

(1) Synthesis of Sub 1-I-1

(3,5-Dichlorophenyl)boronic acid (CAS Registry Number: 67492-50-6) (50 g, 262.04 mmol), 1-bromo-4-iodobenzene (CAS Registry Number: 589-87-7) (111.20 g, 393.06 mmol), Pd(PPh$_3$)$_4$ (9.08 g, 7.86 mmol), and NaOH (31.44 g, 786.12 mmol) were dissolved in anhydrous THF (1000 ml) and a small amount of water (500 ml), and then refluxed for 24 hours. Upon the completion of the reaction, the reaction product was cooled to normal temperature, extracted with CH$_2$Cl$_2$, and washed with water. The small amount of water was removed over anhydrous MgSO$_4$, followed by filtration under reduced pressure. Thereafter, the organic solvent was concentrated to produce a product, which was then separated via silica gel column to give desired 4'-bromo-3,5-dichloro-1,1'-biphenyl 59.35 g. (Yield: 75%)

(2) Synthesis of Sub 1-1

4'-Bromo-3,5-dichloro-1,1'-biphenyl (50 g, 165.57 mmol), N-phenyldibenzo[b,d]thiophen-2-amine (45.59 g, 165.57 mmol), Pd$_2$(dba)$_3$ (4.55 g, 4.97 mmol), P(t-Bu)$_3$ (4.8 ml, 9.93 mmol), and NaOt-Bu (47.74 g, 496.71 mmol) were dissolved in anhydrous Toluene (1100 ml), and then refluxed for 3 hours. Upon the completion of the reaction, the reaction product was cooled to normal temperature, extracted with CH$_2$Cl$_2$, and washed with water. The small amount of water was removed over anhydrous MgSO$_4$, followed by filtration under reduced pressure. Thereafter, the organic solvent was concentrated to produce a product, which was then subjected to silica gel column and recrystallization to give desired N-(3',5'-dichloro-[1,1'-biphenyl]-4-yl)-N-phenyldibenzo[b,d]thiophen-2-amine, 64.11 g. (Yield: 78%)

2. Synthesis Example of Sub 1-44

(1) Synthesis of Sub 1-I-44

(3,5-Dichlorophenyl)boronic acid (CAS Registry Number: 67492-50-6) (50 g, 262.04 mmol), 1-bromo-5-iodonaphthalene (CAS Registry Number: 77332-64-0) (130.88 g, 393.06 mmol), Pd(PPh$_3$)$_4$ (9.08 g, 7.86 mmol), and NaOH (31.44 g, 786.12 mmol) were dissolved in anhydrous THF (1000 ml) and a small amount of water (500 ml), and then refluxed for 24 hours. Upon the completion of the reaction, the reaction product was cooled to normal temperature, extracted with CH$_2$Cl$_2$, and washed with water. The small amount of water was removed over anhydrous MgSO$_4$, followed by filtration under reduced pressure. Thereafter, the organic solvent was concentrated to produce a product, which was then separated via silica gel column to give desired N,9-diphenyl-9H-carbazol-3-amine, 67.34 g. (Yield: 73%)

(2) Synthesis of Sub 1-44

N,9-diphenyl-9H-carbazol-3-amine (50 g, 142.03 mmol), N-phenyldibenzo[b,d]thiophen-2-amine (47.50 g, 142.03 mmol), Pd$_2$(dba)$_3$ (3.90 g, 4.26 mmol), P(t-Bu)$_3$ (4.2 ml, 8.52 mmol), and NaOt-Bu (40.95 g, 426.08 mmol) were dissolved in anhydrous Toluene (950 ml), and then refluxed for 3 hours. Upon the completion of the reaction, the reaction product was cooled to normal temperature, extracted with CH$_2$Cl$_2$, and washed with water. The small amount of water was removed over anhydrous MgSO$_4$, followed by filtration under reduced pressure. Thereafter, the organic solvent was concentrated to produce a product, which was then subjected to silica gel column and recrystallization to give desired N-(5-(3,5-dichlorophenyl)naphthalen-1-yl)-N, 9-diphenyl-9H-carbazol-3-amine, 61.06 g. (Yield: 71%)

3. Synthesis Example of Sub 1-51

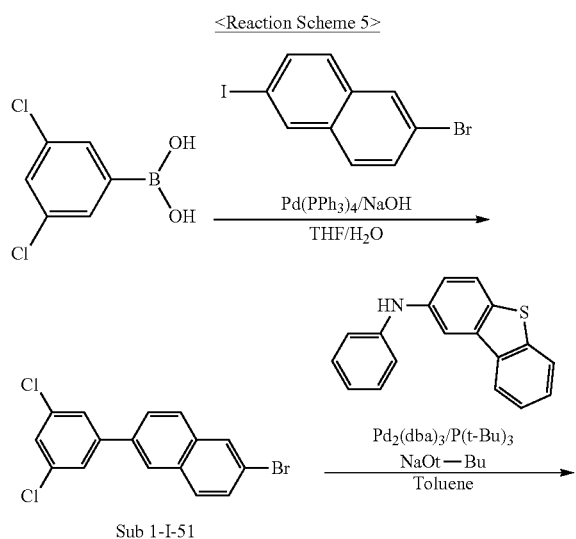

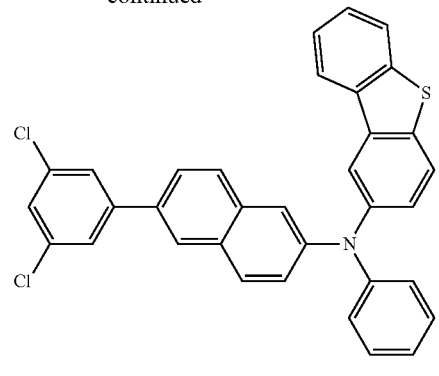

Sub 1-51

(1) Synthesis of Sub 1-I-51

(3,5-Dichlorophenyl)boronic acid (CAS Registry Number: 67492-50-6) (50 g, 262.04 mmol), 2-bromo-6-iodonaphthalene (CAS Registry Number: 389806-32-0) (130.88 g, 393.06 mmol), Pd(PPh$_3$)$_4$ (9.08 g, 7.86 mmol), and NaOH (31.44 g, 786.12 mmol) were dissolved in anhydrous THF (1000 ml) and a small amount of water (500 ml), and then refluxed after 24 hours. Upon the completion of the reaction, the reaction product was cooled to normal temperature, extracted with CH$_2$Cl$_2$, and washed with water. The small amount of water was removed over anhydrous MgSO$_4$, followed by filtration under reduced pressure. Thereafter, the organic solvent was concentrated to produce a product, which was then separated via silica gel column to give desired 2-bromo-6-(3,5-dichlorophenyl)naphthalene, 71.03 g. (Yield: 77%)

(2) Synthesis of Sub 1-26

2-Bromo-6-(3,5-dichlorophenyl)naphthalene (50 g, 142.03 mmol), N-phenyldibenzo[b,d]thiophen-2-amine (39.11 g, 142.03 mmol), Pd$_2$(dba)$_3$ (3.90 g, 4.26 mmol), P(t-Bu)$_3$ (4.2 ml, 8.52 mmol), and NaOt-Bu (40.95 g, 426.08 mmol) were dissolved in anhydrous Toluene (950 ml), and then refluxed for 3 hours. Upon the completion of the reaction, the reaction product was cooled to normal temperature, extracted with CH$_2$Cl$_2$, and washed with water. The small amount of water was removed over anhydrous MgSO$_4$, followed by filtration under reduced pressure. Thereafter, the organic solvent was concentrated to produce a product, which was then subjected to silica gel column and recrystallization to give desired N-(6-(3,5-dichlorophenyl)naphthalen-2-yl)-N-phenyldibenzo[b,d]thiophen-2-amine, 62.09 g. (Yield: 80%)

4. Synthesis Example of Sub 1-72

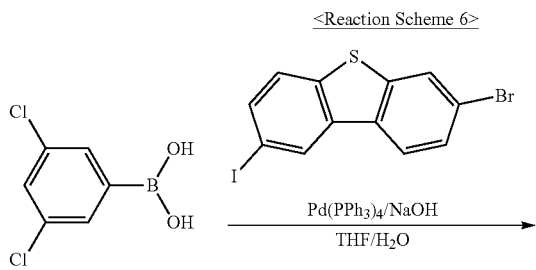

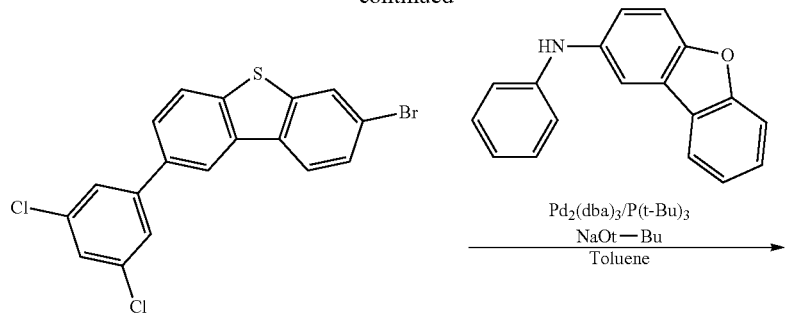

Sub 1-I-72

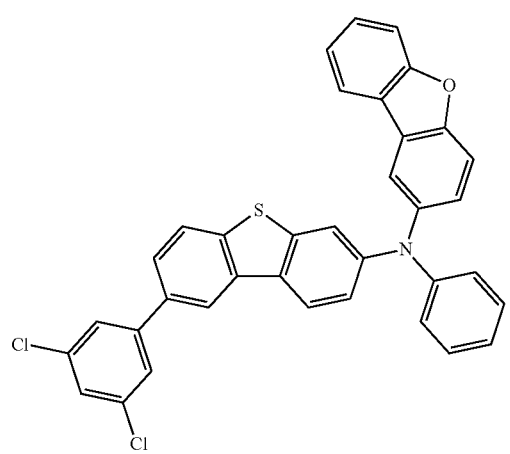

Sub 1-72

(1) Synthesis of Sub 1-I-72

(3,5-Dichlorophenyl)boronic acid (CAS Registry Number: 67492-50-6) (50 g, 262.04 mmol), 7-bromo-2-iodod-ibenzo[b,d]thiophene (CAS Registry Number: 1627589-27-8) (152.92 g, 393.06 mmol), Pd(PPh$_3$)$_4$ (9.08 g, 7.86 mmol), and NaOH (31.44 g, 786.12 mmol) were dissolved in anhydrous THF (1000 ml) and a small amount of water (50 ml), and then refluxed after 24 hours. Upon the completion of the reaction, the reaction product was cooled to normal temperature, extracted with CH$_2$Cl$_2$, and washed with water. The small amount of water was removed over anhydrous MgSO$_4$, followed by filtration under reduced pressure. Thereafter, the organic solvent was concentrated to produce a product, which was then separated via silica gel column to give desired 7-bromo-2-(3,5-dichlorophenyl)dibenzo[b,d] thiophene, 85.56 g. (Yield: 80%)

(2) Synthesis of Sub 1-72

7-Bromo-2-(3,5-dichlorophenyl)dibenzo[b,d]thiophene (50 g, 122.51 mmol), N-phenyldibenzo[b,d]furan-2-amine (31.77 g, 122.51 mmol), Pd$_2$(dba)$_3$ (3.37 g, 3.68 mmol), P(t-Bu)$_3$ (3.6 ml, 7.35 mmol), and NaOt-Bu (35.32 g, 367.53 mmol) were dissolved in anhydrous Toluene (820 ml), and then refluxed for 3 hours. Upon the completion of the reaction, the reaction product was cooled to normal temperature, extracted with CH$_2$Cl$_2$, and washed with water. The small amount of water was removed over anhydrous MgSO$_4$, followed by filtration under reduced pressure. Thereafter, the organic solvent was concentrated to produce a product, which was then subjected to silica gel column and recrystallization to give desired N-(8-(3,5-dichlorophenyl) dibenzo[b,d]thiophen-3-yl)-N-phenyldibenzo[b,d]furan-2-amine, 53.89 g. (Yield: 75%)

The compounds pertaining to Sub 1 may be compounds below, but are not limited thereto. Table 1 below shows FD-MS values of the compounds pertaining to Sub 1.

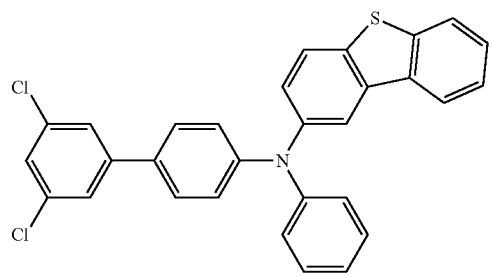

Sub 1-1

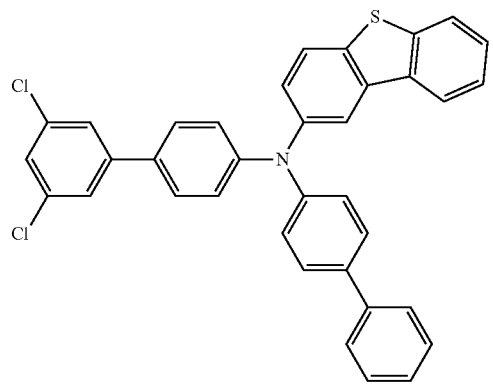

Sub 1-2

-continued
Sub 1-3
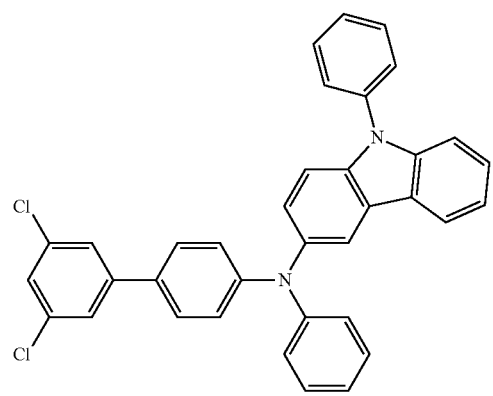
Sub 1-4
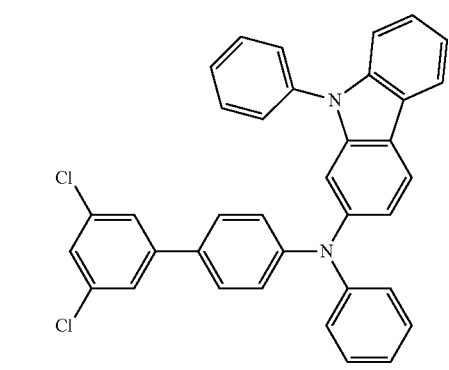
Sub 1-5
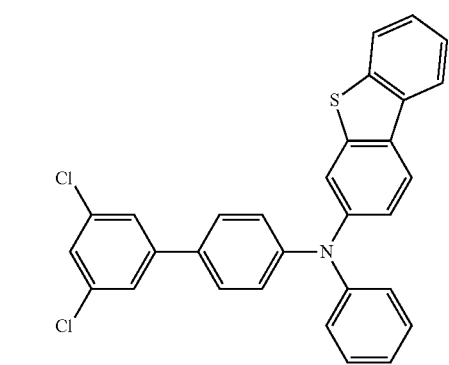
Sub 1-6
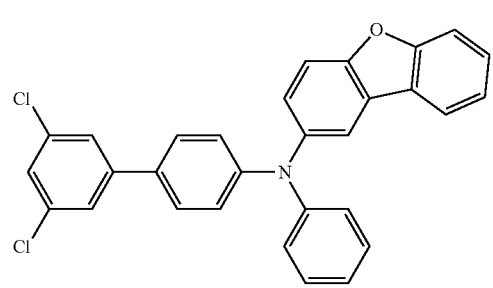
Sub 1-7
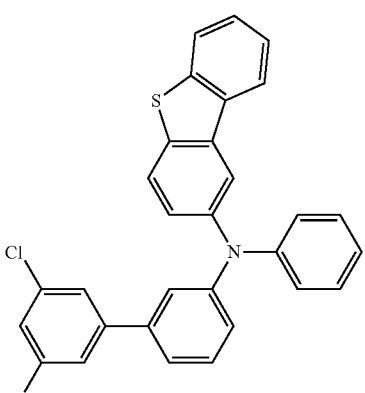
Sub 1-8
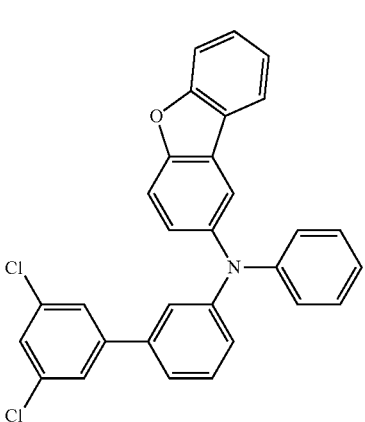
Sub 1-9
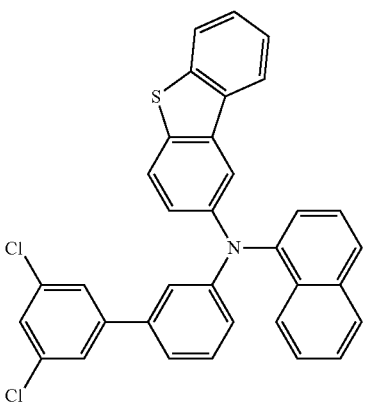
Sub 1-10
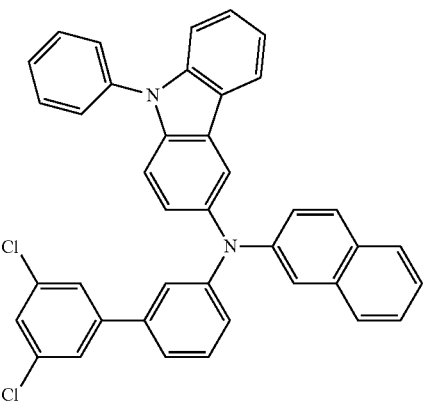

Sub 1-11
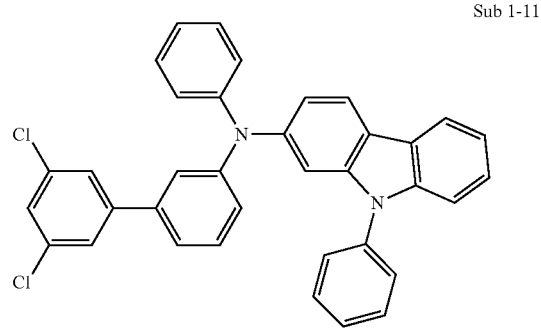
Sub 1-12
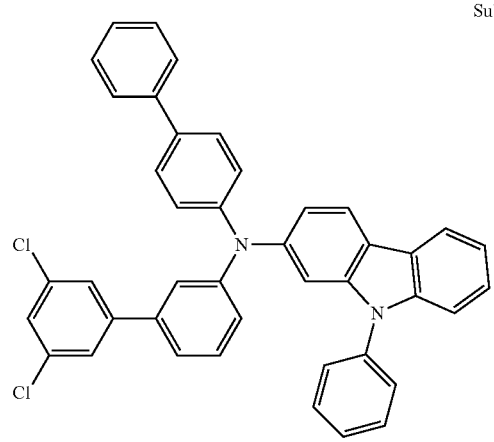
Sub 1-13
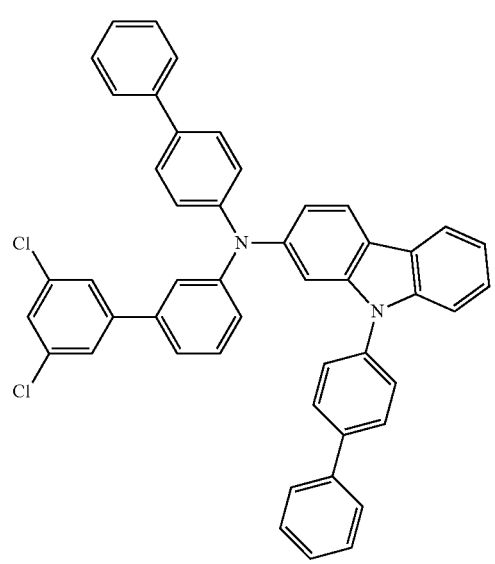
Sub 1-14
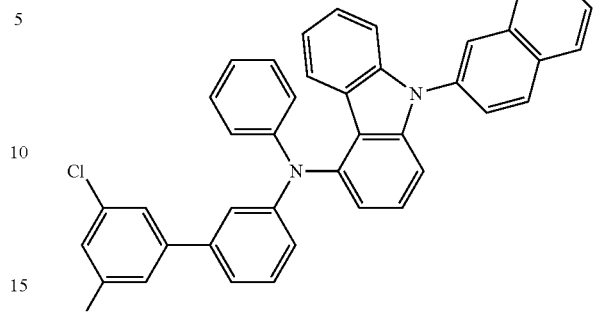
Sub 1-15
Sub 1-16
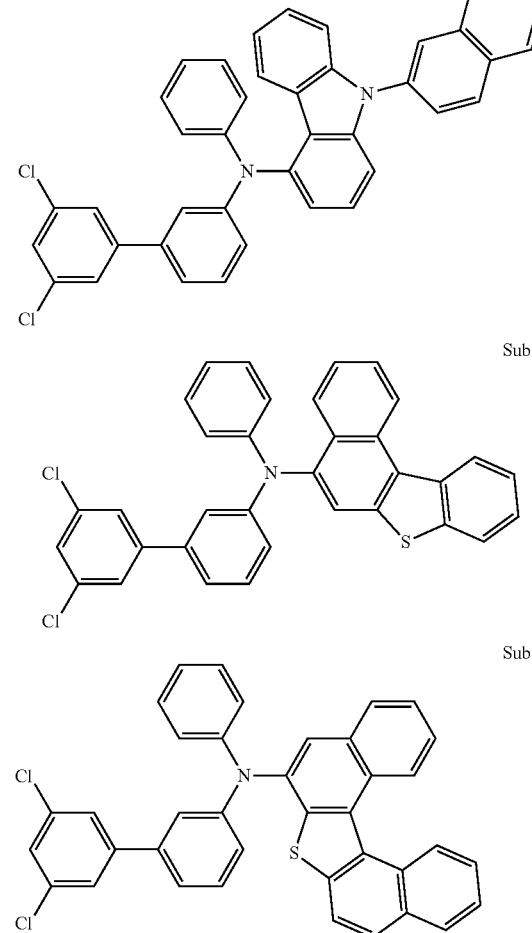
Sub 1-17
Sub 1-18
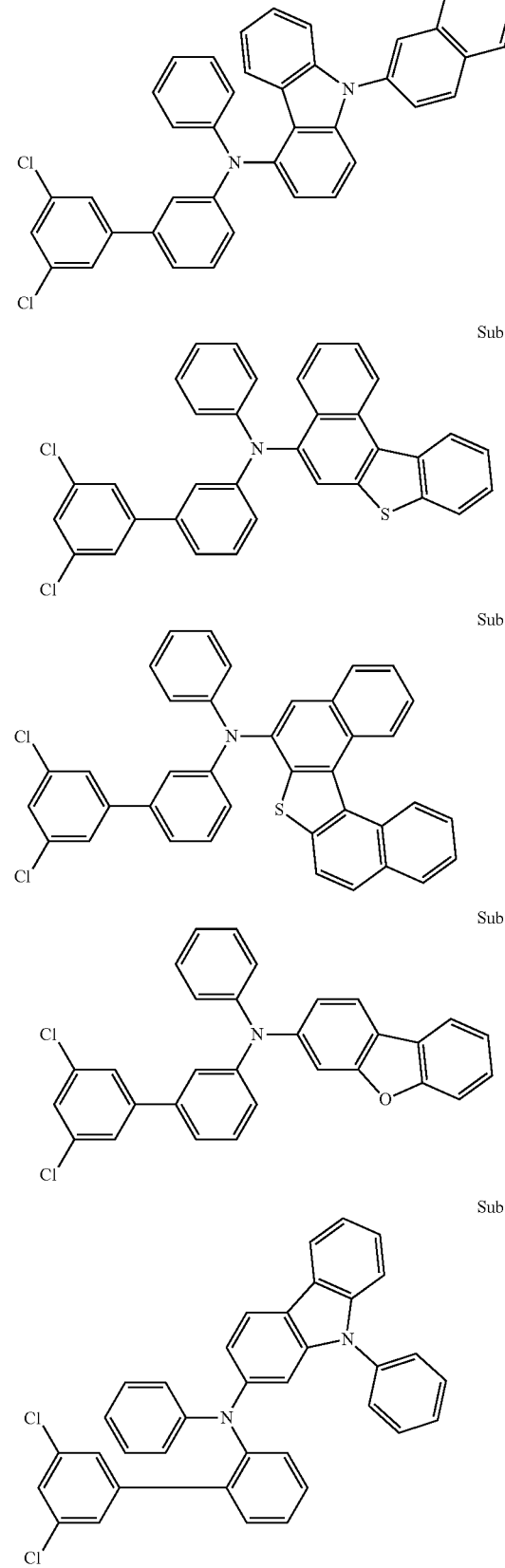

-continued
Sub 1-19
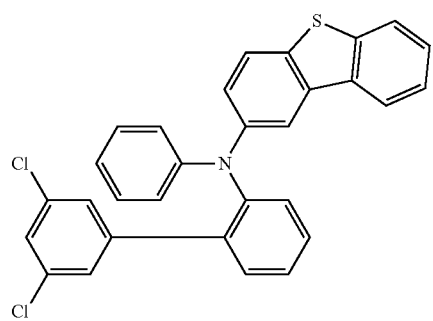
Sub 1-20
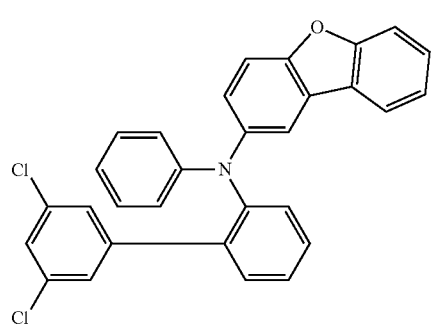
Sub 1-21
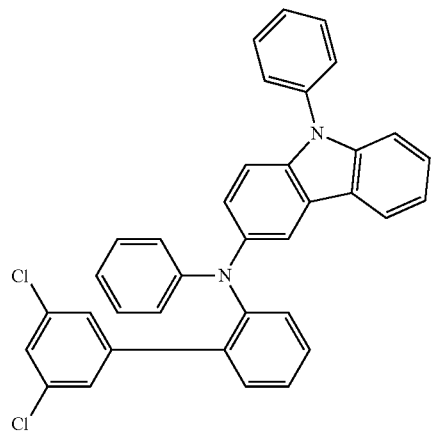
Sub 1-22
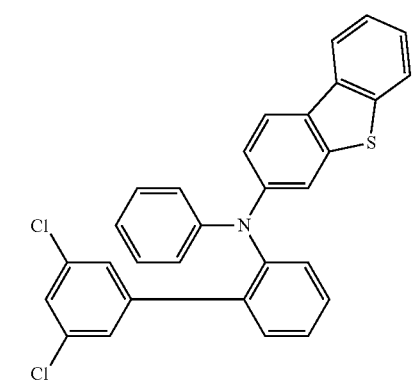
Sub 1-23
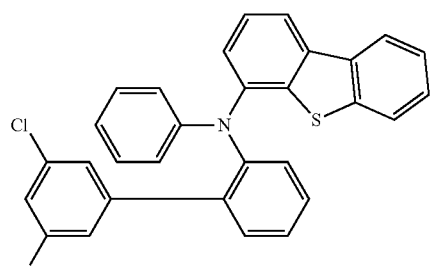
Sub 1-24
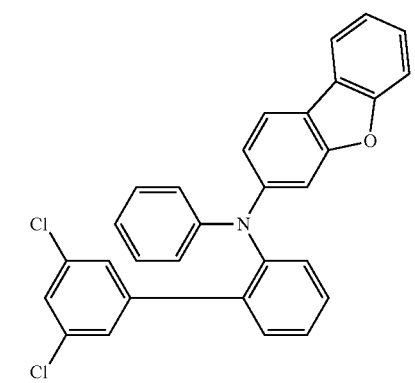
Sub 1-25
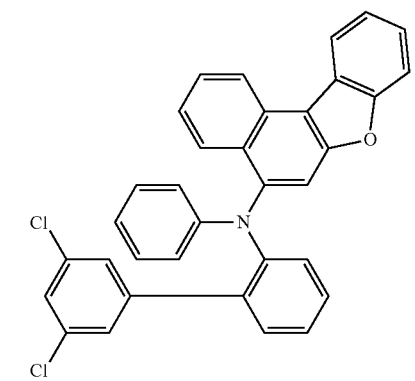
Sub 1-26
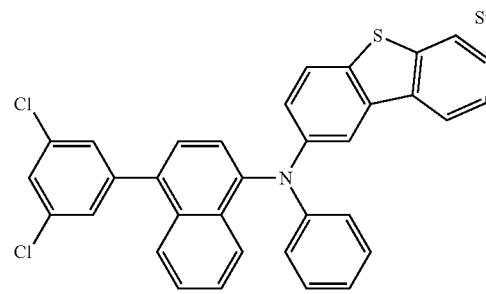
Sub 1-27
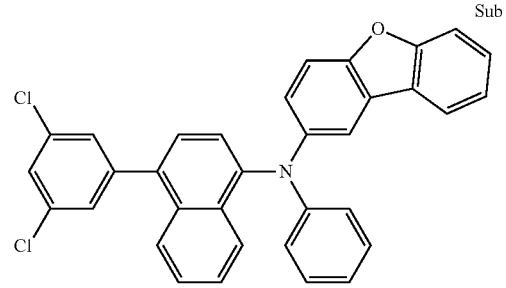

Sub 1-28
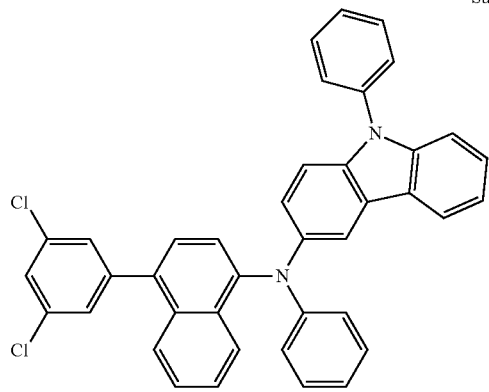
Sub 1-29
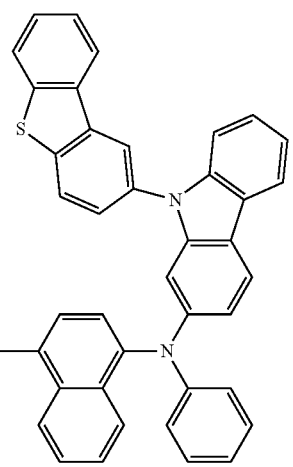
Sub 1-30
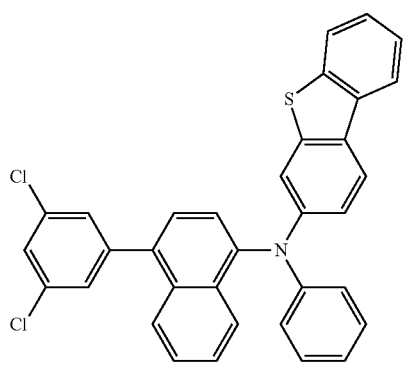
Sub 1-31
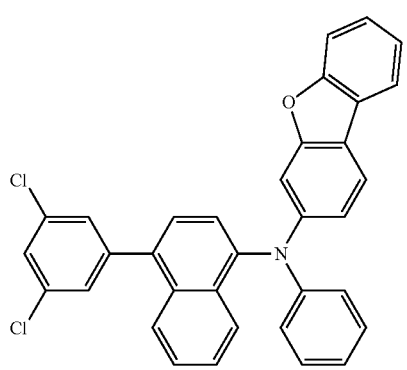
Sub 1-32
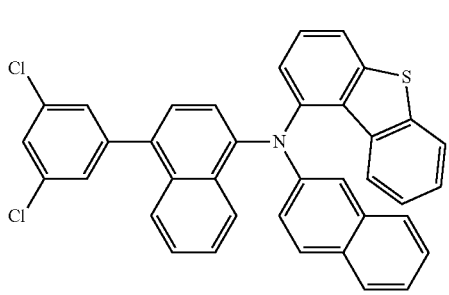
Sub 1-33
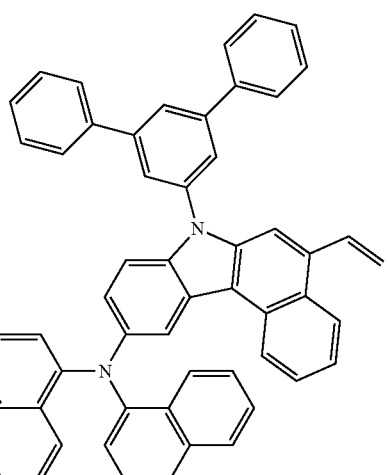
Sub 1-34
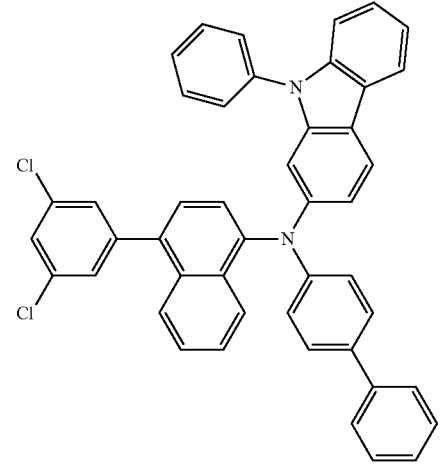
Sub 1-35
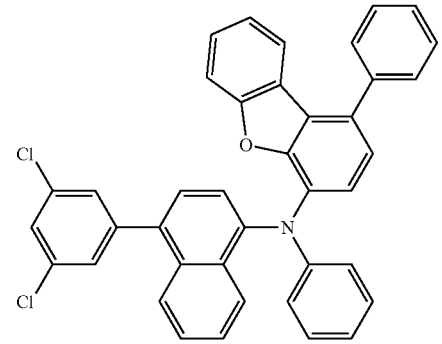

Sub 1-36
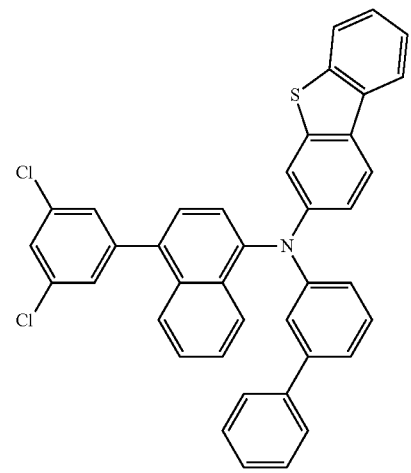
Sub 1-37
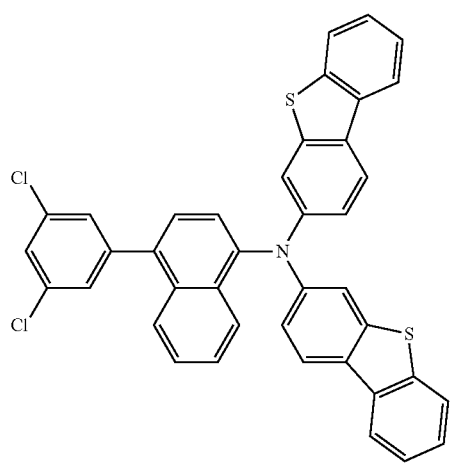
Sub 1-38
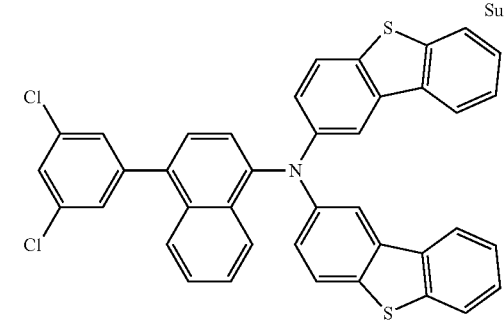
Sub 1-39
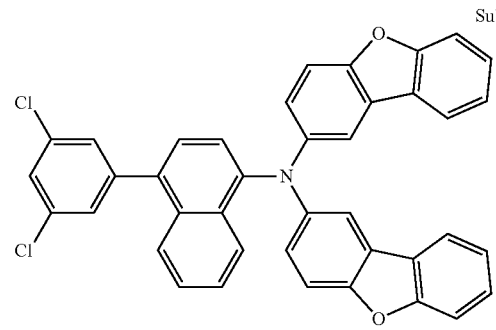
Sub 1-40
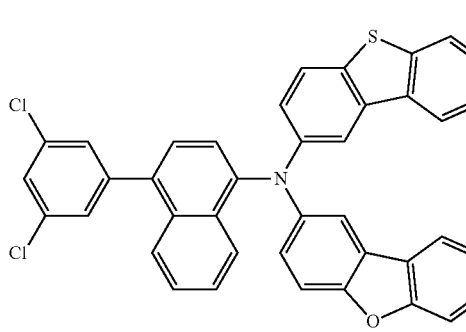
Sub 1-41
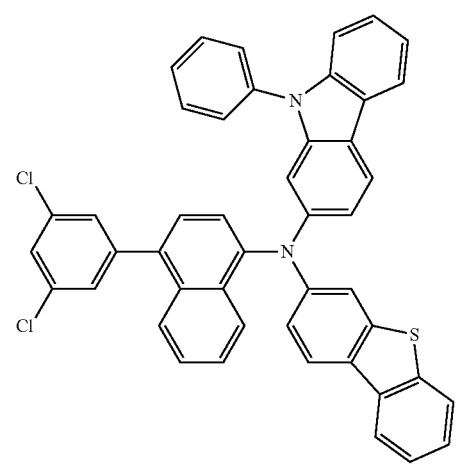
Sub 1-42
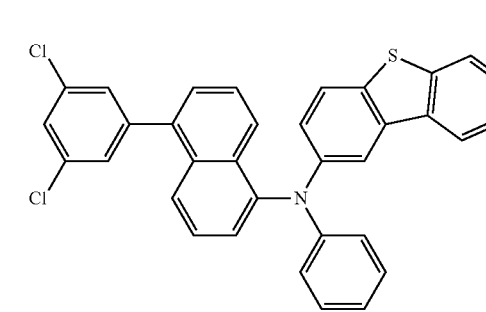
Sub 1-43
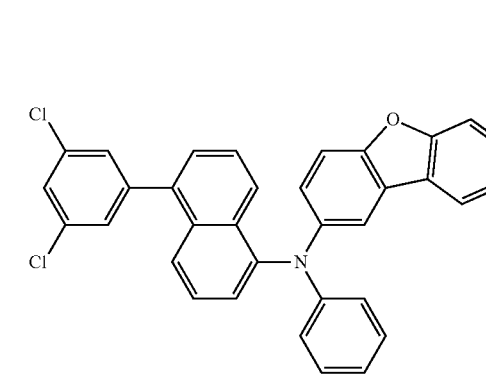

-continued
Sub 1-44
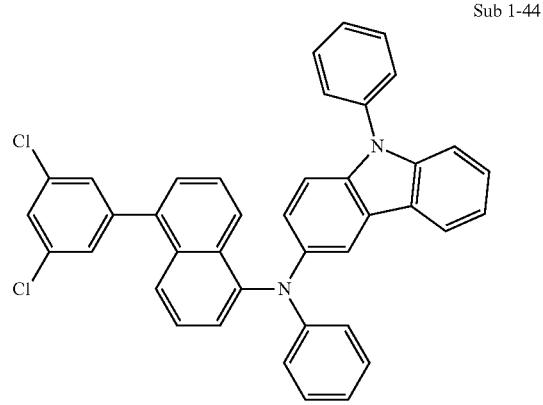
Sub 1-45
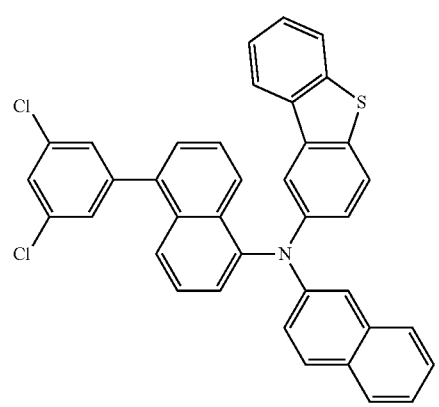
Sub 1-46
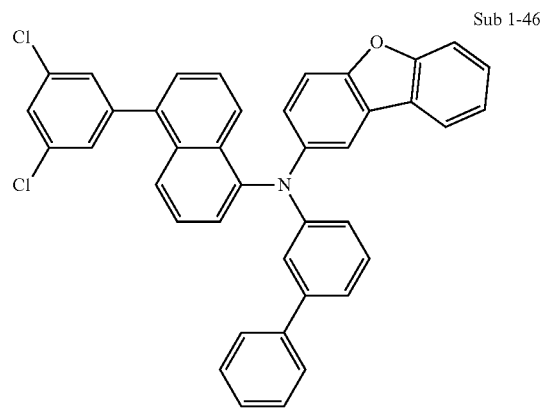
-continued
Sub 1-47
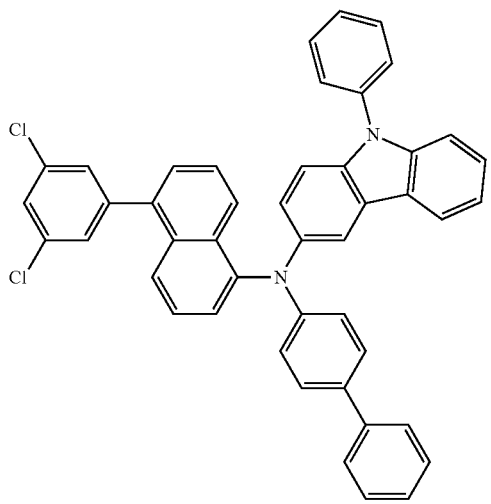
Sub 1-48
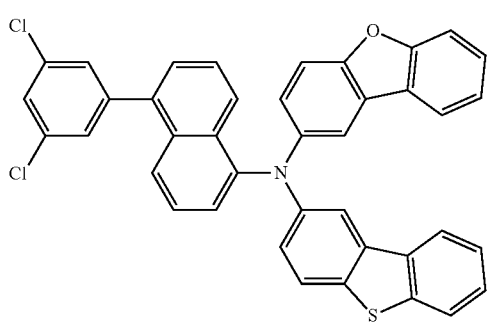
Sub 1-49
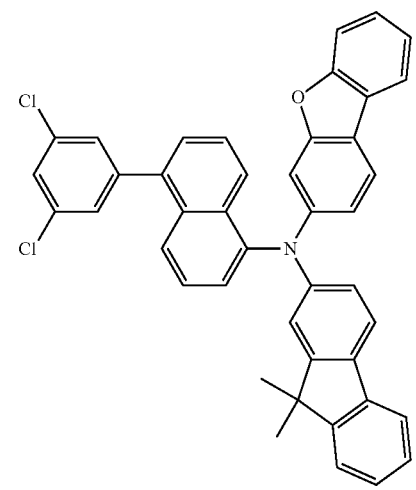

Sub 1-50
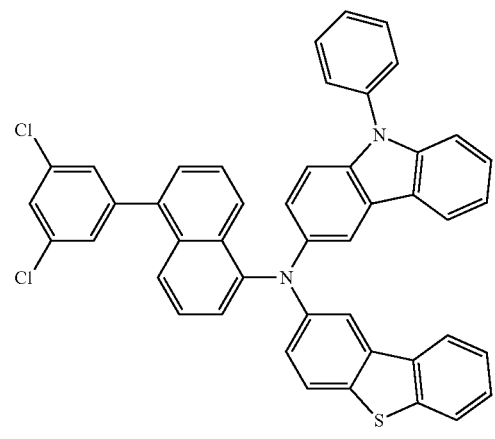
Sub 1-51
Sub 1-54
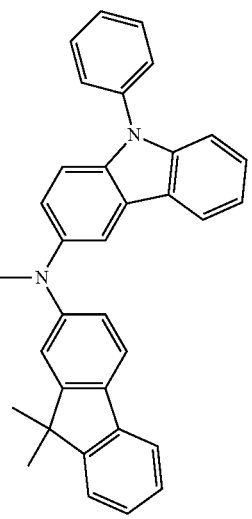
Sub 1-52
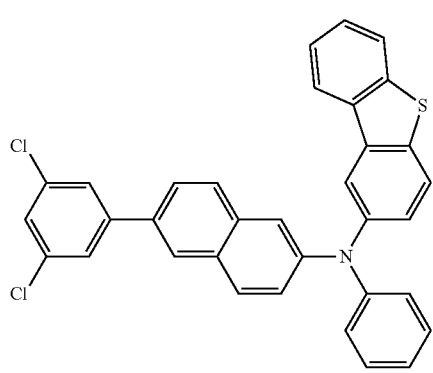
Sub 1-53
Sub 1-55
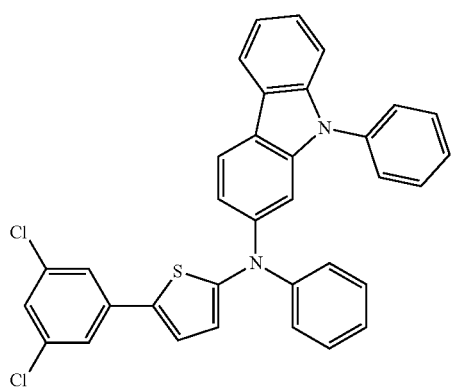
Sub 1-56
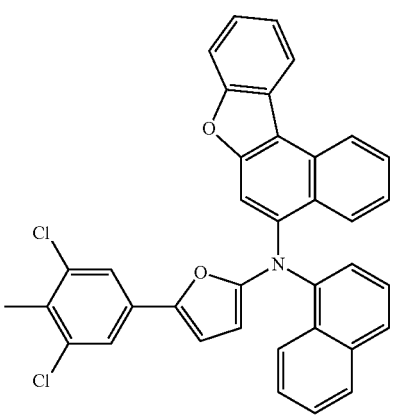

Sub 1-57
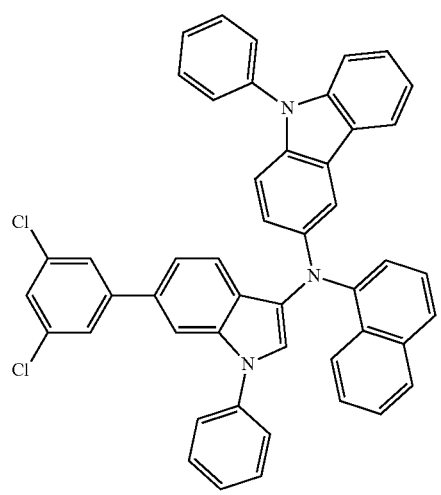
Sub 1-60
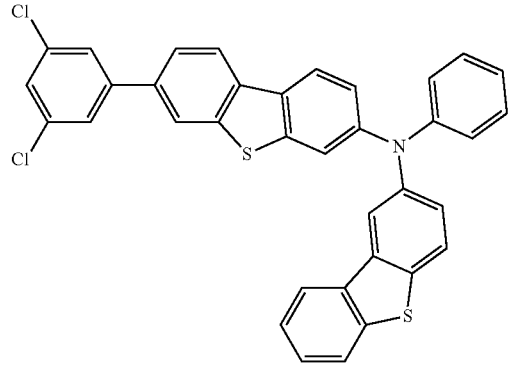
Sub 1-58
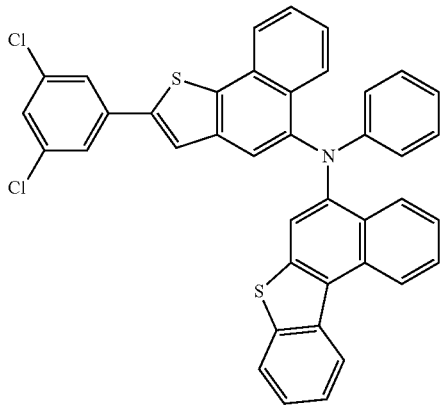
Sub 1-61
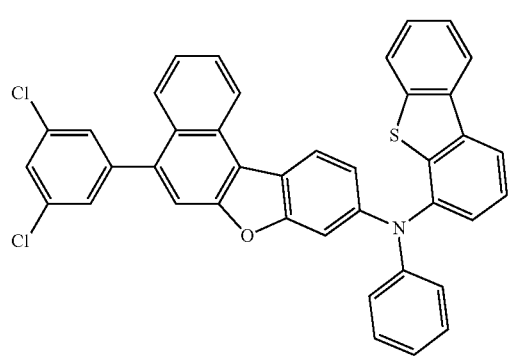
Sub 1-59
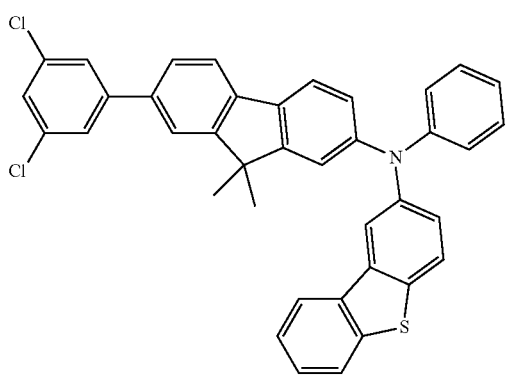
Sub 1-62
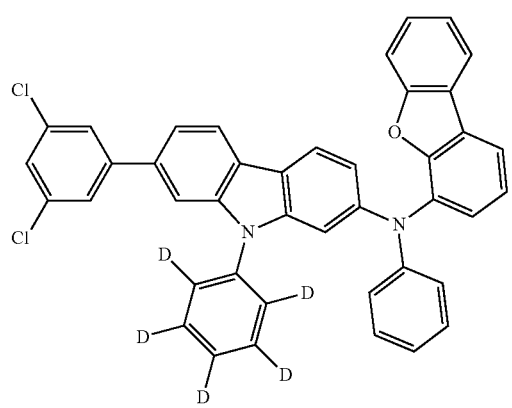

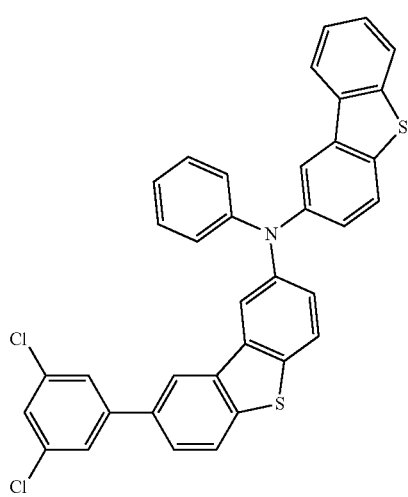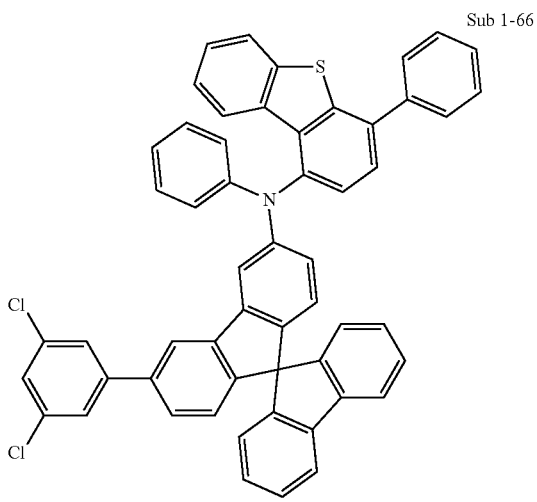

Sub 1-70
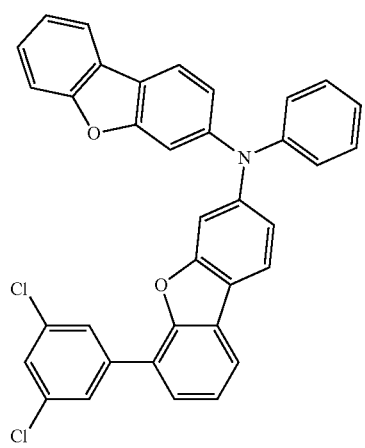
Sub 1-71
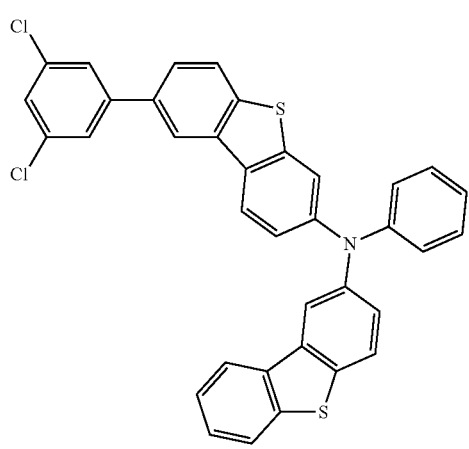
Sub 1-72
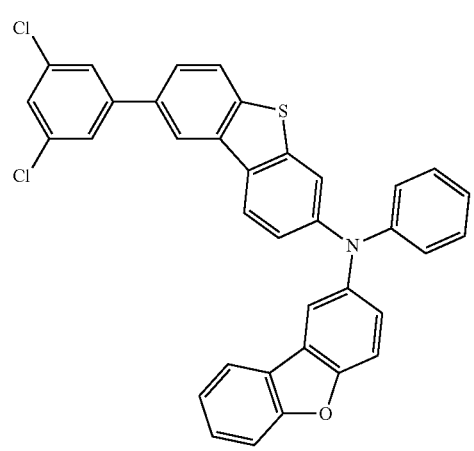
Sub 1-73
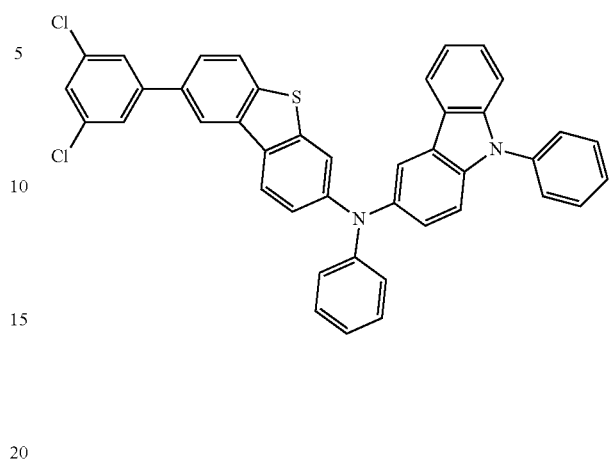
Sub 1-74
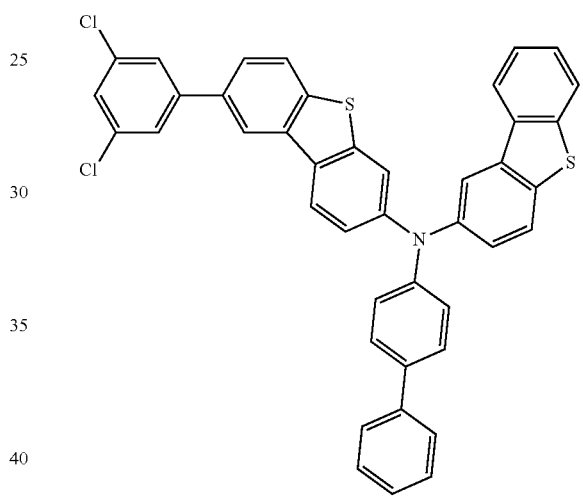
Sub 1-75
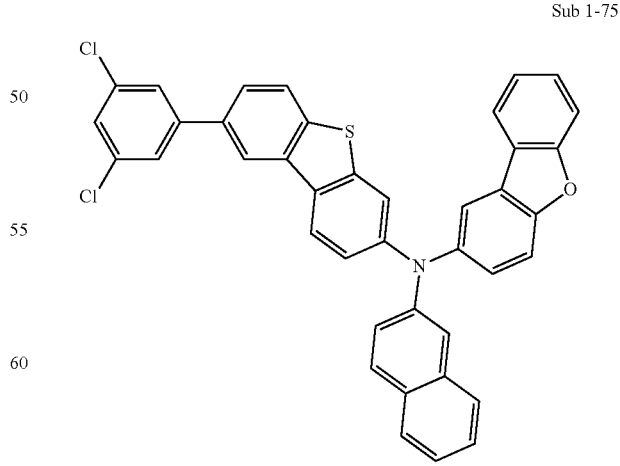

-continued
Sub 1-76
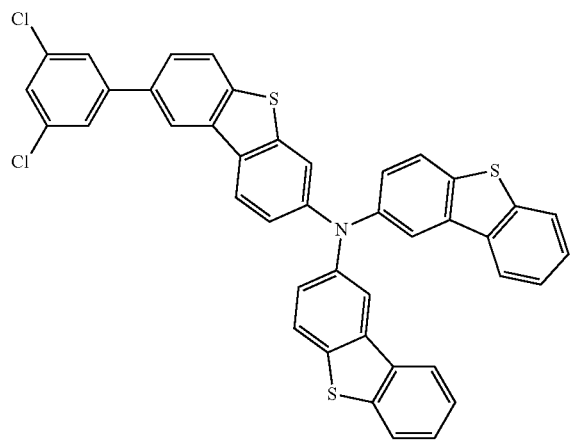
Sub 1-77
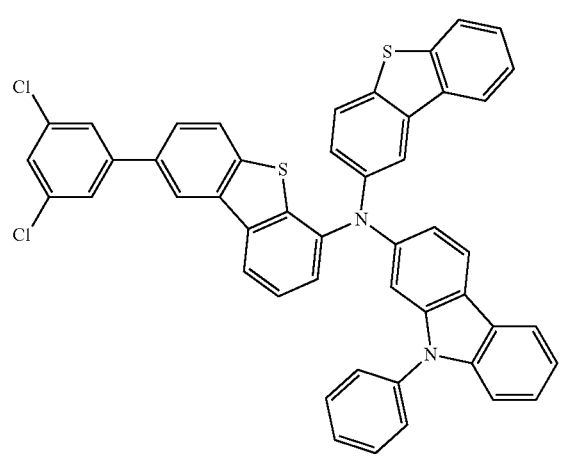
Sub 1-78
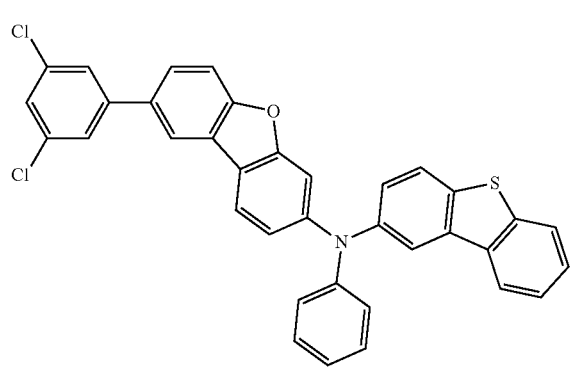
Sub 1-79
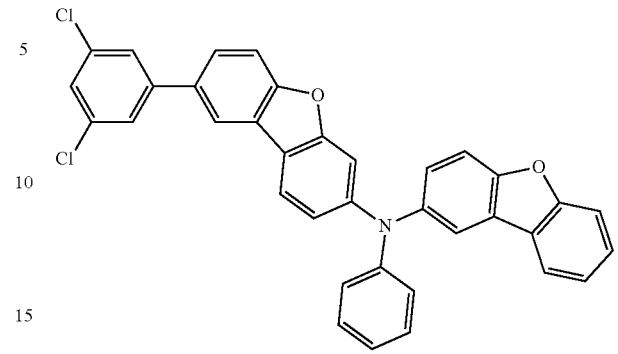
Sub 1-80
Sub 1-81
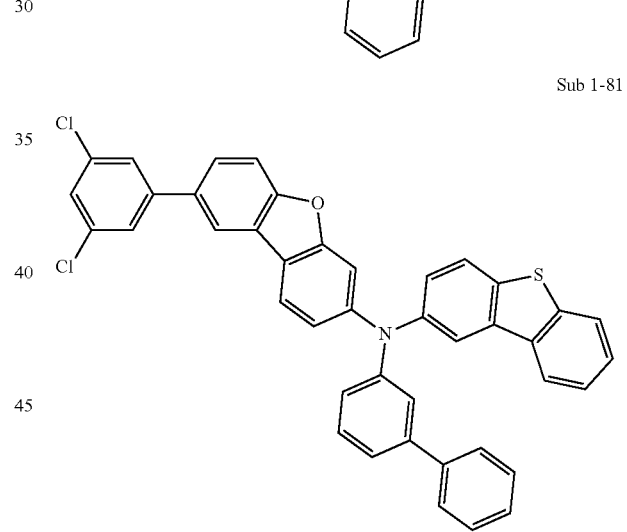
Sub 1-82
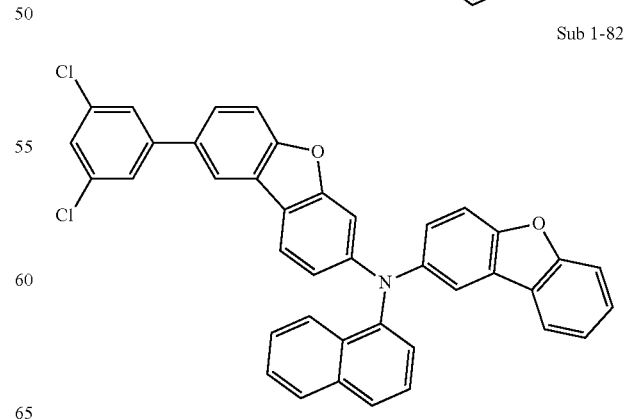

Sub 1-83
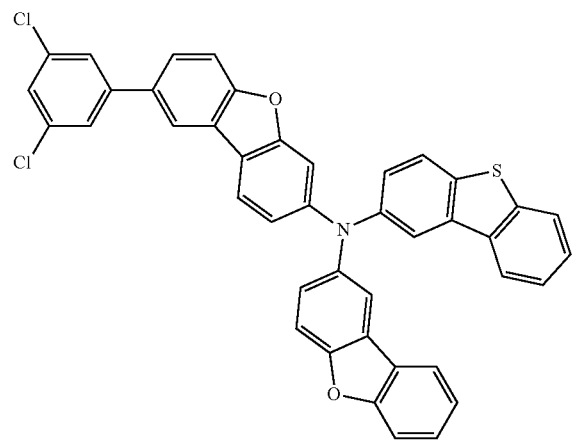
Sub 1-84
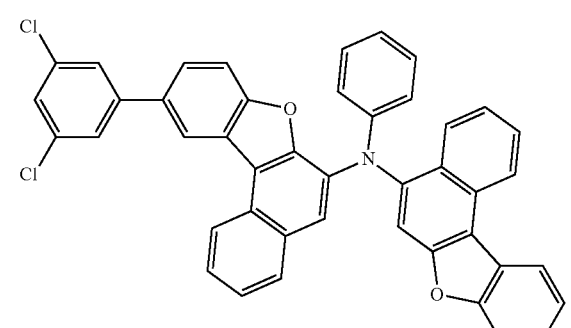
Sub 1-85
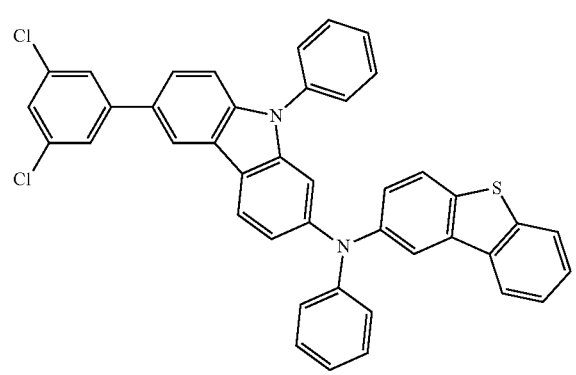
Sub 1-86
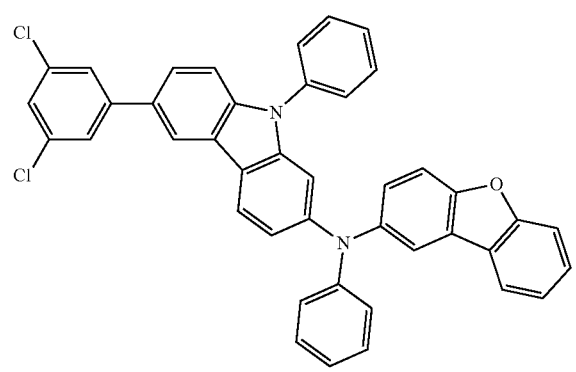
Sub 1-87
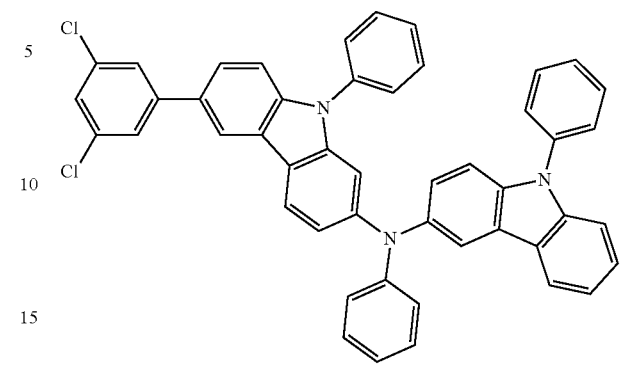
Sub 1-88
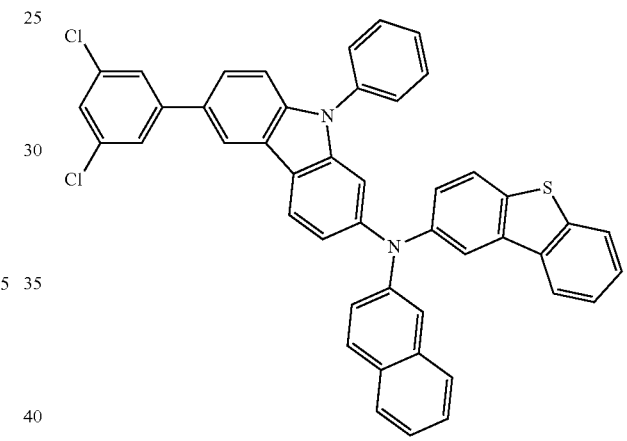
Sub 1-89
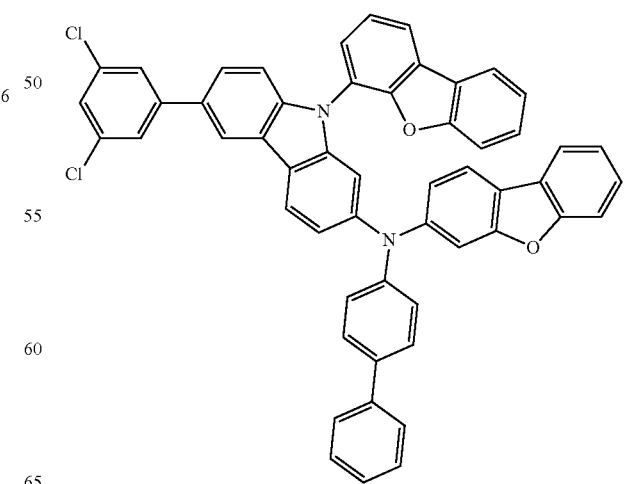

Sub 1-90

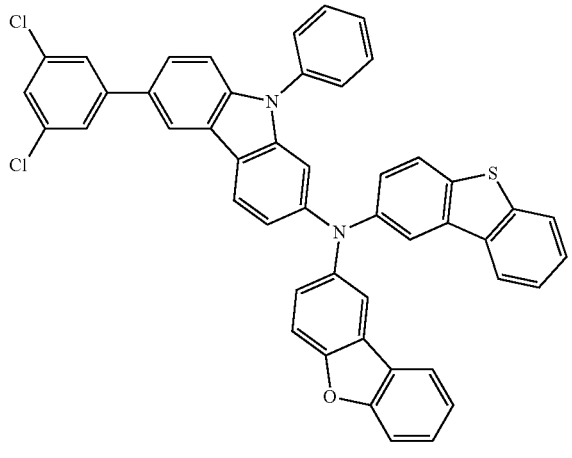

Sub 1-91

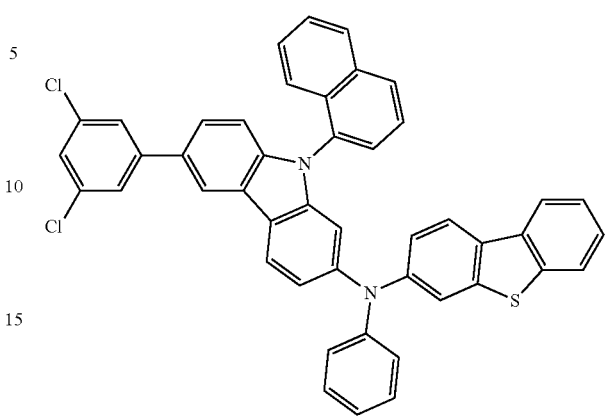

TABLE 1

| Compound | FD-MS | Compound | FD-MS |
|---|---|---|---|
| Sub 1-1 | m/z = 495.06($C_{30}H_{19}Cl_2NS$ = 496.45) | Sub 1-2 | m/z = 571.09($C_{36}H_{23}Cl_2NS$ = 572.55) |
| Sub 1-3 | m/z = 554.13($C_{36}H_{24}Cl_2N_2$ = 555.50) | Sub 1-4 | m/z = 554.13($C_{36}H_{24}Cl_2N_2$ = 555.50) |
| Sub 1-5 | m/z = 495.06($C_{30}H_{19}Cl_2NS$ = 496.45) | Sub 1-6 | m/z = 479.08($C_{30}H_{19}Cl_2NO$ = 480.39) |
| Sub 1-7 | m/z = 495.06($C_{30}H_{19}Cl_2NS$ = 496.45) | Sub 1-8 | m/z = 479.08($C_{30}H_{19}Cl_2NO$ = 480.39) |
| Sub 1-9 | m/z = 545.08($C_{34}H_{21}Cl_2NS$ = 546.51) | Sub 1-10 | m/z = 604.15($C_{40}H_{26}Cl_2N_2$ = 605.56) |
| Sub 1-11 | m/z = 554.13($C_{36}H_{24}Cl_2N_2$ = 555.50) | Sub 1-12 | m/z = 630.16($C_{42}H_{28}Cl_2N_2$ = 631.60) |
| Sub 1-13 | m/z = 630.16($C_{42}H_{28}Cl_2N_2$ = 631.60) | Sub 1-14 | m/z = 604.15($C_{40}H_{26}Cl_2N_2$ = 605.56) |
| Sub 1-15 | m/z = 545.08($C_{34}H_{21}Cl_2NS$ = 546.51) | Sub 1-16 | m/z = 595.09($C_{38}H_{23}Cl_2NS$ = 596.57) |
| Sub 1-17 | m/z = 479.08($C_{30}H_{19}Cl_2NO$ = 480.39) | Sub 1-18 | m/z = 554.13($C_{36}H_{24}Cl_2N_2$ = 555.50) |
| Sub 1-19 | m/z = 495.06($C_{30}H_{19}Cl_2NS$ = 496.45) | Sub 1-20 | m/z = 479.08($C_{30}H_{19}Cl_2NO$ = 480.39) |
| Sub 1-21 | m/z = 554.13($C_{36}H_{24}Cl_2N_2$ = 555.50) | Sub 1-22 | m/z = 495.06($C_{30}H_{19}Cl_2NS$ = 496.45) |
| Sub 1-23 | m/z = 495.06($C_{38}H_{19}Cl_2NS$ = 496.45) | Sub 1-24 | m/z = 479.08($C_{30}H_{19}Cl_2NO$ = 480.39) |
| Sub 1-25 | m/z = 529.10($C_{34}H_{21}Cl_2NO$ = 530.45) | Sub 1-26 | m/z = 545.08($C_{34}H_{21}Cl_2NS$ = 546.51) |
| Sub 1-27 | m/z = 529.10($C_{34}H_{21}Cl_2NO$ = 530.45) | Sub 1-28 | m/z = 604.15($C_{40}H_{26}Cl_2N_2$ = 605.56) |
| Sub 1-29 | m/z = 710.14($C_{46}H_{28}Cl_2N_2S$ = 711.70) | Sub 1-30 | m/z = 545.08($C_{34}H_{21}Cl_2NS$ = 546.51) |
| Sub 1-31 | m/z = 529.10($C_{34}H_{21}Cl_2NO$ = 530.45) | Sub 1-32 | m/z = 595.09($C_{38}H_{23}Cl_2NS$ = 596.57) |
| Sub 1-33 | m/z = 882.26($C_{62}H_{40}Cl_2N_2$ = 883.92) | Sub 1-34 | m/z = 680.18($C_{46}H_{30}Cl_2N_2$ = 681.66) |
| Sub 1-35 | m/z = 605.13($C_{40}H_{25}Cl_2NO$ = 606.55) | Sub 1-36 | m/z = 622.11($C_{40}H_{25}Cl_2NS$ = 622.61) |
| Sub 1-37 | m/z = 651.06($C_{40}H_{23}Cl_2NS_2$ = 652.65) | Sub 1-38 | m/z = 651.06($C_{40}H_{23}Cl_2NS_2$ = 652.65) |
| Sub 1-39 | m/z = 619.11($C_{40}H_{23}Cl_2NO_2$ = 620.53) | Sub 1-40 | m/z = 635.09($C_{40}H_{23}Cl_2NOS$ = 636.59) |
| Sub 1-41 | m/z = 710.14($C_{48}H_{28}Cl_2N_2S$ = 711.70) | Sub 1-42 | m/z = 545.08($C_{34}H_{21}Cl_2NS$ = 546.51) |
| Sub 1-43 | m/z = 529.10($C_{34}H_{21}Cl_2NO$ = 530.45) | Sub 1-44 | m/z = 604.15($C_{40}H_{26}Cl_2N$ = 605.56) |
| Sub 1-45 | m/z = 595.09($C_{38}H_{23}Cl_2NS$ = 596.57) | Sub 1-46 | m/z = 605.13($C_{40}H_{25}Cl_2NO$ = 606.55) |
| Sub 1-47 | m/z = 680.18($C_{46}H_{30}Cl_2N_2$ = 681.66) | Sub 1-48 | m/z = 635.09($C_{40}H_{23}Cl_2NOS$ = 636.59) |
| Sub 1-49 | m/z = 645.16($C_{43}H_{29}Cl_2NO$ = 646.61) | Sub 1-50 | m/z = 710.14($C_{46}H_{28}Cl_2N_2S$ = 711.10) |
| Sub 1-51 | m/z = 545.08($C_{34}H_{21}Cl_2NS$ = 546.51) | Sub 1-52 | m/z = 605.13($C_{40}H_{25}Cl_2NO$ = 606.55) |
| Sub 1-53 | m/z = 604.15($C_{40}H_{26}Cl_2N_2$ = 605.56) | Sub 1-54 | m/z = 720.21($C_{49}H_{34}Cl_2N_2$ = 721.73) |
| Sub 1-55 | m/z = 560.09($C_{34}H_{22}Cl_2N_2S$ = 561.52) | Sub 1-56 | m/z = 583.11($C_{37}H_{23}Cl_2NO_2$ = 584.50) |
| Sub 1-57 | m/z = 719.19($C_{48}H_{31}Cl_2N_3$ = 720.70) | Sub 1-58 | m/z = 651.06($C_{40}H_{23}Cl_2NS_2$ = 652.65) |
| Sub 1-59 | m/z = 611.12(C39H27Cl2NS = 612.61) | Sub 1-60 | m/z = 601.05($C_{36}H_{21}Cl_2NS_2$ = 602.59) |
| Sub 1-61 | m/z = 635.09($C_{40}H_{23}Cl_2NOS$ = 636.59) | Sub 1-62 | m/z = 649.17($C_{42}H_{21}D_5Cl_2N_2O$ = 650.61) |
| Sub 1-63 | m/z = 601.05($C_{36}H_{21}Cl_2NS_2$ = 602.59) | Sub 1-64 | m/z = 660.12($C_{42}H_{26}Cl_2N_2S$ = 661.64) |
| Sub 1-65 | m/z = 645.13($C_{42}H_{25}Cl_2NO_2$ = 646.57) | Sub 1-66 | m/z = 809.17($C_{35}H_{33}Cl_2NS$ = 810.84) |
| Sub 1-67 | m/z = 601.05($C_{36}H_{21}Cl_2NS_2$ = 602.59) | Sub 1-68 | m/z = 685.10($C_{44}H_{35}Cl_2NOS$ = 686.65) |
| Sub 1-69 | m/z = 601.05($C_{36}H_{21}Cl_2NS_2$ = 602.59) | Sub 1-70 | m/z = 569.09($C_{36}H_{21}Cl_2NO_2$ = 570.47) |
| Sub 1-71 | m/z = 601.05($C_{36}H_{21}Cl_2NS_2$ = 602.59) | Sub 1-72 | m/z = 585.07($C_{36}H_{21}Cl_2NOS$ = 586.53) |
| Sub 1-73 | m/z = 660.12($C_{42}H_{26}Cl_2N_2S$ = 661.64) | Sub 1-74 | m/z = 667.08($C_{42}H_{25}Cl_2NS_2$ = 678.69) |
| Sub 1-75 | m/z = 635.09($C_{40}H_{23}Cl_2NOS$ = 636.59) | Sub 1-76 | m/z = 707.04($C_{42}H_{23}Cl_2NS_3$ = 708.73) |
| Sub 1-77 | m/z = 766.11($C_{48}H_{28}Cl_2N_2S_2$ = 767.79) | Sub 1-78 | m/z = 585.07($C_{36}H_{21}Cl_2NOS$ = 586.53) |
| Sub 1-79 | m/z = 569.09($C_{36}H_{21}Cl_2NO_2$ = 570.47) | Sub 1-80 | m/z = 644.14($C_{42}H_{26}Cl_2N_2O$ = 645.58) |
| Sub 1-81 | m/z = 661.10($C_{42}H_{25}Cl_2NOS$ = 662.63) | Sub 1-82 | m/z = 619.11($C_{40}H_{23}Cl_2NO_2$ = 620.53) |
| Sub 1-83 | m/z = 675.08($C_{42}H_{23}Cl_2NO_2S$ = 676.61) | Sub 1-84 | m/z = 669.13($C_{44}H_{25}Cl_2NO_2$ = 670.59) |
| Sub 1-85 | m/z = 660.12($C_{42}H_{26}Cl_2N_3S$ = 661.64) | Sub 1-86 | m/z = 644.14($C_{42}H_{26}Cl_2N_2O$ = 645.58) |
| Sub 1-87 | m/z = 719.19($C_{48}H_{31}Cl_2N_3$ = 720.70) | Sub 1-88 | m/z = 710.14($C_{46}H_{28}Cl_2N_2S$ = 711.70) |
| Sub 1-89 | m/z = 810.18($C_{54}H_{32}Cl_2N_2O_2$ = 811.76) | Sub 1-90 | m/z = 750.13($C_{48}H_{28}Cl_2N_2OS$ = 751.73) |
| Sub 1-91 | m/z = 710.14($C_{46}H_{25}Cl_2N_2S$ = 711.70) | | |

II. Product Synthesis

Method A (in cases of the same amine (HN-Ar$^1$Ar$^2$, HN-Ar$^3$Ar$^4$) reaction products)

After Sub 1 (1 eq) was dissolved in Toluene in a round-bottom flask, the amine (HN-Ar$^1$Ar$^2$, HN-Ar$^3$Ar$^4$) reaction products (2 eq), Pd$_2$(dba)$_3$ (0.03 eq), P(t-Bu)$_3$ (0.06 eq), and NaOt-Bu (5 eq) were added, followed by stirred at 80° C. for 3 hours. Upon completion of the reaction, the reaction product was extracted with CH$_2$Cl$_2$ and water. The organic layer was dried over MgSO$_4$ and concentrated, and then the formed compound was subjected to silica gel column and recrystallization to give a final product.

Method B (in Cases of Different Amine (HN-Ar$^1$Ar$^2$, HN-Ar$^3$Ar$^4$) Reaction Products)

After Sub 1 (1 eq) was dissolved in Toluene in a round-bottom flask, the amine (HN-Ar$^1$Ar$^2$) reaction product (1.2 eq), Pd$_2$(dba)$_3$ (0.03 eq), P(t-Bu)$_3$ (0.06 eq), and NaOt-Bu (3 eq) were added, followed by stirring at 80° C. for 3 hours. Upon completion of the reaction, the reaction product was extracted with CH$_2$Cl$_2$ and water. The organic layer was dried over MgSO$_4$ and concentrated, and then the formed compound was subjected to silica gel column and recrystallization to give P-1. After P-I (1 eq) obtained from the synthesis was dissolved in Toluene in a round-bottom flask, the amine (HN-Ar$^3$Ar$^4$) reaction product (1 eq), Pd$_2$(dba)$_3$ (0.03 eq), P(t-Bu)$_3$ (0.06 eq), and NaOt-Bu (3 eq) were added, followed by stirring at 80° C. for 3 hours. Upon completion of the reaction, the reaction product was extracted with CH$_2$Cl$_2$ and water. The organic layer was dried over MgSO$_4$ and concentrated, and then the formed compound was subjected to silica gel column and recrystallization to give a final product.

1. Synthesis Example of P-1

<Reaction Scheme 7>

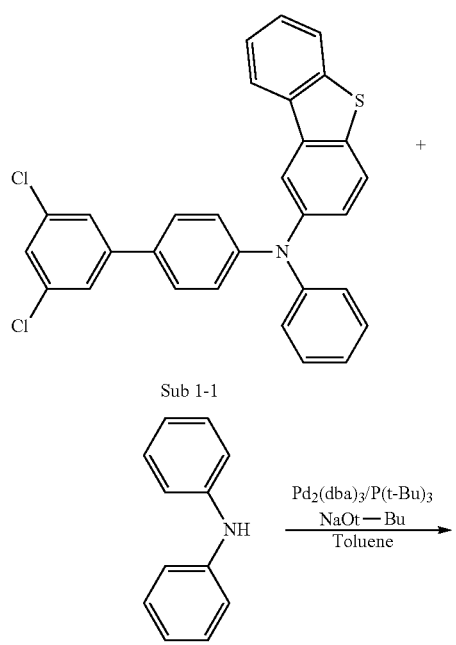

Sub 1-1

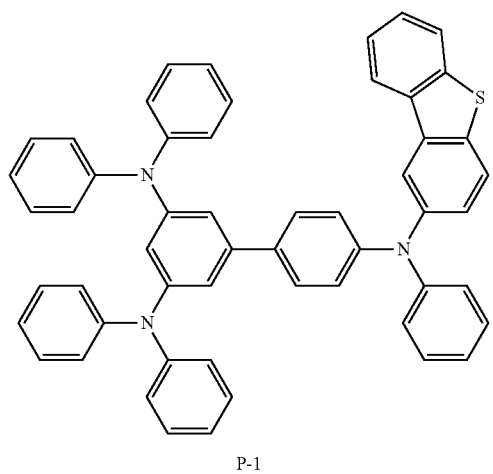

P-1

Sub 1-1 (10 g, 20.14 mmol) obtained from the synthesis, diphenylamine (6.82 g, 40.29 mmol), Pd$_2$(dba)$_3$ (0.55 g, 0.60 mmol), P(t-Bu)$_3$ (0.6 ml, 1.21 mmol), and NaOt-Bu (9.68 g, 100.72 mmol) were dissolved in anhydrous Toluene (300 ml), and then refluxed for 3 hours. Upon the completion of the reaction, the reaction product was cooled to normal temperature, extracted with CH$_2$Cl$_2$, and washed with water. The small amount of water was removed over anhydrous MgSO$_4$, followed by filtration under reduced pressure. Thereafter, the organic solvent was concentrated to produce a product, which was then subjected to silica gel column and recrystallization to give desired P-1, 12.28 g. (Yield: 80%)

2. Synthesis Example of P-6

<Reaction Scheme 8>

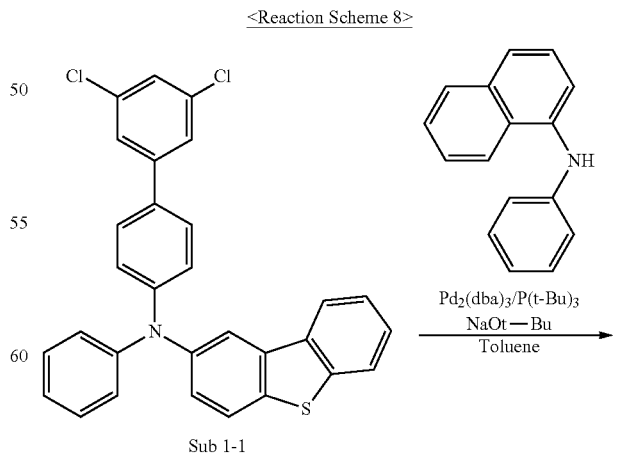

Sub 1-1

-continued

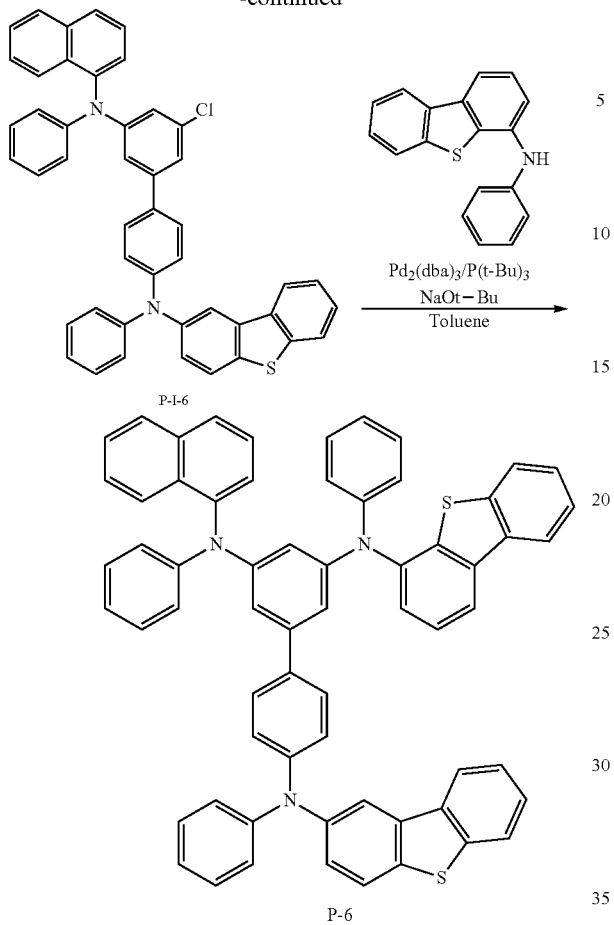

3. Synthesis Example of P-59

<Reaction Scheme 9>

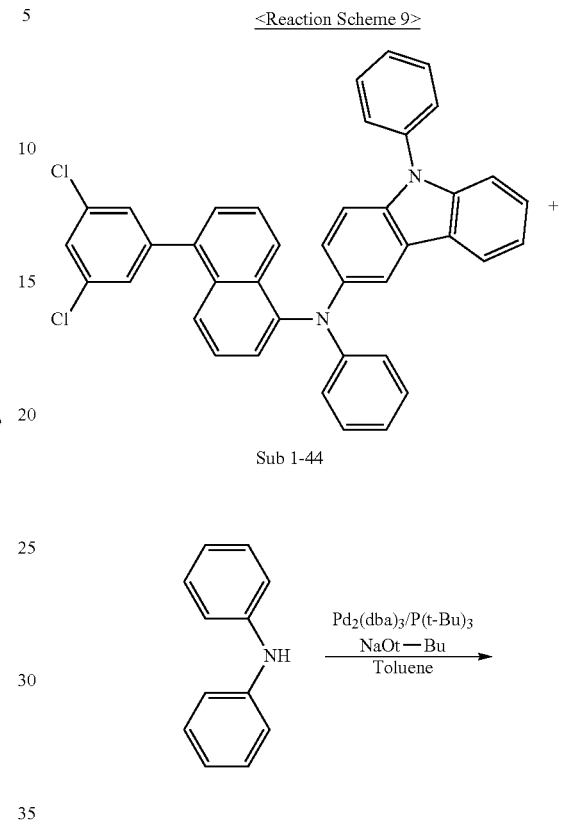

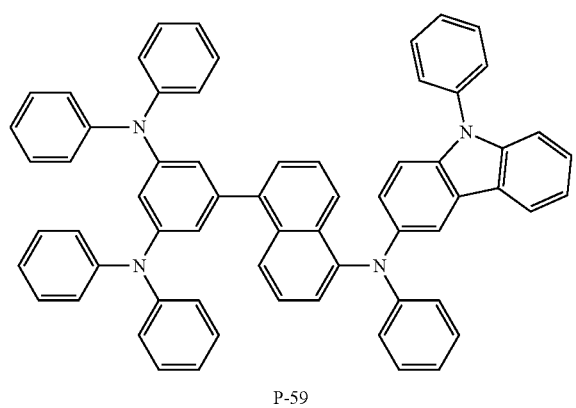

(1) Synthesis of P-I-6

Sub 1-1 (20 g, 40.29 mmol) obtained from the synthesis, N-phenylnaphthalen-1-amine (10.60 g, 48.34 mmol), Pd$_2$(dba)$_3$ (1.11 g, 1.21 mmol), P(t-Bu)$_3$ (1.2 ml, 2.42 mmol), and NaOt-Bu (11.62 g, 120.86 mmol) were dissolved in anhydrous Toluene (440 ml), and then refluxed for 3 hours. Upon the completion of the reaction, the reaction product was cooled to normal temperature, extracted with CH$_2$Cl$_2$, and washed with water. The small amount of water was removed over anhydrous MgSO$_4$, followed by filtration under reduced pressure. Thereafter, the organic solvent was concentrated to produce a product, when was then subjected to a silica gel column and recrystallization to give desired P-I-6, 15.32 g. (Yield: 56%)

(2) Synthesis of P-6

P-I-6 (10 g, 14.72 mmol) obtained from the synthesis, N-phenyldibenzo[b,d]thiophen-4-amine (4.05 g, 14.72 mmol), Pd$_2$(dba)$_3$ (0.40 g, 0.44 mmol), P(t-Bu)$_3$ (0.4 ml, 0.88 mmol), and NaOt-Bu (4.24 g, 44.16 mmol) were dissolved in anhydrous Toluene (150 ml), and then refluxed for 3 hours. Upon the completion of the reaction, the reaction product was cooled to normal temperature, extracted with CH$_2$Cl$_2$, and washed with water. The small amount of water was removed over anhydrous MgSO$_4$, followed by filtration under reduced pressure. Thereafter, the organic solvent was concentrated to produce a product, when was then subjected to silica gel column and recrystallization to give desired P-6, 9.73 g. (Yield: 72%)

Sub 1-44 (10 g, 16.51 mmol) obtained from the synthesis, diphenylamine (5.59 g, 33.03 mmol), Pd$_2$(dba)$_3$ (0.45 g, 0.50 mmol), P(t-Bu)$_3$ (0.5 ml, 0.99 mmol), and NaOt-Bu (7.94 g, 82.57 mmol) were dissolved in Toluene (250 ml), and then refluxed for 3 hours. Upon the completion of the reaction, the reaction product was cooled to normal temperature, extracted with CH$_2$Cl$_2$, and washed with water. The small amount of water was removed over anhydrous MgSO$_4$, followed by filtration under reduced pressure. Thereafter, the organic solvent was concentrated to produce a product, when was then subjected to silica gel column and recrystallization to give desired P-59, 10.79 g. (Yield: 75%)

4. Synthesis Example of P-69

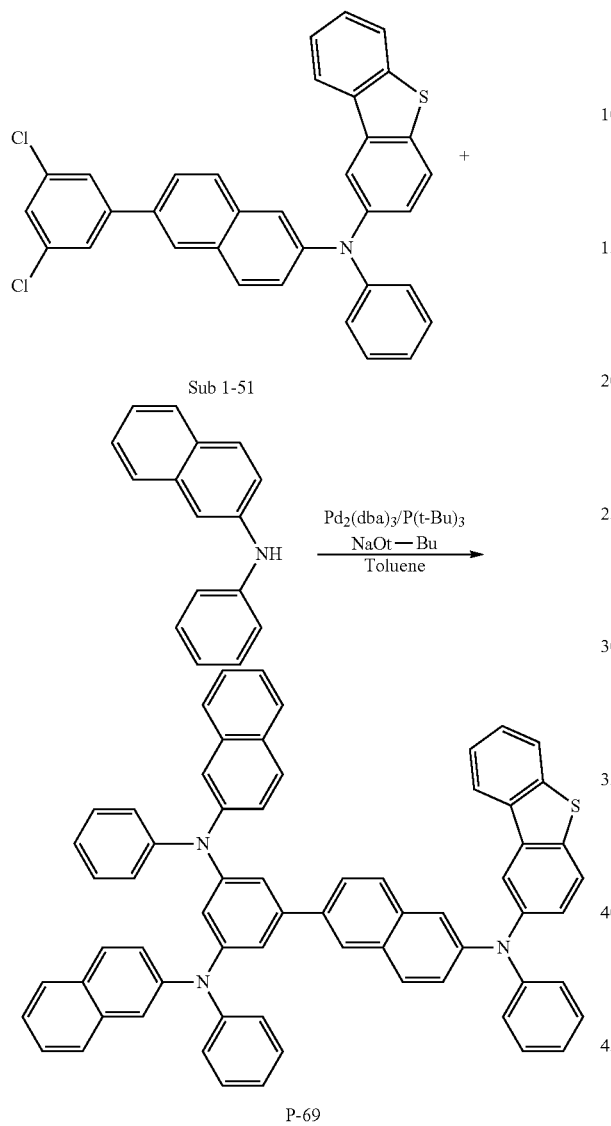

5. Synthesis Example of P-90

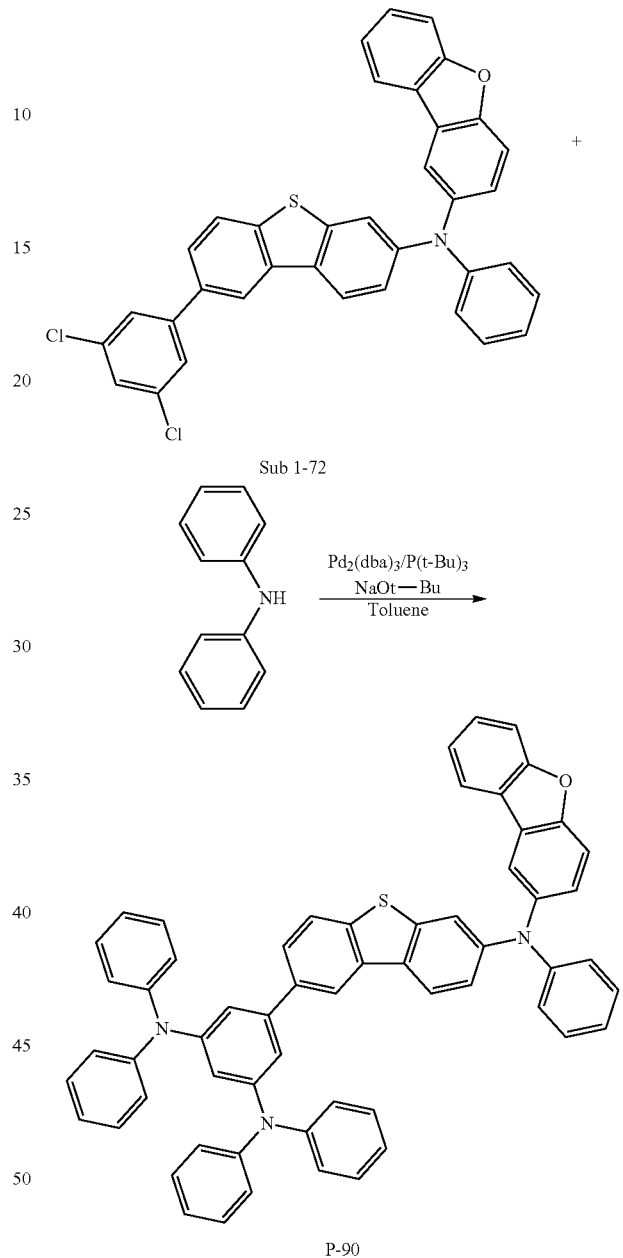

Sub 1-51 (10 g, 18.30 mmol) obtained from the synthesis, N-phenylnaphthalen-2-amine (8.03 g, 36.60 mmol), Pd$_2$(dba)$_3$ (0.50 g, 0.55 mmol), P(t-Bu)$_3$ (0.5 ml, 1.10 mmol), and NaOt-Bu (8.79 g, 91.49 mmol) were dissolved in anhydrous Toluene (275 ml), and then refluxed for 3 hours. Upon the completion of the reaction, the reaction product was cooled to normal temperature, extracted with CH$_2$Cl$_2$, and washed with water. The small amount of water was removed over anhydrous MgSO$_4$, followed by filtration under reduced pressure. Thereafter, the organic solvent was concentrated to produce a product, when was then subjected to silica gel column and recrystallization to give desired P-69, 13.69 g. (Yield: 82%)

Sub 1-72 (10 g, 17.05 mmol) obtained from the synthesis, diphenylamine (5.77 g, 34.10 mmol), Pd$_2$(dba)$_3$ (0.47 g, 0.51 mmol), P(t-Bu)$_3$ (0.5 ml, 1.02 mmol), and NaOt-Bu (8.19 g, 85.25 mmol) were dissolved in anhydrous Toluene (260 ml), and then refluxed for 3 hours. Upon the completion of the reaction, the reaction product was cooled to normal temperature, extracted with CH$_2$Cl$_2$, and washed with water. The small amount of water was removed over anhydrous MgSO$_4$, followed by filtration under reduced pressure. Thereafter, the organic solvent was concentrated to produce a product, when was then subjected to silica gel column and recrystallization to give desired P-90, 9.88 g. (Yield: 68%)

FD-MS values of Compounds P-1 to P-112 of the present disclosure produced by the synthesis examples above are shown in Table 2 below.

TABLE 2

| Compound | FD-MS | Compound | FD-MS |
|---|---|---|---|
| P-1 | m/z = 761.29($C_{54}H_{39}N_3S$ = 761.99) | P-2 | m/z = 837.32($C_{60}H_{43}N_3S$ = 838.09) |
| P-3 | m/z = 820.36($C_{60}H_{44}N_4$ = 821.04) | P-4 | m/z = 820.36($C_{60}H_{44}N_4$ = 821.04) |
| P-5 | m/z = 761.29($C_{54}H_{39}N_3S$ = 761.99) | P-6 | m/z = 917.29($C_{64}H_{43}N_3S_2$ = 918.19) |
| P-7 | m/z = 845.34($C_{62}H_{43}N_3O$ = 846.05) | P-8 | m/z = 821.34($C_{60}H_{43}N_3O$ = 822.02) |
| P-9 | m/z = 805.39($C_{58}H_{31}D_{10}N_3O$ = 806.05) | P-10 | m/z = 811.30($C_{58}H_{41}N_3S$ = 812.05) |
| P-11 | m/z = 761.29($C_{54}H_{39}N_3S$ = 761.99) | P-12 | m/z = 845.34($C_{62}H_{43}N_3O$ = 846.05) |
| P-13 | m/z = 795.32($C_{58}H_{43}N_3O$ = 795.99) | P-14 | m/z = 837.32($C_{60}H_{43}N_3S$ = 838.09) |
| P-15 | m/z = 913.35($C_{66}H_{47}N_3S$ = 914.18) | P-16 | m/z = 811.30($C_{58}H_{41}N_3S$ = 812.05) |
| P-17 | m/z = 870.37($C_{64}H_{46}N_4$ = 871.10) | P-18 | m/z = 820.36($C_{60}H_{44}N_4$ = 821.04) |
| P-19 | m/z = 896.39($C_{66}H_{48}N_4$ = 897.14) | P-20 | m/z = 896.39($C_{66}H_{48}N_4$ = 897.14) |
| P-21 | m/z = 995.40($C_{73}H_{49}N_5$ = 996.23) | P-22 | m/z = 811.30($C_{58}H_{41}N_3S$ = 812.05) |
| P-23 | m/z = 943.31($C_{66}H_{45}N_3S_2$ = 944.23) | P-24 | m/z = 911.39($C_{67}H_{49}N_3O$ = 912.15) |
| P-25 | m/z = 820.36($C_{60}H_{44}N_4$ = 821.04) | P-26 | m/z = 761.29($C_{54}H_{39}N_3S$ = 761.99) |
| P-27 | m/z = 745.31($C_{54}H_{39}N_3O$ = 745.93) | P-28 | m/z = 905.37($C_{60}H_{55}N_3SSi_2$ = 906.35) |
| P-29 | m/z = 1051.40($C_{77}H_{53}N_3S$ = 1052.35) | P-30 | m/z = 811.30($C_{58}H_{41}N_3S$ = 812.05) |
| P-31 | m/z = 863.35($C_{62}H_{45}N_3O_2$ = 864.06) | P-32 | m/z = 946.40($C_{70}H_{50}N_4$ = 947.20) |
| P-33 | m/z = 761.29($C_{54}H_{39}N_3S$ = 761.99) | P-34 | m/z = 961.35($C_{70}H_{47}N_3S$ = 962.23) |
| P-35 | m/z = 795.32($C_{58}H_{41}N_3O$ = 795.99) | P-36 | m/z = 871.36($C_{64}H_{45}N_3O$ = 872.08) |
| P-37 | m/z = 811.30($C_{58}H_{41}N_3S$ = 812.05) | P-38 | m/z = 795.32($C_{58}H_{41}N_3O$ = 795.99) |
| P-39 | m/z = 870.37($C_{64}H_{46}N_4$ = 871.10) | P-40 | m/z = 976.36($C_{70}H_{48}N_4S$ = 977.24) |
| P-41 | m/z = 811.30($C_{58}H_{41}N_3S$ = 812.05) | P-42 | m/z = 895.36($C_{66}H_{45}N_3O$ = 869.11) |
| P-43 | m/z = 887.33($C_{64}H_{45}N_3S$ = 888.15) | P-44 | m/z = 937.35($C_{68}H_{47}N_3S$ = 938.21) |
| P-45 | m/z = 921.37($C_{68}H_{47}N_3O$ = 922.14) | P-46 | m/z = 921.37($C_{68}H_{47}N_3O$ = 922.14) |
| P-47 | m/z = 977.38($C_{71}H_{51}N_3S$ = 978.27) | P-48 | m/z = 1372.60($C_{102}H_{76}N_4O$ = 1373.76) |
| P-49 | m/z = 946.40($C_{70}H_{50}N_4$ = 947.20) | P-50 | m/z = 977.34($C_{70}H_{47}N_3OS$ = 978.23) |
| P-51 | m/z = 963.36($C_{70}H_{49}N_3S$ = 964.24) | P-52 | m/z = 917.29($C_{64}H_{43}N_3S_2$ = 918.19) |
| P-53 | m/z = 917.29($C_{64}H_{43}N_3S_2$ = 918.19) | P-54 | m/z = 935.35($C_{68}H_{45}N_3O_2$ = 936.13) |
| P-55 | m/z = 973.27($C_{64}H_{39}F_4N_3OS$ = 974.09) | P-56 | m/z = 976.36($C_{70}H_{48}N_4S$ = 977.24) |
| P-57 | m/z = 811.30($C_{50}H_{41}N_3S$ = 812.05) | P-58 | m/z = 795.32($C_{58}H_{41}N_3O$ = 795.99) |
| P-59 | m/z = 870.37($C_{64}H_{46}N_4$ = 871.10) | P-60 | m/z = 861.32($C_{82}H_{43}N_3S$ = 862.11) |
| P-61 | m/z = 871.36($C_{64}H_{45}N_3O$ = 872.08) | P-62 | m/z = 946.40($C_{70}H_{50}N_4$ = 947.20) |
| P-63 | m/z = 861.32($C_{62}H_{43}N_3S$ = 862.11) | P-64 | m/z = 871.36($C_{64}H_{45}N_3O$ = 872.08) |
| P-65 | m/z = 901.31($C_{64}H_{43}N_3OS$ = 902.13) | P-66 | m/z = 911.39($C_{67}H_{49}N_3O$ = 912.15) |
| P-67 | m/z = 895.36($C_{66}H_{45}N_3O$ = 869.11) | P-68 | m/z = 976.36($C_{70}H_{48}N_4S$ = 977.24) |
| P-69 | m/z = 911.33($C_{66}H_{45}N_3S$ = 912.17) | P-70 | m/z = 947.39($C_{70}H_{49}N_3O$ = 948.18) |
| P-71 | m/z = 870.37($C_{64}H_{46}N_4$ = 871.10) | P-72 | m/z = 986.43($C_{73}H_{54}N_4$ = 987.26) |
| P-73 | m/z = 932.30($C_{64}H_{44}N_4S_2$ = 933.20) | P-74 | m/z = 915.35($C_{65}H_{45}N_3O_3$ = 916.09) |
| P-75 | m/z = 985.41($C_{72}H_{51}N_5$ = 986.24) | P-76 | m/z = 917.29($C_{64}H_{43}N_3S_2$ = 918.19) |
| P-77 | m/z = 877.35($C_{63}H_{47}N_3S$ = 878.15) | P-78 | m/z = 867.27($C_{60}H_{41}N_3S_2$ = 868.13) |
| P-79 | m/z = 965.26($C_{64}H_{43}N_3OS_3$ = 966.25) | P-80 | m/z = 915.40($C_{66}H_{41}D_5N_4O$ = 916.15) |
| P-81 | m/z = 867.27($C_{60}H_{41}N_3S_2$ = 868.13) | P-82 | m/z = 976.36($C_{70}H_{48}N_4S$ = 977.24) |
| P-83 | m/z = 911.35($C_{66}H_{45}N_3O_2$ = 912.11) | P-84 | m/z = 1261.50($C_{92}H_{67}N_3OS$ = 1262.63) |
| P-85 | m/z = 867.27($C_{60}H_{41}N_3S_2$ = 868.13) | P-86 | m/z = 951.33($C_{68}H_{45}N_3OS$ = 952.19) |
| P-87 | m/z = 967.31($C_{68}H_{45}N_3S_2$ = 968.25) | P-88 | m/z = 925.33($C_{66}H_{43}N_3O_3$ = 926.09) |
| P-89 | m/z = 867.27($C_{60}H_{41}N_3S_2$ = 868.13) | P-90 | m/z = 851.30($C_{60}H_{41}N_3OS$ = 852.07) |
| P-91 | m/z = 926.34($C_{66}H_{46}N_4S$ = 927.18) | P-92 | m/z = 943.31($C_{66}H_{45}N_3S_2$ = 944.23) |
| P-93 | m/z = 951.33($C_{68}H_{45}N_3OS$ = 952.19) | P-94 | m/z = 973.26($C_{66}H_{43}N_3S_3$ = 974.27) |
| P-95 | m/z = 957.28($C_{66}H_{43}N_3OS_2$ = 958.21) | P-96 | m/z = 1032.33($C_{72}H_{48}N_4S_2$ = 1033.32) |
| P-97 | m/z = 851.30($C_{60}H_{41}N_3OS$ = 852.07) | P-98 | m/z = 916.38($C_{66}H_{40}D_5N_3O_2$ = 917.14) |
| P-99 | m/z = 910.37($C_{66}H_{46}N_4O$ = 911.12) | P-100 | m/z = 927.33($C_{66}H_{45}N_3OS$ = 928.17) |
| P-101 | m/z = 885.34($C_{64}H_{43}N_3O_2$ = 886.07) | P-102 | m/z = 941.32($C_{66}H_{43}N_3O_2S$ = 942.15) |
| P-103 | m/z = 1016.35($C_{72}H_{48}N_4OS$ = 1017.26) | P-104 | m/z = 935.35($C_{68}H_{45}N_3O_2$ = 936.13) |
| P-105 | m/z = 926.34($C_{66}H_{46}N_4S$ = 927.18) | P-106 | m/z = 910.37($C_{66}H_{46}N_4O$ = 911.12) |
| P-107 | m/z = 985.41($C_{72}H_{51}N_5$ = 986.24) | P-108 | m/z = 976.36($C_{70}H_{48}N_4S$ = 977.24) |
| P-109 | m/z = 960.38($C_{70}H_{48}N_4O$ = 961.18) | P-110 | m/z = 1368.53($C_{101}H_{68}N_4O_2$ = 1369.68) |
| P-111 | m/z = 1016.35($C_{72}H_{48}N_4OS$ = 1017.26) | P-112 | m/z = 976.36($C_{70}H_{48}N_4S$ = 977.24) |

Although the exemplary synthesis examples of the present disclosure represented by Formula 1 have been described above, the synthesis examples are on the basis of Buchwald-Hartwig cross coupling, Suzuki cross-coupling, or the like. A person skilled in the art could easily understand that the above reactions proceed even though, besides the substituents specified in the specific synthesis examples, other substituents (X, $Ar^1$ to $Ar^6$, L, $R^1$ to $R^3$, m, n, and o) defined in Formula 1 are bound. For example, the reaction of Sub 1→P-I→Final Product in Reaction scheme 1, the reaction of Sub 1-I→Sub 1 in Reaction Scheme 2 were on the basis of Buchwald-Hartwig cross coupling, and the reaction of start material→Sub 1-I in Reaction Scheme 2 was on the basis of Suzuki cross-coupling. The above reactions would proceed even though clearly specified substituents are bound.

Manufacturing and Evaluation of Organic Electronic Element

[Example 1] Green Organic Light Emitting Diode (Hole Transport Layer)

An organic light emitting diode was manufactured by an ordinary method using the compound of the present disclosure as a material for a hole transport layer. First, 4,4',4'-tris[2-naphthyl(phenyl)amino]triphenylamine (hereinafter, abbreviated as "2-TNATA") was vacuum-deposited with a thickness of 60 nm on an ITO layer (anode) formed on a galas substrate to form a hole injection layer, and then, Compound P-1 of the present disclosure was vacuum-deposited with a thickness of 60 nm on the hole injection layer to form a hole transport layer. Subsequently, 4,4'-N, N'-dicarbazole-biphenyl (hereinafter, abbreviated as "CBP") as a host material and tris(2-phenylpyridine)-iridium (hereinafter, abbreviated as "Ir(ppy)$_3$") as a dopant material were doped at a weight ratio of 90:10 and thus vacuum-deposited with a thickness of 30 nm on the hole transport layer to form a light emitting layer. Then, (1,1'-bisphenyl)-4-olato)bis(2-methyl-8-quinolinolato)aluminum (hereinafter, abbreviated as "BAlq") was vacuum-deposited with a thickness of 10 nm on the light emitting layer to form a hole blocking layer, and tris(8-quinolinolato)aluminum (hereinafter abbreviated as "Alq$_3$") was vacuum-deposited with a thickness of 40 nm on the hole blocking layer to form an electron transport layer. Thereafter, LiF as a halogenated alkali metal was deposited with a thickness of 0.2 nm to form an electron injection layer, and then Al was deposited with a thickness of 150 nm to form a cathode, and in this way, an organic light emitting diode was manufactured.

[Example 2] to [Example 22] Green Organic Light Emitting Diode (Hole Transport Layer)

Organic light emitting diodes were manufactured by the same method as in Example 1 except that as a material for the hole transport layer, Compounds P-3 to P-109 of the present disclosure shown in table 3 below were used instead of Compound P-1 of the present disclosure.

[Comparative Example 1] to [Comparative Example 3] Green Organic Light Emitting Diodes (Hole Transport Layer)

Organic light emitting diodes were manufactured by the same method as in Example 1 except that as a material for the hole transport layer, Comparative Compounds 1 to 3 of the present disclosure shown in table 3 below were used instead of Compound P-1 of the present disclosure.

<Comparatie Compound 1>

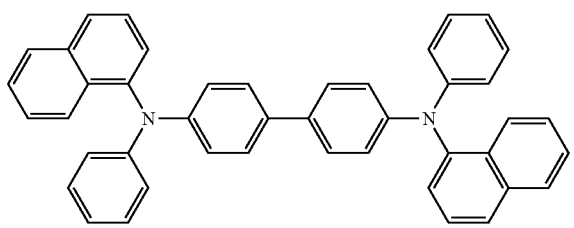

<Comparatie Compound 2>

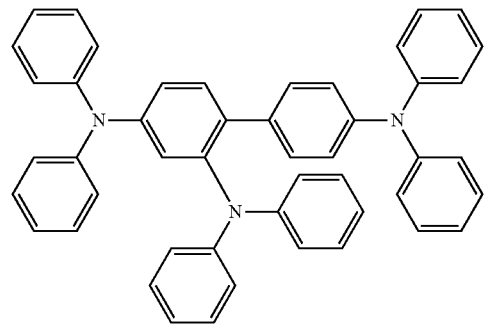

<Comparatie Compound 3>

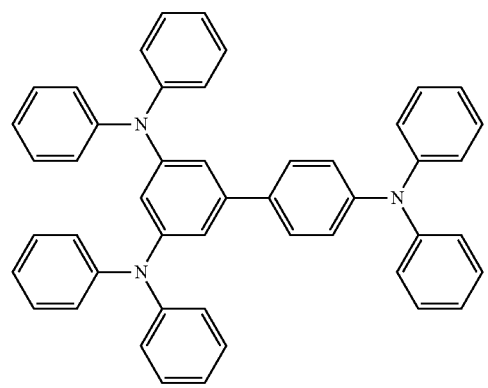

A forward bias DC voltage was applied to each of the organic light emitting diodes manufactured in Examples 1 to 22 and Comparative Examples 1 to 3 of the present disclosure to measure electro-luminescent (EL) characteristics thereof by PR-650 (Photoresearch). As a result, the T95 lifetime was measured by a lifetime measurement equipment (fabricated by Mcscience) at reference brightness of 5000 cd/m$^2$. The measurement results are shown in table 3 below.

TABLE 3

| | Compound | Voltage (V) | Current Density (mA/cm2) | Brightness (cd/m2) | Efficiency (cd/A) | Lifetime T(95) | CIE x | CIE y |
|---|---|---|---|---|---|---|---|---|
| Comparative Example (1) | Comparative Compound 1 | 6.0 | 21.5 | 5000 | 23.3 | 57.4 | 0.33 | 0.62 |
| Comparative Example (2) | Comparative Compound 2 | 5.6 | 18.9 | 5000 | 26.4 | 73.4 | 0.33 | 0.61 |
| Comparative Example (3) | Comparative Compound 3 | 5.6 | 18.1 | 5000 | 27.6 | 84.4 | 0.33 | 0.61 |
| Example (1) | Compound (P-1) | 5.7 | 14.1 | 5000 | 35.4 | 120.3 | 0.33 | 0.61 |
| Example (2) | Compound (P-3) | 5.7 | 12.9 | 5000 | 38.7 | 127.9 | 0.33 | 0.62 |
| Example (3) | Compound (P-4) | 5.6 | 12.7 | 5000 | 39.3 | 137.0 | 0.33 | 0.61 |
| Example (4) | Compound (P-8) | 5.7 | 14.2 | 5000 | 35.3 | 123.2 | 0.33 | 0.61 |
| Example (5) | Compound (P-17) | 5.6 | 11.9 | 5000 | 42.1 | 144.2 | 0.33 | 0.62 |
| Example (6) | Compound (P-18) | 5.6 | 11.7 | 5000 | 42.7 | 150.9 | 0.33 | 0.61 |
| Example (7) | Compound (P-19) | 5.6 | 11.7 | 5000 | 42.6 | 150.8 | 0.33 | 0.62 |

TABLE 3-continued

| | Compound | Voltage (V) | Current Density (mA/cm2) | Brightness (cd/m2) | Efficiency (cd/A) | Lifetime T(95) | CIE x | CIE y |
|---|---|---|---|---|---|---|---|---|
| Example (8) | Compound (P-20) | 5.6 | 11.8 | 5000 | 42.4 | 150.5 | 0.33 | 0.61 |
| Example (9) | Compound (P-22) | 5.6 | 12.7 | 5000 | 39.4 | 137.9 | 0.33 | 0.62 |
| Example (10) | Compound (P-24) | 5.6 | 12.6 | 5000 | 39.8 | 135.4 | 0.33 | 0.62 |
| Example (11) | Compound (P-25) | 5.6 | 14.1 | 5000 | 35.4 | 117.4 | 0.33 | 0.62 |
| Example (12) | Compound (P-33) | 5.7 | 15.6 | 5000 | 32.0 | 111.3 | 0.33 | 0.62 |
| Example (13) | Compound (P-35) | 5.7 | 15.7 | 5000 | 31.9 | 112.2 | 0.33 | 0.61 |
| Example (14) | Compound (P-49) | 5.6 | 13.8 | 5000 | 36.2 | 119.0 | 0.33 | 0.61 |
| Example (15) | Compound (P-598 | 5.6 | 14.7 | 5000 | 34.1 | 122.3 | 0.33 | 0.61 |
| Example (16) | Compound (P-66) | 5.7 | 15.8 | 5000 | 31.6 | 111.0 | 0.33 | 0.62 |
| Example (17) | Compound (P-72) | 5.7 | 14.8 | 5000 | 33.7 | 121.1 | 0.33 | 0.62 |
| Example (18) | Compound (P-80) | 5.6 | 12.9 | 5000 | 38.8 | 125.1 | 0.33 | 0.62 |
| Example (19) | Compound (P-91) | 5.7 | 13.4 | 5000 | 37.4 | 126.3 | 0.33 | 0.62 |
| Example (20) | Compound (P-99) | 5.7 | 14.2 | 5000 | 35.3 | 118.6 | 0.33 | 0.61 |
| Example (21) | Compound (P-105) | 5.6 | 12.7 | 5000 | 39.4 | 132.3 | 0.33 | 0.61 |
| Example (22) | Compound (P-109) | 5.5 | 12.8 | 5000 | 39.0 | 137.5 | 0.33 | 0.61 |

As can be seen from the results of Table 3 above, compared with the organic light emitting diodes of Comparative Examples 1 to 3, the organic light emitting diodes using the present inventive compounds as a material for the hole transport layer showed significantly improved light emission efficiency and lifetime.

Compared with the cases in which diaryl amine was bound (Comparative Compounds 1 to 3), the cases in which dibenzothiophene, dibenzofurane, carbazole, or the like, but not an aryl group, is introduced as at least one of the substituents substituted at an amine group linked to the linker L like in the present inventive compounds showed high Tg values and high refractive indexes, and thus the light emission efficiency and thermal stability were improved and the lifetime was increased.

Meanwhile, the correlation between the hole transport layer and the light emitting layer (host) needs to be considered, and thus even a person skilled in the art would have great difficulty in deriving features of the hole transport layer employing the compounds of the present disclosure in spite of using similar cores.

[Example 23] Red Organic Light Emitting Diode (Light Emitting Auxiliary Layer)

An organic light emitting diode was manufactured by an ordinary method using the compound of the present disclosure as a material for the hole transport layer. First, 2-TNATA was vacuum-deposited with a thickness of 60 nm on an ITO layer (anode) formed on a galas substrate to form a hole injection layer, and then, NPB was vacuum-deposited with a thickness of 60 nm on the hole injection layer to form a hole transport layer. Subsequently, Compound P-1 of the present disclosure was vacuum-deposited with a thickness of 20 nm on the hole transport layer to form a light emitting auxiliary layer, and then CBP as a host material and bis-(1-phenylisoquinolyl) iridium ($Y^2$) acetylacetonate (hereinafter, abbreviated as "(piq)$_2$Ir(acac)") as a dopant material were doped at a weight ratio of 95:5 onto the light emitting auxiliary layer, and thus vacuum-deposited with a thickness of 30 nm, thereby forming a light emitting layer. Then, BAlq was vacuum-deposited with a thickness of 5 nm on the light emitting layer to form a hole blocking layer, and bis(10-hydroxybenzo[h]quinolinato) beryllium (hereinafter, abbreviated as "BeBq$_2$") was vacuum-deposited with a thickness of 40 nm on the hole blocking layer to form an electron transport layer. Thereafter, LiF as a halogenated alkali metal was deposited with a thickness of 0.2 nm to form an electron injection layer, and then Al was deposited with a thickness of 150 nm to form a cathode, and in this way, an organic light emitting diode was manufactured.

[Example 24] to [Example 72] Red Organic Light Emitting Diodes (Light Emitting Auxiliary Layer)

Organic light emitting diodes were manufactured by the same method as in Example 23 except that as a material for the light emitting auxiliary layer, Compounds P-2 to P-107 of the present disclosure shown in table 4 below were used instead of Compound P-1 of the present disclosure.

Comparative Example 4

An organic light emitting diode was manufactured by the same method as in Example 23 except that the light emitting auxiliary was not formed.

Comparative Example 5 and Comparative Example 6

Organic light emitting diodes were manufactured by the same method as in Example 23 except that as a material for the light emitting auxiliary layer, Comparative Compounds 2 and 3 shown in table 4 below were used instead of Compound P-1 of the present disclosure.

A forward bias DC voltage was applied to each of the organic light emitting diodes manufactured in Examples 23 to 72 and Comparative Examples 4 to 6 of the present disclosure to measure electro-luminescent (EL) characteristics thereof by PR-650 (Photoresearch). As a result, the T95 lifetime was measured by a lifetime measurement equipment (fabricated by Mcscience) at reference brightness of 2500 cd/m$^2$. The measurement results are shown in table 4 below.

TABLE 4

|  | Compound | Voltage (V) | Current Density (mA/cm2) | Brightness (cd/m2) | Efficiency (cd/A) | Lifetime T(95) | CIE x | CIE y |
|---|---|---|---|---|---|---|---|---|
| Comparative Example (4) | — | 5.3 | 33.3 | 2500 | 7.5 | 62.7 | 0.66 | 0.32 |
| Comparative Example (5) | Comparative Compound 2 | 5.8 | 29.0 | 2500 | 8.6 | 79.0 | 0.66 | 0.33 |
| Comparative Example (6) | Comparative Compound 3 | 5.7 | 23.1 | 2500 | 10.8 | 84.5 | 0.66 | 0.33 |
| Example (23) | Compound (P-1) | 5.5 | 10.5 | 2500 | 23.8 | 142.0 | 0.66 | 0.32 |
| Example (24) | Compound (P-2) | 5.5 | 10.5 | 2500 | 23.8 | 140.9 | 0.66 | 0.32 |
| Example (25) | Compound (P-3) | 5.3 | 11.6 | 2500 | 21.6 | 136.8 | 0.66 | 0.33 |
| Example (26) | Compound (P-4) | 5.3 | 11.4 | 2500 | 22.0 | 139.9 | 0.66 | 0.33 |
| Example (27) | Compound (P-5) | 5.5 | 10.8 | 2500 | 23.2 | 138.9 | 0.66 | 0.33 |
| Example (28) | Compound (P-6) | 5.6 | 10.6 | 2500 | 23.5 | 139.6 | 0.66 | 0.32 |
| Example (29) | Compound (P-8) | 5.6 | 10.9 | 2500 | 22.9 | 138.1 | 0.66 | 0.32 |
| Example (30) | Compound (P-9) | 5.6 | 11.1 | 2500 | 22.4 | 138.2 | 0.66 | 0.32 |
| Example (31) | Compound (P-10) | 5.5 | 10.5 | 2500 | 23.8 | 144.9 | 0.66 | 0.32 |
| Example (32) | Compound (P-11) | 5.5 | 9.5 | 2500 | 26.3 | 168.5 | 0.66 | 0.33 |
| Example (33) | Compound (P-13) | 5.6 | 10.0 | 2500 | 25.0 | 152.6 | 0.66 | 0.32 |
| Example (34) | Compound (P-14) | 5.6 | 9.6 | 2500 | 26.0 | 162.4 | 0.66 | 0.33 |
| Example (35) | Compound (P-16) | 5.5 | 9.6 | 2500 | 25.9 | 161.5 | 0.66 | 0.33 |
| Example (36) | Compound (P-17) | 5.3 | 10.5 | 2500 | 23.7 | 142.5 | 0.66 | 0.32 |
| Example (37) | Compound (P-18) | 5.3 | 10.3 | 2500 | 24.4 | 148.7 | 0.66 | 0.32 |
| Example (38) | Compound (P-20) | 5.3 | 10.3 | 2500 | 24.2 | 148.4 | 0.66 | 0.32 |
| Example (39) | Compound (P-22) | 5.5 | 9.7 | 2500 | 25.6 | 157.7 | 0.66 | 0.33 |
| Example (40) | Compound (P-25) | 5.4 | 12.6 | 2500 | 19.8 | 132.1 | 0.66 | 0.32 |
| Example (41) | Compound (P-26) | 5.7 | 11.5 | 2500 | 21.7 | 136.0 | 0.66 | 0.33 |
| Example (42) | Compound (P-27) | 5.7 | 12.0 | 2500 | 20.8 | 133.6 | 0.66 | 0.32 |
| Example (43) | Compound (P-37) | 5.6 | 11.5 | 2500 | 21.7 | 136.1 | 0.66 | 0.33 |
| Example (44) | Compound (P-38) | 5.6 | 12.2 | 2500 | 20.5 | 134.2 | 0.66 | 0.32 |
| Example (45) | Compound (P-39) | 5.4 | 12.7 | 2500 | 19.7 | 130.7 | 0.66 | 0.32 |
| Example (46) | Compound (P-40) | 5.4 | 12.8 | 2500 | 19.6 | 130.1 | 0.66 | 0.32 |
| Example (47) | Compound (P-41) | 5.6 | 11.9 | 2500 | 21.0 | 136.2 | 0.66 | 0.33 |
| Example (48) | Compound (P-50) | 5.7 | 12.4 | 2500 | 20.1 | 133.9 | 0.66 | 0.33 |
| Example (49) | Compound (P-52) | 5.7 | 11.8 | 2500 | 21.2 | 135.5 | 0.66 | 0.33 |
| Example (50) | Compound (P-57) | 5.5 | 11.6 | 2500 | 21.6 | 136.6 | 0.66 | 0.33 |
| Example (51) | Compound (P-59) | 5.4 | 12.7 | 2500 | 19.6 | 132.9 | 0.66 | 0.33 |
| Example (52) | Compound (P-69) | 5.7 | 11.8 | 2500 | 21.2 | 136.0 | 0.66 | 0.32 |
| Example (53) | Compound (P-73) | 5.5 | 13.4 | 2500 | 18.7 | 128.3 | 0.66 | 0.33 |
| Example (54) | Compound (P-76) | 5.7 | 12.9 | 2500 | 19.3 | 132.3 | 0.66 | 0.33 |
| Example (55) | Compound (P-77) | 5.7 | 12.9 | 2500 | 19.4 | 130.8 | 0.66 | 0.33 |
| Example (56) | Compound (P-78) | 5.6 | 11.6 | 2500 | 21.5 | 135.6 | 0.66 | 0.32 |
| Example (57) | Compound (P-81) | 5.7 | 11.6 | 2500 | 21.5 | 136.2 | 0.66 | 0.32 |
| Example (58) | Compound (P-83) | 5.6 | 12.1 | 2500 | 20.7 | 134.4 | 0.66 | 0.32 |
| Example (59) | Compound (P-85) | 5.6 | 10.7 | 2500 | 23.4 | 139.7 | 0.66 | 0.33 |
| Example (60) | Compound (P-88) | 5.7 | 11.6 | 2500 | 21.6 | 135.4 | 0.66 | 0.32 |
| Example (61) | Compound (P-89) | 5.5 | 10.5 | 2500 | 23.8 | 144.7 | 0.66 | 0.32 |
| Example (62) | Compound (P-90) | 5.6 | 10.7 | 2500 | 23.5 | 137.3 | 0.66 | 0.33 |
| Example (63) | Compound (P-91) | 5.3 | 10.9 | 2500 | 22.9 | 137.5 | 0.66 | 0.32 |
| Example (64) | Compound (P-91) | 5.5 | 10.5 | 2500 | 23.8 | 144.3 | 0.66 | 0.33 |
| Example (65) | Compound (P-96) | 5.4 | 11.1 | 2500 | 22.4 | 139.2 | 0.66 | 0.33 |
| Example (66) | Compound (P-97) | 5.5 | 10.9 | 2500 | 22.9 | 138.0 | 0.66 | 0.33 |
| Example (67) | Compound (P-99) | 5.3 | 11.3 | 2500 | 22.1 | 138.3 | 0.66 | 0.32 |
| Example (68) | Compound (P-101) | 5.6 | 11.1 | 2500 | 22.6 | 139.7 | 0.66 | 0.32 |
| Example (69) | Compound (P-103) | 5.4 | 11.3 | 2500 | 22.1 | 138.8 | 0.66 | 0.32 |
| Example (70) | Compound (P-105) | 5.4 | 11.3 | 2500 | 22.0 | 138.3 | 0.66 | 0.33 |
| Example (71) | Compound (P-106) | 5.4 | 11.5 | 2500 | 21.7 | 136.4 | 0.66 | 0.32 |
| Example (72) | Compound (P-107) | 5.3 | 11.9 | 2500 | 21.1 | 136.2 | 0.66 | 0.32 |

As can be seen from the results of Table 4 above, compared with the organic light emitting diodes of Comparative Examples 4 to 6, the organic light emitting diodes using the present inventive compounds as a material for the light emitting auxiliary layer showed significantly improved light emission efficiency and lifetime.

In Comparative Compounds 2 and 3 having different binding positions of the amine substituent, Comparative Compound 3 showed higher results in view of light emission efficiency than Comparative Compound 2. Compared with Comparative Compound 3 in which aryl groups are introduced as the substituents substituted on an amine, the present inventive compounds in which heterocyclic substituents, such as dibenzothiophene, dibenzofurane, and carbazole, are introduced as the substituents substituted on an amine showed significantly higher results in light emission efficiency and lifetime.

Compared with Comparative Example 3 in which diaryl amine was bound, the present inventive compounds in which carbazole but not an aryl group is introduced as at least one of the substituents substituted at an amine group linked to the linker L had higher hole mobility and thus a lower driving voltage. Compared with Comparative Compound 3, the present inventive compounds in which dibenzothiophene or dibenzofurane, but not an aryl group, is introduced as at least one of the substituents substituted on an amine group bound to the linker L showed higher refractive indexes, and as a result, the manufactured elements had higher light transmittances, leading to significantly increased light emission efficiency.

Collectively considering the above-described characteristics (high Tg value, high refractive index, and fast hole mobility), it can be confirmed that the band gap, electric characteristics, interface characteristics, and the like can be significantly changed depending on the kind, binding position, and number of amine groups, and these function as important factors in the improvement of element performance.

In addition, the evaluation results of the above-described manufactured elements provide characteristics of elements in which the compounds of the present disclosure were applied to only one layer between the hole transport layer and the light emitting auxiliary layer, but the compounds of the present disclosure can be applied to both of the hole transport layer and the light emitting auxiliary layer.

Although exemplary embodiments of the present disclosure have been described for illustrative purposes, a person skilled in the art will appreciate that various modifications, additions and substitutions are possible, without departing from the scope and spirit of the invention as disclosed in the accompanying claims. Therefore, the embodiment disclosed in the present disclosure is intended to illustrate the scope of the technical idea of the present disclosure, and the scope of the present disclosure is not limited by the embodiment. The scope of the present disclosure shall be construed on the basis of the accompanying claims, and it shall be construed that all of the technical ideas included within the scope equivalent to the claims belong to the present disclosure.

The invention claimed is:

1. An organic electric element comprising:
   a first electrode;
   a second electrode; and
   at least one organic material layer including a light emitting layer positioned between the first electrode and the second electrode,
   wherein the organic material layer includes a hole transport layer between the first electrode and light emitting layer,
   wherein the hole transport layer contains a compound represented by Formula 1:

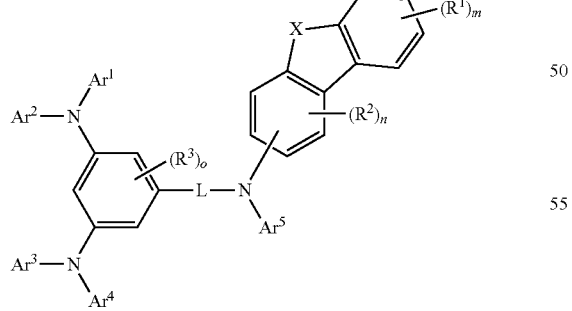

<Formula 1> in Formula-1:
1) X is any one of S, O, and $NAr^6$;
2) $Ar^1$ to $Ar^6$ each are independently selected from the group consisting of a $C_6$-$C_{60}$ aryl group, a $C_2$-$C_{60}$ heterocyclic group containing at least one heteroatom of O, N, S, Si, a fluorenyl group, a fused ring group of a $C_6$-$C_{60}$ aromatic ring and a $C_3$-$C_{60}$ aliphatic ring, a $C_1$-$C_{50}$ alkyl group, a $C_2$-$C_{20}$ alkenyl group, a $C_2$-$C_{20}$ alkynyl group, a $C_1$-$C_{30}$ alkoxy group, and a $C_6$-$C_{30}$ aryloxy group;

3) $R^1$ to $R^3$ each are independently selected from the group consisting of deuterium, tritium, halogen, a cyano group, a nitro group, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxy group, and a $C_6$-$C_{30}$ aryloxy group, in the presence of a plurality of $R^1$'s and $R^2$'s, at least one pair of neighboring $R^1$'s and $R^2$'s independently may bind to each other to form a ring, provided that $R^1$'s and $R^2$'s forming no ring are the same as defined above;

4) m is an integer of 0 to 4, and when m is an integer of 2 or greater, $R^1$'s are the same as or different from each other;

5) n and o each are independently an integer of 0 to 3, and when n and o each are an integer of 2 or greater, $R^2$'s and $R^3$'s each are the same as or different from each other; and 6) L is represented by one of Formula L1 to L6 below:

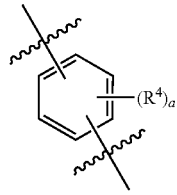

<Formula L1>

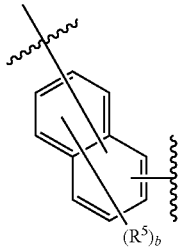

<Formula L2>

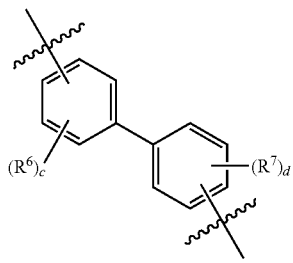

<Formula L3>

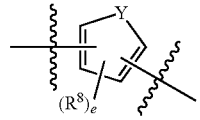

<Formula L4>

-continued

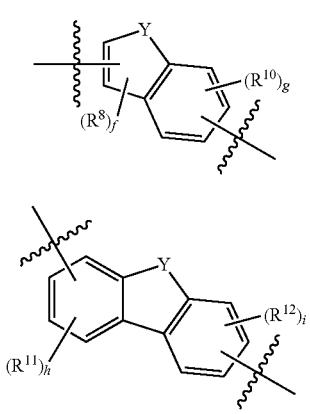

<Formula L5>

<Formula L6> wherein in Formulas L1 to L6:
7) Y is any one of S, O, $NAr^7$, and $CAr^8Ar^9$;
8) $Ar^7$ to $Ar^9$ each are independently selected from the group consisting of a $C_6$-$C_{60}$ aryl group, a fluorenyl group, a $C_2$-$C_{60}$ heterocyclic group containing at least one heteroatom of O, N, S, Si, and P, a fused ring group of a $C_6$-$C_{60}$ aromatic ring and a $C_3$-$C_{60}$ aliphatic ring, a $C_1$-$C_{50}$ alkyl group, a $C_2$-$C_{20}$ alkenyl group, a $C_2$-$C_{20}$ alkynyl group, a $C_1$-$C_{30}$ alkoxy group, and a $C_6$-$C_{30}$ aryloxy group, and $Ar^8$ to $Ar^9$ may bind to each other to form a spiro compound together with a carbon atom to which they are bound;
9) $R^4$ to $R^{12}$ each are independently selected from the group consisting of deuterium, tritium, halogen, a cyano group, a nitro group, an aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxy group, and a $C_6$-$C_{30}$ aryloxy group, in the presence of a plurality of $R^{10}$'s and $R^{12}$'s, at least one pair of neighboring $R^{10}$'s, $R^{11}$'s, and $R^{12}$'s independently may bind to each other to form a ring, provided that $R^{10}$'s to $R^{12}$'s forming no ring are the same as defined above;
10) a, c, and d each are independently an integer of 0 to 4, and when a, c, and d are each an integer of 2 or greater, $R^4$'s, $R^6$'s, and $R^7$'s are the same as or different from each other;
11) b is an integer of 0 to 8, and when b is an integer of 2 or greater, $R^5$'s are the same as or different from each other;
12) e is an integer of 0 to 2, and when e is an integer of 2 or greater, $R^8$'s are the same as or different from each other;
13) f is an integer of 0 or 1; and
14) g, h, and i each are independently an integer of 0 to 3, and when g, h, and i are each an integer of 2 or greater, $R^{10}$'s to $R^{12}$'s are the same as or different from each other,
wherein the aryl group, fluorenyl group, heterocyclic group, fused ring group, alkyl group, alkenyl group, alkynyl group, alkoxy group, and aryloxy group of $Ar^1$ to $Ar^6$, $R^1$ to $R^3$, $Ar^7$ to $Ar^9$, and $R^4$ to $R^{12}$ each may be further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group, and when the substituents are adjacent to each other, the substituents may bind to each other to form a ring,
with the proviso that, if X is O or S, L is not L1.

2. The organic electric element of claim 1, wherein the compound is contained as a single kind of compound alone or a mixture of two or more kinds of compounds.

3. The organic electric element of claim 1, wherein the organic material layer is formed by a spin coating process, a nozzle printing process, an inkjet printing process, a slot coating process, a dip coating process, or a roll-to-roll process.

4. An electronic device comprising:
a display device comprising the organic electric element of claim 1, and
a controller for driving the display device.

5. The electronic device of claim 4, wherein the organic electric element is one of an organic light emitting diode, an organic solar cell, an organic photo conductor, an organic transistor, and an element for a monochromatic or white illumination.

6. The organic electric element of claim 1, wherein Formula 1 is any one of the compounds below:

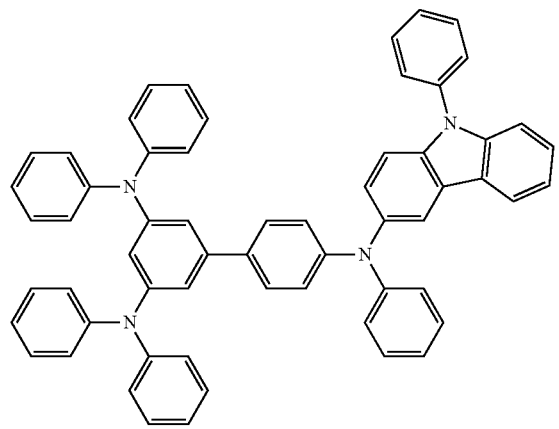

P-3

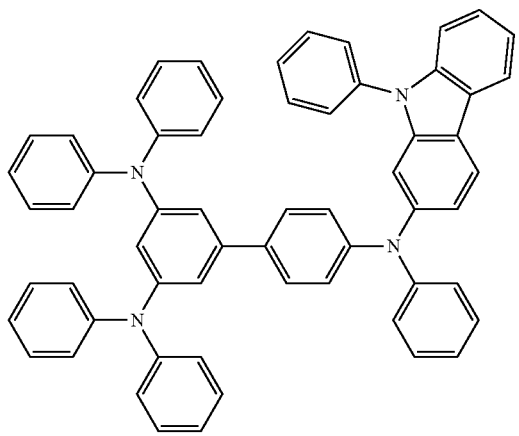

P-4

-continued
P-17
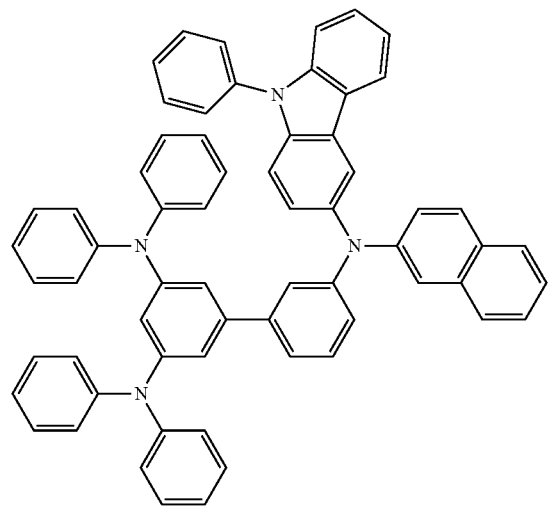
P-18
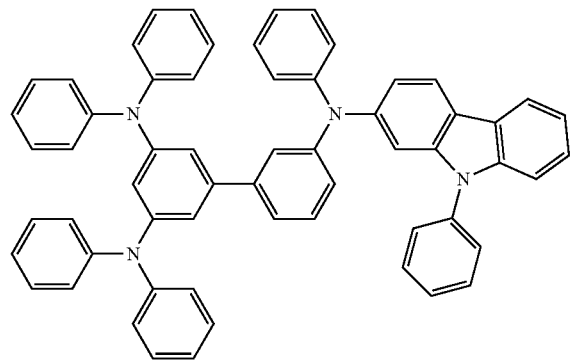
P-19
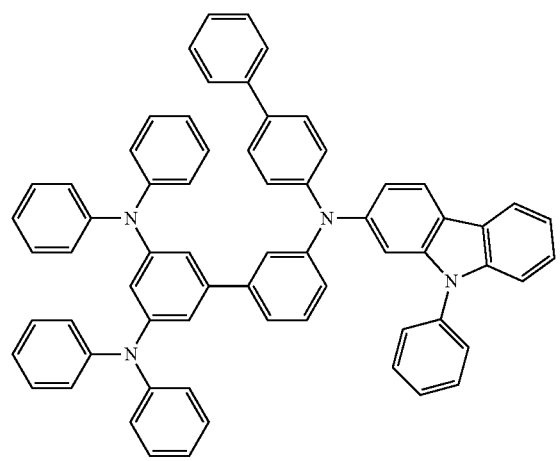
P-20
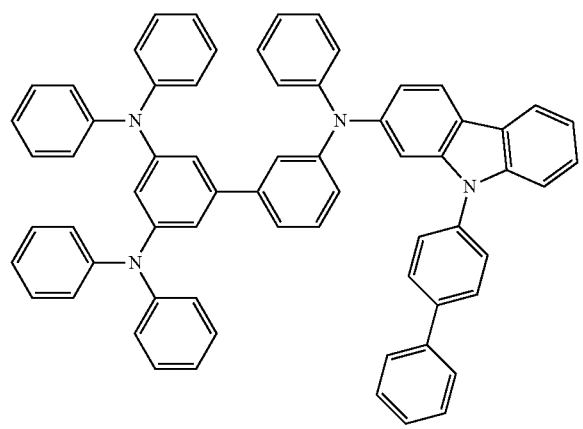
P-21
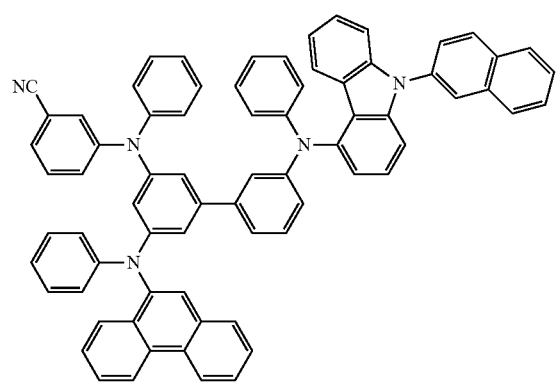
P-25
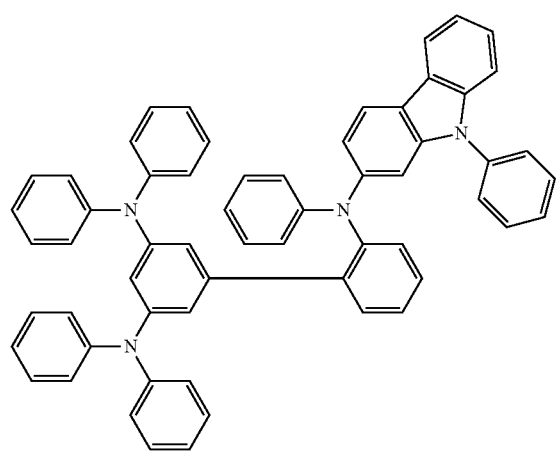

-continued
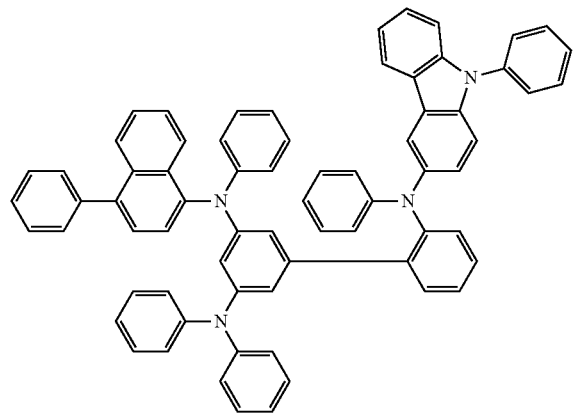
P-32
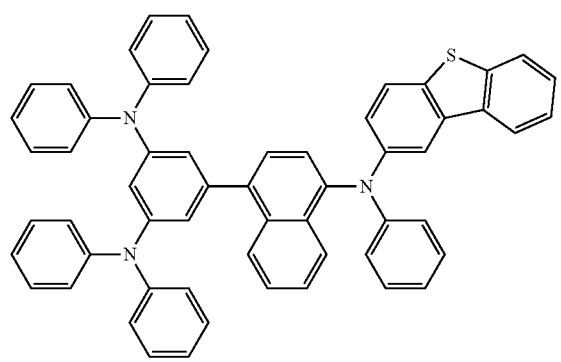
P-37
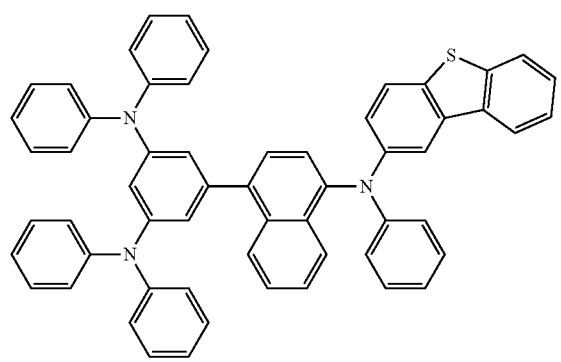
P-38
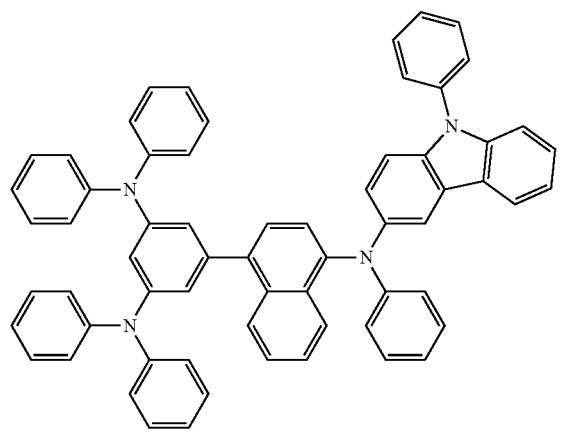
P-39
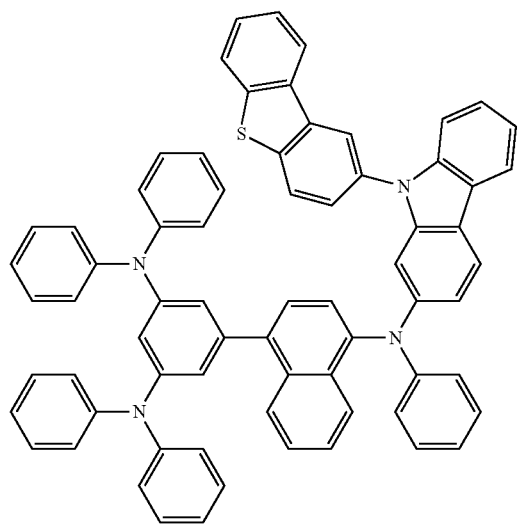
P-40

-continued
P-41
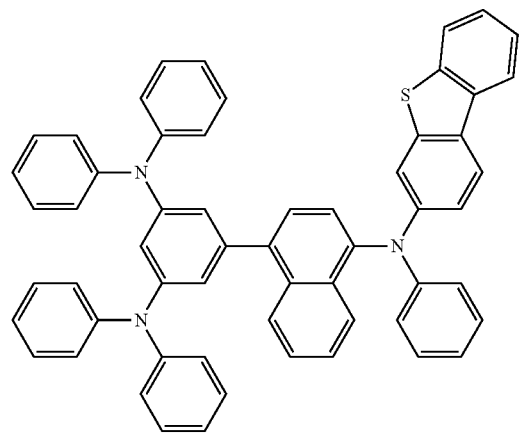
P-42
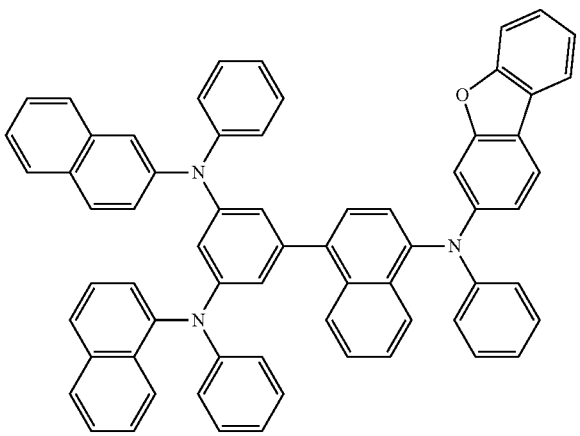
P-43
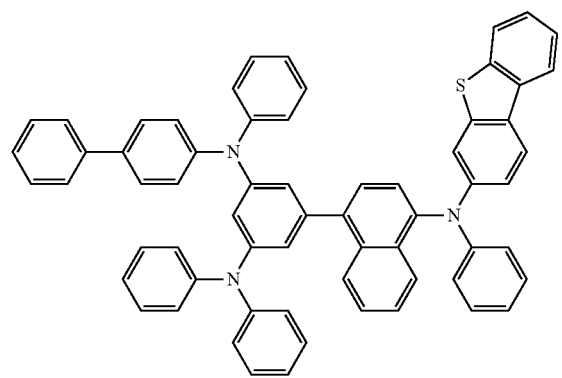
P-44
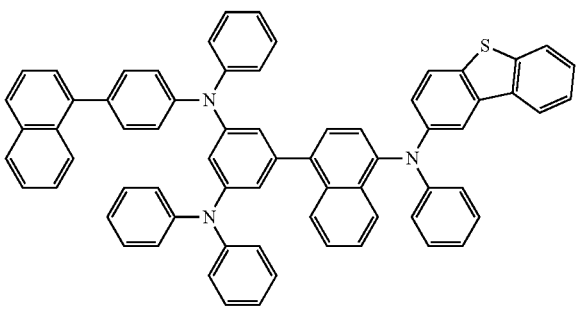
P-45
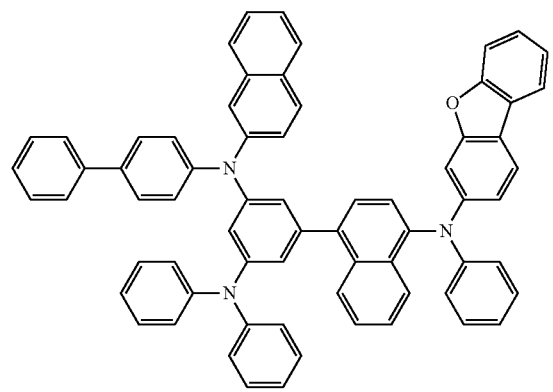
P-46
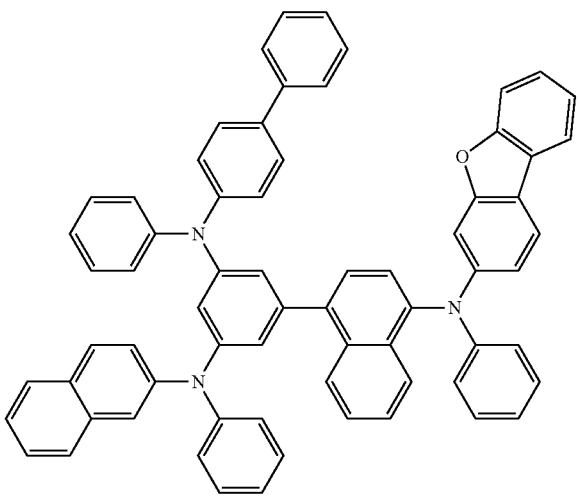

-continued
P-47
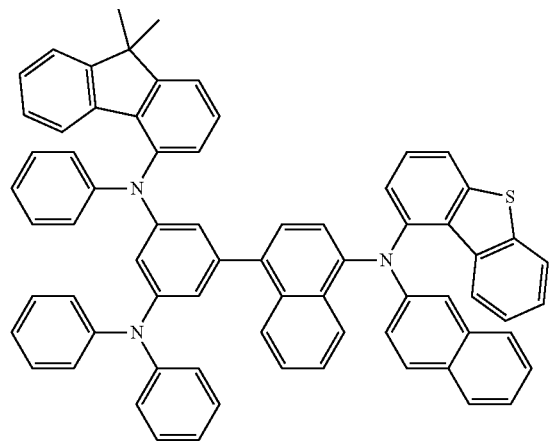
P-48
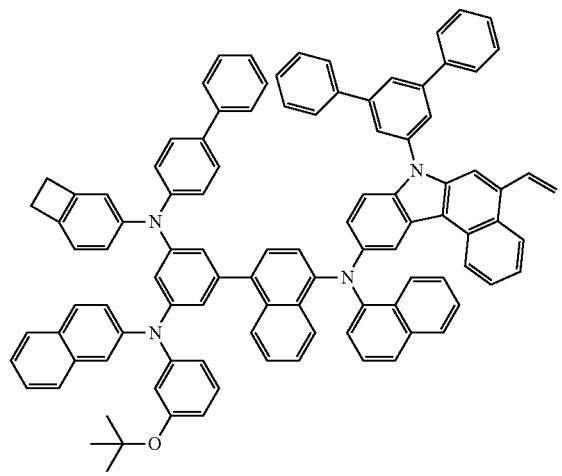
P-49
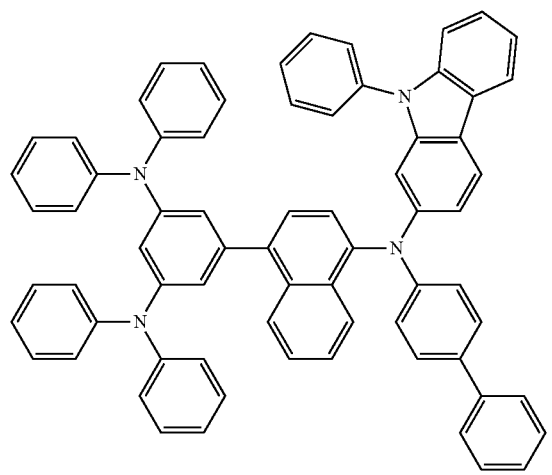
P-50
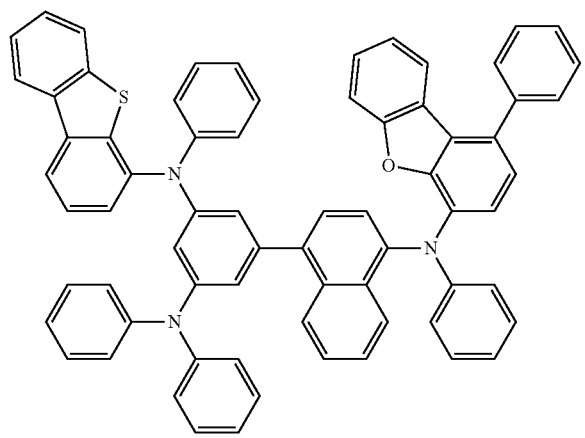
P-51
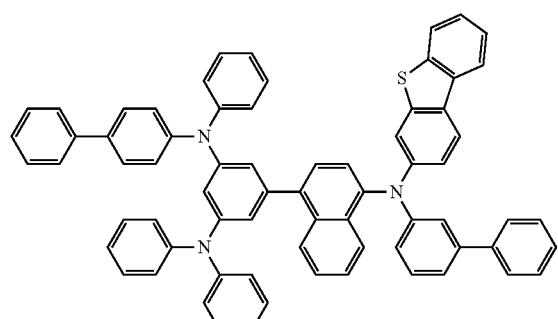
P-52
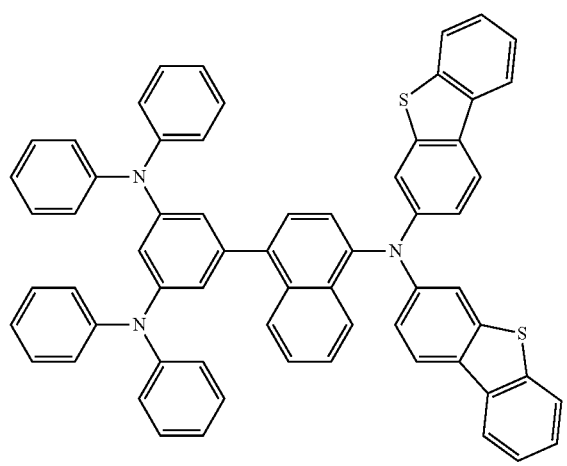

-continued
P-53
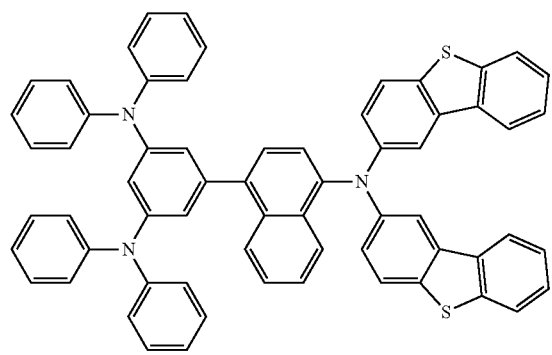
P-54
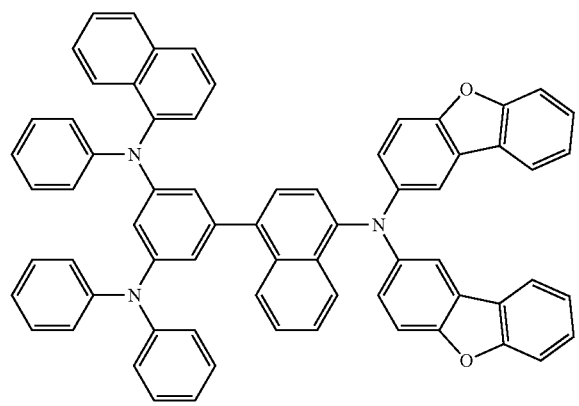
P-55
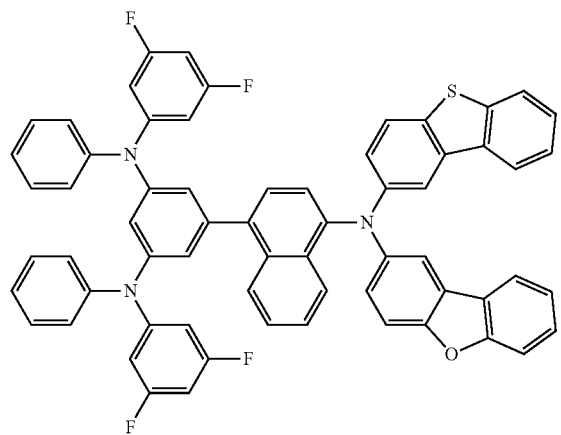
P-56
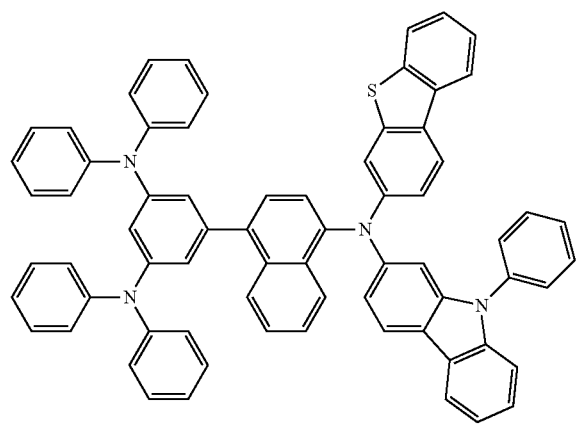
P-57
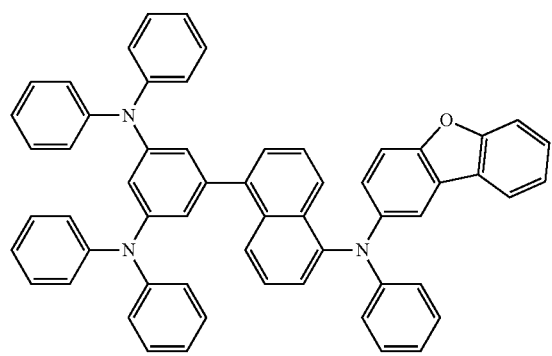
P-58
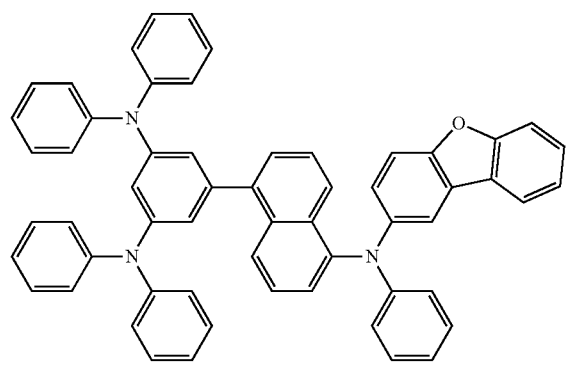

-continued
P-59
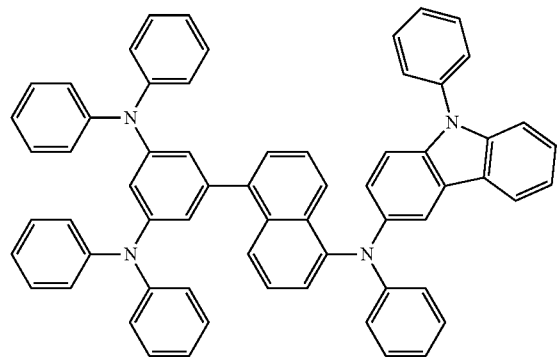
P-60
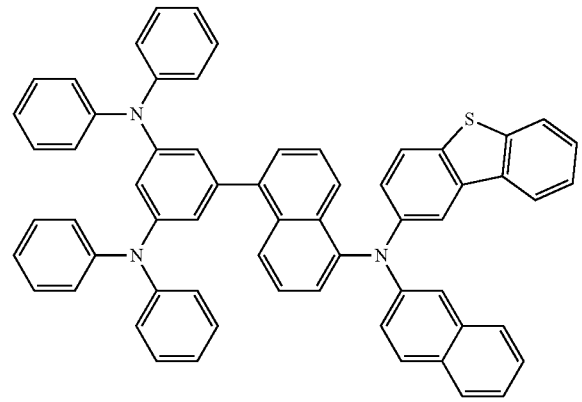
P-61
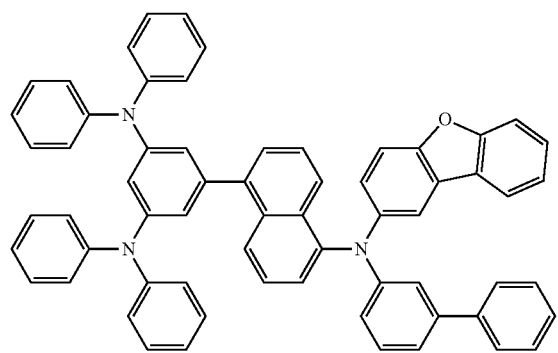
P-62
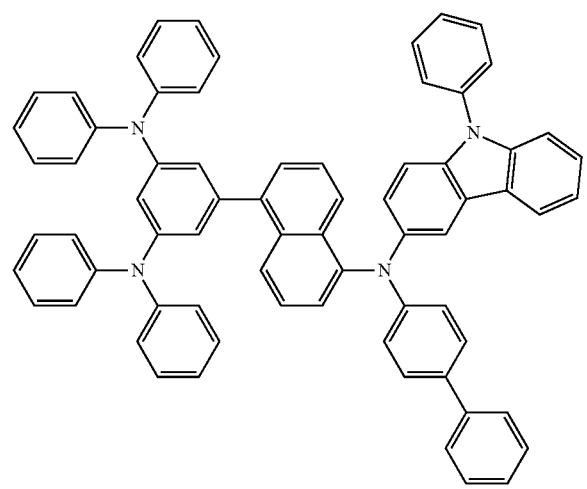
P-63
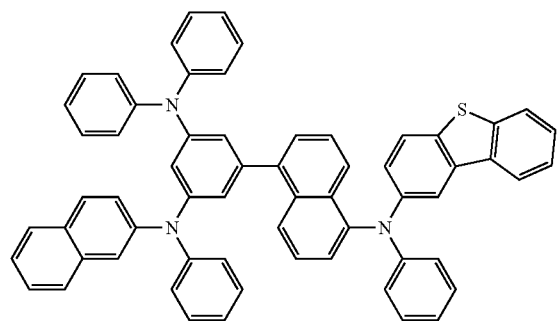
P-64
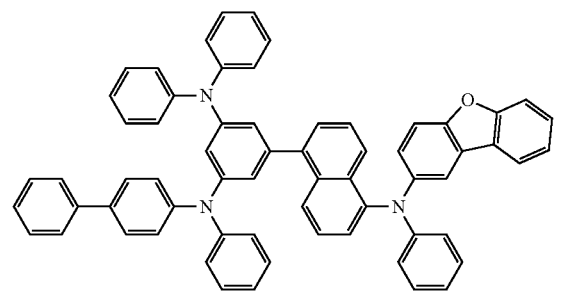

-continued
P-65
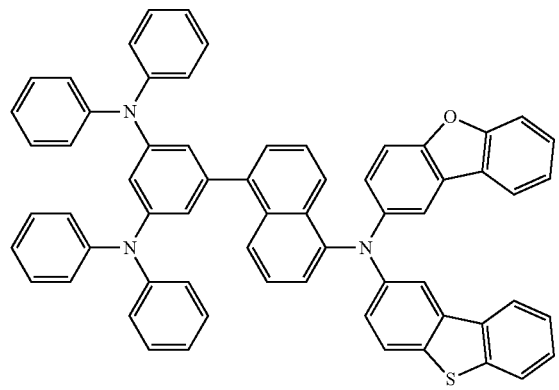
P-66
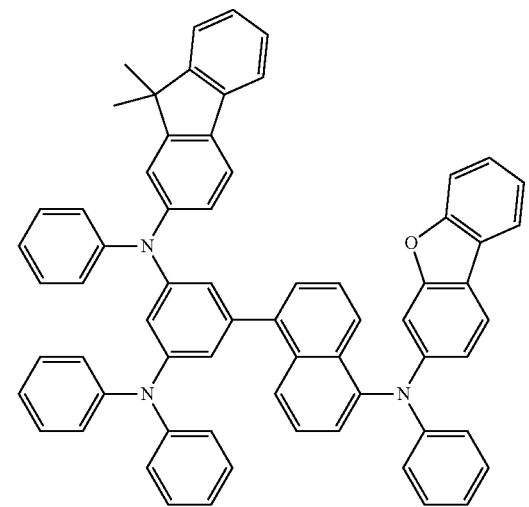
P-67
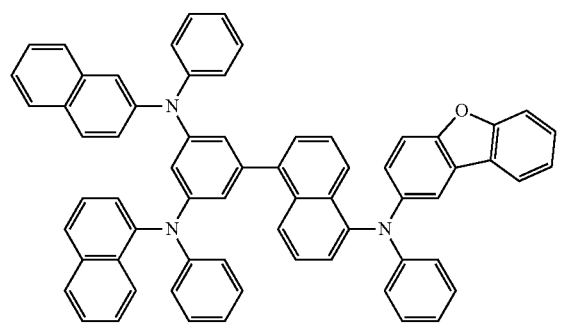
P-68
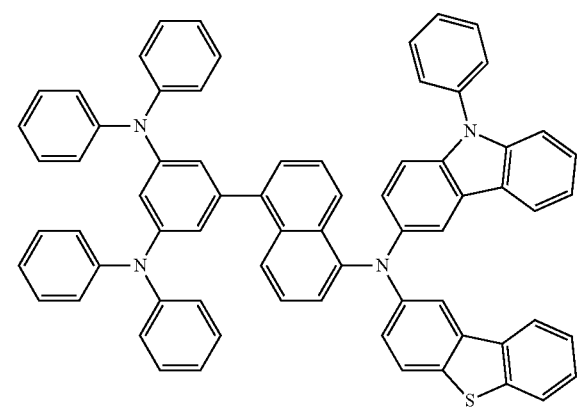
P-69
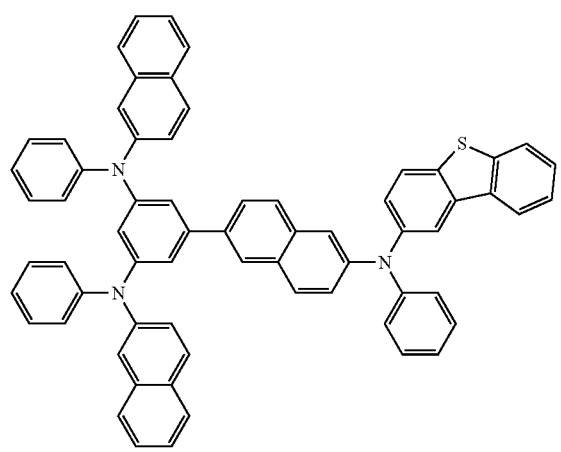
P-70
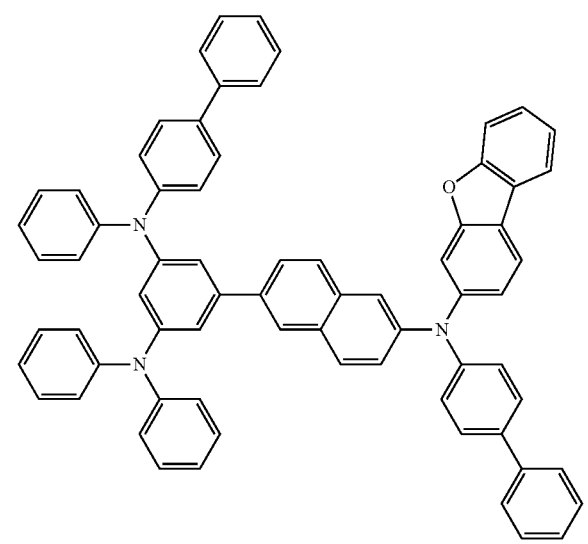

-continued
P-71
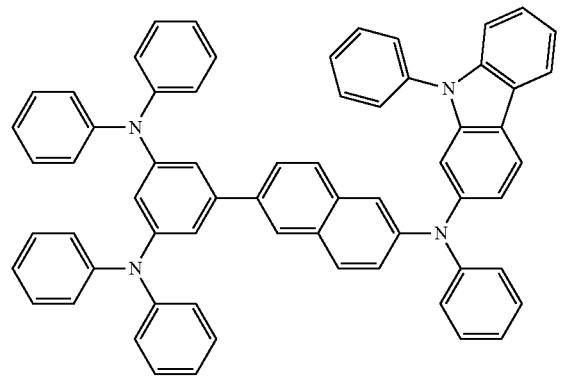
P-72
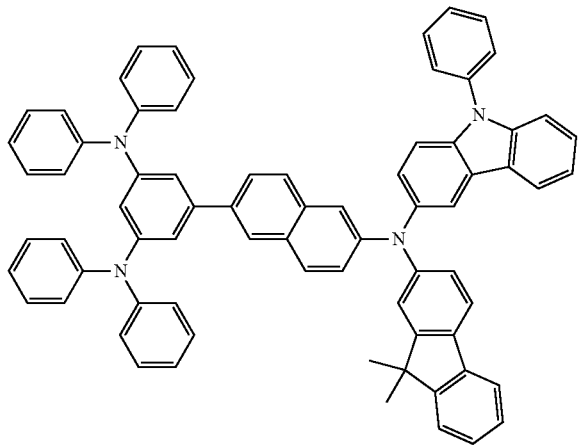
P-71
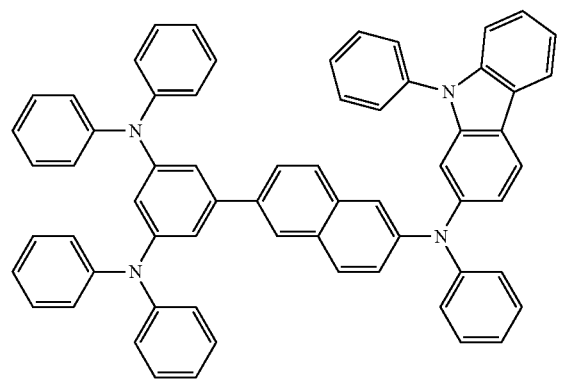
P-73
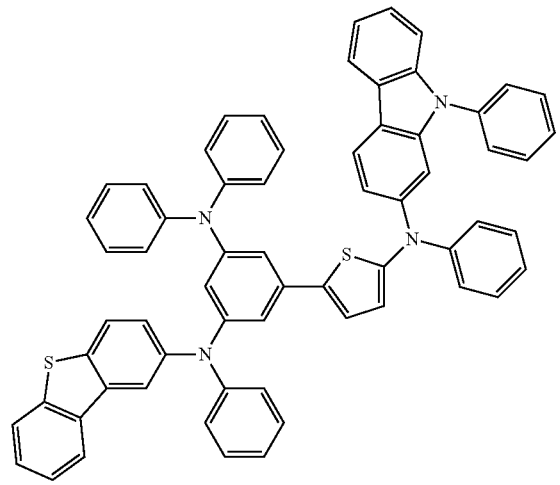
P-74
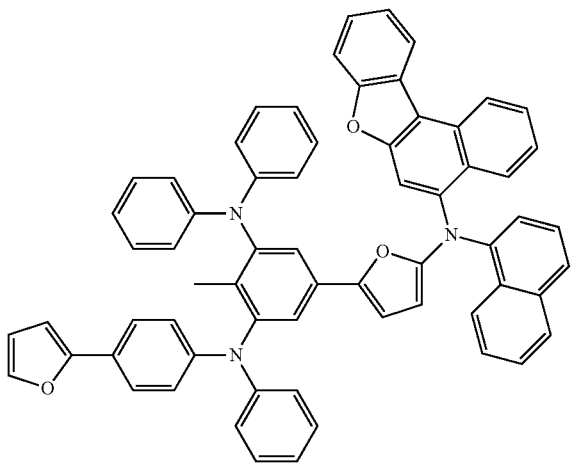

-continued
P-75
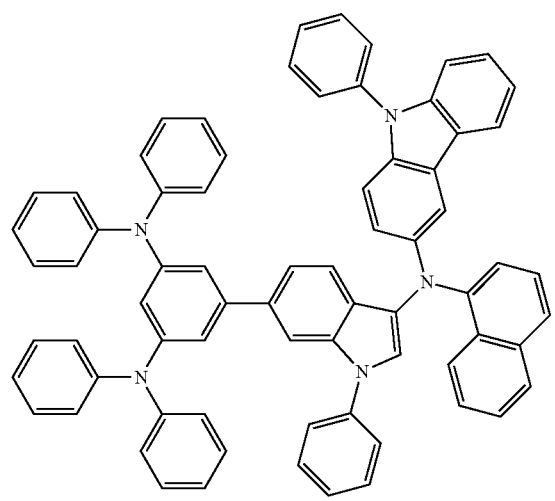
P-76
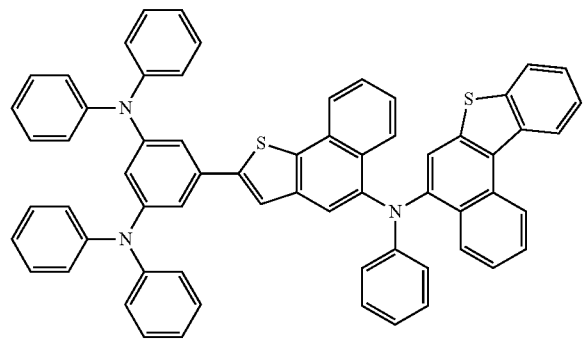
P-71
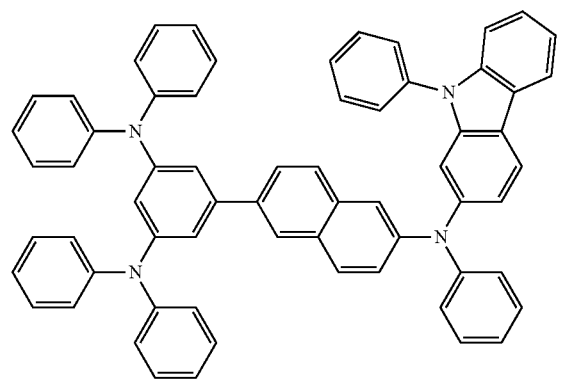
P-72
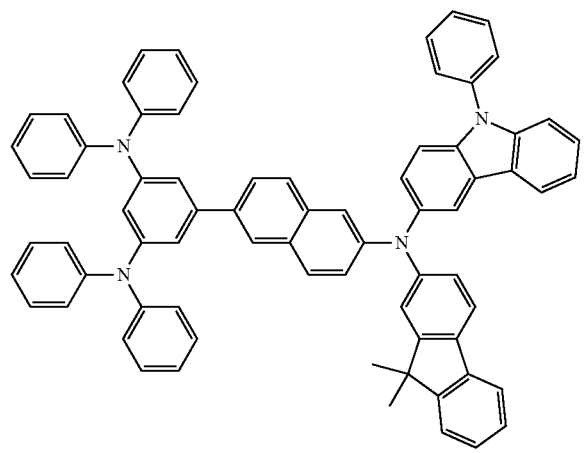
P-77
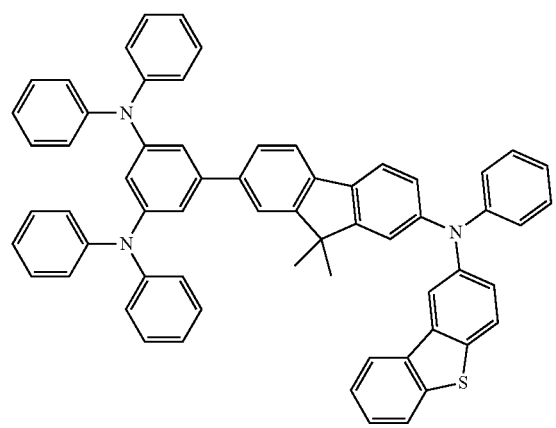
P-78
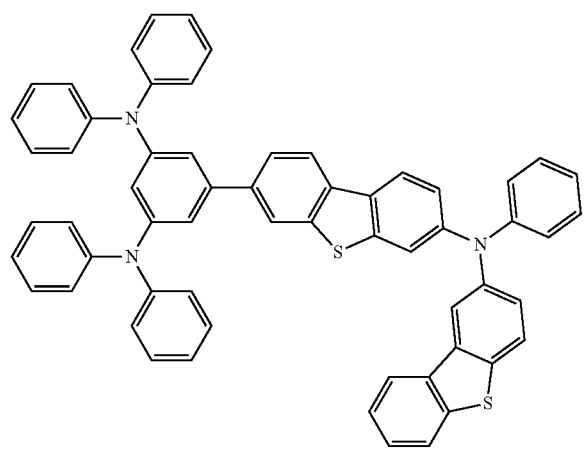

-continued
P-79
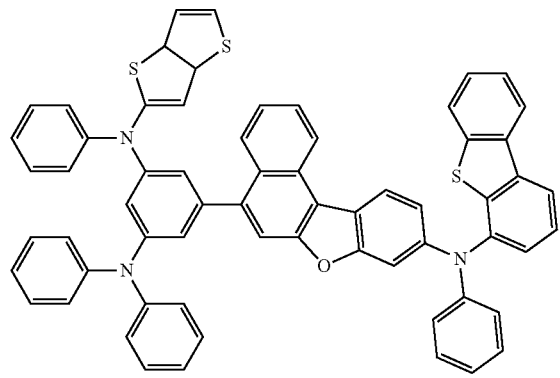
P-80
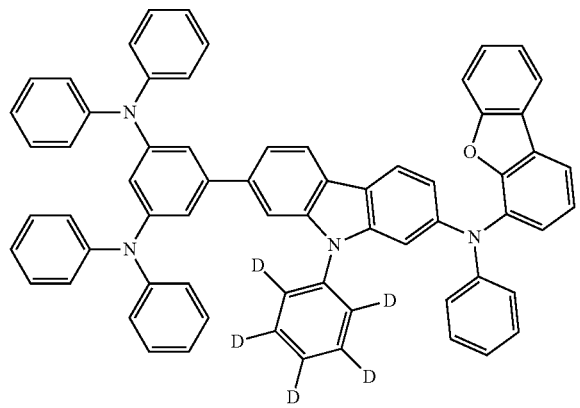
P-81
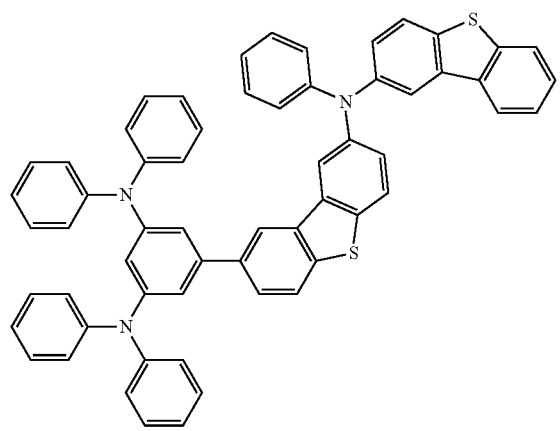
P-82
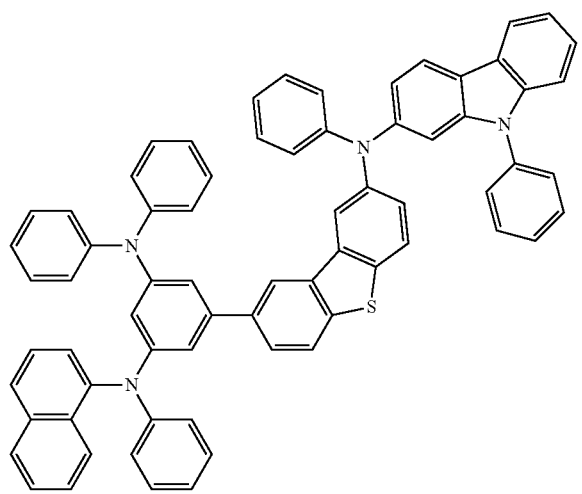
P-83
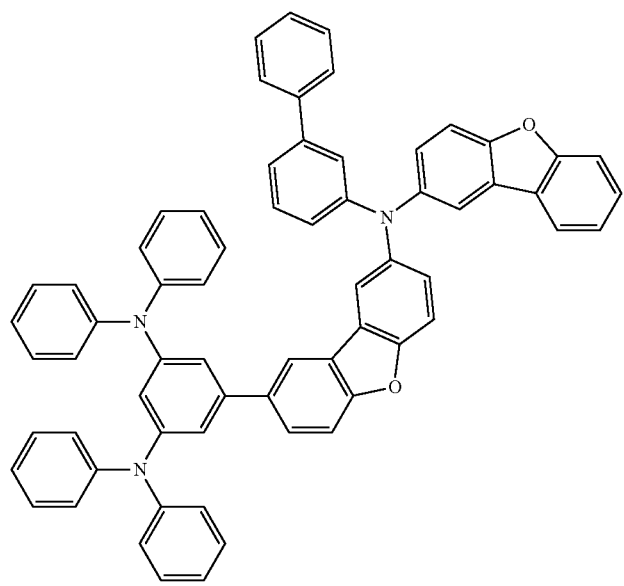

-continued
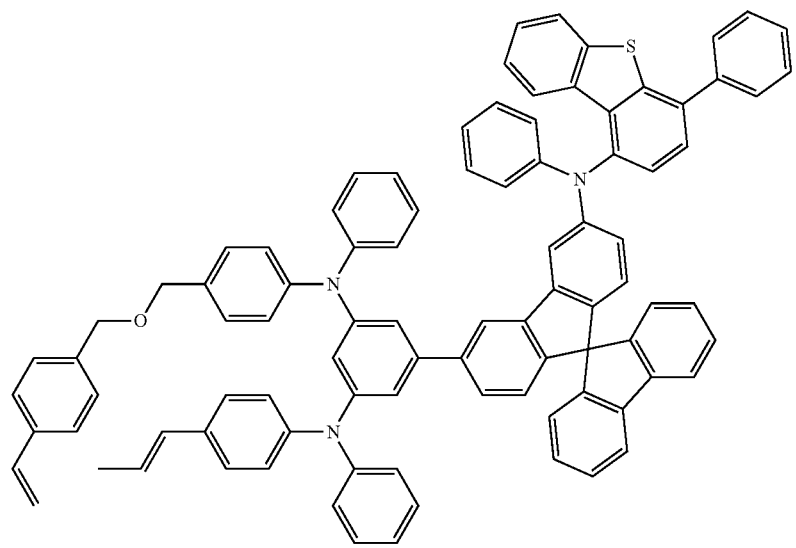
P-84
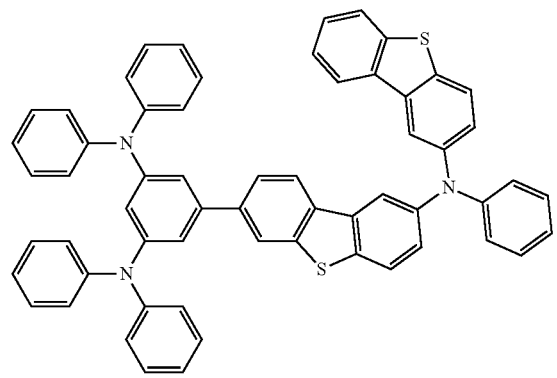
P-85
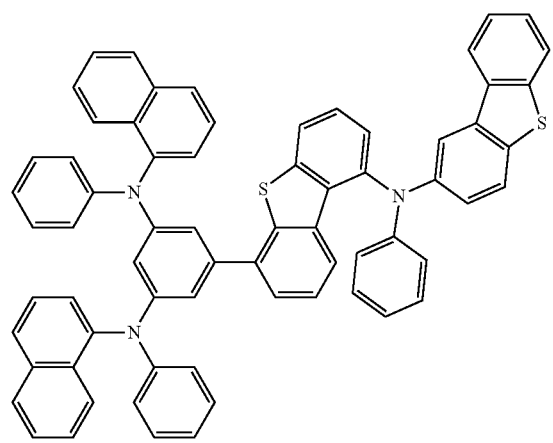
P-87
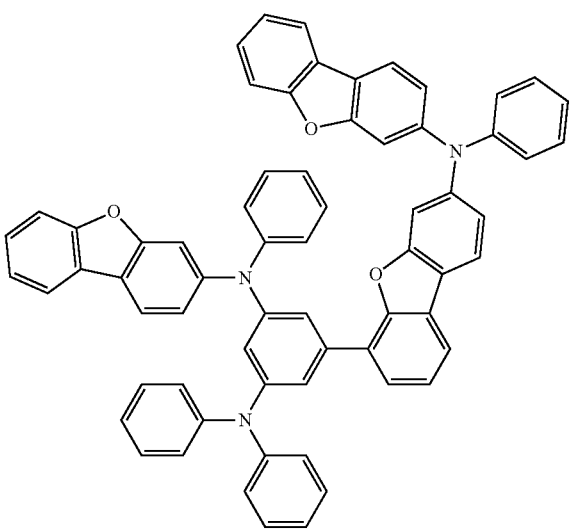
P-88

-continued
P-89
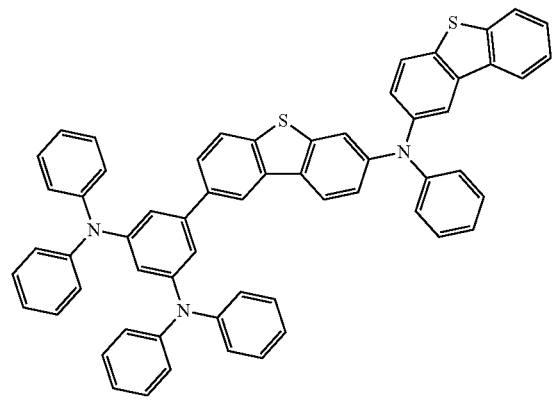
P-90
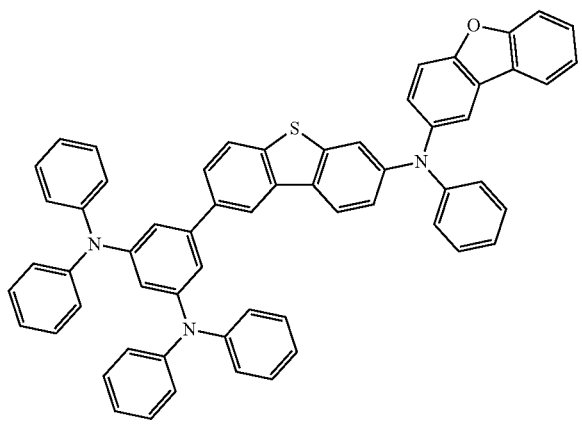
P-91
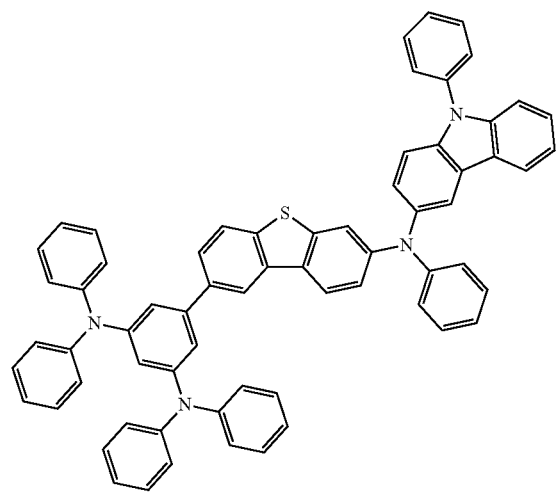
P-92
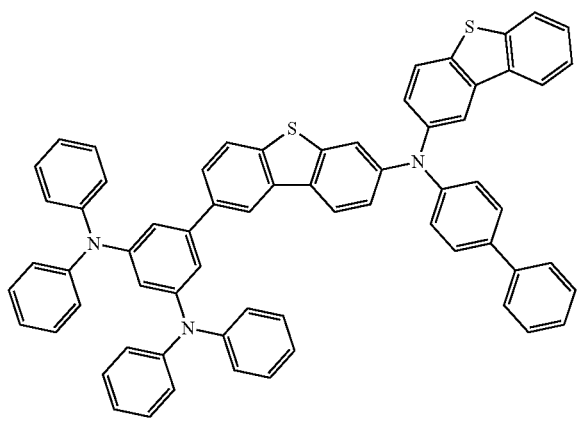
P-93
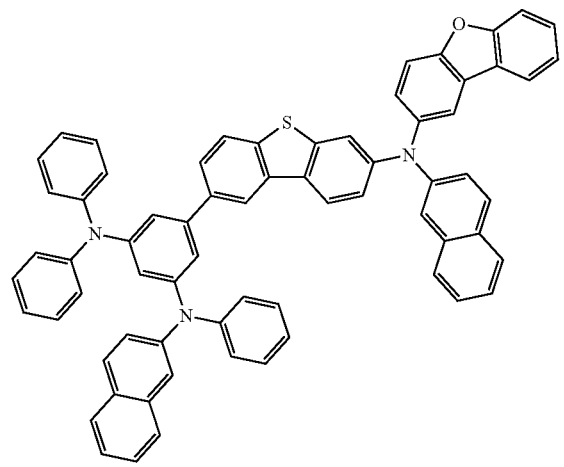
P-94
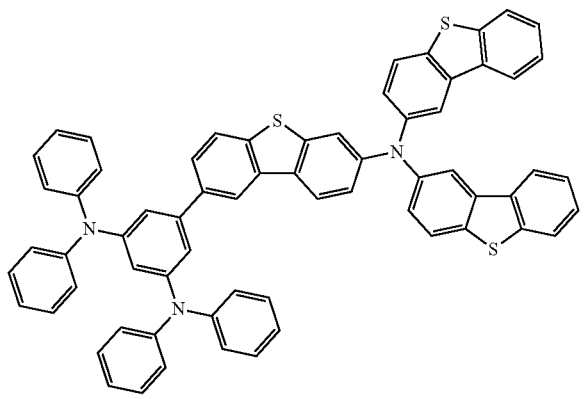

-continued
P-95
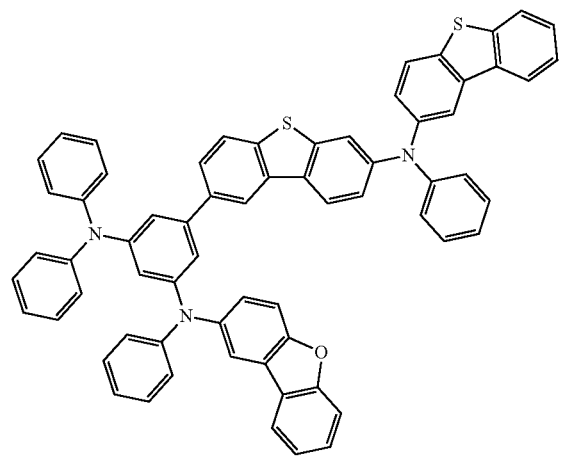
P-96
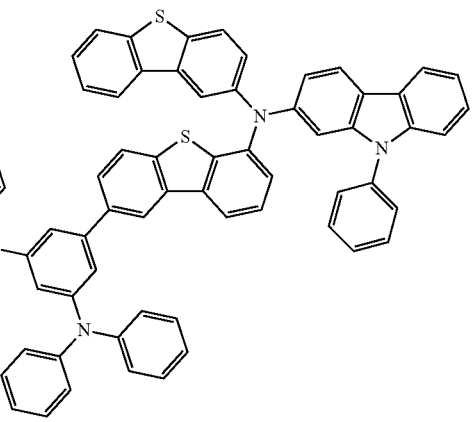
P-97
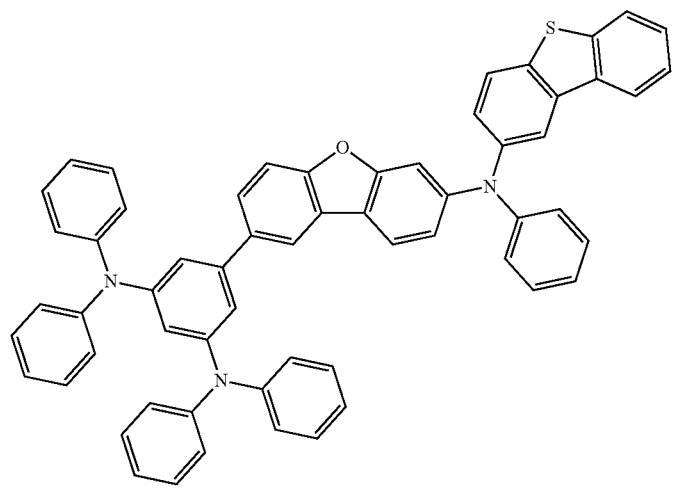
P-98
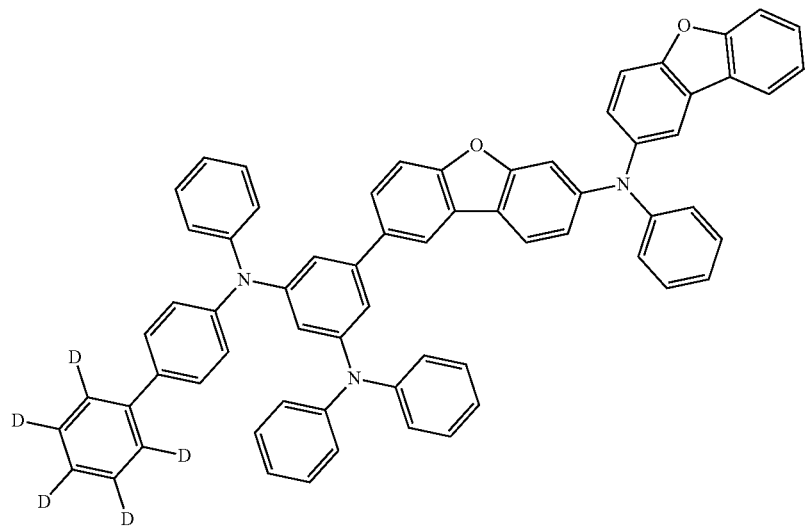

-continued
P-99
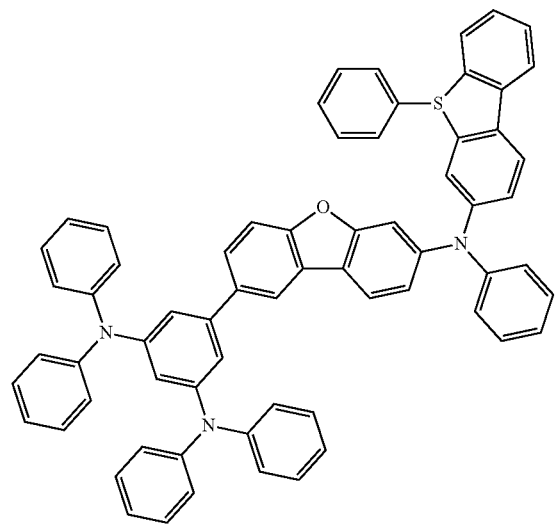
P-100
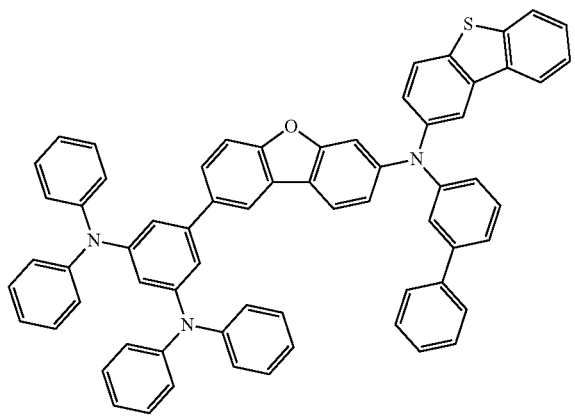
P-101
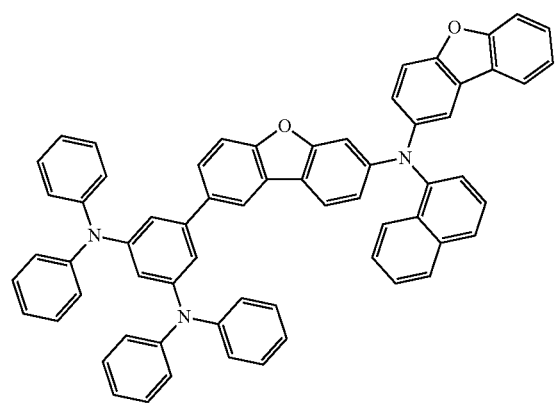
P-102
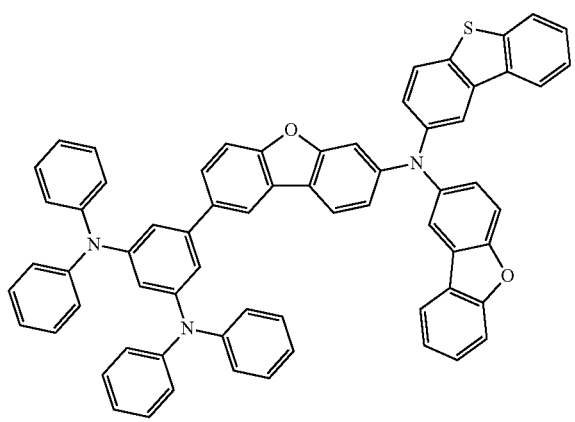
P-103
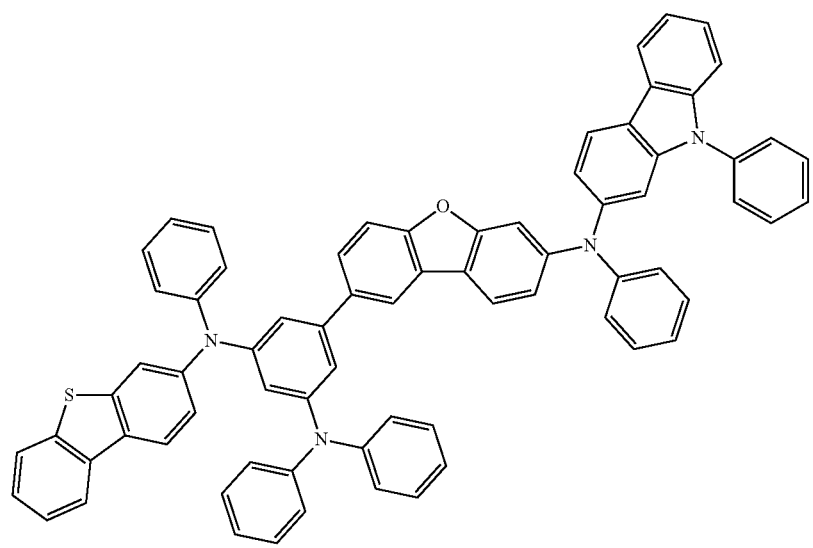

-continued
P-104
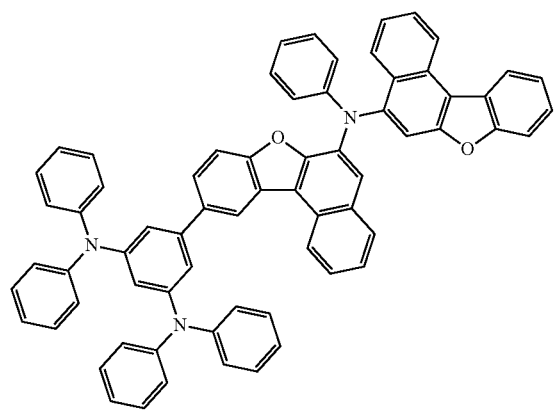
P-105
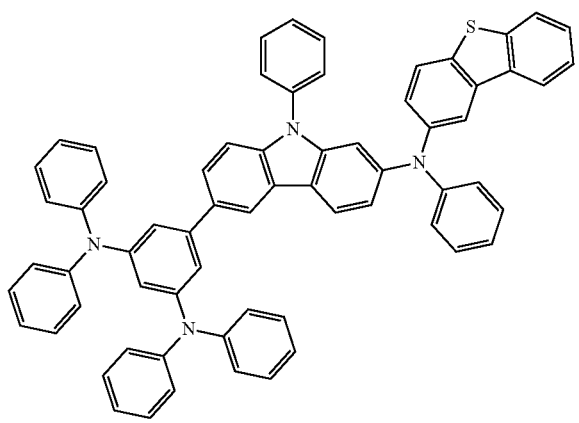
P-106
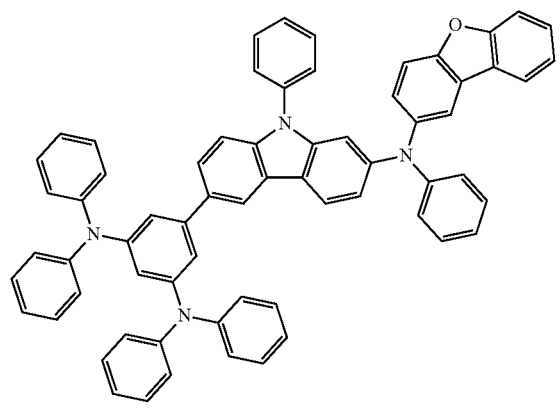
P-107
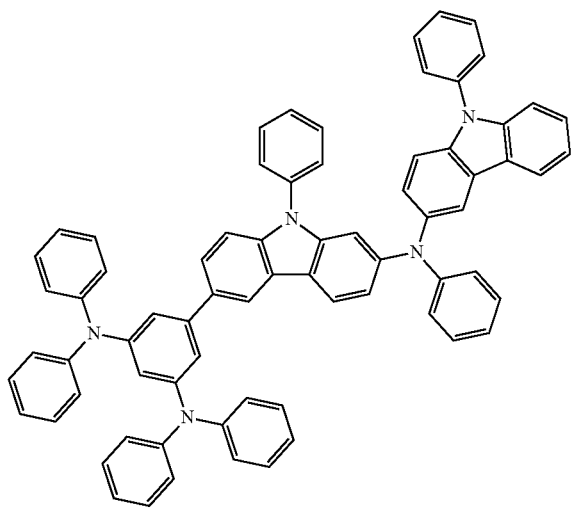
P-108
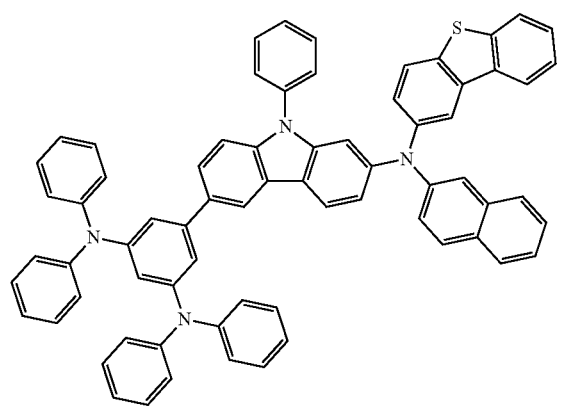
P-109
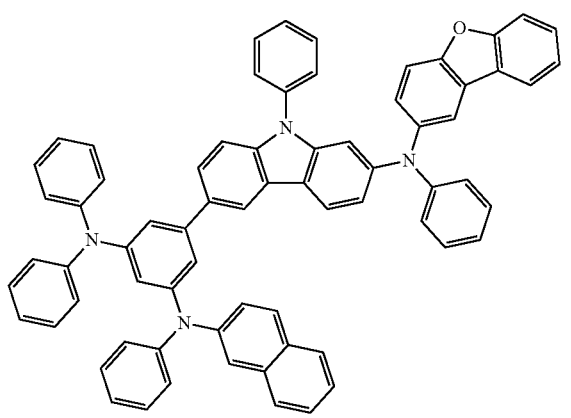

-continued

P-110

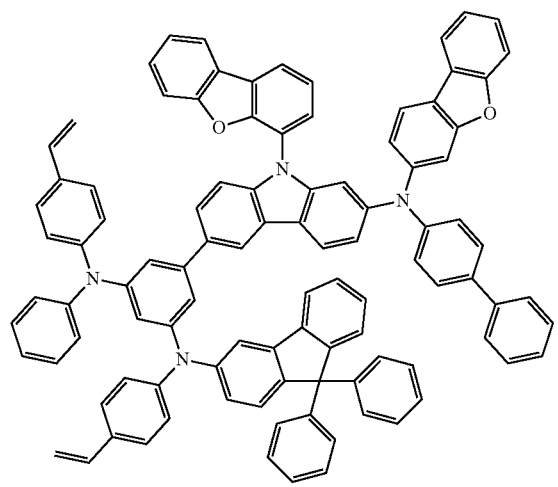

P-111

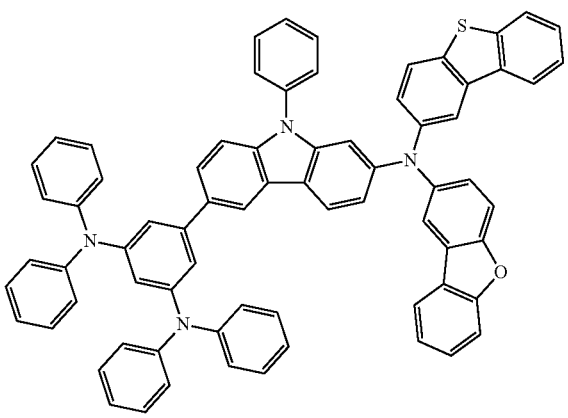

P-112

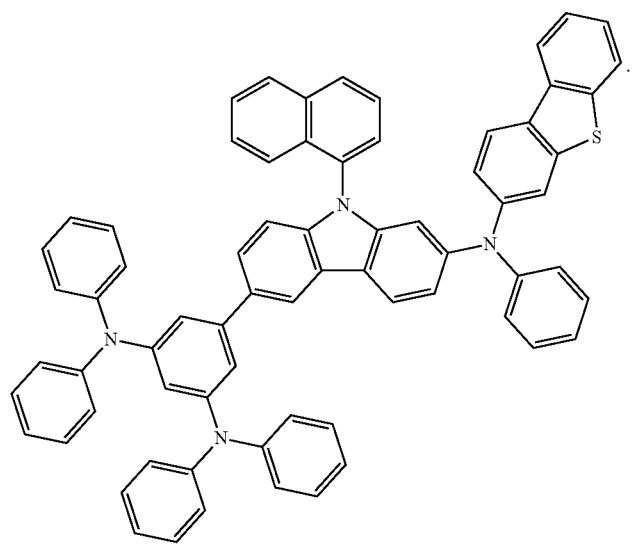

7. An organic electric element comprising:
a first electrode;
a second electrode; and
at least one organic material layer including a light emitting layer positioned between the first electrode and the second electrode,
wherein the organic material layer includes a light emitting auxiliary layer between the first electrode and light emitting layer,
wherein the light emitting layer contains a red phosphorescent emitter and the light emitting auxiliary layer contains a compound represented by Formula 1:

<Formula 1>

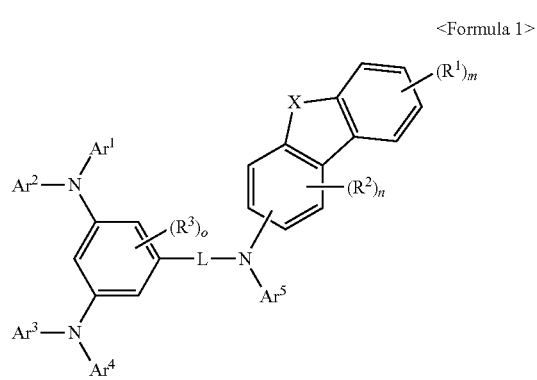

in Formula 1:
1) X is any one of S, O, and NAr$^6$;
2) Ar$^1$ to Ar$^6$ each are independently selected from the group consisting of a C$_6$-C$_{60}$ aryl group, a C$_2$-C$_{60}$ heterocyclic group containing at least one heteroatom of O, N, S, Si, a fluorenyl group, a fused ring group of a C$_6$-C$_{60}$ aromatic ring and a C$_3$-C$_{60}$ aliphatic ring, a C$_1$-C$_{50}$ alkyl group, a C$_2$-C$_{20}$ alkenyl group, a C$_2$-C$_{20}$ alkynyl group, a C$_1$-C$_{30}$ alkoxy group, and a C$_6$-C$_{30}$ aryloxy group;
3) R$^1$ to R$^3$ each are independently selected from the group consisting of deuterium, tritium, halogen, a cyano group, a nitro group, a C$_6$-C$_{60}$ aryl group, a fluorenyl group, a C$_2$-C$_{60}$ heterocyclic group containing at least one heteroatom selected from the group consisting of O, N, S, Si, and P, a fused ring group of a C$_3$-C$_{60}$ aliphatic ring and a C$_6$-C$_{60}$ aromatic ring, a C$_1$-C$_{50}$ alkyl group, a C$_2$-C$_{20}$ alkenyl group, a C$_2$-C$_{20}$ alkynyl group, a C$_1$-C$_{30}$ alkoxy group, and a C$_6$-C$_{30}$ aryloxy group, in the presence of a plurality of R$^1$'s and R$^2$'s, at least one pair of neighboring R$^1$'s and R$^2$'s independently may bind to each other to form a ring, provided that R$^1$'s and R$^2$'s forming no ring are the same as defined above;
4) m is an integer of 0 to 4, and when m is an integer of 2 or greater, R$^1$'s are the same as or different from each other;
5) n and o each are independently an integer of 0 to 3, and when n and o each are an integer of 2 or greater, R$^2$'s and R$^3$'s each are the same as or different from each other; and
6) L is represented by one of Formula L1 to L6 below:

<Formula L1>

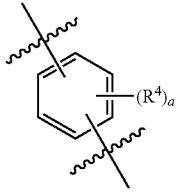

<Formula L2>

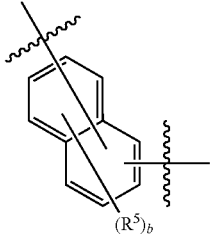

<Formula L3>

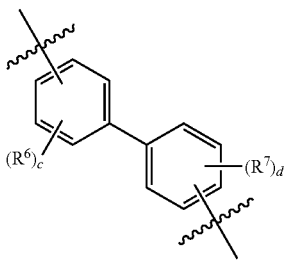

<Formula L4>

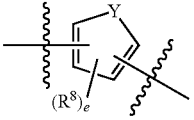

<Formula L5>

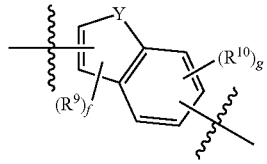

<Formula L6>

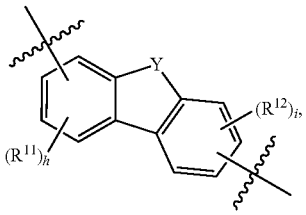

wherein in Formulas L1 to L6:
7) Y is any one of S, O, NAr$^7$, and CAr$^8$Ar$^9$;
8) Ar$^7$ to Ar$^9$ each are independently selected from the group consisting of a C$_6$-C$_{60}$ aryl group, a fluorenyl group, a C$_2$-C$_{60}$ heterocyclic group containing at least one heteroatom of O, N, S, Si, and P, a fused ring group of a C$_6$-C$_{60}$ aromatic ring and a C$_3$-C$_{60}$ aliphatic ring, a C$_1$-C$_{50}$ alkyl group, a C$_2$-C$_{20}$ alkenyl group, a C$_2$-C$_{20}$ alkynyl group, a C$_1$-C$_{30}$ alkoxy group, and a C$_6$-C$_{30}$ aryloxy group, and Ar$^8$ to Ar$^9$ may bind to each other to form a spiro compound together with a carbon atom to which they are bound;
9) R$^4$ to R$^{12}$ each are independently selected from the group consisting of deuterium, tritium, halogen, a cyano group, a nitro group, an aryl group, a fluorenyl group, a C$_2$-C$_{60}$ heterocyclic group containing at least one heteroatom selected from the group consisting of O, N, S, Si, and P, a fused ring group of a C$_3$-C$_{60}$ aliphatic ring and a C$_6$-C$_{60}$ aromatic ring, a C$_1$-C$_{50}$ alkyl group, a C$_2$-C$_{20}$ alkenyl group, a C$_2$-C$_{20}$ alkynyl group, a C$_1$-C$_{30}$ alkoxy group, and a C$_6$-C$_{30}$ aryloxy group, in the presence of a plurality of R$^{10}$'s and R$^{12}$'s, at least one pair of neighboring R$^{10}$'s, R$^{11}$'s, and R$^{12}$'s independently may bind to each other to form a ring, provided that R$^{10}$'s to R$^{12}$'s forming no ring are the same as defined above;
10) a, c, and d each are independently an integer of 0 to 4, and when a, c, and d are each an integer of 2 or greater, R$^4$'s, R$^6$'s, and R$^7$'s are the same as or different from each other;
11) b is an integer of 0 to 8, and when b is an integer of 2 or greater, R$^5$'s are the same as or different from each other;
12) e is an integer of 0 to 2, and when e is an integer of 2 or greater, R$^8$'s are the same as or different from each other;
13) f is an integer of 0 or 1; and
14) g, h, and i each are independently an integer of 0 to 3, and when g, h, and i are each an integer of 2 or greater, R$^{10}$'s to R$^{12}$'s are the same as or different from each other,
wherein the aryl group, fluorenyl group, heterocyclic group, fused ring group, alkyl group, alkenyl group, alkynyl group, alkoxy group, and aryloxy group of $Ar^1$ to $Ar^6$, $R^1$ to $R^3$, $Ar^7$ to $Ar^9$ and $R^4$ to $R^{12}$ each may be further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group, and when the substituents are adjacent to each other, the substituents may bind to each other to form a ring, with the proviso that, if X is O or S, L is not L1.

8. The organic electric element of claim 7, wherein the compound is a single compound or a mixture of two or more compounds.

9. The organic electric element of claim 7, wherein the organic material layer is formed by a spin coating process, a nozzle printing process, an inkjet printing process, a slot coating process, a dip coating process, or a roll-to-roll process.

10. An electronic device comprising:
a display device comprising the organic electric element of claim 7; and
a controller for driving the display device.

11. The electronic device of claim 10, wherein the organic electric element is one of an organic light emitting diode, an organic solar cell, an organic photo conductor, an organic transistor, and an element for a monochromatic or white illumination.

12. The organic electric element of claim 7, wherein Formula 1 is any one of the compounds below:

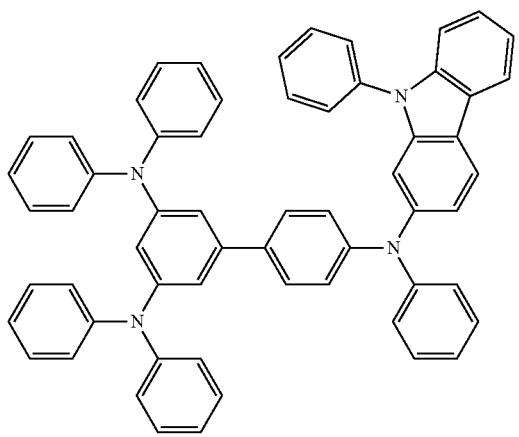

P-4

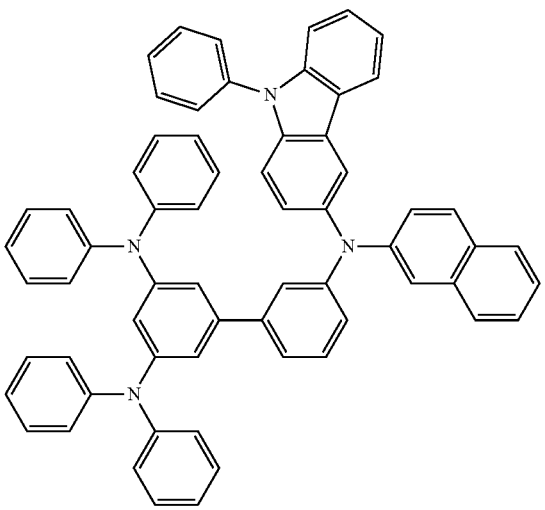

P-17

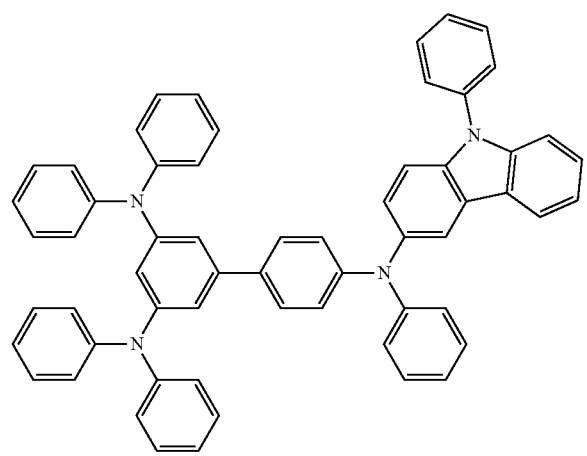

P-3

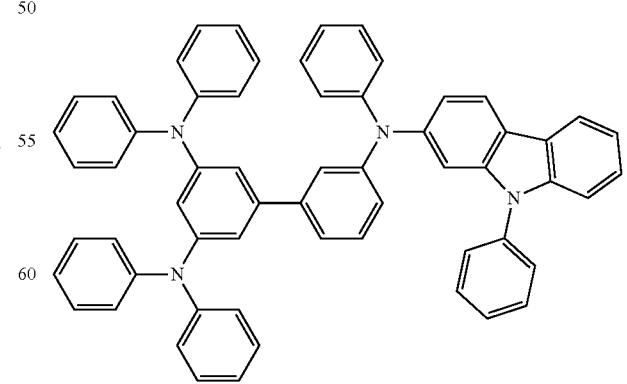

P-18

-continued
P-19
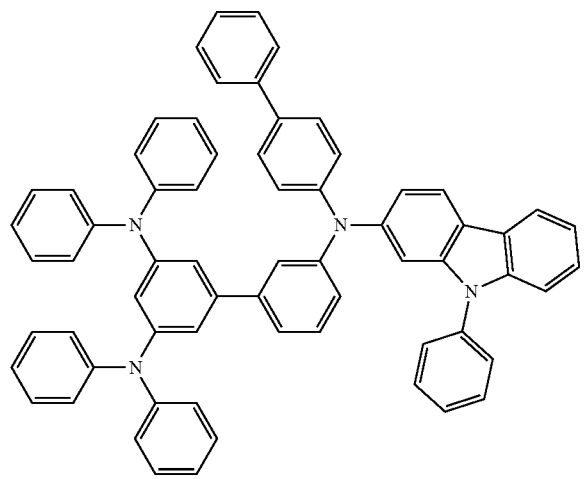
P-20
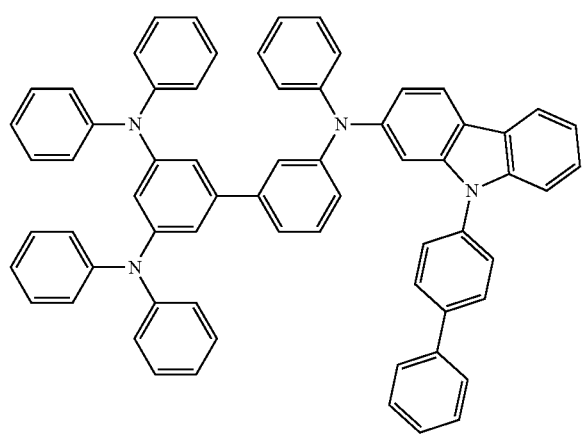
P-21
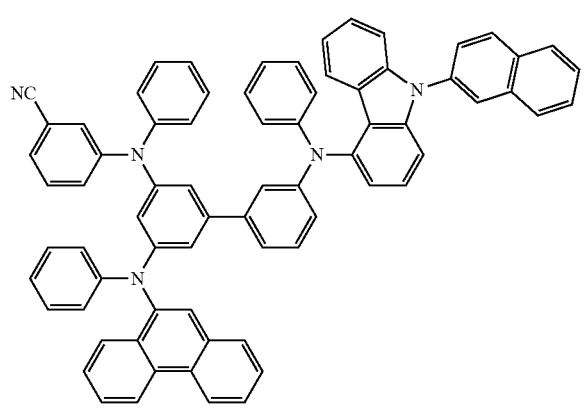
-continued
P-25
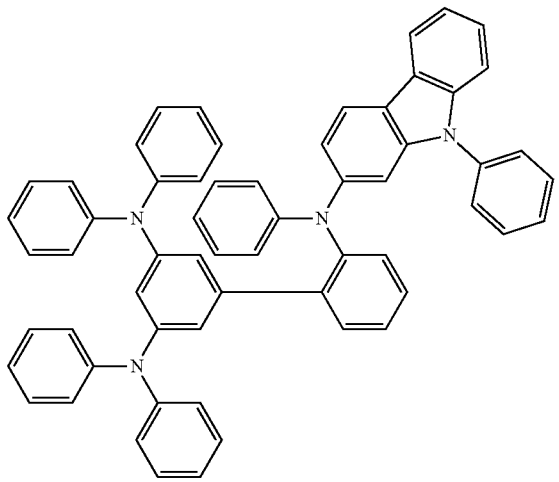
P-32
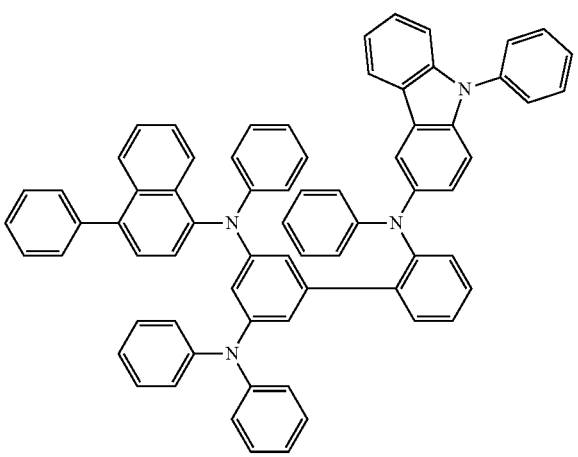
P-37

-continued
P-38
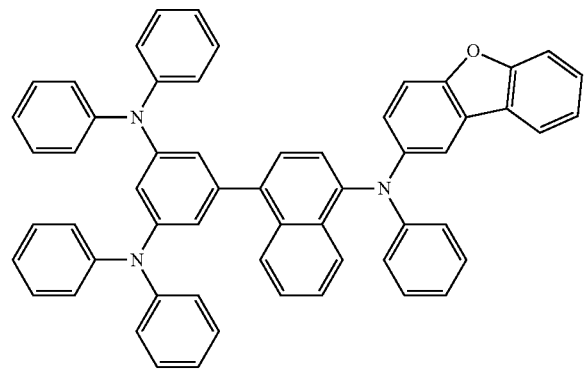
P-39
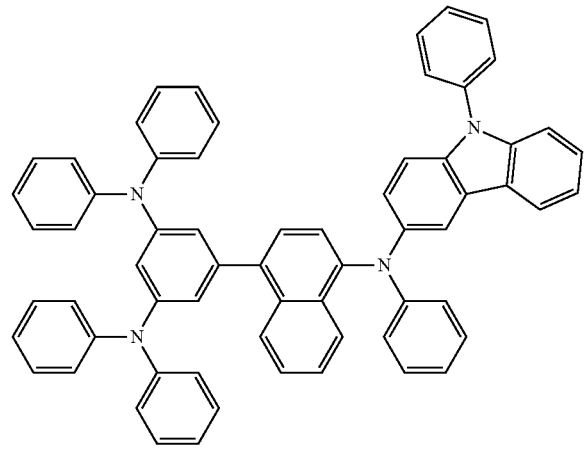
P-40
P-41
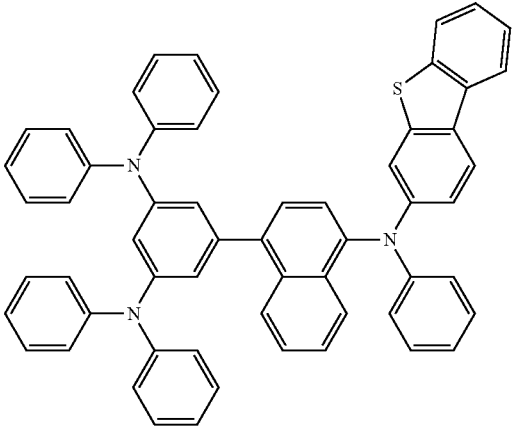
P-42
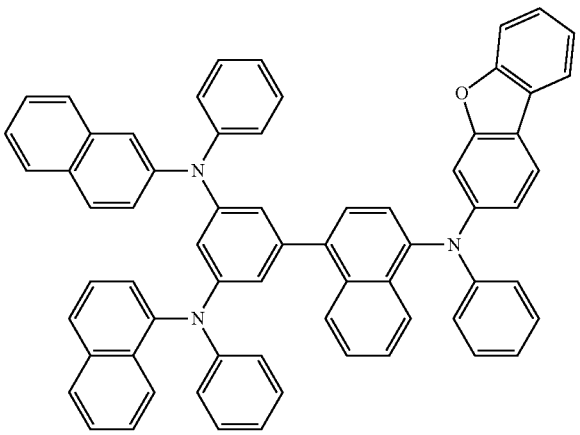
P-43
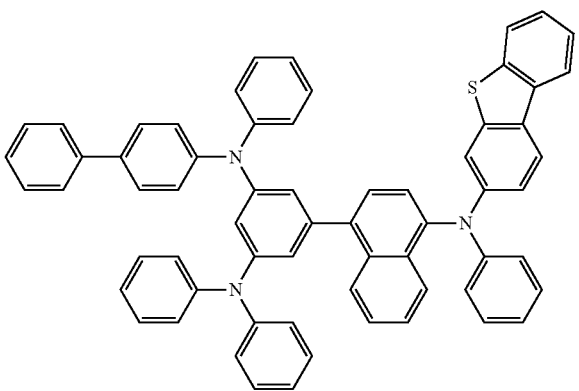
P-44
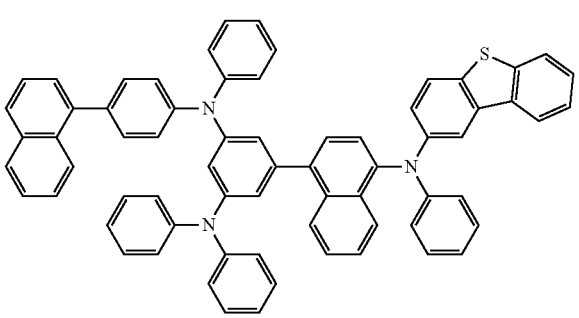

-continued
P-45
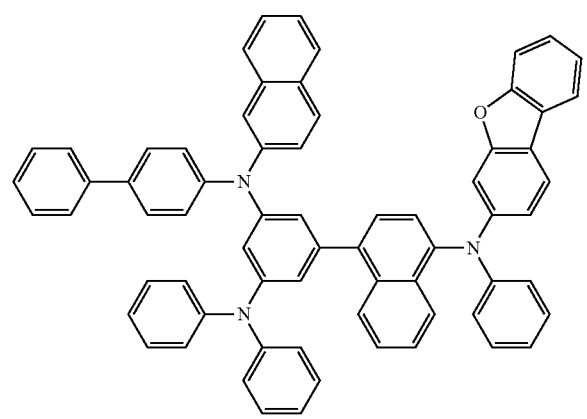
P-48
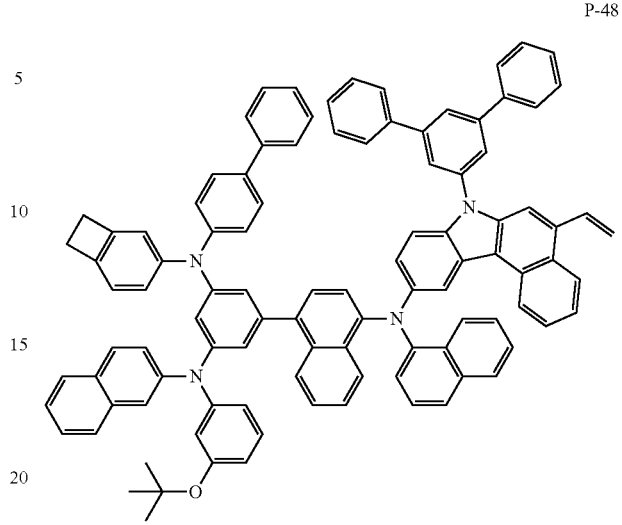
P-46
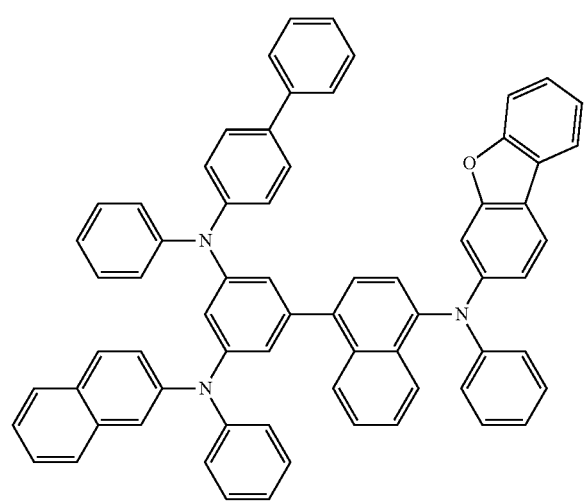
P-49
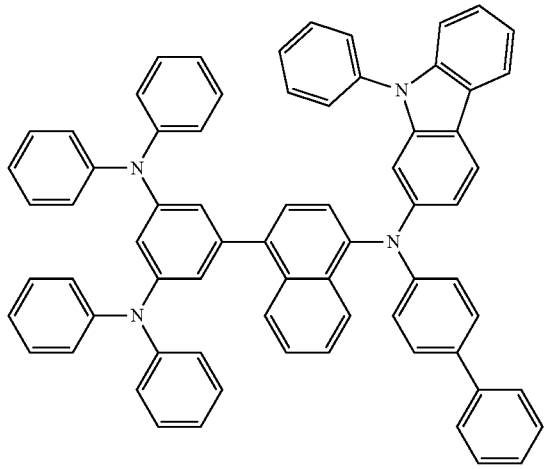
P-47
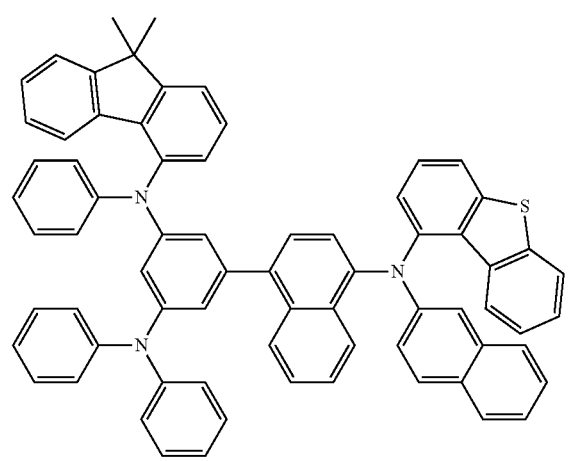
P-50
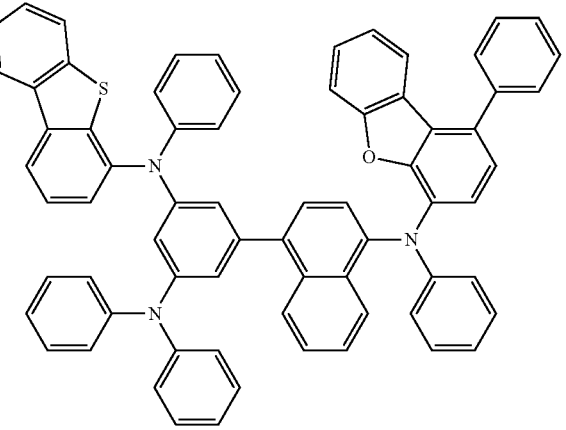

P-51
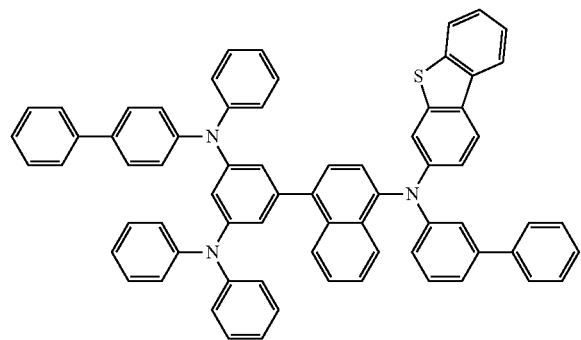
P-52
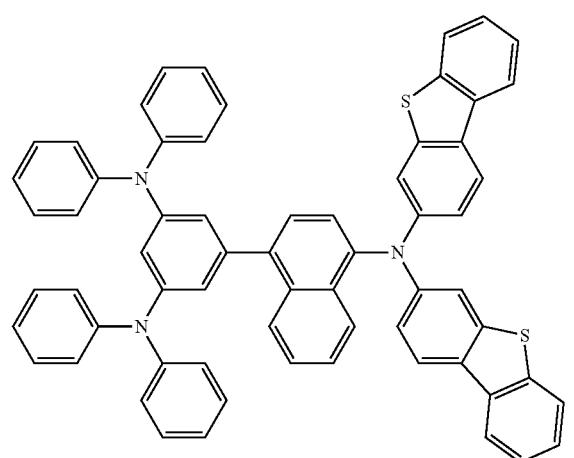
P-53
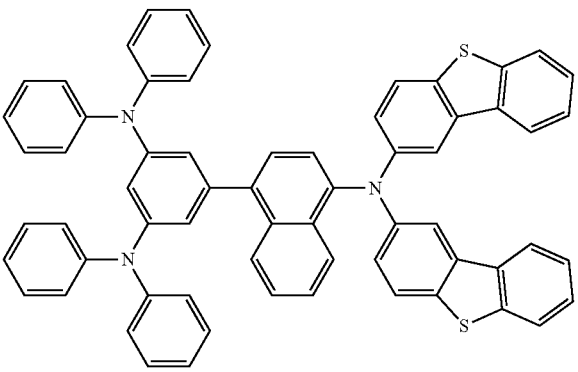
P-54
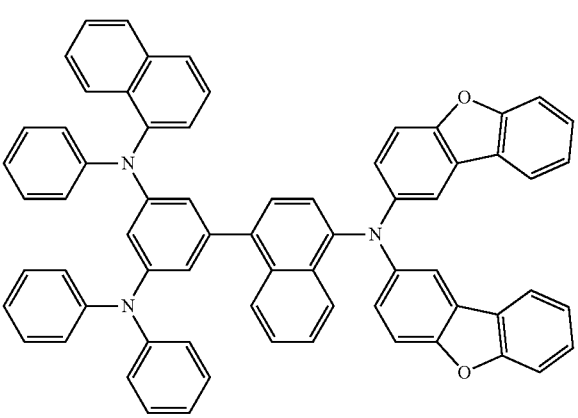
P-55
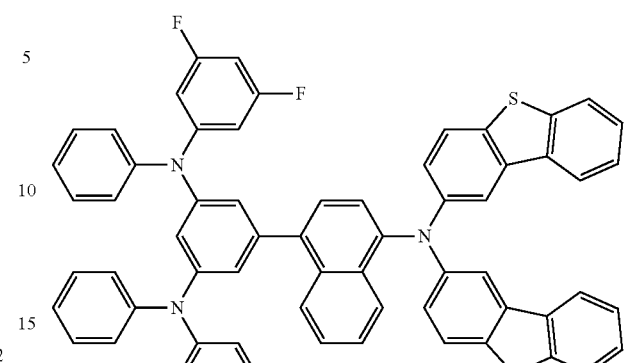
P-56
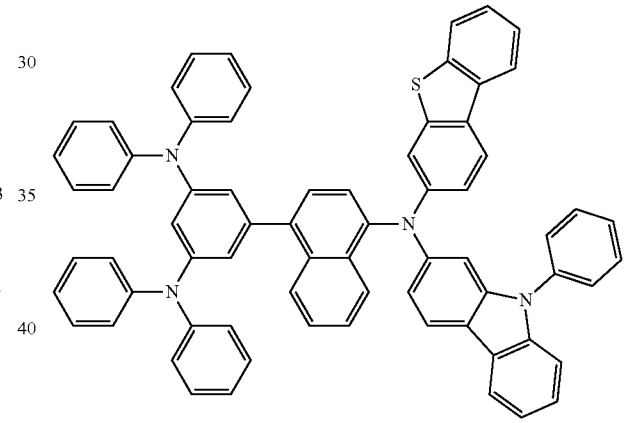
P-57
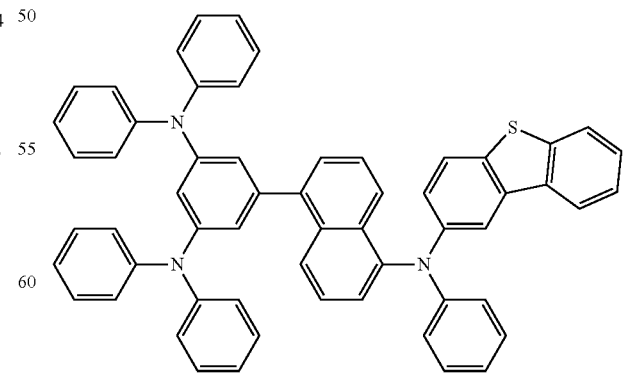

P-58
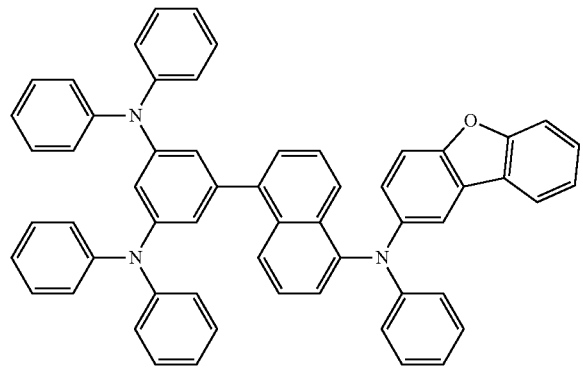
P-59
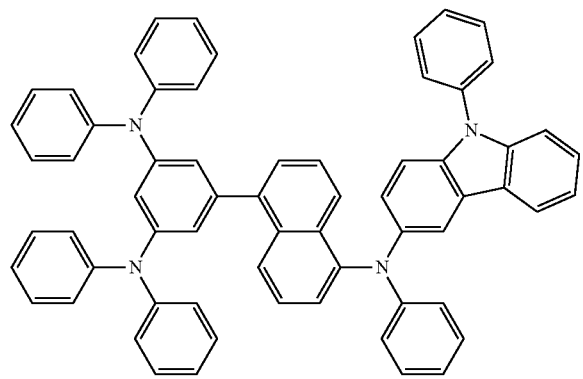
P-60
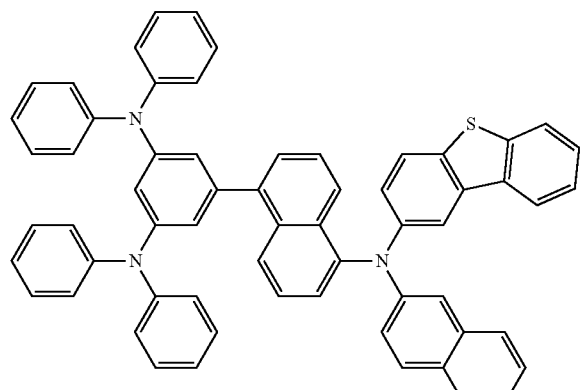
P-61
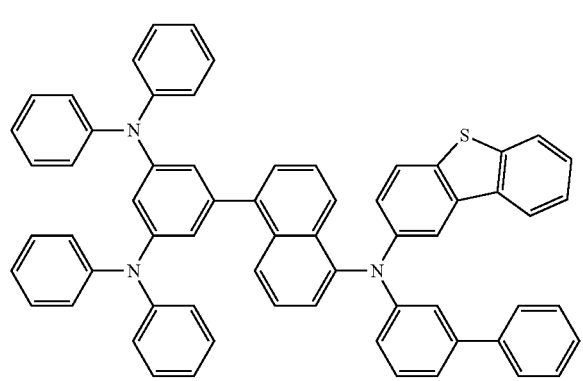
P-62
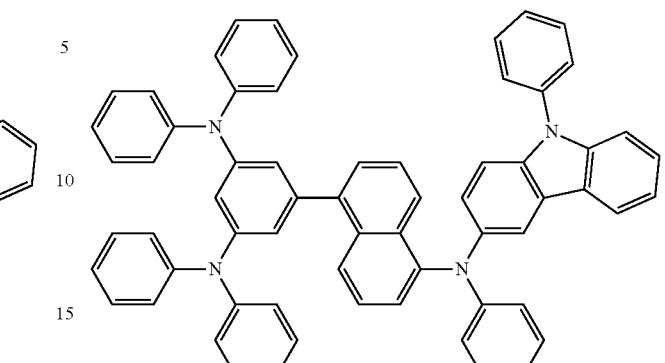
P-63
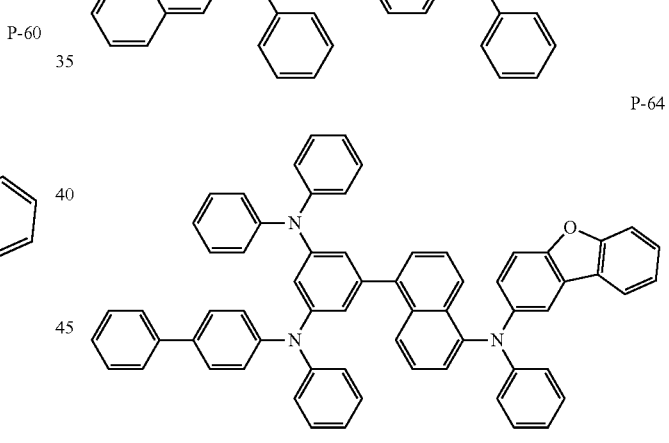
P-64
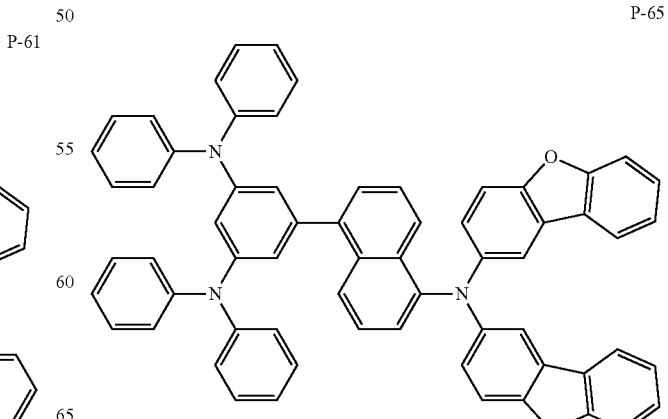
P-65

P-66
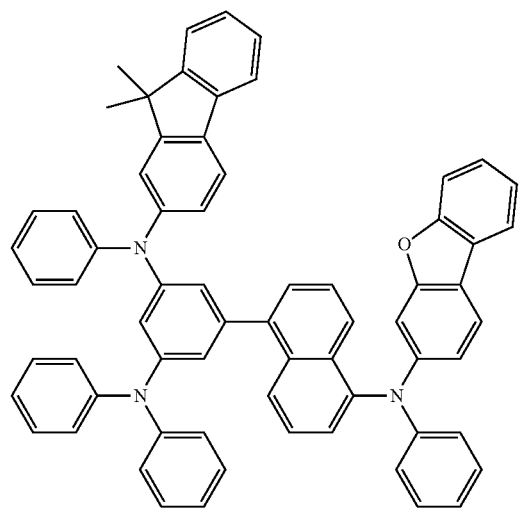
P-67
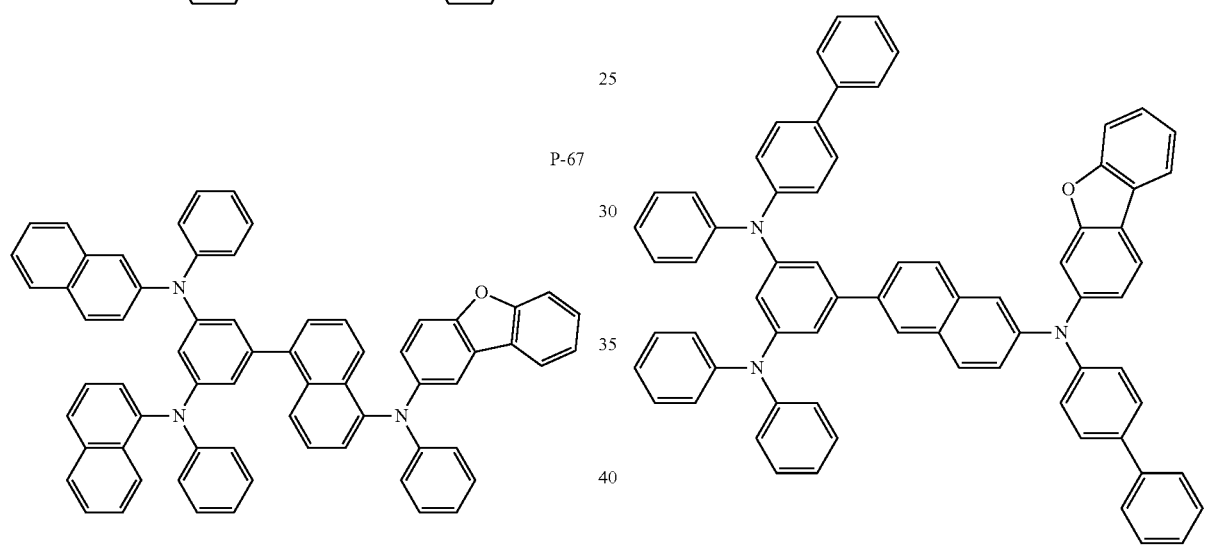
P-68
P-69
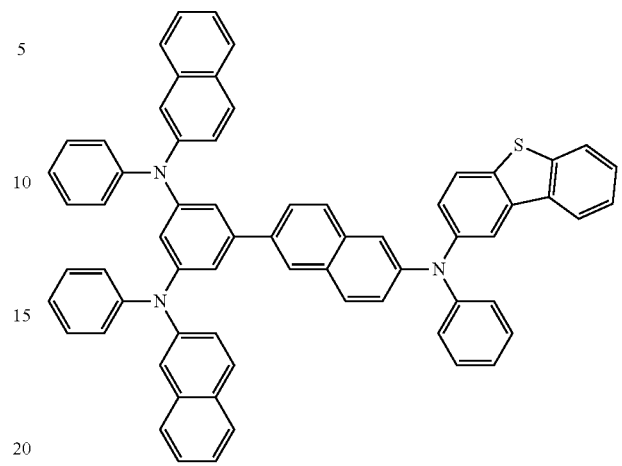
P-70
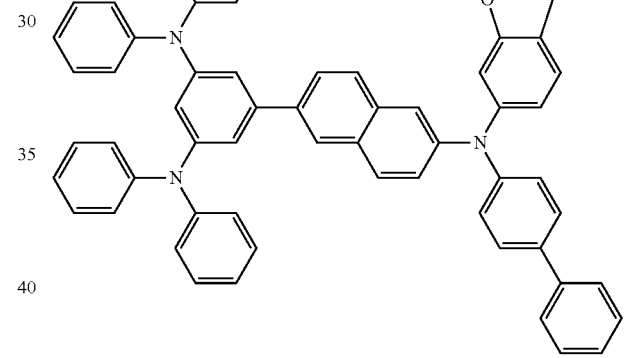
P-71
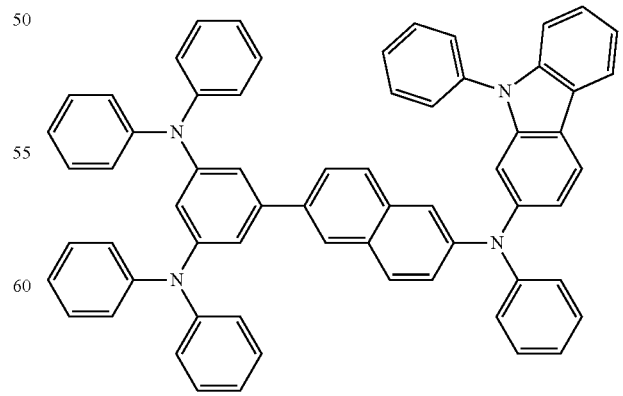

-continued
P-73
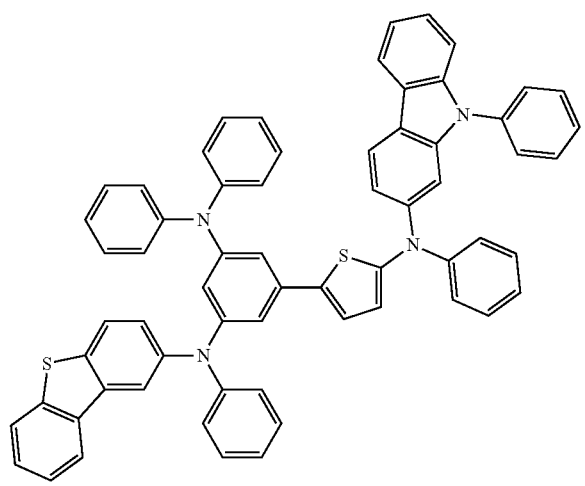
P-74
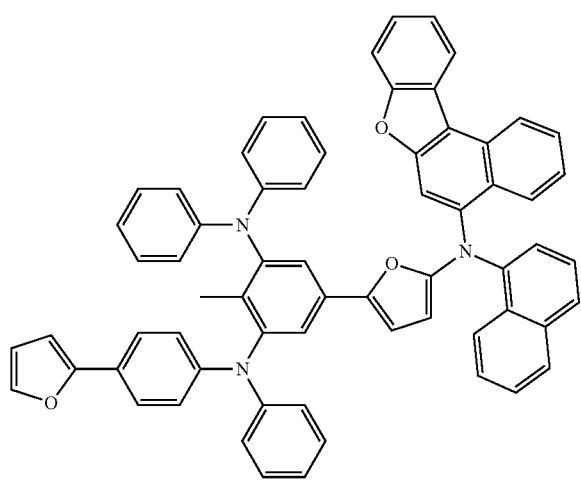
P-75
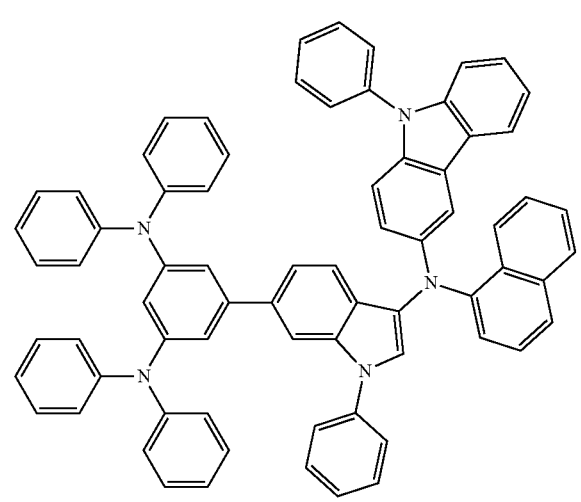
-continued
P-76
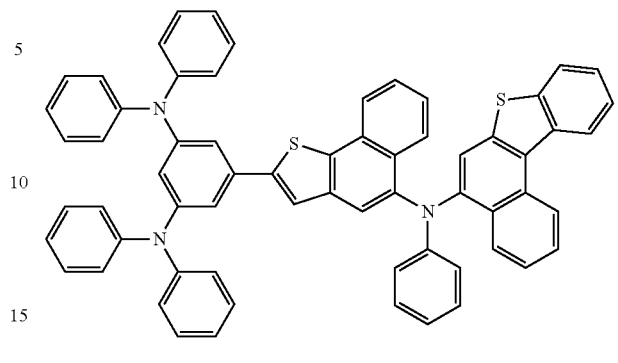
P-77
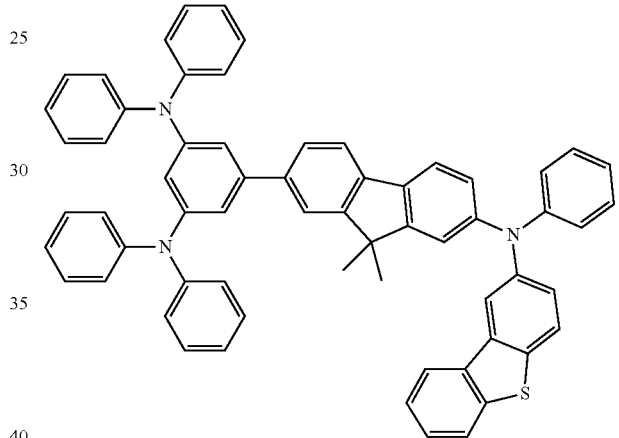
P-78
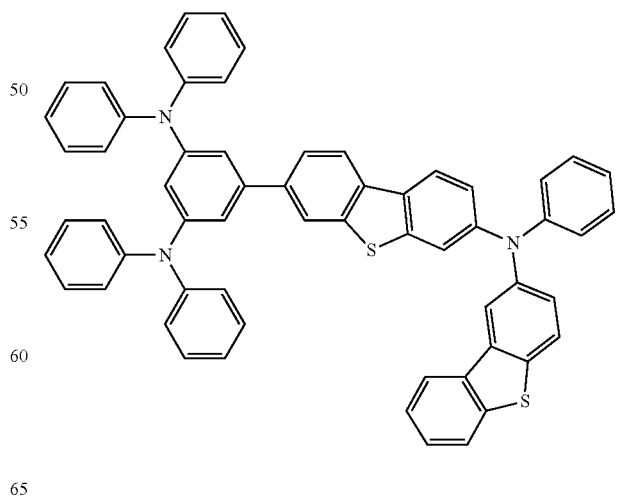

P-79
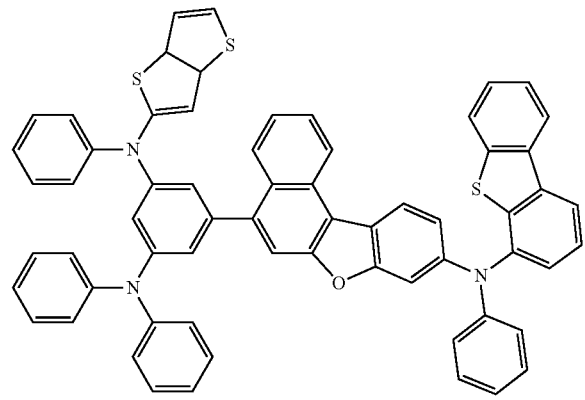
P-82
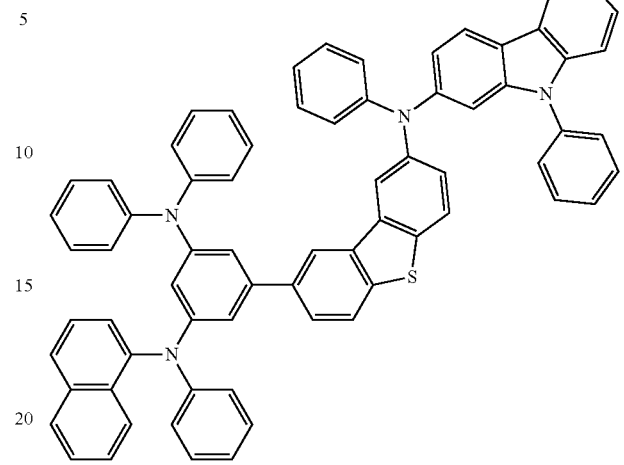
P-80
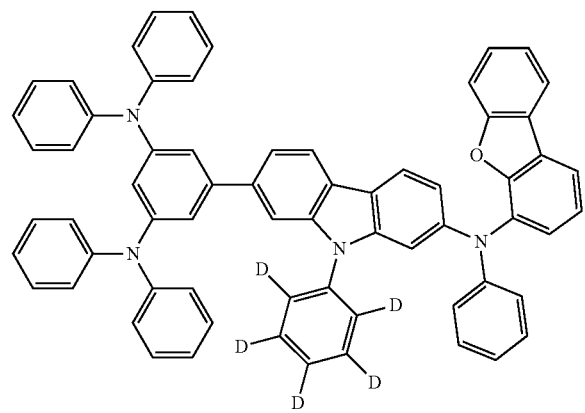
P-83
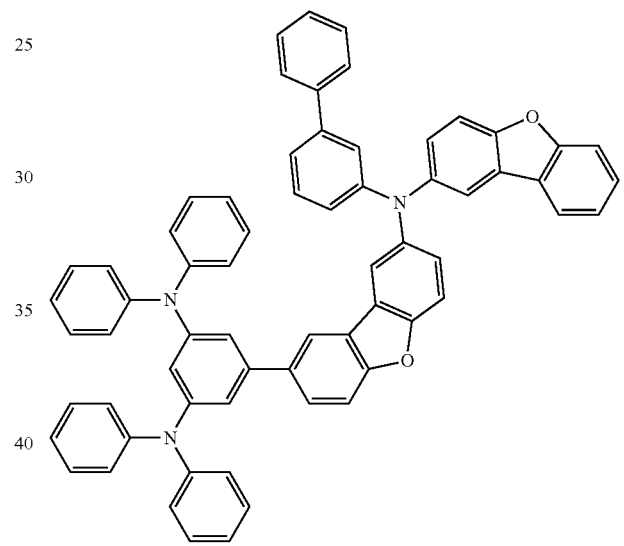
P-81
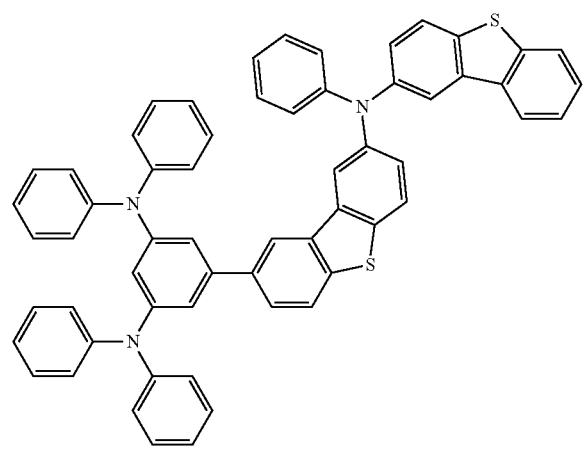
P-84
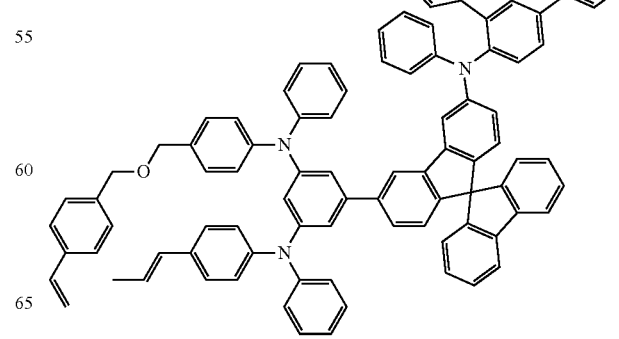

-continued
P-85
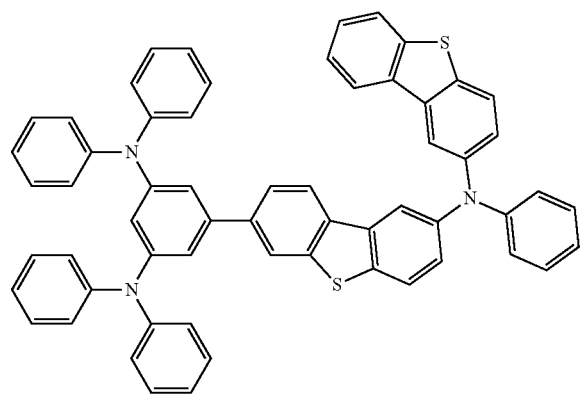
P-87
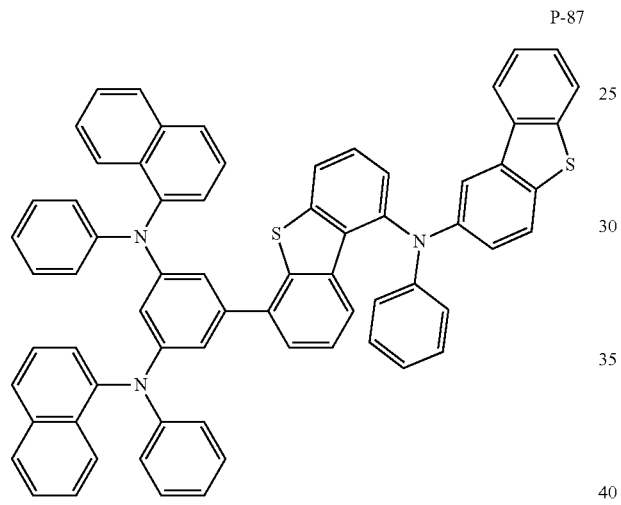
P-88
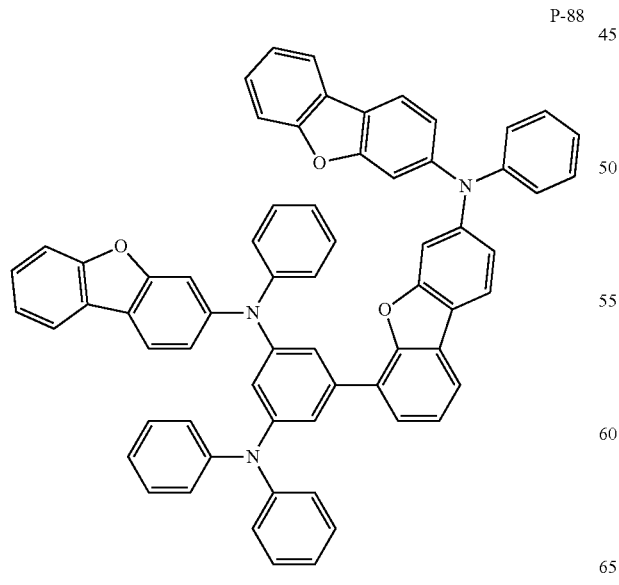
-continued
P-89
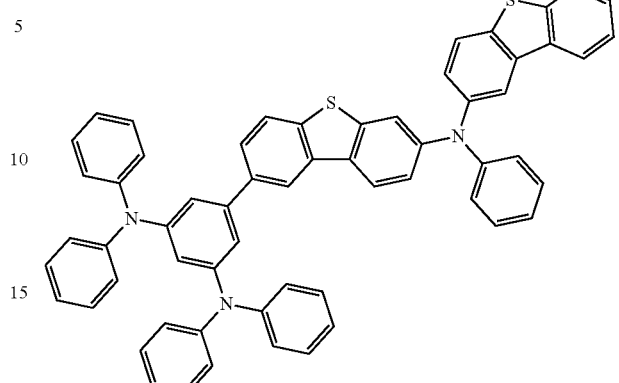
P-90
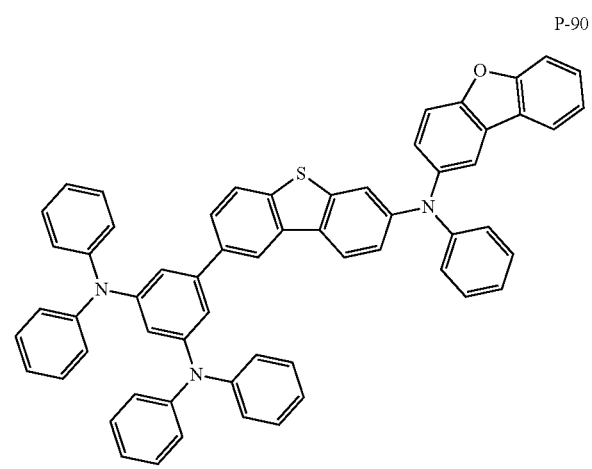
P-91
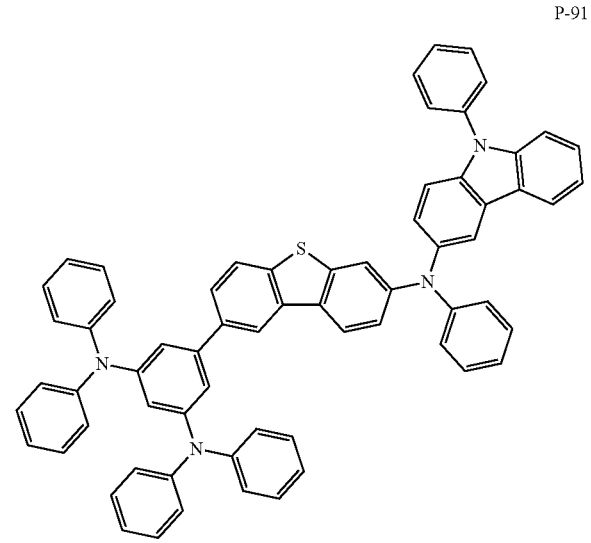

P-92
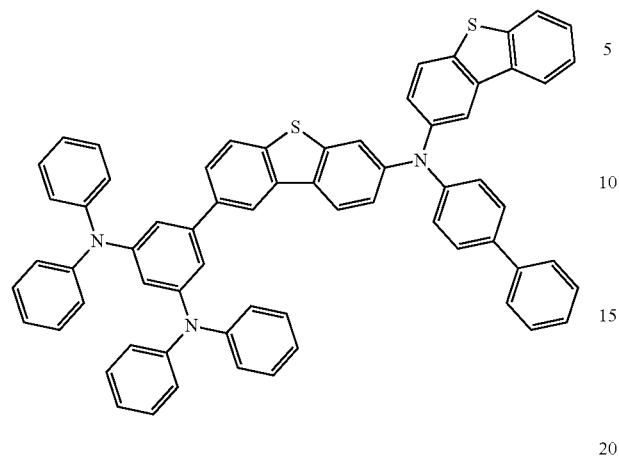
P-95
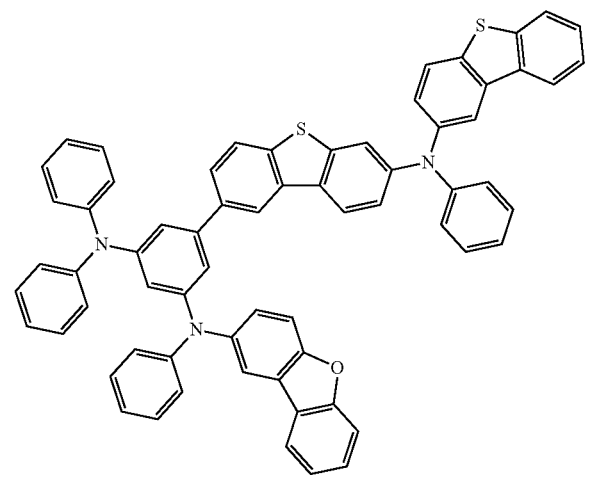
P-93
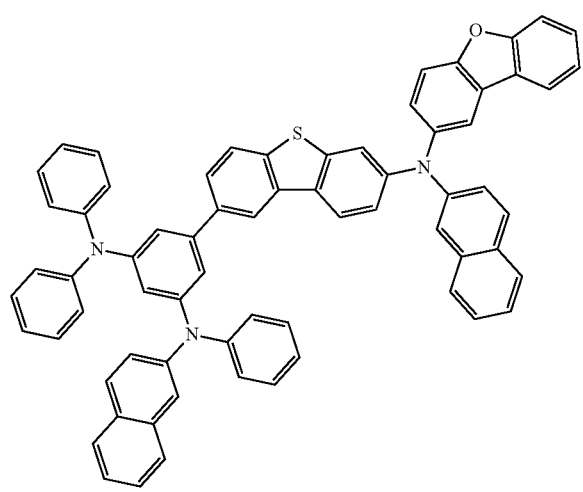
P-96
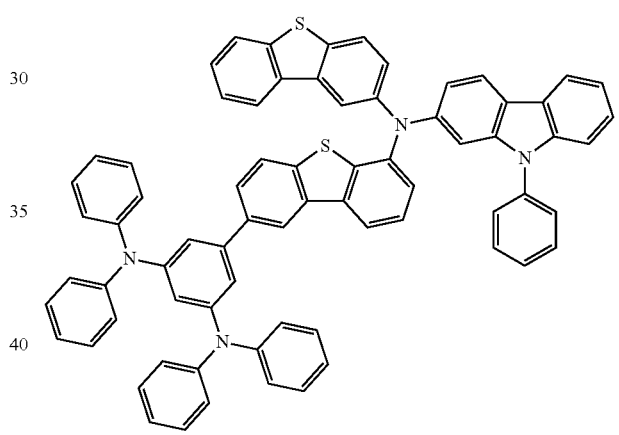
P-94
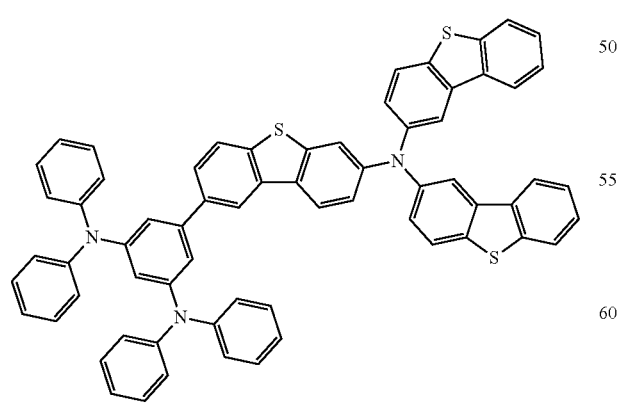
P-97
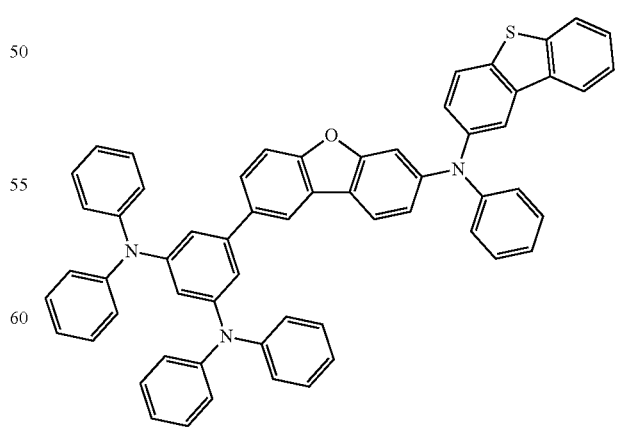

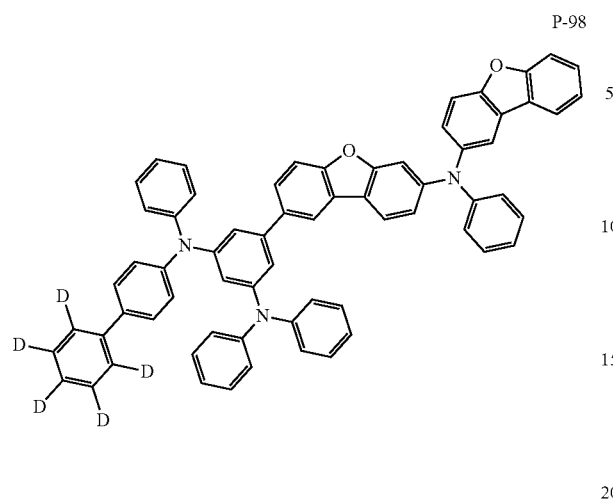
P-98
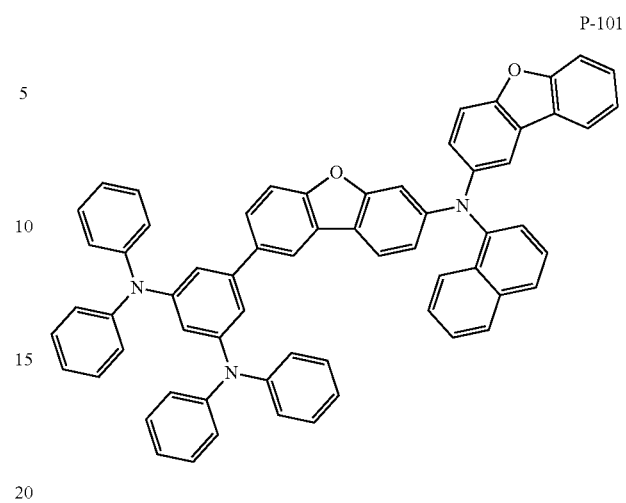
P-101
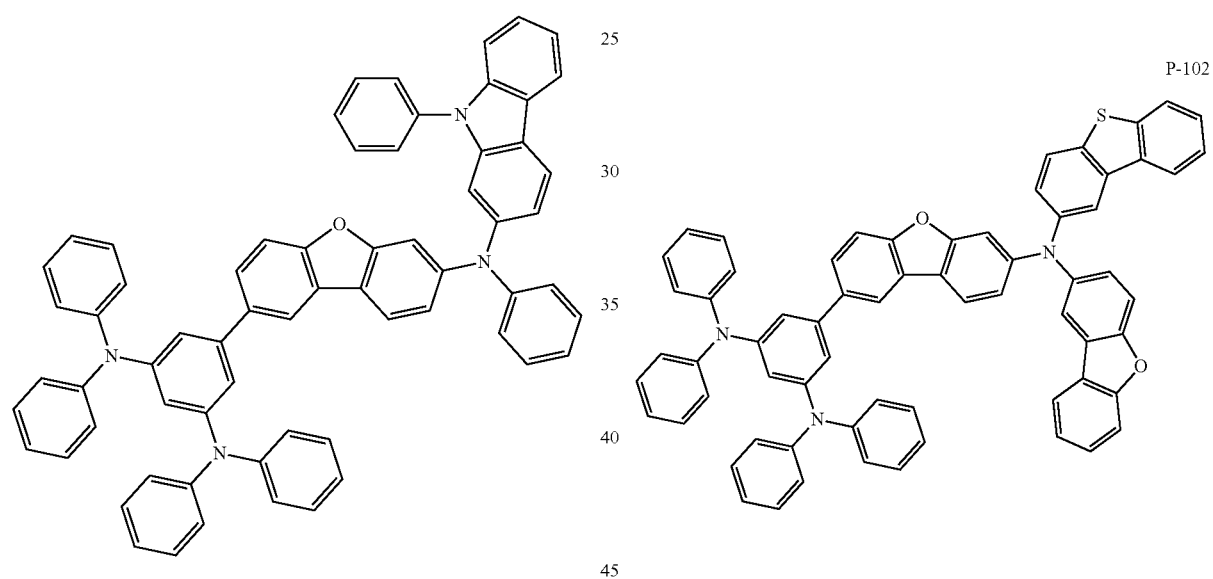
P-99
P-102
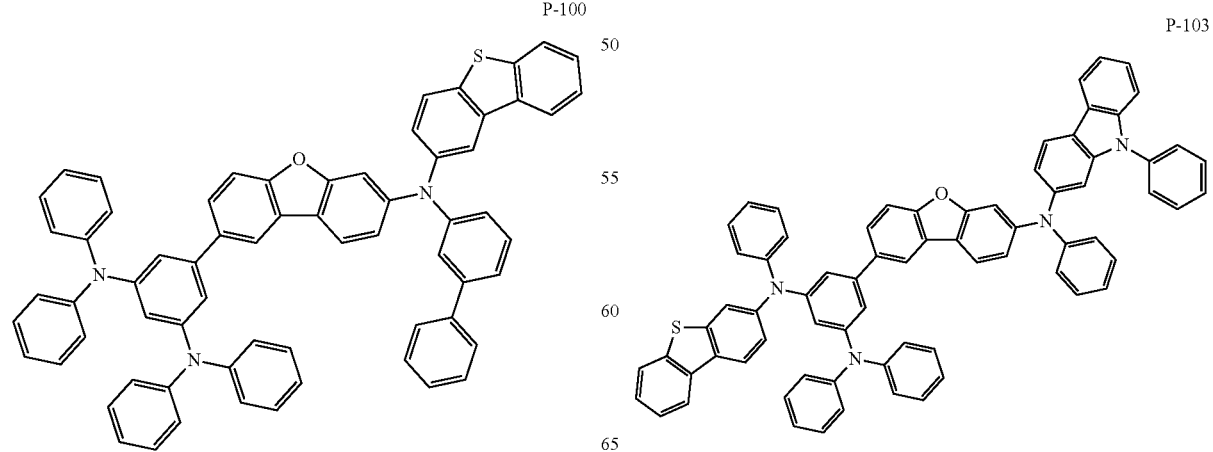
P-100
P-103

P-104
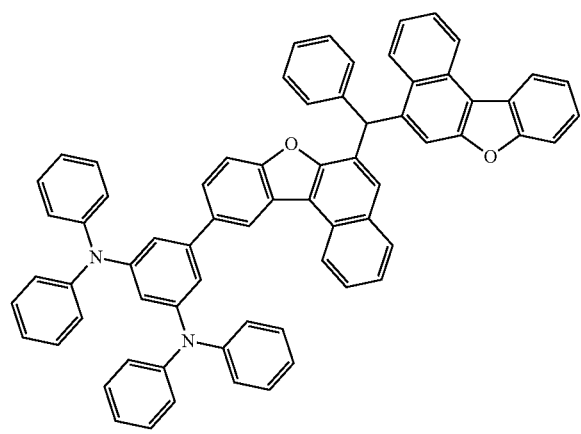
P-105
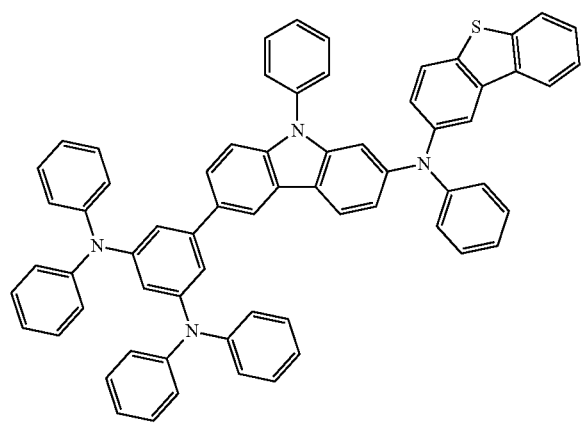
P-106
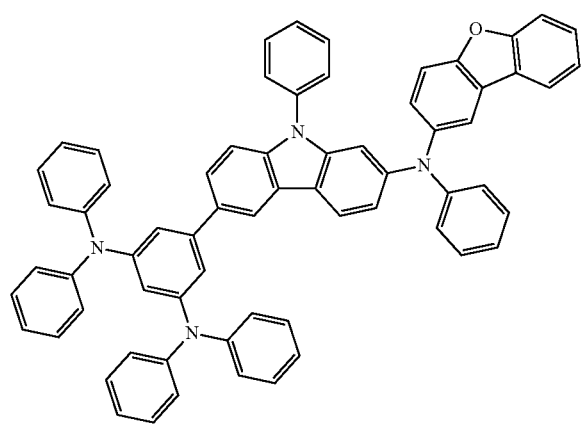
P-107
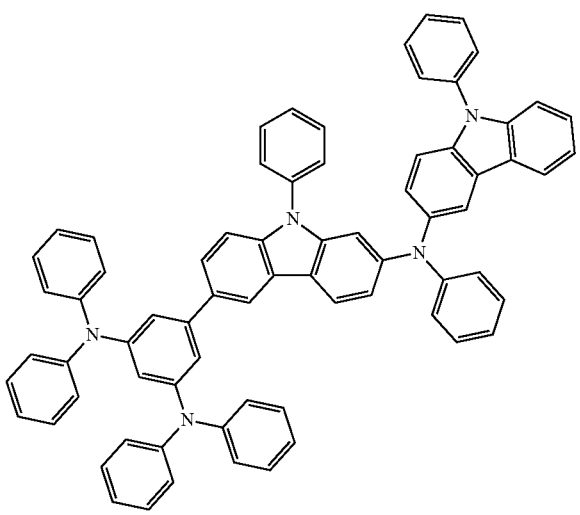
P-108
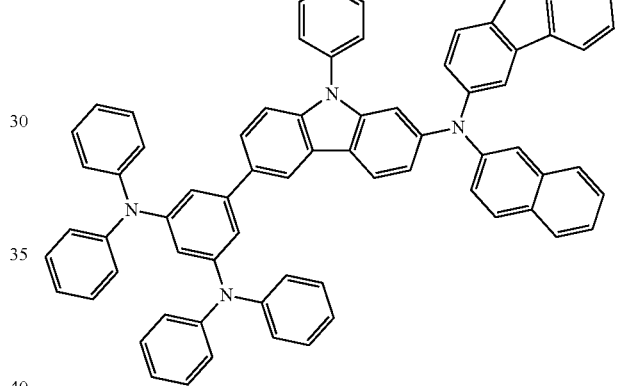
P-109
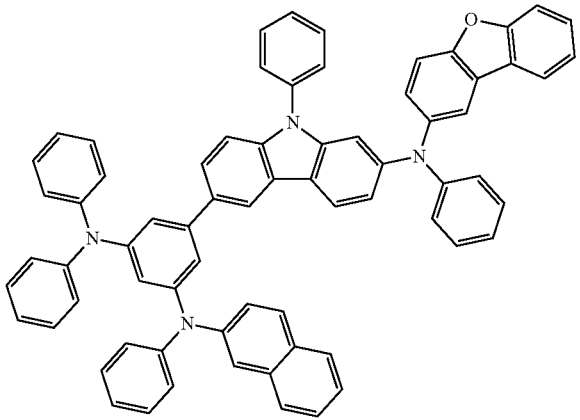

-continued
P-110
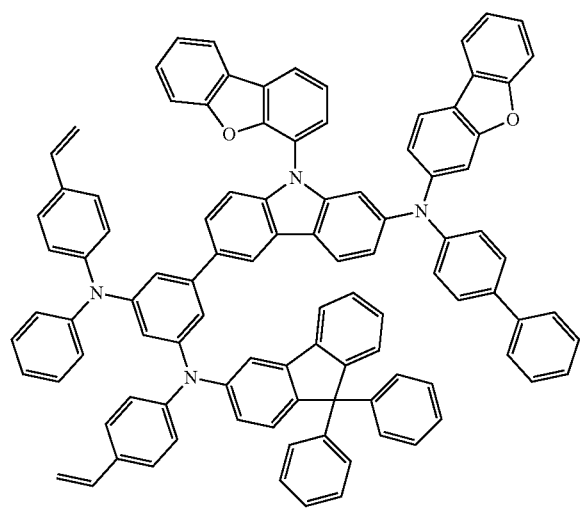
P-111
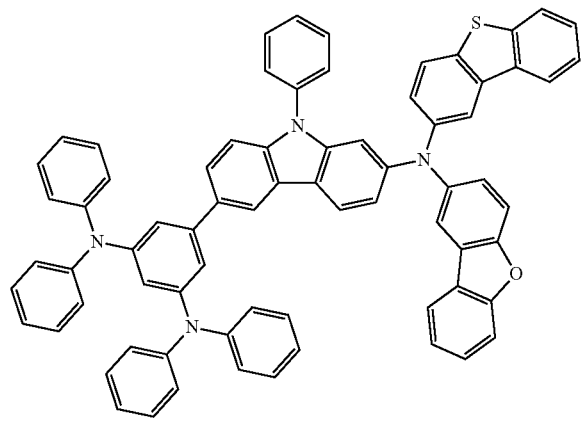
P-112
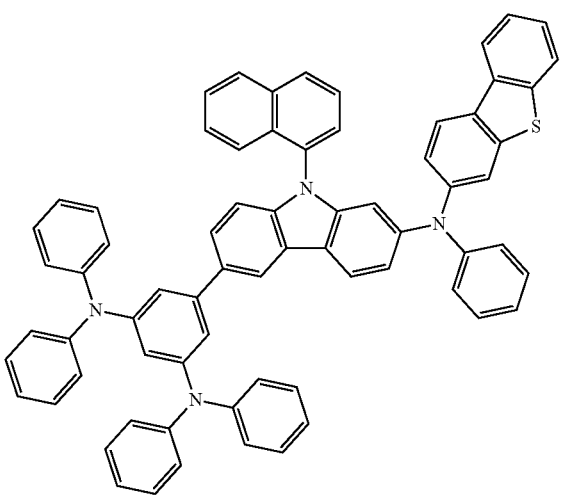
* * * * *